(12) United States Patent
Graham et al.

(10) Patent No.: US 9,334,515 B2
(45) Date of Patent: May 10, 2016

(54) POLYPEPTIDES FOR USE IN THE DECONSTRUCTION OF CELLULOSE

(75) Inventors: Joel Edward Graham, Baltimore, MD (US); Melinda E. Clark, San Francisco, CA (US); Frank Thomson Robb, Gaithersburg, MD (US); Douglas S. Clark, Orinda, CA (US); Harvey W. Blanch, San Francisco, CA (US)

(73) Assignees: THE REGENTS OF THE UNIVERSITY OF CALIFORNIA, Oakland, CA (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 129 days.

(21) Appl. No.: 13/813,154

(22) PCT Filed: Jul. 14, 2011

(86) PCT No.: PCT/US2011/044074
§ 371 (c)(1),
(2), (4) Date: Mar. 20, 2014

(87) PCT Pub. No.: WO2012/015605
PCT Pub. Date: Feb. 2, 2012

(65) Prior Publication Data
US 2015/0211037 A1 Jul. 30, 2015

Related U.S. Application Data

(60) Provisional application No. 61/369,588, filed on Jul. 30, 2010.

(51) Int. Cl.
| | |
|---|---|
| C12N 9/26 | (2006.01) |
| C12P 7/00 | (2006.01) |
| C12N 15/00 | (2006.01) |
| C12N 1/20 | (2006.01) |
| C07H 21/04 | (2006.01) |
| C12P 19/14 | (2006.01) |
| C12P 19/02 | (2006.01) |
| C13K 1/02 | (2006.01) |
| C12N 9/42 | (2006.01) |
| C12N 9/24 | (2006.01) |

(52) U.S. Cl.
CPC ............ *C12P 19/14* (2013.01); *C12N 9/2402* (2013.01); *C12N 9/2437* (2013.01); *C12P 7/00* (2013.01); *C12P 19/02* (2013.01); *C13K 1/02* (2013.01)

(58) Field of Classification Search
CPC ............................... C12N 9/2402; C12P 7/00
See application file for complete search history.

(56) References Cited

FOREIGN PATENT DOCUMENTS

| WO | 2007/118935 A1 | 10/2007 |
|---|---|---|
| WO | 2008/025164 A1 | 3/2008 |

OTHER PUBLICATIONS

Graham et al. F6M085_9CREN—UniProtKB/TrEMBL. 2011.*
International Search Report and Written Opinion received for PCT Patent Application No. PCT/US2011/044074, mailed on Dec. 8, 2011, 12 pages.
International Preliminary Report on Patentability received for PCT Patent Application No. PCT/US2011/044074 issued on Feb. 5, 2013, 6 pages.
Copeland et al., "Unirpot Direct Submission Accession A4XMG8 [online].", May 29, 2007, Document Available at <URL:http://www.uniprot.org/uniprot/A4XMG8.txt?version=1>, Retrieved on Dec. 2, 2011, 1 page.
Finan et al., "Uniprot Direct Submission Accession Q92TY9 [online]. Dec. 1, 2001", Document Available at <URL:http://www.uniprot.org/uniprot/Q92TY9.txt?version=1>, Retrieved on Dec. 2, 2011, 1 page.
Muzny et al., "EMBL Database Entry AC133618.3 [online]. Jun. 3, 2003", Document Available at <http://www.ebi.ac.uk/ena/data/view/AC133618>, Retrieved on Nov. 17, 2011], 3 pages.
Rusch et al., "EMBL Database Entry EK682540.1 [online]. Jun. 3, 2010", Document Available at <http://www.ebi.ac.uk/ena/data/view/EK682540>, Retrieved on Nov. 17, 2011], 2 pages.
Sudarsanam et al., "Uniprot Direct Submission Accession A7VX72 [online]. Oct. 23, 2007", Document Available at < http://www.uniprot.org/uniprot/A7VX72.txt?version=1>, Retrieved on Dec. 2, 2011, 1 page.
Office Action Received for Australian Patent Application No. 2011283091, issued on Sep. 23, 2013, 5 pages.
Office Action Received for Australian Patent Application No. 2011283091, mailed on Mar. 26, 2014, 3 pages.
Office Action Received for European Patent Application No. 11812939.4, mailed on Jul. 8, 2014, 4 pages.
Office Action Received for Chinese Patent Application No. 201180035220.2, mailed on Feb. 11, 2015, 9 pages (5 pages of English Translation and 4 pages of Official Copy).
Extended European Search Report (includes Supplementary European Search Report and Search Opinion) received for European Patent Application No. 11812939.4, mailed on Nov. 22, 2013, 5 pages.
Pottkaemper et al., "Applying Metagenomics for the Identification of Bacterial Cellulases that are Stable in Ionic Liquids", Green Chemistry, vol. 11. No. 7, 2009, pp. 957-965.

* cited by examiner

*Primary Examiner* — Yong Pak
(74) *Attorney, Agent, or Firm* — Morrison & Foerster LLP

(57) ABSTRACT

Hydrolysis and degradation of cellulose-containing biomass by use of a polypeptide having cellulase activity is provided. Also provided are polypeptides having cellulase activity, such as archaeal cellulases, polynucleotides encoding the polypeptides, and compositions containing the polypeptides, and methods of use thereof.

8 Claims, 28 Drawing Sheets

FIG. 1A
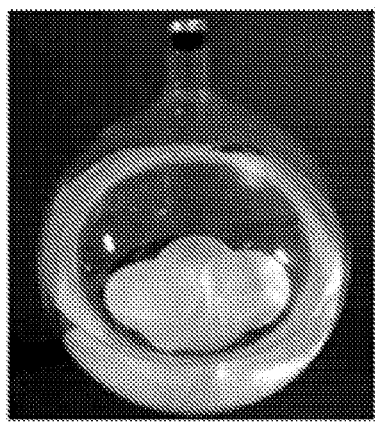 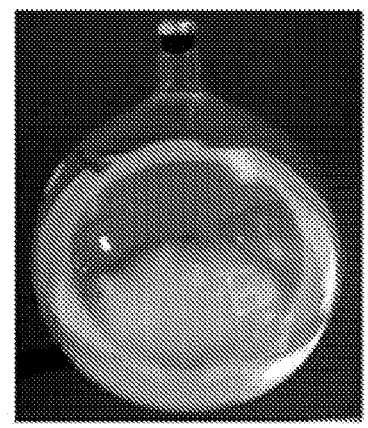
FIG. 1B  FIG. 1C

| | |
|---|---|
| gi\|294054782\|ref\|YP_003548440.1\| | 50 MQWHKVMLTFDGPGTST-ATPNPF-- |
| gi\|182415705\|ref\|YP_001820771.1\| | 41 KQWHKVSLTFAGPSTSETNSVNPF-- |
| gi\|294054225\|ref\|YP_003547883.1\| | 32 RTWHKVTLSWNGPQTNELATPNPF-- |
| gi\|294054029\|ref\|YP_003547687.1\| | 51 MQWHNVILTMNGPNSSS-ATPNPF-- |
| gi\|182413656\|ref\|YP_001818722.1\| | 36 EQWHKITLSIDGPEARTDTSPNPF-- |
| gi\|324476360\|ref\|NP_869354.1\| | 45 RMWHKVTVTLNGPYAHQDNTPNPY-- |
| gi\|260062629\|ref\|YP_003195709.1\| | 31 QKWHRIQILFDGPQTSESASQNPF-- |
| gi\|269839032\|ref\|YP_003323724.1\| | 12 GEWEV-----TSTREYE------NPF-- |
| gi\|171742388\|ref\|ZP_02918195.1\| | 9 EQHRLFEINLTGTTEG-------NPY-- |
| gi\|182414093\|ref\|YP_001819159.1\| | 34 ERWNTFELTLHGPATG-------NPF-- |
| gi\|294776617\|ref\|ZP_06742086.1\| | 27 ECWDRFELSFKQVTKG-------NPF-- |
| gi\|284038044\|ref\|YP_003387974.1\| | 25 EQWGRFEKTFTAKATG-------NPF-- |
| gi\|261406849\|ref\|YP_003243090.1\| | 15 ERWGIFEVALSGPSAG-------NPF-- |
| gi\|156437l2\|ref\|NP_228758.1\| | 10 EKWGTYEITLKGKAEG-------NPF-- |
| tr\|A7HFC4\|A7HFC4_ANADF | 33 LANQMVEWTFTSTRPYK------DPF-- |
| tr\|C7PTR3\|C7PTR3_CHIPD | 46 SANVMVEVSFTANRTYS------DPF-- |
| gi\|295135314\|ref\|YP_003585990.1\| VIMSS5326244 | 24 KKYDRFEEEFQSDKTYE------NPL-- |
| tr\|D1N449\|D1N449_9BACT | 47 PKFGLVEIAFNISGLSS----NPFDT |
| tr\|A7VX72\|A7VX72_9CLOT | 46 PEQGEANALFOGRFRLLREFFNPFDP |
| tr\|A9AYF5\|A9AYF5_HERA2 | 20 PAFEKFEAAFAFEKVFE-----NPYCP |
| tr\|A4XMG8\|A4XMG8_CALS8 | 42 AVFGTIELAIDTTITVA------NPYDP |
| tr\|B1ZN60\|B1ZN60_OPITP | 45 YKYSKFEISFKTPAFKG-----NCFDP |
| | 35 HAWFGAFFRTAGAPVAF-----NNFDP |

| FIG. 8C |
|---|
| FIG. 8CA |
| FIG. 8CB |

FIG. 8CA

```
RDYRMDVTFTGPSS-QSYVVPGYYAADGNSGETSLGSGNRWRVAFAPDEAGTWNYSVSFVTGTDIA
TNYRLNVTFKHSASNRTLIVPGYFAADGNAANTGAVSGDKWRVDFTPDATGTWTYVASFRTGSNVA
TDYRLDVRFTHQSG-TSYLVPGYYAADGDAANTGADSGSVWRVHFAPDAIGNWDYAVSFRTGEAVA
KDYRMNVTFTHPNSGLSYTVPGYFAADGNAGQTGATSGGKWRAHLCPDHAGQWTYSVSFRSGTDVA
LDYRMDVTFTHESGAPSYRVPGYFAVDGNAAETSAFAGRIWRAHLAPDKPGMWRYAVSFRRGPEVA
LDHRMEVEFKHESG-KQYLVPGYFAADGNAANTSAESGTQWRAHFAPDETGEWTYTVHFATGKDAA
LNYRLNVLFTAPDG-REFTVPGFFAADGNAAESSATSGNKWAVRFSPDQVGTWTYTASFRTGDEVA
VDVEVIGRFISPSG-REWRVPGFY------------DDGVWKVRFNPGEEGRWAYRLE--------
QDVTLSADFTNETG-QIVVVGGFY------------RGNGNYSVRFMASSAGRWAFTTR--------
VDVRLGARFTD---GTRTIEVPGFY-----------DGDGVYRVRFMPDATGAWHYETS--------
-DIRLSATFVC---GKEKKTVEGFY-----------DGENTYRIRFMPAVAGEWRYVTS--------
TEVTLTAELSN---GYTTYSVAGFY-----------DGKDTFKIRFMPPKTGKWRYKTS--------
EEVAVSATFEYRN--DRVEVEGFY------------DGDGIYRVRFMPDREGTWRYVTK--------
TDVEIKAVFTSEAG-DSFEVEGFY------------DGEDTFKIRFMPNRTGLWKYEVR--------
NQIELNVTFTTPSG-KKLLVPAFW------------DGGDIWHVRYSSTETGIHHFSTV--------
NEVTLDVTFIDPKG-QELRVPAFW------------AGKNVWKVRYASPVVGTHSFQSE--------
YDVEFDVKFISPSG-REQVVRGFW------------DGGSTWRVRFMPDEIGTWQFSTS--------
QDITLSVEFTSPQG-EKIKTYGFW------------DGARIWKFRFSPDQAGKWTYQTS--------
---PVRAEVLAPSG-ARIHVPAF-------------PVPGGWAARFRPREPGRHRWVAR--------
REIKLDMCLVSPSG-KPLLLPAYFD-----------QVNHHWQSRFAPQETGQYQYYFE--------
EDIAVDIKMQSPSG-KEILLPCFYVSGES-------GEASEWEARFAPQEIGRYTYHLV--------
SDIDVWHIETPSG-SRVAVPAFYFQNYTVEI IVRVGRPYWLARFAPVEEGVHKFYVK--------
DEVTVDFEIKAPNG-KLTRLPAFYSRDYERETATPIGQGFWEFRFTPPVPGEYRLRAV--------
EEVDLKAYILKPNG-DQKQISGFWYEGFQREILISTLEKDWRIRYSAQVPGEYRYVT--------
NQIDLMVSFISATG-QIYRVPAFWYQDFDQLSLQPKGNPEWRVRFTPSEPGAWQVKAE--------
DEIDIWGEFVSPSG-KKYVMPAFWYQDYKREVLTKVGQPEWRIRFCPVEIGKWKYTIY--------
PQIRLDAIFTGPSG-ETRSVAAFWYQDYTREVLTPQGTPEWRLRYTPTEAGEHRVTLH--------
```

FIG. 8CB

| FIG. 8D |
|---|
| FIG. 8DA | FIG. 8DB |

FIG. 8DA

```
gi|294054782|ref|YP_003548440.1| 275 -----------------DIWRYDCSKLCDWQVLFCHFDRKCNMMH--FVMTCQQHCQLFEYADP
gi|182415705|ref|YP_001820771.1| 270 -----------------DRTRFDVSKLADWEIVFSHMQKLGINLH--VVTCECCCDCL------
gi|294054225|ref|YP_003547883.1| 260 -----------------ERYRNQCSKLADWCVVFCHAQSKCHFLH--FKTCETQHECL------
gi|294054029|ref|YP_003547687.1| 279 -----------------HPLQFDCSKLQDWCIVFSHGQKMCNYLM--FKTCLHQHECLDCPGSA
gi|182413656|ref|YP_001818722.1| 265 -----------------DPLHFDCSKLQDWCIIFQHATALCLHLM--FKLCCTCHDCNHPGGCG
gi|324763601|ref|NP_869354.1  | 273 -----------------QKLHYDCSKLQDWCIVFQHGTENCHYLM--FKLCETEHQCHRQGKA
gi|260062629|ref|YP_003195709.1| 261 GLFPGGQDSSNRLRYDVSKLEDWLILFQHAQSKCHFIM--FKTCFFENCAL------
gi|269839032|ref|YP_003323724.1| 174 -----------------APVRFNLEYFATWQRVVRKVEELCLGLEVIH-----------EAWC
gi|171742388|ref|ZP_02918195.1| 175 -----------------ETGFQHTCFDEEFFAHLCCRIACLDELCIEAQITLLHPYQK-----PIWC
gi|182414093|ref|YP_001819159.1| 196 ------------PRDWDFARFNPEYFRAFCKAVACLRELCIEAQITLTHPYG------KAWC
gi|294776617|ref|ZP_06742086.1| 190 KDEGHERKEWDFDREDPAFFQHLCKRIDQLHRLCIEADLTLFHPYQK---GRWC
gi|284038044|ref|YP_003387974.1| 189 KDDGKPVTVWHFDREDPAFFQHLCKRIDQLHRLCIEADLTLFHPYQK---GRWC
gi|261406849|ref|YP_003243090.1| 172 --AGTCPEPADTTRENPAFFAHLCERIGDLMKLCVEADLILFHPYDKQ---GRWC
gi|156437121|ref|NP_228758.1  | 168 -----------------EEDGRYEFNVKFFQHFCRLVKELHDMCIEADVILFHPY------DKWC
gi|223936397|ref|ZP_03628309.1| 202 ------------EGGFPWETHFTRINPKYFQHPCDRIAFLWDSCLAPC--LF------GRWC
gi|223934736|ref|ZP_03626656.1| 216 ------------EAGYTWETHYTRIRPEYFQAACKRMMHLVDCCFTPCIV---------GRWC
gi|126645445|ref|ZP_01717989.1| 189 ------------GEVAFTGSGKISLNPEFFQRICQKIEEANAKCLLVSPVVLWAIPFGQGTEYSPGYY
gi|223936533|ref|ZP_03628444.1| 204 ------------OSVFESTSTTLTINLHLFQQLCSRIETLNRACLLSAILPLRDLEAQA------PGLE
tr|A7HFC4|A7HFC4_ANADF         | 202 -----------------EPVAFDEAAARYCAIFAAAEAHCVKVVLSVFAIGFTPGDALI---KGWE
tr|C7PTR3|C7PTR3_CHIPD         | 200 PRTKRYQPSAE--YFHPGAIRRYCOLVDNCDSLCLYFMLTDWHGHLHEH------GGWK
gi|295135314|ref|YP_003585990.1| 175 NFNSRYTASDA--YYNPSAVAKLCSLVDLSKKCLHM-NLTLGPGNYSKED------GGFA
VIMSS5326244                    220 LH------------YYSLDDAARICEIVKLAEKYDIYIVFVFHWHGELA------DNWG
tr|D1N449|D1N449_9BACT         | 235 ----TRAGNYGRYNLEAALIKLCHIFEQARKNGIYLNLILDNHGRLSDRSD--PEWQ
tr|A7VX72|A7VX72_9CLOT         | 204 LH------------EYNQDNALKLCRRFQTAEELGIFFRLSLFHWEDFDDETEKFPDWG
tr|A9AYF5|A9AYF5_HERA2         | 213 ----TGLGDYSKRMQQALMLCOIFXLAEQRNITINLTLINHGAFSTSTD--SEWA
tr|A4XMG8|A4XMG8_CALS8         | 217 ----TGIYDFTNALDRAYQLCKVLELAEQKGIYIHLTFINHGOFSTKVN---POWN
tr|B1ZN60|B1ZN60_OPITP         | 207 ----KGTHYPLQAAWQLCQIFALAETRGLYLLLCFQHHQYYHAND---PAWG
```

FIG. 8DB

```
gi|294054782|ref|YP_003548440.1|   364 TIYAGACSDQRKDFSDHGRALLPYEDHIS--------
gi|182415705|ref|YP_001820771.1|   345 -----NTDAQREAFADYLNALDPYFSLIA--------
gi|294054225|ref|YP_003547883.1|   342 VKEHFQSTECRQAMAQWFYDNDPYKHMLV--------
gi|294054029|ref|YP_003547687.1|   362 -------QSTSQRQAMAQYFRDTDPYGHNIV-------
gi|182413656|ref|YP_001818722.1|   354 ------LSTECQQAMAAFIRDTDPYHHPIV-------
gi|324763360|ref|NP_869354.1|      361 ------QTTDEHLAMLNYIEEMDPYGHMRV-------
gi|260062629|ref|YP_003195709.1|   348 DELGDTNNTRVRAYASYIKSLDPYNHMIV--------
gi|269839032|ref|YP_003323724.1|   258 WHYKPTADRWAIRIARWLRANAPWGHIVS--------
gi|171742388|ref|YP_001819159.1|   255 UMPQKSLEDWR-EYARVVMANDAFGHLRS--------
gi|182414093|ref|YP_001819159.1|   275 LVRTKTEEHWQ-OLGRLVOATDPFDHLRS--------
gi|294776617|ref|ZP_06742086.1|    276 YVKAKTVDDWK-LLTKTVENDPYRHLCS---------
gi|284038044|ref|YP_003387974.1|   275 YVKSKTVSDWD-LLAKTVAQNDPYKHLCS--------
gi|261406849|ref|YP_003243090.1|   257 FNKHKTIEDWQ-RLLQVYQRXDPYQRLRS--------
gi|156437121|ref|NP_228758.1|      245 --LIKPOKDWQ-GYFNFIVEXDPYNHLRS--------
gi|223936397|ref|ZP_03628309.1|    287 AKDQAQLLKWT-KVTRYVROVDPYNRPLS--------
gi|223934736|ref|ZP_03626656.1|    301 PYDQRKOVKWT-EVTRYNRATDPFNRPITIHPTG---
gi|126645445|ref|ZP_01717989.1|    276 --YYGDLEDWK-SIGSQVTGDGKHQGLVTLHPHG---
gi|223936533|ref|ZP_03628444.1|    287 -NLSTQVARWK-RVGRSVTAN-OHHAPVI--------
tr|A7HFC4|A7HFC4_ANADF             306 AIPEDHWIPWAEDLARTWRAEDPYGHPVIAGPVG---
tr|C7PTR3|C7PTR3_CHIPD             314 LIPLPVIAQWMLCHSRYLKDIDPYHHLVSTSI-----
gi|295135314|ref|YP_003585990.1|   277 PIDAKTIVDWMCCMSNYIDKIDPYNHIITTSI-----
VIMSS5326244                       321 FSARSAFVSWVKCISSYIKSVDPYNRIVTVNLAQ---
tr|D1N449|D1N449_9BACT             347 RYNOGSAIRWACKAAAFLOANSPVSIHFCSQYNN---
tr|A7VX72|A7VX72_9CLOT             313 DDEASKVIGWM3CHGSYLKOLD3-KHLVT3SFAO---
tr|A9AYF5|A9AYF5_HERA2             319 PINDALHOPWISCHTRWLAOFDPYCHLVSTSYA----
tr|A4XMG8|A4XMG8_CALS8             323 DNYOPEKSNWMKDHALFIKSIDPYKHLVSSSSAV---
tr|B1ZN60|B1ZN60_OPITP             314 DLVHADVVAWMRDHARWLPAHDPYOHLITTSLTG---
```

FIG. 8EA

| FIG. 8E |
|---|
| FIG. 8EA |
| FIG. 8EB |

```
IHNGPSSTDAIFNALVGHTSFT-GPAFOWNINT---NIAAKTK-OURDASIASGHKWVFCMDEPYLGGN----------------------PN
VHTYPSOPDTIYTGHLGSELIS-GASLOLESPS--IVHEOTL-KWVKKSAAAGSKWVSVDELGPSSAGVV-PDANDP---------AH
IHNGOSPND------LLGDASKLTGFSLOTNLEDFANVPGTVA-SWIRKSAEAGKPWAVACDEPGOASHAIR-PDONAGS----SH
LHTYPGEWEOVYRPLLGSASELTGASIOTNYN----TVHSRTL-OWLNESTAAGKVWVVANDEOGPASHANP-PDNGWPGYTGSTSO
LHTFPDWOERVYRPLLGDRSALTGVSLOT-------GWEQSHRRVL-OWIEESAAAGKOWVVAHDEQNPHYTGVP-PDTGWEGFDGTATA
LHTYPGEODKKYDPLLGDKSNLTGVSLONSHIK---DTHWOTV-KWSEKAREAGKPWVVAFDESGSAAHGQC-PDLGYRGYDGRDTO
IHSYPNSOSELYEPLLGDSDLT-GPSLOIOIN----NIHRDVK-RWINDSKASGKOWVVTNDEOGDWTTGVA-ADASYGGDKGSRNR
LHNG---PWDPPFAHRFRSDOFWGGRDDAWLAAGIEDRIAYSLGGWYG-------TAVFA--EYGYERNP--ALPLNIPGHEF---CO
IHNCIPIYDYNE-PWCTHCSIORVDVTRT------TECIAD----WRKA---YGKPVVCO--EPGYEGNI----YWGWGNLTG--EE
IHHSQ--LLFDNROPWTHASIONGSAVEEP----GRAELYRDVWRK------PVVYD--EVKYEGNA-----RRRWGOLSG--PE
IHGATATYFDYWMPEFTHV------SIODEAPVLSSTASATLRKIYRK-----PVICO--EYGYEGNL---PYRWGRLS---PQ
IHGATATYDYRKPEFTMVSIODETPVOSPNAAAMLRHIYNK-------PVIAO--EVGYEGNL----KSRWGRYS----PE
IHNGTKSLYDFESKSWLTHO--------SIOHWOTSPTT---CWREA----VRKPIVVO--EISYEGNV----AKRWGNITG--LE
VHOCFKFYDHTK-PWITHASIOWGSLRSWSGEPEIDIGIHLIPKWREM---VKKPVIID--FCGYEGNI----EYGWGNLPP--OE
IHPPIEROOVSDPNLLDFDMLOSGWDDRASVPYTISLVRRSRSSSPRM----PTIDA--EVCYEGILNCORYMEWRCLLGGTAG
IGRLSARHAMDDLSLIOIDMLOTPHGORDAVAP---TVHTMRE-SYADKPVM----PVING--EASFEMLSSLTRRMFWLCLMNGAAG
LSWIGDIYE--NOCWYDVITYOSSNSNSENTVNWINKGPIAK-OWDNLRPM---PLINT--EPNYECIFITRNASYWSVFAA--PP
LHPGTTLOEFRAEPWVDVLSYQSGOEADDNALOWLLAGPLAI-DWQRVPLK---PFINL--APYYENSSTORRLIYWSLLNA--PT
LHWYVEWWASAACOIVOWHRY--GPDVHDVHDLAEALVETTR----DTARYGKPVLIG--EFG-------WGGDAK--PE
SHRD---IIGMNAIPYIOFN----------OKHIYKHTEKIPGIYP-DYIOT---FGKPYVVG--EFGYRWED---ODPKYATEANY---
SHRD---LEGLNSLPAIDIN----------OKHIYNRTKDIPGEII-DYEKR---FGKPYVIG--EFSYDWDW---SKNFDEFPE--EN
YNSEPRVWSVESIOINVNRY--GPEGFKDIAL---AIPSIVEGLWNT-----YRKPIIIT--EFGVDYRWIGKGTPYWA--YD--KS
VRRFIKLFDNPSITHLAGDAYRS-------PQINFVDHLRGYEONMRYNKPQUIT--EFGGN-----PQGSSERQVL--AD
SRRDLNLWOLPCIDLTTVHRYTYEEYGQROYDTEGALSAVLKERESO----VEKPVLFG--EFALS------PGGDIOKDYD--PE
SNTSTSMWVOPEINFTQHHDYT-GRDLGQAFPLVIRELNAAA-------PQKPALVS--ELGYAGTG--RDEVINRDVW-----
LYDP---LEKVKELDFININDYGI------TNFCKNIPSKQR-DIADM--YNKPAFFC--ENGIA------SDPTTTKRLD-RX
GSDRPEHWOLPEMEFSMYHSYWDPAPARKAAVLAEDFHHR----------YGKPVMIG--EFGVSGAN------WARPMD--PH
```

FIG. 8EB

POLYPEPTIDES FOR USE IN THE DECONSTRUCTION OF CELLULOSE

CROSS-REFERENCE TO RELATED APPLICATION

This is a U.S. National Phase patent application of PCT/US2011/044074, filed Jul. 14, 2011, which claims the benefit U.S. Provisional Patent Application No. 61/369,588, filed Jul. 30, 2010, each of which is hereby incorporated by reference in the present disclosure in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 677792000900SUBSEQLIST.txt, date recorded: Dec. 04, 2015, size: 280 KB).

FIELD

The present disclosure relates to hydrolysis of cellulose-containing polysaccharides and degradation of biomass using polypeptides having cellulase activity, including hyperthermophilic polypeptides. In particular the present disclosure relates to archaeal polynucleotides encoding the polypeptides, the polypeptides themselves, and compositions, methods and uses thereof.

BACKGROUND

Cellulose, the major component of plant biomass, is considered the most abundant biopolymer. Bayer, E. A., Chanzy, H., Lamed, R., Shoham, Y. (1998) Cellulose, cellulases and cellulosomes. Curr. Opin. Struct. Biol. 8, 548-557. Certain microorganisms are able to convert the monomer of cellulose, glucose, into various products useful in the production of biofuels and other methods. Cellulose is highly stable, has a high storage potential, low cost, and plentiful supply. Based on these and other properties, cellulose and enzymes capable of degrading and hydrolyzing it are useful in the sequestration, storage, and production of bioenergy. Lynd L R, Weimer P J, van Zyl W H, Pretorius I S (2002), "Microbial cellulose utilization: fundamentals and biotechnology," Microbiol Mol Biol Rev 66: 506-577.

Crystalline cellulose is composed of linear polymers of β1-4 linked glucose, held in a tightly crosslinked crystalline lattice by a high degree of intermolecular hydrogen bonding. This structure confers stability but also hinders efficient deconstruction of cellulose. Strategies for commercial depolymerization of cellulose typically combine pretreatment to disrupt the crystalline structure, followed by enzymatic hydrolysis. Hilden L, Johansson G (2004), "Recent developments on cellulases and carbohydrate-binding modules with cellulose affinity," Biotechnol Lett, 26: 1683-1693. Disruption of the crystalline structure and chemical hydrolysis typically requires high temperatures and low pH. See Kim J S, Lee Y Y, Torget, R W. (2001) "Cellulose hydrolysis under extremely low sulfuric acid and high-temperature conditions, Appl. Biochem. Biotechnol. 91-93 331-340. Enzymatic hydrolysis generally occurs under milder conditions. The degree of pretreatment required and the expense of subsequent cleanup steps are affected by properties of the enzymes used.

Bacteria capable of degrading cellulose include those belonging to the genera Aquifex, Rhodothermus, Thermobifida, Anaerocellum, and Caldicellulosiruptor. A recombinant thermostable endoglucanase of Aquifex aeolicus produced in E. coli showed maximal activity at 80° C. and pH 7.0 with a half-life of 2 h at 100° C. (Kim J S, Lee Y Y, Torget, R W (2001). Cellulose hydrolysis under extremely low sulfuric acid and high-temperature conditions. Appl. Biochem. Biotechnol. 91-93. 331-340)). The endoglucanases produced by Anaerocellum thermophilum and Caldicellulosiruptor saccharolyticus are multidomain enzymes composed of two catalytic domains, linked to carbohydrate binding domains by proline-threonine-rich regions (Zverlov V, Mahr S, Riedel K, Bronnenmeier K (1998a), "Properties and gene structure of a bifunctional cellulolytic enzyme (CelA) from the extreme thermophile 'Anaerocellum thermophilum' with separate glycosyl hydrolase family 9 and 48 catalytic domains," Microbiology 144 (Pt 2): 457-465; Te'o V S, Saul D J, Bergquist P L (1995), "celA, another gene coding for a multidomain cellulase from the extreme thermophile Caldocellum saccharolyticum," Appl Microbiol Biotechnol 43: 291-296; Saul et al. 1990. The recombinant endoglucanase of Rhodothermus marinus has a pH optimum of 6.0-7.0 and a temperature optimum at 100° C. (Halldórsdóttir S, Thórólfsdóttir E T, Spilliaert R, Johansson M, Thorbjarnardóttir S H, Palsdottir A, Hreggvidsson G O, Kristjánsson J K, Holst O, Eggertsson G. (1998), "Cloning, sequencing and overexpression of a Rhodothermus marinus gene encoding a thermostable cellulase of glycosyl hydrolase family 12," Appl Microbiol Biotechnol 49: 277-284). The aerobic thermophilic bacterium Thermus caldophilus also produces an endoglucanase which exhibits high activity on CMC with cellobiose and cellotriose as products (Kim D, Park B H, Jung B-W, Kim M-K, Hong S I, Lee, D S (2006) Identification and molecular modeling of a family 5 endocellulase from Thermus caldophilus GK24, a cellulolytic strain of Thermus thermophilus. Int J Mol Sci 7: 571-589). In contrast, high-temperature, crystalline deconstructing cellulases from hyperthermophilic Archaea are few in number, despite efforts to identify such enzymes. Hyperthermophilic enzymes that act on cellulose typically lack identifiable cellulose binding domains.

Thus there is a need for improved cellulases, including cellulases encoded by hyperthermophilic archaea, and cellulases having high stability and tolerance to a range of chemical and physical parameters, including cellulases with activity at high temperatures and over a broad range of temperatures and pH, cellulases with higher catalytic activity and rate of conversion, activity in the presence of salts, ionic detergents, sulfhydryl reagents, and ionic liquids. Provided are polypeptides, compositions and methods that meet this need.

BRIEF SUMMARY

The present disclosure relates to isolated polypeptides (proteins), and in particular cellulases, including cellulases encoded by hyperthermophilic archaea, and cellulases having high stability and tolerance to a range of chemical and physical parameters, including cellulases with activity at high temperatures and over a broad range of temperatures and pH, cellulases with higher catalytic activity and rate of conversion, activity in the presence of salts, ionic detergents, sulfhydryl reagents, and ionic liquids. For example, provided are polypeptides, such as EBI244, having cellulase activity, e.g., endoglucanase, exoglucanase and/or β-Glucosidase or β-Glucosidaseglucohydrolase activity, such as cellulases produced by archaea. Certain aspects of the present disclosure relate to an isolated EBI244 protein having the amino acid sequence of SEQ ID NO: 1, and variants and fragments thereof. The present disclosure also relates to isolated polynucleotides encoding the polypeptides, as well as vectors and genetically modified host cells containing such isolated polynucleotides.

The present disclosure further relates to compositions comprising the isolated polypeptides or enriched in such polypeptides. Moreover the present disclosure relates to methods for the identification and production of the polypeptides, and methods for their use in the degradation and hydrolysis of poly- and oligo-saccharides, such as biomass, e.g., hemicellulose, for example, in the conversion of biomass, such as lignocellulocytic biomass, including pretreated lignocellulocytic biomass, into soluble sugars, including for use in the fermentive production of biofuels, polishing of cotton fabrics, production of laundry detergents, production of polished crystalline cellulose, assays of cellulases, expansins, and cellulose binding proteins, and in pulping cellulolytic materials.

In some embodiments, the provided polypeptides are isolated proteins that include a domain having an amino acid sequence at least at or about 30%, 40%, 50%, 60%, typically at least at or about 70%, 75%, 80%, 85%, 90%, 91%, 92%, 93%, 94%, 95%, 96%, 97%, 98%, or 99% identical or at or about 100% identical to a domain of SEQ ID NO: 1, such as to amino acids 250-580 of SEQ ID NO: 1, where the protein is a cellulase. In some embodiments, the protein includes or further includes a domain at least at or about 30%, 40%, 50%, 60%, typically at least at or about 70%, 75%, 80%, 85%, 90%, 91%, 92%, 93%, 94%, 95%, 96%, 97%, 98%, or 99% identical or at or about 100% identical to amino acids 130-250 of SEQ ID NO: 1. In some embodiments, the protein includes or further includes a domain at least at or about 30%, 40%, 50%, 60%, typically at least at or about 70%, 75%, 80%, 85%, 90%, 91%, 92%, 93%, 94%, 95%, 96%, 97%, 98%, or 99% identical or at or about 100% identical to amino acids 750-842 of SEQ ID NO: 1. In some embodiments, the protein includes or further includes a domain at least at or about 30%, 40%, 50%, 60%, typically at least at or about 70%, 75%, 80%, 85%, 90%, 91%, 92%, 93%, 94%, 95%, 96%, 97%, 98%, or 99% identical or at or about 100% identical to amino acids 580-750 of SEQ ID NO: 1.

In one aspect, the protein contains a domain having an amino acid sequence at least 70%, 75%, 80%, 85%, 90%, 91%, 92%, 93%, 94%, 95%, 96%, 97%, 98%, or 99% identical or 100% identical to amino acids 250 through 580 of SEQ ID NO: 1, amino acids 130-250 of SEQ ID NO: 1, amino acids 750-842 of SEQ ID NO: 1, or amino acids 580-750 of SEQ ID NO: 1, where the protein is a cellulase.

In one embodiment, the isolated protein has an amino acid sequence that is at least 70%, 75%, 80%, 85%, 90%, 91%, 92%, 93%, 94%, 95%, 96%, 97%, 98%, or 99% identical or 100% identical to SEQ ID NO: 1. In another embodiment, the protein is a mature cellulase protein, containing an amino acid sequence having at least 70%, 75%, 80%, 85%, 90%, 91%, 92%, 93%, 94%, 95%, 96%, 97%, 98%, or 99% identity or 100% identity to (i) amino acids 5-842 of SEQ ID NO: 1, (ii) amino acids 10-842 of SEQ ID NO: 1, (iii), amino acids 15-842 of SEQ ID NO: 1, (iv) amino acids 20-842 of SEQ ID NO: 1, (v) amino acids 24-482 of SEQ ID NO: 1; (vi) amino acids 25-482 of SEQ ID NO: 1; (vii) amino acids 30-842 of SEQ ID NO: 1; (viii) amino acids 35-842 of SEQ ID NO: 1; (ix) amino acids 40-842 of SEQ ID NO: 1; (x) amino acids 45-842 of SEQ ID NO: 1; (xi) amino acids 50-842 of SEQ ID NO: 1; or (xii) amino acids 130-842 of SEQ ID NO: 1. In one such aspect, the isolated mature cellulase protein includes an amino acid sequence having at least 70%, 75%, 80%, 85%, 90%, 91%, 92%, 93%, 94%, 95%, 96%, 97%, 98%, or 99% identity or 100% identity to amino acids 24-482 of SEQ ID NO: 1.

In one embodiment, the protein contains an amino acid sequence at least 30%, 40%, 50%, 60%, 70%, 75%, 80%, 85%, 90%, 91%, 92%, 93%, 94%, 95%, 96%, 97%, 98%, or 99% identical or 100% identical to SEQ ID NO: 1, such as a protein of SEQ ID NO: 1 or a protein variant thereof. In one aspect, the protein has identity at glutamates 413 and 506 of SEQ ID NO: 1. In another embodiment, the protein contains an amino acid sequence that is at least 70%, 75%, 80%, 85%, 90%, 91%, 92%, 93%, 94%, 95%, 96%, 97%, 98%, or 99% identical or 100% identical to SEQ ID NO: 5. In yet another embodiment, the protein contains an amino acid sequence that is at least 70%, 75%, 80%, 85%, 90%, 91%, 92%, 93%, 94%, 95%, 96%, 97%, 98%, or 99% identical or 100% identical to SEQ ID NO: 16.

In another embodiment, the protein contains an amino acid sequence encoded by a nucleic acid sequence with at least 30%, 40%, 50%, 60%, 70%, 75%, 80%, 85%, 90%, 91%, 92%, 93%, 94%, 95%, 96%, 97%, 98%, or 99% identity or 100% identity to SEQ ID NO: 2, SEQ ID NO: 3, SEQ ID NO: 4, or SEQ ID NO: 15.

In some embodiments, the protein is a protein of SEQ ID NO: 1, SEQ ID NO: 5, or SEQ ID NO: 16.

Other aspects of the present disclosure relate to an isolated protein having amino acids 250-580 of SEQ ID NO: 1, where the protein is a cellulase. Still other aspects of the present disclosure relate to an isolated protein having amino acids 130-250 of SEQ ID NO: 1, where the protein is a cellulase. Yet other aspects of the present disclosure relate to an isolated protein having amino acids 750-842 of SEQ ID NO: 1, where the protein is a cellulase. Further aspects of the present disclosure relate to an isolated protein having amino acids 580-750 of SEQ ID NO: 1, where the protein is a cellulase.

In some embodiments, the protein further includes a domain, such as a catalytic domain or cellulose binding domain of a bacterial or archaeal enzyme. In one aspect, such proteins are fusion proteins, containing one or more domains of SEQ ID NO: 1, 5, or SEQ ID NO: 6-13, such as a catalytic or cellulose binding domain, and one or more domains of another protein, such as another cellulase. In one embodiment, the domain, e.g., catalytic domain or cellulose binding domain, is from another organism, for example, B. fibrisolvens, S. solfataricus, A. cellulolyticus, P. furiosus, P. horikoshii, P. abyssi, A. cellulolyticus, S. lividans, B. fibrisolvens, or T. reesei, or other cellulase-encoding organism disclosed herein or well know in the art.

In some embodiments, the protein includes a modification, such as a tag, for example, an N-terminal or C-terminal histidine tag.

In some embodiments, the protein exhibits cellulase activity, for example, one or more of endoglucanase activity, exoglucanase activity, and β-Glucosidase activity. In some embodiments, the protein exhibits such activity over a range of physical and chemical conditions, such as at a high temperature or over a broad temperature range, such as at a temperature greater than 105° C., 95° C. to 110° C., or at a temperature exceeding 90, 91, 92, 93, 94, 95, 96, 07, 98, 99, or 100° C., or over a broad temperature range, such as between at or about 60° C. and 110° C. or between 65° C. and 110° C., such as between 90 and 110° C., between 65 and 70° C., between 85 and 105° C., or between 95 and 105° C.

In some embodiments, the activity has a half-life of at least one, two, three, four, or five hours at 100° C., or 105° C., for example, a half-life of at least five hours at 100° C., or a half-life of at least one hour at 105° C., at a pH of about 6.8. In some embodiments, the activity has a half-life of at least five, six, seven, eight, nine, 10, 11, 12, 13, 14, 15, 20, 25, 30, 35, 45, or 60 minutes at 108° C., for example, a half-life of at least 15 minutes at 108° C., or a at a pH of about 6.8. In some embodiments, the protein exhibits the activity at 90° C., in a solution containing up to 50% ionic liquid, 3.2 M KCl, or 4 M NaCl. In some embodiments, the cellulase activity is at least 50% maximum over a pH range of between about 4.5 and 8.75, or is at least 70% maximum at a pH of greater than about 7 or at a pH of about 8.5.

Also provided are compositions containing the isolated proteins, and nucleic acids encoding the proteins, such as polynucleotides encoding any of the proteins, for example, an isolated nucleic acid encoding a protein that comprises an amino acid sequence at least 30%, 40%, 50%, 60%, typically at least 70%, 75%, 80%, 85%, 90%, 91%, 92%, 93%, 94%, 95%, 96%, 97%, 98%, or 99% identical or 100% identical to SEQ ID NO: 1, SEQ ID NO: 5, or SEQ ID NO: 16, and isolated nucleic acids having a nucleotide sequence at least at least 30%, 40%, 50%, 60%, typically at least 70%, 75%, 80%, 85%, 90%, 91%, 92%, 93%, 94%, 95%, 96%, 97%, 98%, or 99% identical or 100% identical to SEQ ID NO: 2, SEQ ID NO: 3, SEQ ID NO: 4, or SEQ ID NO: 15.

Also provided are expression vectors containing the isolated nucleic acids, operably linked to a regulatory sequence, and host cells containing the expression vectors, and methods for producing a protein by culturing the host cell in a culture medium, under suitable conditions to produce a protein encoded by the expression vector. Also provided are compositions containing the host cells in culture medium, and compositions containing the provided proteins in the supernatant of culture medium.

In some embodiments, the composition contains a high salt or ionic solution, such as a solution including NaCl or KCl at a concentration of at least 1 M, 2M, 3M, or 4M. In some embodiments, the composition has a pH of at least at or about 5.5, 6.5, 7, 7.5, 8, or 8.5. In some embodiments, the composition includes an ionic liquid at a concentration of between at or about 20% and 50% or up to at or about 50%.

Also provided are methods of reducing the viscosity of a pretreated biomass mixture, by contacting a pretreated biomass mixture having an initial viscosity with the provided compositions and/or proteins, and incubating the contacted biomass mixture under conditions sufficient to reduce the initial viscosity of said pretreated biomass mixture.

Also provided are methods for converting a biomass to sugars, hydrolyzing or degrading a biomass, by contacting the biomass with the provided compositions and/or proteins. Also provided are methods for producing a fermentation product by contacting biomass with the compositions or proteins to form a first product, and then culturing the first product with one or more fermentive microorganisms under conditions sufficient to produce a fermentation product, or incubating the first product with a chemical solution, under conditions sufficient to produce a fermentation product by a chemical process. Also provided are methods for producing a fermentation product, by hydrolyzing or degrading biomass with the provided compositions and proteins to form a first product and then culturing the first product with one or more fermentive microorganisms under conditions sufficient to produce a fermentation product, or incubating the first product with a chemical solution, under conditions sufficient to produce a fermentation product by a chemical process. In some aspects, the fermentation product is a biofuel.

Also provided are methods for fermenting biomass by fermenting the biomass with one or more fermenting microorganisms, wherein the biomass is or has been treated by a provided composition or protein.

Also provided are methods for producing a fuel by contacting a biomass with the composition or protein to yield a sugar solution and culturing the sugar solution with a fermentative microorganism under conditions sufficient to produce a fuel or under conditions sufficient to produce a fermentation product by a chemical process.

Also provided are methods for food production, by contacting a plant material with the provided composition or protein, yield a treated plant material, and methods for textile cleaning by contacting a soiled textile with the composition or protein, to yield a clean textile. Also provided are methods for paper pulp bleaching by contacting paper pulp with the composition or protein to yield bleached paper pulp.

Also provided are laundry detergent compositions, containing the provided proteins and detergent, and methods for use of such compositions in cleaning, anti-deposition, or color care, by contacting the laundry detergent composition with a textile.

In some aspects, the methods, e.g., the contacting, are conducted at a pH between 4.5 and 8.5, such as a pH of at least 5.5 or at least 6.5, for example, at least 7, at least 7.5, at least 8, at least 8.5. In some aspects, the methods or contacting are performed at a temperature between 90 and 110° C., between 60 and 70° C., between 95 and 105° C., or at least 100° C. In some aspects, the method or contacting is performed in a solution containing KCl or NaCl, for example, at a concentration of at least 1 M, 2 M, 3 M, or 4 M, or at a saturating condition. In one aspect, the method or contacting is performed in a solution containing at least 10%, at least 20%, at least 30% or at least 40% ionic liquid.

In some aspects, the biomass is a lignocellulose. In some embodiments, the biomass is pretreated prior to contacting.

BRIEF DESCRIPTION OF THE DRAWINGS

FIG. 1A shows the source of lignocellulose-degrading consortium of hyperthermophilic Archea enrichment, and degradation of filter paper. A circumneutral geothermal pool at 94° C., with a level-maintaining syphon. Sediment from the floor of this site was enriched on pulverized Miscanthus at 90° C. and subsequently transferred to filter paper enriched media. FIG. 1B depicts the degradation of filter paper by the enrichment culture in a spherical 2 L culture flask. Circular discs of Whatman® #3 filter paper were shredded and partially dissolved after incubation for 30 days at 90° C. FIG. 1C depicts control Whatman® #3 filter paper discs. Incubation as in panel B.

FIG. 2A shows Whatman® #1 filter paper in media without (C) and with (E) inoculation with the enrichment at 90° C. Lettering was applied with a number 2 graphite pencil. FIG. 2B shows Whatman® #3 filter paper strip (2 mm×40 mm) in growth media supported by a glass tube, without (C) and with (E) inoculation with the enrichment at 90° C. The inoculated sampled showed complete dissolution of the filter paper strip.

FIG. 8C shows a multiple sequence alignment of a non-redundant sample of the thirty-eight sequences identified using Hidden Markov Model (HMM) searching and analysis based on domain 1 of EBI244, as described in Example 1. YP_003548440.1 (SEQ ID NO: 42), YP_001820771.1 (SEQ ID NO: 43), YP_003547883.1 (SEQ ID NO: 44), YP_003547687.1 (SEQ ID NO: 45), YP_001818722.1 (SEQ ID NO: 46), NP_869354.1 (SEQ ID NO: 47), YP_003195709.1 (SEQ ID NO: 48), YP_003323724.1 (SEQ ID NO: 49), ZP_02918195.1 (SEQ ID NO: 50), YP_001819159.1 (SEQ ID NO: 51), ZP_06742086.1 (SEQ ID NO: 52), YP_003387974.1 (SEQ ID NO: 53), YP_003243090.1 (SEQ ID NO: 54), NP_228758.1 (SEQ ID NO: 55), ZP_03628309.1 (SEQ ID NO: 56), ZP_03626656.1 (SEQ ID NO: 57), ZP_01717989.1 (SEQ ID NO: 58), ZP_03628444.1 (SEQ ID NO: 59), A7HFC4_ANADF (SEQ ID NO: 60), C7PTR3_CHIPD (SEQ ID NO: 61), YP_003585990.1 (SEQ ID NO: 62), VIMSS5326244 (SEQ ID NO: 63), D1N449_9BACT (SEQ ID NO: 64), A7VX72_9CLOT (SEQ ID NO: 65), A9AYF5_HERA2 (SEQ ID NO: 66), A4XMG8_CALS8 (SEQ ID NO: 67), B1ZN60_OPITP (SEQ ID NO: 68). FIG. 8D shows a multiple sequence alignment of EBI244 domain 2 with sequences identified in the domain 1 HMM search/analysis (see FIG. 8C). Catalytic residues of EBI244 predicted from Pfam analysis (glutamates 413 and 506) both glutamates) are highlighted in yellow. YP_003548440.1 (SEQ ID NO: 69), YP_001820771.1 (SEQ ID NO: 70), YP_003547883.1 (SEQ ID NO: 71), YP_003547687.1 (SEQ ID NO: 72), YP_001818722.1 (SEQ ID NO: 73), NP_869354.1 (SEQ ID NO: 74), YP_003195709.1 (SEQ ID NO: 75), YP_003323724.1 (SEQ ID NO: 76), ZP_02918195.1 (SEQ ID NO: 77), YP_001819159.1 (SEQ ID NO: 78), ZP_06742086.1 (SEQ ID NO: 79), YP_003387974.1 (SEQ ID NO: 80), YP_003243090.1 (SEQ ID NO: 81), NP_228758.1 (SEQ ID NO: 82), ZP_03628309.1 (SEQ ID NO: 83), ZP_03626656.1 (SEQ ID NO: 84), ZP_01717989.1 (SEQ ID NO: 85), ZP_03628444.1 (SEQ ID NO: 86), A7HFC4_ANADF (SEQ ID NO: 87), C7PTR3_CHIPD (SEQ ID NO: 88), YP_003585990.1 (SEQ ID NO: 89), VIMSS5326244 (SEQ ID NO: 90), D1N449_9BACT (SEQ ID NO: 91), A7VX72_9CLOT (SEQ ID NO: 92), A9AYF5_HERA2 (SEQ ID NO: 93), A4XMG8_CALS8 (SEQ ID NO: 94), B1ZN60_OPITP (SEQ ID NO: 95). FIG. 8E shows a Multiple sequence alignment of all hits to domain 4 HMM searching. Domain 4 search area is highlighted in orange. All sequences were globally aligned using the MUSCLE program. YP_003548440.1 (SEQ ID NO: 96), YP_001820771.1 (SEQ ID NO: 97), YP_003547883.1 (SEQ ID NO: 98), YP_003547687.1 (SEQ ID NO: 99), YP_001818722.1 (SEQ ID NO: 100), NP_869354.1 (SEQ ID NO: 101), YP_003195709.1 (SEQ ID NO: 102), YP_003323724.1 (SEQ ID NO: 103), ZP_02918195.1 (SEQ ID NO: 104), YP_001819159.1 (SEQ ID NO: 105), ZP_06742086.1 (SEQ ID NO: 106), YP_003387974.1 (SEQ ID NO: 107), YP_003243090.1 (SEQ ID NO: 108), NP_228758.1 (SEQ ID NO: 109), ZP_03628309.1 (SEQ ID NO: 110), ZP_03626656.1 (SEQ ID NO: 111), ZP_01717989.1 (SEQ ID NO: 112), ZP_03628444.1 (SEQ ID NO: 113), A7HFC4_ANADF (SEQ ID NO: 114), C7PTR3_CHIPD (SEQ ID NO: 115), YP_003585990.1 (SEQ ID NO: 116), VIMSS5326244 (SEQ ID NO: 117), D1N449_9BACT (SEQ ID NO: 118), A7VX72_9CLOT (SEQ ID NO: 119), A9AYF5_HERA2 (SEQ ID NO: 120), A4XMG8_CALS8 (SEQ ID NO: 121), B1ZN60_OPITP (SEQ ID NO: 122).

FIG. 12A depicts cellohexaose (0.33 mM) substrate. FIG. 12B depicts cellopentaose (0.4 mM) and glucose (0.4 mM) substrates. FIG. 12C depicts cellotriose (0.67 mM) substrates. FIG. 12D depicts cellobiose (1 mM) substrate. Standards were a mixture of glucose, cellotriose and cellopentaose (m1) and mixture of cellobiose, cellotetraose and cellopentaose (m2). Time points (minutes, label) were (0,0), (1:20,1), (2:40, 2), (6:20, 3), (12:40, 4), (25:20, 5), (50:40, 6), (120:00, 7). Oligomers higher than cellohexaose up to dp~11 were rapidly formed then degraded over time.

DEFINITIONS

Figure 2:
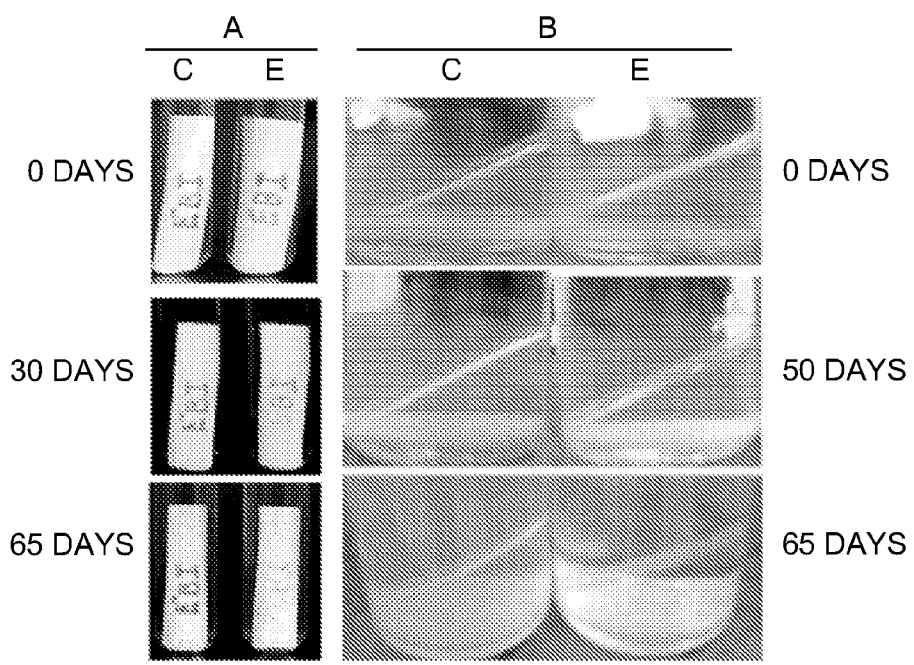
FIG. 2 depicts results of additional experiments showing filter degradation by the enrichment.

The term "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. The term "specific activity" describes quantitatively the catalytic activity per amount of enzyme under defined reaction conditions.

The term "thermostability" describes the property of a protein to withstand a limited exposure to certain temperatures, such as high temperatures, without losing the activity it possesses at temperatures where its activity is measurable or is optimal. The term "thermoactive" describes a property of a protein which retains activity at high temperatures.

The term "pH-stability" describes the property of a protein to withstand a limited exposure to pH-values significantly deviating from the pH where its stability is optimal (e.g., more than one pH-unit above or below the pH-optimum, without losing its activity under conditions where its activity is measurable). The term "pH active" describes a property of a protein which retains activity at a pH value deviating significantly from pH values typically optimal for such activities.

The term "cellulase" refers to an enzyme (or enzymatic activity thereof) that catalyzes an enzymatic reaction in which cellulose is hydrolyzed into glucose, cellobiose, or cellooligotose, including enzymes having endoglucanase, exoglucanase, e.g., glucanohydrolase or cellobiohydrolase, β-Glucosidase or β-Glucosidaseglucohydrolase activity, and the corresponding enzymatic activity of such enzymes.

The term "lignocellulose" refers to any material primarily consisting of cellulose, hemicellulose, and lignin.

The term "hemicellulose" refers to a polymer of short, highly-branched chains of mostly five-carbon pentose sugars (e.g., xylose and arabinose) and to a lesser extent six-carbon hexose sugars (e.g., galactose, glucose and mannose).

The term "renewable resources" refers to biomass substrates that are grown and harvested, like crops, straw, wood and wood products. The term "biological fuels" refers to solid, liquid, or gas fuel including or derived from biomass, such as biodiesel, biogas, vegetable oil, bioethanol, and biohydrogen.

As used herein, when it is generally stated that a polypeptide or nucleic acid molecule or region thereof contains or has "identity" or "homology," per se (without specifying a particular percent identity), to another polypeptide or nucleic acid molecule or region thereof, the two molecules and/or regions share at least at or about 40%, and typically at least at or about 50%, 60% or 70% sequence identity, such as at least at or about 60%, 65%, 70%, 75%, 80%, 85%, 90%, 95%, 96%, 97%, 98%, 99% or 100% sequence identity. The precise percentage of identity can be specified.

Sequence "identity" has an art-recognized meaning. The percentage of sequence identity between two nucleic acid or polypeptide molecules and/or regions can be calculated using well-known and published techniques, such as those described below. In general, for determination of the percentage sequence identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073). For sequence identity, the number of conserved amino acids or nucleotides is determined by standard alignment algorithms programs, and can be used with default gap penalties established by each supplier. Substantially homologous nucleic acid molecules specifically hybridize typically at moderate stringency or at high stringency all along the length of the nucleic acid of interest.

The term "identity," when associated with a particular number, represents a comparison between the sequences of a first and a second polypeptide or polynucleotide or regions thereof. As used herein, the term at least "90% identical to" refers to percent identities from 90 to 99.99 of one nucleotide or amino acid sequence to the other. Identity of 90% or more is indicative of the fact that, assuming for exemplification purposes, the full length of a first and second polypeptide, each 100 amino acids in length, are compared, no more than 10% (i.e., 10 out of 100) of the amino acids in the first polypeptide differs from that of the second polypeptide. Similar comparisons can be made between first and second polynucleotides. Such differences among the first and second sequences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleotide or amino acid residue substitutions, insertions, additions or deletions. At the level of homologies or identities above about 85-90%, the result should be independent of the program and gap parameters set; such high levels of identity can be assessed readily, often by manual alignment without relying on software.

Sequence identity can be measured along the full length of a polynucleotide or polypeptide or along a region thereof. Sequence identity compared along the full length of two polynucleotides or polypeptides refers to the percentage of identical nucleotide or amino acid residues along the full-length of the molecule. Alternatively, sequence identity can be compared along the length of a molecule, compared to a region of another molecule.

DETAILED DESCRIPTION

Crystalline cellulose is composed of linear polymers of β1-4 linked glucose, held in the crystalline lattice by a high degree of intermolecular hydrogen bonding. The tightly crosslinked structure is primarily responsible for the inherent stability of cellulose, but also can hinder efficient deconstruction. The conversion of cellulose to glucose is generally accomplished by chemical hydrolysis (typically using a single step of acid treatment) or enzymatic hydrolysis (generally involving acid pretreatment followed by hydrolysis with cellulase enzymes). High temperatures combined with low pH are generally required for the disruption of the crystalline structure and chemical hydrolysis. See Kim J S, Lee Y Y, Torget, R W. (2001) "Cellulose hydrolysis under extremely low sulfuric acid and high-temperature conditions, *Appl. Biochem. Biotechnol.* 91-93. 331-340. Enzymatic hydrolysis generally occurs under milder conditions. Strategies for commercial depolymerization of cellulose typically combine pretreatment and enzymatic hydrolysis. Hilden L, Johansson G (2004), "Recent developments on cellulases and carbohydrate-binding modules with cellulose affinity," *Biotechnol Lett,* 26: 1683-1693. The degree of pretreatment required and the expense of subsequent cleanup steps required depend upon the properties of the enzymes that will be used.

Embodiments

The present disclosure relates to isolated polypeptides, including cellulases and other polypeptides, for example, cellulases having endoglucanase, exoglucanase and/or β-Glucosidase or β-Glucosidaseglucohydrolase activity, activity, including those produced by archaea, such as an EBI244 polypeptide (SEQ ID NO: 1) and variants and fragments thereof. The present disclosure also relates to isolated polynucleotides encoding the polypeptides, as well as vectors and genetically modified host cells containing such isolated polynucleotides. The present disclosure further relates to compositions comprising the isolated polypeptides or enriched in such polypeptides. Moreover the present disclosure relates to methods for the identification and production of the polypeptides, and methods for their use in the degradation and hydrolysis of poly- and oligo-saccharides, such as biomass, e.g., hemicellulose, for example, in the conversion of biomass, such as lignocellulocytic biomass, including pretreated lignocellulocytic biomass, into soluble sugars, including for use in the fermentive production of biofuels, polishing of cotton fabrics, production of laundry detergents, production of polished crystalline cellulose, assays of cellulases, expansins, and cellulose binding proteins, and in pulping cellulolytic materials. Also provided herein are hyperthermophilic organisms and polypeptides encoded by the organisms, capable of utilizing crystalline cellulose, and methods for their identification and production.

Polypeptides

The present disclosure relates to isolated polypeptides having cellulase activity and fragments thereof. In particular, the present disclosure provides polypeptides of SEQ ID NO: 1, SEQ ID NO: 5, SEQ ID NO: 16, and fragments and variants thereof. In some embodiments, the polypeptide includes a sequence having at least 50%, 60%, typically at least 70%, 75%, 80%, 85%, 90%, 91%, 92%, 93%, 94%, 95%, 96%, 97%, 98%, 99% or 100% sequence identity to SEQ ID NO: 1, or to one or more regions or domains thereof, including amino acid residues 1-25 of SEQ ID NO: 1, amino acid residues 30-130 of SEQ ID NO: 1, amino acid residues 250 through 580 of SEQ ID NO: 1 (Domain 2), amino acids 130-250 of SEQ ID NO: 1 (domain 1), amino acids 750-842 of SEQ ID NO: 1 (Domain 4), or amino acids 580-750 proline-threonine rich region, Domain 1, Domain 2, Domain 3, or Domain 4 of SEQ ID NO: 1, where the polypeptide is a cellulase.

In some embodiments, the polypeptide is a variant or fragment of SEQ ID NO: 1, SEQ ID NO: 5, or SEQ ID NO: 16, with one or more amino acid deletions, insertions, modifications, or substitutions, such as a polypeptide having at least 30%, 40%, 50%, 60%, typically at least 70%, 75%, 80%, 85%, 90%, 91%, 92%, 93%, 94%, 95%, 96%, 97%, 98%, 99% or 100% sequence identity to SEQ ID NO: 1, SEQ ID NO: 5, or SEQ ID NO: 16, or containing a domain, such as a catalytic domain or carbohydrate binding motif (CBM) that is at least 30%, 40%, 50%, 60%, typically at least 30%, 40%, 50%, 60%, 70%, 75%, 80%, 85%, 90%, 91%, 92%, 93%, 94%, 95%, 96%, 97%, 98%, 99% or 100% identical to a domain thereof. Typically, the variant or fragment retains a substantial amount of the cellulase or other enzymatic activity or cellulose binding capability of the wild-type protein. For example, in some embodiments, the variant or fragment retains one, typically both, of the wild type active site residues at E413 and E506. In some embodiments, the variants include a protein comprising the sequence of a protein listed in any of Tables 1, 2, 3, and 4, such as a polypeptide having a sequence at least 30%, 40%, 50%, 60%, typically at least 70%, 75%, 80%, 85%, 90%, 91%, 92%, 93%, 94%, 95%, 96%, 97%, 98%, 99% or 100% identical to SEQ ID NO: 6, 7, 8, 9, 10, 11, 12, or 13.

Whether any two nucleic acid or polypeptide molecules have sequences that contain, or contain at least, a certain percent (e.g. 60%, 70%, 80%, 85%, 90%, 95%, 96%, 97%, 98% or 99%) sequence identity can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Altschul, S. F., et al., *J Molec Biol* 215: 403 (1990); Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). The extent of sequence identity (homology) and complementarity may be determined using any computer program and associated parameters, including those described herein, such as BLAST 2.2.2. or FASTA version 3.0t78, with the default parameters. It is understood that for the purposes of determining sequence identity among DNA and RNA sequences thymidine nucleotide is equivalent to (represents identity with) a uracil nucleotide. Percent identity further can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps. Various programs and methods for assessing identity are known to those of skill in the art. High levels of identity, such as 90% or 95% identity, readily can be determined without software.

In some embodiments, the polypeptides are produced recombinantly, while in others the polypeptides are produced synthetically, or are purified from a native source, such as an archaea, such as one described herein.

The provided polypeptides generally have cellulase activity, for example, endoglucanase, exoglucanase, e.g., glucanohydrolase or cellobiohydrolase, $\beta$-Glucosidase or $\beta$-Glucosidaseglucohydrolase activity, and/or cellulose binding ability. In one aspect, the provided polypeptides exhibit the cellulase activity or binding ability, for example, an activity or binding ability of at least 40%, 50%, 60%, 70%, 75%, or more of maximum (or with a half-life of activity or binding ability of at least 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 3 hours, 4 hours, 5 hours, or more hours) over a broad range of conditions, for example, over range of conditions that is broader than that observed for one or more known cellulases, such as bacterial cellulases, including those produced by *Anaerocellum thermophilum, Caldicellulosiruptor saccharolyticus, Rhodothermus marinus,* or *Thermus caldophilus*. For example, in some aspects, the polypeptides exhibit activity or binding ability in the presence of high salt solution, such as in the presence of a saturating concentration of salt, such as in a solution containing sodium chloride (NaCl) at a concentration of at least at or about 0.5 M, 1 M, 1.5 M, 2 M, 2.5 M, 3 M, 3.5 M, or 4 M sodium chloride, or potassium chloride (KCl), at a concentration at or about 0.5 M, 1 M, 1.5 M, 2 M, 2.5 M 3.0 M or 3.2 M KCl and/or ionic liquids, such as 1,3-dimethylimidazolium dimethyl phosphate ([DMIM]DMP) or [EMIM]OAc, or in the presence of one or more detergents, such as ionic detergents (e.g., SDS, CHAPS), sulfhydryl reagents, such as in saturating ammonium sulfate or ammonium sulfate between at or about 0 and 1 M.

In some aspects, the polypeptides exhibit the activity or binding ability at high temperatures, such as a temperature exceeding 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., or 110° C., or over a broad temperature range, such as between at or about 60° C. and 110° C. or between 65° C. and 110° C., such as between 90° C. and 110° C., between 6° C. 5 and 70° C., between 85° C. and 105° C., between 85° C. and 110° C., between 95° C. and 105° C., or between 95° C. and 110° C. In some aspects, the polypeptides exhibit the activity or binding ability over a broad pH range, for example, at a pH of between about 4.5 and 8.75, at a pH of greater than 7 or at a pH of 8.5, or at a pH of at least 5.0, 5.5, 6.0, 6.5, 7.0, 7.5, 83.0, or 8.5.

Cellulase activity and binding capabilities can be measured by a number of well-known methods, including zymograms, reducing sugar assays (e.g., DNS Micro or Macro, Nelson-Somogyi Micro or Macro, Nelson Semi-Micro, Ferricyanide-1, Ferricyanide-2, PAHBAH Micro or Macro, BCA, and Modified BCA), assays using paranitrophenol-labeled glycosides, product analysis, total sugar assays, such as Phenol-$H_2SO_4$ or Anthrone $H_2SO_4$, enzymatic glucose assays, and cellulose binding assays, for example, using the methods described herein.

Substrates for cellulase activity and binding assays include soluble and insoluble substrates. Soluble substrates include, for example, cellodextrins and their derivatives, including radiolabelled versions thereof, short chain cellulase, β-methylumbelliferyl-oligosaccharides, p-nitrophenol-oligosaccharides, Long chain cellulose derivatives, Carboxymethyl cellulose (CMC), hydroxyethyl cellulose (HEC), dyed CMC. Insoluble substrates, include, for example, cotton, Whatman No. 1 filter paper, pulp (e.g., Solka Floc), crystalline cellulose, such as cotton, microcrystalline cellulose (e.g., Avicel®), valonia cellulose, bacterial cellulose, amorphous cellulose (e.g., PASC, alkali-swollen cellulose), dyed cellulose, fluorescent cellulose, chromogenic and fluorephoric derivatives, such as trinitrophenyl-carboxymethylcellulose (TNP-CMC) and fluram-cellulose, practical cellulose-containing substrates, α-cellulose, and pretreated lignocellulosic biomass.

In some embodiments, the polypeptides are produced as N- and/or C-terminal fusion proteins, for example to aid in extraction, detection and/or purification and/or to add functional properties to the cellulases. Examples of fusion protein partners include, but are not limited to, glutathione-S-transferase (GST), 6XHis, GAL4 (DNA binding and/or transcriptional activation domains), FLAG-, MYC-tags or other tags well known to anyone skilled in the art. In some embodiments, a proteolytic cleavage site is provided between the fusion protein partner and the protein sequence of interest to allow removal of fusion protein sequences. Preferably, the fusion protein does not hinder the cellulase activity of the polypeptides.

In some embodiments, the polypeptide is fused to one or more domains, for example, of other proteins, such as other cellulases or sugar-reducing enzyme, including a bacterial, archaeal, and/or hyperthermophilic cellulase or enzyme, for example, cellulases and enzymes belonging to glycosyl hydrolase family GH5 or GH12 or CBM family 1 or 2, such as those encoded by mesophiles, such as B. fibrisolvens, and cellulases encoded by thermophiles such as S. solfataricus, R. marinus, A. cellulolyticus, P. furiosus, P. horikoshii, P. abyssi, or A. cellulolyticus, S. lividans, B. fibrisolvens, or T. reesei.

Such domains can include a leader peptide, propeptide, binding domain and/or catalytic domain. Suitable binding domains include, but are not limited to, carbohydrate-binding domains (e.g., CBM) of various specificities, providing increased affinity to carbohydrate components present during the application of the cellulase. Suitable enzymatically active domains possess an activity that supports the action of the polypeptide in producing the desired product. Non-limiting examples of catalytic domains include: cellulases, hemicellulases such as xylanase, mannanases, exo-mannanases, glucanases, arabinases, galactosidases, pectinases, and/or other activities such as proteases, lipases, acid phosphatases and/or others or functional fragments thereof.

In some embodiments, the fusion proteins contain the catalytic or enzymatically active domain of another cellulase or sugar-reducing enzyme, such as fused to one or more domains of the provided polypeptides, such as a CMB domain, for example, to Domain 1, Domain 4, or Domain 3 of SEQ ID NO: 1 or a variant thereof. In another embodiment, the fusion protein contains a catalytic domain of one of the provided peptides, such as a domain having a certain percent identity to domain 2 of SEQ ID NO: 1, amino acid residues 250 through 580. Typically, the fusion proteins exhibit improved stability, cellulase activity, tolerance for various conditions, and/or cellulose binding compared to the other enzyme, e.g., cellulase, alone.

For example, the tight binding of the provided polypeptides to crystalline cellulose as described herein, makes it useful in methods for identifying and producing new hyperstable cellulases. In one embodiment, the hyperstable cellulases are produced using well-known engineering methods, which have been used to engineer thermophilic and hyperthermophilic cellulases to improve the activity on crystalline substrates. In one example, the methods involve the addition of a thermostable cellulose binding domain provided herein to a catalytic domain, for example, as carried out to introduce chitin binding domains to increase binding and activity toward crystalline cellulose.

Domains of the fusion proteins are optionally linked to the polypeptides through a linker sequence that simply joins the provided cellulose polypeptide or fragment thereof and the fusion domain without significantly affecting the properties of either component, or the linker optionally has a functional importance for the intended application.

In some embodiments, the provided polypeptides are used in conjunction with one or more additional proteins of interest. Non-limiting examples of proteins of interest include: hemicellulases, alpha-galactosidases, beta-galactosidases, lactases, beta-glucanases, endo-beta-1,4-glucanases, cellulases, xylosidases, xylanases, xyloglucanases, xylan acetylesterases, galactanases, exo-mannanases, pectinases, pectin lyases, pectinesterases, mannanases, polygalacturonases, arabinases, rhamnogalacturonases, laccases, reductases, oxidases, phenoloxidases, ligninases, proteases, amylases, phosphatases, lipolytic enzymes, cutinases and/or other enzymes.

Polynucleotides

Also provided are isolated and/or purified nucleic acid molecules, e.g., polynucleotides, encoding the provided polypeptides, e.g., cellulases. In some embodiments, the isolated polynucleotide encodes SEQ ID NO: 1, SEQ ID NO: 5, SEQ ID NO: 15, or a fragment or variant thereof, such as fragments thereof including amino acid residues 1-25 of SEQ ID NO: 1, amino acid residues 30-130 of SEQ ID NO: 1, amino acid residues 250 through 580 of SEQ ID NO: 1 (Domain 2), amino acids 130-250 of SEQ ID NO: 1 (domain 1), amino acids 750-842 of SEQ ID NO: 1 (Domain 4), or amino acids 580-750 proline-threonine rich region, Domain 1, Domain 2, Domain 3, or Domain 4 of SEQ ID NO: 1, or containing a sequence of SEQ ID NO: 1, or a sequence that is at least 30%, 40%, 50%, 60%, typically at least 70%, 75%, 80%, 85%, 90%, 91%, 92%, 93%, 94%, 95%, 96%, 97%, 98%, 99% or 100% identical to such a protein or region thereof. For example, provided are polynucleotides encoding polypeptides containing a domain of the provided polypeptide, such as a catalytic domain or carbohydrate binding motif (CBM) that is at least 50%, 60%, typically at least 30%, 40%, 50%, 60%, 70%, 75%, 80%, 85%, 90%, 91%, 92%, 93%, 94%, 95%, 96%, 97%, 98%, 99% or 100% identical to such a domain thereof, where the encoded polypeptide is a cellulase. In one embodiment, provided are polynucleotides containing a nucleic acid sequence having at least 50%, 60%, typically at least 70%, 75%, 80%, 85%, 90%, 91%, 92%, 93%, 94%, 95%, 96%, 97%, 98%, 99% or 100% sequence identity to SEQ ID NO: 3, SEQ ID NO: 4, SEQ ID NO: 15, or to one or more regions or domains thereof. Also provided are polynucleotides encoding the polypeptides listed in Tables 1-4.

Typically, the variant or fragment encodes a protein retaining a substantial amount of the cellulase or other enzymatic activity or cellulose binding capability of the wild-type protein. For example, in some embodiments, the variant or fragment retains one, typically both, of the wild type active site residues at E413 and E506. In some embodiments, the variants include polypeptides encoding a protein comprising the sequence of a protein listed in any of Tables 1, 2, 3, and 4.

Methods for the Identification of Hyperthermophiles and Hyperthermophilic Cellulases and Characterization Assays There is an absence of known archaeal hyperthermophiles subsisting on plant biomass as exclusive carbon sources. Despite the discovery of multiple endo and exocellulases in thermophiles, the upper temperature limit for organisms known to grow on crystalline cellulose has risen slowly. The compositions provided here are based in part on the discovery that a known method for identifying thermophilic cellulases is the isolate-centric nature of these studies. Thus, provided are high throughput metagenomic, transcriptomic, and proteomic methods for identification of cellulases, including for the identification of hyperthermophilic cellulases. For example, provided is a metagenomic approach for identification of cellulases, such as stable and thermoactive endoglucanase from a lignocellulose-degrading consortium of hyperthermophilic Archaea.

In one embodiment, such methods are carried out by cultivating archaea growing on a cellulose-containing carbon source, such as crystalline cellulose, at above a certain temperature, such as at or about at least 90° C., 94° C., or 100° C., and selection of organisms capable of utilizing cellulose under these conditions. In one aspect, the method allows for selection of a minimal consortium, rather than a single isolates. An exemplary method is the isolation described herein in Example 1.

Also provided are methods for identifying and producing new hyperstable cellulases by mutating known enzymes to include one or more domains, such as the cellulose binding domain, for example, any of domains 1, 3, and/or 4, of the provided polypeptides, for example, to improve the activity on crystalline substrates. In one example, the methods involve the addition of a thermostable cellulose binding domain provided herein to a catalytic domain, for example, as carried out to introduce chitin binding domains to increase binding and activity toward crystalline cellulose.

Also provided are methods using the provide polypeptides for the characterization of cellulose degradation and production of polished crystalline cellulose for assays of cellulases, expansins, and cellulose binding proteins.

Vectors and Host Cells

Also provided are vectors, host cells, and methods for the production of the provided polypeptides and polynucleotides. In some embodiments, DNA encoding the polypeptide is chemically synthesized based on the provided sequences or obtained directly from host cells harboring the gene (e.g., by cDNA library screening or PCR amplification). In some embodiments, the provided polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker.

Expression vector/host cell combinations are well known and can be used in the provided methods. Typically, the expression cassette or vector is introduced in a suitable expression host cell, which then expresses the corresponding polypeptide. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces, Staphylococcus* (e.g., *S. carnosus*), *Lactococcus* (e.g., *L. lactis*), or *Bacillus* (*subtilis, megaterium, licheniformis*, etc.). Also particularly suitable are yeast expression hosts such as *Saccharomyces cerevisiae, Schizosaccharomyces pombe, Yarrowia lipolytica, Hansenula polymorpha, Kluyveromyces lactis* or *Pichia pastoris*, and fungal expression hosts such as *Aspergillus niger, Chrysosporium lucknowense, Aspergillus* (e.g., *A. oryzae, A. niger, A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable.

Promoters and/or signal sequences associated with secreted proteins in a particular host of interest are candidates for use in the heterologous production and secretion of the provided polypeptides in that host or in other hosts. Such sequences are well known. In some embodiments, the provided polynucleotide is recombinantly associated with a polynucleotide encoding a suitable homologous or heterologous signal sequence that leads to secretion of the enzyme into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage GIII genes. For *Bacillus subtilis*, Gram-positive organisms and other organisms known in the art, particularly suitable signal sequences further include those that drive expression of the AprE, NprB, Mpr, AmyA, AmyE, Blac, SacB, and for *S. cerevisiae* or other yeast, include the killer toxin, Bar1, Suc2, Mating factor alpha, Inu1A or Ggplp signal sequence. Signal sequences can be cleaved by a number of signal peptidases, thus removing them from the rest of the expressed protein. In some embodiments, the provided polypeptide is expressed alone or as a fusion with other peptides, tags or proteins located at the N- or C-terminus (e.g., 6XHis, HA or FLAG tags). Suitable fusions include tags, peptides or proteins that facilitate affinity purification or detection (e.g., 6XHis, HA, chitin binding protein, thioredoxin or FLAG tags), as well as those that facilitate expression, secretion or processing of the provided polypeptide. Suitable processing sites include enterokinase, STE13, Kex2 or other protease cleavage sites for cleavage in vivo or in vitro.

In some embodiments, the provided polynucleotides are introduced into expression host cells by any of a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the polypeptides are expressed intracellularly. Optionally, after intracellular expression of the polypeptides, or secretion into the periplasmic space using signal sequences such as those mentioned above, a permeabilisation or lysis step can be used to release the cellulase into the supernatant. The disruption of the membrane barrier is effected by the use of mechanical means such as ultrasonic waves, pressure treatment (French press), cavitation or the use of membrane-digesting enzymes such as lysozyme or enzyme mixtures. As a further alternative, the polynucleotides encoding the polypeptides are expressed by use of a suitable cell-free expression system. In cell-free systems, the polynucleotide of interest is typically transcribed with the assistance of a promoter, but ligation to form a circular expression vector is optional. In other embodiments, RNA is exogenously added or generated without transcription and translated in cell free systems.

Reduction of the Viscosity of Pretreated Biomass Mixtures

The provided polypeptides and compositions containing the polypeptides find use in a variety of industrial applications, including in the reduction of the viscosity of pretreated biomass mixtures prior to their degradation into monosaccharides and oligosaccharides, for example, in biofuel production.

Biomass that is used for as a feedstock, for example, in biofuel production generally contains high levels of lignin, which can block hydrolysis of the cellulosic component of the biomass. Typically, biomass is pretreated with, for example, high temperature and/or high pressure to increase the accessibility of the cellulosic component to hydrolysis. However, pretreatment generally results in a biomass mixture that is highly viscous. The high viscosity of the pretreated biomass mixture can also interfere with effective hydrolysis of the pretreated biomass. Advantageously, the polypeptides and compositions of the present disclosure can be used to reduce the viscosity of pretreated biomass mixtures prior to further degradation of the biomass.

Accordingly, certain embodiments of the present disclosure relate to methods of reducing the viscosity of a pretreated biomass mixture, by contacting a pretreated biomass mixture having an initial viscosity with any of the polypeptides or compositions of the present disclosure; and incubating the contacted biomass mixture under conditions sufficient to reduce the initial viscosity of the pretreated biomass mixture.

In some embodiments, the disclosed methods are carried out as part of a pretreatment process. The pretreatment process may include the additional step of adding any of the polypeptides or compositions of the present disclosure to pretreated biomass mixtures after the step of pretreating the biomass under high temperature, and incubating the pretreated biomass with the polypeptides or compositions under conditions sufficient to reduce the viscosity of the mixture. The polypeptides or compositions may be added to the pretreated biomass mixture while the temperature of the mixture is high, or after the temperature of the mixture has decreased. In some embodiments, the methods are carried out in the same vessel or container where the heat pretreatment was performed. In other embodiments, the methods are carried out in a separate vessel or container where the heat pretreatment was performed.

In some embodiments, the methods are carried out in the presence of high salt, such as solutions containing saturating concentrations of salts, solutions containing sodium chloride (NaCl) at a concentration of at least at or about 0.5 M, 1 M, 1.5 M, 2 M, 2.5 M, 3 M, 3.5 M, or 4 M sodium chloride, or potassium chloride (KCl), at a concentration at or about 0.5 M, 1 M, 1.5 M, 2 M, 2.5 M 3.0 M or 3.2 M KCl and/or ionic liquids, such as 1,3-dimethylimidazolium dimethyl phosphate ([DMIM]DMP) or [EMIM]OAc, or in the presence of one or more detergents, such as ionic detergents (e.g., SDS, CHAPS), sulfydryl reagents, such as in saturating ammonium sulfate or ammonium sulfate between at or about 0 and 1 M. In other embodiments, the polypeptides or compositions of the present disclosure are contacted with the pretreated biomass mixture at a temperature exceeding 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., or 110° C., or over a broad temperature range, such as between at or about 60° C. and 110° C. or between 65° C. and 110° C., such as between 90° C. and 110° C., between 65° C. and 70° C., between 85° C. and 105° C., between 85° C. and 110° C., between 95° C. and 105° C., or between 95° C. and 110° C. In some aspects, the polypeptides exhibit the activity or binding ability over a broad pH range, for example, at a pH of between about 4.5 and 8.75, at a pH of greater than 7 or at a pH of 8.5, or at a pH of at least 5.0, 5.5, 6.0, 6.5, 7.0, 7.5, 83.0, or 8.5.

Biomass includes, but is not limited to, plant material, municipal solid waste, and wastepaper, including lignocellulosic feedstocks, e.g., agricultural residues such as corn stover, wheat straw, barley straw, oat straw, rice straw, canola straw, and soybean stover, grasses such as switch grass, *miscanthus*, cord grass, and reed canary grass, fiber process residues such as corn fiber, beet pulp, pulp mill fines and rejects and sugar cane bagasse, forestry wastes such as aspen wood, other hardwoods, softwood and sawdust, and post-consumer waste paper products; palm kernel, coconut, konjac, locust bean gum, gum guar, soy beans. Suitable crop residue for production of biomass includes but is not limited to palm kernel meal, palm kernel expellers, copra meal, copra pellets and soy bean hulls.

Degradation of Biomass to Mono- and Oligosaccharides

The polypeptides, polynucleotides, vectors, and host cells of the present disclosure find use in a variety of industrial applications, including in the degradation of biomass, e.g., cellulase and lignocellulose, into monosaccharides and oligosaccharides, for example, in biofuel production, textile methods, including cleaning, cotton softening, and denim finishing, in production and uses of detergents, for example, for color care, cleaning, and anti-deposition; for food-based methods, including food processing and mashing; for pulp and paper methods, such as paper pulp bleaching, deinking, drainage improvement, and fiber modification. Thus, also provided are methods and uses of the provided polypeptides, polynucleotides, and compositions for such purposes, for example, in degrading or hydrolyzing cellulose-containing compositions to produce soluble sugars, for example, followed by enzymatic or chemical fermentation.

In some embodiments, the methods are carried out in the presence of high salt, such as solutions containing saturating concentrations of salts, solutions containing sodium chloride (NaCl) at a concentration of at least at or about 0.5 M, 1 M, 1.5 M, 2 M, 2.5 M, 3 M, 3.5 M, or 4 M sodium chloride, or potassium chloride (KCl), at a concentration at or about 0.5 M, 1 M, 1.5 M, 2 M, 2.5 M 3.0 M or 3.2 M KCl and/or ionic liquids, such as 1,3-dimethylimidazolium dimethyl phosphate ([DMIM]DMP) or [EMIM]OAc, or in the presence of one or more detergents, such as ionic detergents (e.g., SDS, CHAPS), sulfydryl reagents, such as in saturating ammonium sulfate or ammonium sulfate between at or about 0 and 1 M. In some embodiments, the conversion occurs at a temperature exceeding 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., or 110° C., or over a broad temperature range, such as between at or about 60° C. and 110° C. or between 65° C. and 110° C., such as between 90° C. and 110° C., between 65° C. and 70° C., between 85° C. and 105° C., between 85° C. and 110° C., between 95° C. and 105° C., or between 95° C. and 110° C. In some aspects, the polypeptides exhibit the activity or binding ability over a broad pH range, for example, at a pH of between about 4.5 and 8.75, at a pH of greater than 7 or at a pH of 8.5, or at a pH of at least 5.0, 5.5, 6.0, 6.5, 7.0, 7.5, 83.0, or 8.5.

Bioenergy feedstocks consist primarily of the plant cell wall components cellulose and hemicellulose. Hydrolysis of these polysaccharides to their monomeric sugars involves a set of enzymes acting synergistically to cleave the different chemical linkages (Dodd and Cann, GCB Bioenergy, 1:2, 2009). Cellulose is the predominant polysaccharide in biomass (with others including hemicellulose, lignin, and pectin). Cellulose is a homopolymer of anhydrocellobiose (a linear beta-(1-4)-D-glucan), and includes glucose units linked together in β-1,4-glycosidic linkages. The hemicellulosic component can vary in chemical composition. Hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains.

The provided polypeptides may be used to degrade various types of cellulosic biomass, which are well-known in the art, including plant biomass, microbial biomass, purified cellulose, and lignocellulosic feedstocks. Cellulosic biomass includes lignocellulose biomass, containing cellulose, hemicellulose, and lignin. Purified celluloses include holocellulases, such as Solka Flok, microcrystalline celluloses, such as Avicel® and Sigmacell®, and the highly soluble cellulose ether, carboxymethylcellulose (CMC). Cellulose-containing substrates include soluble and substrates, such as cellodextrins and their derivatives, short chain cellulase, β-methylumbelliferyl-oligosaccharides, p-nitrophenol-oligosaccharides, long chain cellulose derivatives, carboxymethyl cellulose (CMC), hydroxyethyl cellulose (HEC), and insoluble substrates, including cotton, Whatman No. 1 filter paper, Pulp (e.g., Solka Floc), Crystalline cellulose, such as cotton, microcrystalline cellulose (e.g., Avicel®), Valonia cellulose, bacterial cellulose, Amorphous cellulose (e.g., PASC, alkali-swollen cellulose), dyed cellulose, fluorescent cellulose, chromogenic and fluorephoric derivatives, such as trinitrophenyl-carboxymethylcellulose (TNP-CMC) and Fluram-cellulose, practical cellulose-containing substrates, α-cellulose, and pretreated lignocellulosic biomass.

Biofuel Production

The provided polypeptides and compositions containing the polypeptides find use in the degradation and hydrolysis of cellulase and cellulase-containing biomass and feedstocks, for example, for the production of monosaccharides, disaccharides, and oligosaccharides from biomass, such as chemical or fermentation feedstocks, for the production of biofuel, such as ethanol, butanol, other products, and intermediates. Provided are methods and compositions for such uses of the provided polypeptides, such as conversion of lignocellulocytic biomass into soluble sugars for fermentative production of biofuels, conversion of pretreated lignocelluose into soluble sugars, conversion of lignocellulose into soluble sugars in the presence of high salt or ionic liquids, conversion of crystalline cellulose into soluble sugars at high temperatures, such as those exceeding 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., or over a broad temperature range, such as between at or about 60° C. and 110° C. or between 65° C. and 110° C., such as between 90° C. and 110° C., between 65° C. and 70° C., between 85° C. and 105° C., between 85° C. and 1110° C., between 95° C. and 105° C., or between 95° C. and 110° C., or under other conditions as described herein above.

In one embodiment, the provided composition includes the peptide in a composition of crude fermentation broth, with or without the cells removed, or in the form of a semi-purified or purified enzyme preparation. In another embodiment, the provided host cells are used as a source of the polypeptide in a fermentation process with the biomass.

In one embodiment, the polypeptides of the present disclosure find use in the degradation of cellulose to aid in the degradation of biomass, to form biofuels, such as ethanol. Ethanol is produced by enzymatic degradation of biomass and conversion of the released saccharides to ethanol (often referred to as bioethanol or biofuel, used as a fuel additive or extender in blends of from less than 1% and up to 100% (a fuel substitute)). In one embodiment, for the production of biofuels from biomass, the provided polypeptides, compositions, and methods are used in the conversion of cellulose to its monomer (glucose) or other soluble sugar, for subsequent conversion to biofuel (e.g., ethanol) by fermentation, such as by microbial or chemical fermentation. For example, the provided polypeptides and methods may be used for such conversion by enzymatic hydrolysis, optionally including acid pretreatment, typically carried out at high temperatures, followed by hydrolysis with the provided polypeptides.

In one embodiment, the polypeptides are used in combination with other carbohydrases (e.g., mannanases, glucanase, xylanase, alpha-galactosidase and/or cellulase) for more extensive hydrolysis of the plant material.

Food Processing

Compositions comprising the polypeptides of the present disclosure also find use in the processing and manufacturing of food or animal feed, such as in mashing. Provided are methods employing the provided compositions in such uses. Several anti-nutritional factors limit the use of specific plant material in the preparation of animal feed and food for humans. Plant material containing oligosaccharides can reduce the digestibility and absorption of nutritional compounds such as minerals, vitamins, sugars and fats by the animals. Provided are methods for food processing using the provided compositions. In one embodiment, the polypeptides and compositions are used to degrade or hydrolyze polymers into simpler sugars, which can be more readily assimilated to provide additional energy.

Polypeptides of the present disclosure also are useful as additives to feed for monogastric animals such as poultry and swine, as well as for human food. In some embodiments, the polypeptides are used to pretreat the feed instead of as a feed additive. In some embodiments, the polypeptides are added to or used to pretreat feed for weanling pigs, nursery pigs, piglets, fattening pigs, growing pigs, finishing pigs, laying hens, broiler chicks, turkeys, for example, added to or used to pretreat feed from plant material such as palm kernel, coconut, konjac, locust bean gum, gum guar, soy beans, barley, oats, flax, wheat, corn, linseed, citrus pulp, cottonseed, groundnut, rapeseed, sunflower, peas, and lupines.

Because of their stability, e.g., thermostability, they find used in processes of producing pelleted feed in which heat is applied to the feed mixture before the pelleting step, as it is the case in most commercial pellet mills. In one example, the polypeptides are added to the other feed ingredients in advance of the pelleting step or after the pelleting step to the already formed feed pellets.

In some embodiments, the provided compositions containing the provided polypeptide for use in food processing or as a feed supplement contain other substituents, such as coloring agents, aroma compounds, stabilizers, vitamins, minerals, other feed or food enhancing enzymes and the like. This applies in particular to the so-called pre-mixes. Food additives according to this present disclosure may be combined with other food components to produce processed food products. The resulting, combined food additive is mixed in an appropriate amount with other food components such as cereal or plant proteins to form a processed food product.

Textile Cleaning and Laundry Detergents

The provided polypeptides, methods, and compositions also find use in textile methods, including cleaning, cotton softening, and denim finishing, the polishing of cotton fabrics under high temperature treatments, and in production and uses of detergents, for example, for color care, cleaning, and anti-deposition. For example, the provided polypeptides find use in detergent compositions to facilitate the removal of cellulose-containing stains and soils. In one embodiment, the polypeptides are used in detergent compositions; provided are such detergent compositions and methods for their use. In one embodiment, the detergent compositions contain the polypeptides in combination with other enzymes from the group of amylases, mannases, cellulases, lipases, pectinases, proteases, endoglucanases, and exoglucanases.

The detergent compositions include those in any convenient form, including in a bar, a tablet, a powder, a granule, a paste or a liquid. A liquid detergent is generally aqueous, typically containing up to 70% water and 0-30% organic solvent(s), or non-aqueous component(s). Typically, the detergent composition comprises one or more surfactants (e.g., non-ionic including semi-polar, anionic, cationic and/or zwitterionic). The surfactants are typically present at a level of from 0.1% to 60% by weight. When included, detergents typically contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap. When included, detergents typically contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine (glucamides).

Detergent compositions optionally comprise 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic add, soluble silicates, or layered silicates. Detergent compositions optionally comprise one or more polymers such as carboxymethylcellulose (CMC), poly(vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers, and lauryl methacrylate/acrylic acid copolymers. The detergent optionally comprises a bleaching system (e.g., hydrogen peroxide source) such as perborate or percarbonate, which may be combined with a peracid-forming bleach activator such as tetraacetylethylenediamine or nonanoyloxybenzenesulfonate. Alternatively, the bleaching system comprise peroxyacids of the amide, imide, or sulfone type.

In one embodiment, the provided polypeptides are added to the detergent composition in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

Paper Pulp Processes

In another embodiment, the provided compositions and polypeptides find use in pulp and paper methods, such as in paper pulp bleaching, deinking, drainage improvement, and fiber modification, for example, in high temperature applications for the pulping of cellulolytic materials. Provided are methods and compositions for use of the provided polypeptides for such purposes. For example, in some embodiments, the polypeptides find use in the enzyme aided bleaching of paper pulps such as chemical pulps, semi-chemical pulps, kraft pulps, mechanical pulps or pulps prepared by the sulfite method. In some embodiments, the pulps are chlorine free pulps bleached with oxygen, ozone, peroxide or peroxyacids. In some embodiments, the provided polypeptides are used in enzyme aided bleaching of pulps produced by modified or continuous pulping methods that exhibit low lignin contents. In some embodiments, the provided polypeptides are applied alone; in other embodiments, they are provided in combination with other enzymes, such as xylanase and/or endoglucanase and/or alpha-galactosidase and/or cellobiohydrolase enzymes.

The following examples are offered to illustrate provided embodiments and are not intended to limit the scope of the invention.

EXAMPLES

The following examples describe the results of a metagenomic approach to identify extremely stable and thermoactive endoglucanases from a lignocellulose-degrading consortium of hyperthermophilic Archaea, including the endoglucanase EBI244, with a capacity to tightly bind microcrystalline cellulose (Avicel® PH-101).

Example 1

Enrichment of Hyperthermophilic Archaea and Metagenomic Sequencing

Hyperthermophilic Archaea were enriched on pulverized plant biomass (microcrystalline cellulose). For this process, a sample of sediment collected from a continental volcanic hot spring at 94° C. and neutral pH was selectively enriched to obtain a consortium of hyperthermophilic Archaea growing on lignocellulose as sole carbon source. A secondary minimal enrichment of three hyperthermophilic Archaea was isolated on minimal salts medium containing microcrystalline cellulose (Avicel®) as the major carbon source.

Source Material

Sediment was sampled from great boiling springs near Gerlach Nev., from a pool having a temperature of 94° C., known to maintain temperatures around 90° C. (FIG. 1A). A small glass jar (4 oz) was filled with sediment, topped off with spring water, closed, and sealed with Parafilm® M. Samples were transported on ice; long-term storage was carried out in anaerobic jars at 4° C.

Enrichment of Hyperthermophilic Archaea

Approximately 3 mL of sediment was used as inoculum to generate an anaerobic microbial enrichment on minimal salts medium (90 mL). The medium was similar to DSMZ medium #516 (ANAEROCELLUM MEDIUM), except that pulverized lignocellulosic feedstock *Miscanthus gigas*, ground to 80 uM particle size, was used as the carbon source feedstock, and yeast extract was reduced to 0.2 g/L. Specifically, the medium contained NH4Cl (0.33 g), KH2PO4 (0.33 g), KCl (0.33 g), MgCl2×6 H2O (0.33 g), CaCl2×2 H2O (0.33 g), Trace element solution (Nitrilotriacetic acid 1.500 g, MgSO4×7 H2O 3.000 g, MnSO4×H2O 0.500 g, NaCl 1.000 g, FeSO4×7 H2O 0.100 g, CoSO4×7 H2O 0.180 g, CaCl2×2 H2O 0.100 g, ZnSO4×7 H2O 0.180 g, CuSO4×5 H2O 0.010 g, KAl(SO4)2×12 H2O 0.020 g, H3BO3 0.010 g, Na2MoO4×2 H2O 0.010 g, NiCl2×6 H2O 0.025 g, Na2SeO3×5 H2O 0.300 mg, Distilled water 1000.000 ml, made by first dissolving nitrilotriacetic acid and adjusting pH to 6.5 with KOH, then adding minerals, adjusting pH to 7.0 with KOH), Distilled water 1000.000 ml) (1.00 ml), Yeast extract (0.2 g), Resazurin (0.50 mg), Vitamin solution (Biotin 2.000 mg, Folic acid 2.000 mg, Pyridoxine-HCl 10.000 mg, Thiamine-HCl×2H2O 5.000 mg, Riboflavin 5.000 mg, Nicotinic acid 5.000 mg, D-Ca-pantothenate 5.000 mg, Vitamin B12 0.100 mg, p-Aminobenzoic acid 5.000 mg, Lipoic acid 5.000 mg) (10.00 ml), NaHCO3 (1.50 g), pulverized lignocellulosic feedstock *Miscanthus gigas*, ground to 80 uM particle size for use as the carbon source (5.00 g), Na2S×9H2O 0.50 g, Distilled water 1000.00 ml, with ingredients (except vitamins, bicarbonate, cellobiose and sulfide) dissolved, boiled for 1 min., then cooled to room temperature under 80% N2 and 20% CO2 gas atmosphere, adding vitamins, feedstock solutions and bicarbonate from a sterile stock solution, prior to inoculation, adjusted to a pH of 7.1-7.3.

After incubation for three weeks at 90° C., a secondary enrichment was performed by innoculating with microcrystalline cellulose, with ~50 μm particle size (Avicel® pH101 Fluka, Ireland), as the carbon source. The minimal enrichment obtained on microcrystalline cellulose (Avicel®) was transferred to the same salts medium described above, with Whatman® #3 (Qualitative Grade 3) Filter Paper as a carbon source, (FIGS. 1B and 1C). Enrichment on Avicel® was chosen for scaled up production of the consortium because this finely divided crystalline substrate resulted in more rapid growth.

This enrichment strategy yielded a three-organism consortium, capable of deconstructing crystalline filter paper at 90° C., as demonstrated by pitting, shredding or complete dissolution of strips of Whatman® #1 (Qualitative Grade 1) or Whatman® #3 (Qualitative Grade 3) filter paper (FIG. 2). Specifically, the consortium degraded a strip of Whatman #1 filter paper supported by glass tubing, a circular piece of Whatman® #3 filter paper (confirmed by visible pits). Pits were more often seen with the thicker Whatman® #3 filter paper (FIG. 2B), while shredding/dissolution was more often seen with the thinner Whatman® #1 filter paper (FIG. 2A).

Repeated efforts to separate the three species of the consortium failed.

Extraction, Purification, and Analysis of Native Protein

Avicel® from a 17.5 L enrichment, grown on Avicel® PH 101 in a 20 L specialized fermentor, was washed and extracted with CHAPS detergent and SDS as follows. The enrichment was harvested by centrifugation and the pellet, principally Avicel®, was washed 3 times with Tris buffer (100 mM sodium chloride and 0.05% Tween® 20) to remove soluble proteins. The remaining pellet was washed with 0.6% CHAPS detergent in TE (Tris-EDTA) buffer, then twice with 2% CHAPS in TE buffer, 20 minutes each, at 90° C., then boiled in 1% SDS for 20 minutes, and in 2% SDS for 20 minutes. The 1% SDS and 2% SDS fractions contained proteins determined to have been transferred to Avicel® during growth, and tightly bound to partly digested cellulose fibrils.

Preliminary Assay of Endoglucanase Function Using Zymograms

Figure 3:
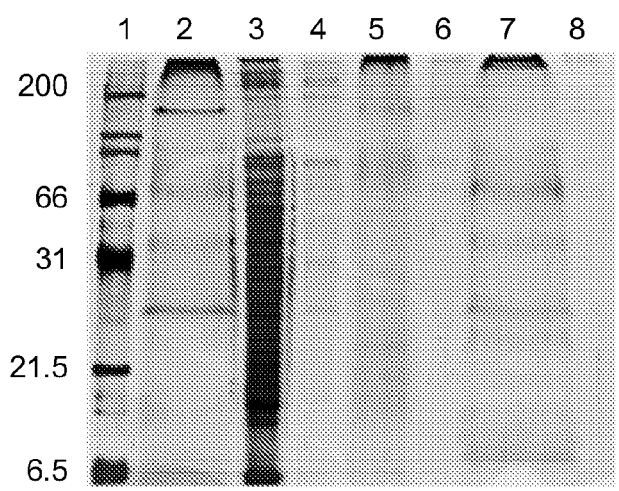
FIG. 3 shows endoglucanase activity of protein in the three-organism hyperthermophilic Archaea consortium enriched on Avicel® as described in Example 1A, measured by zymograms on SDS-PAGE fractions from detergent wash of Avicel® from the enrichment culture. The lanes are labeled as follows: 1 (Marker), (2) 1% SDS wash (experiment 1); (3) whole cell extract; (4) Avicel®; (5) CHAPS fraction; (6) Pellet after CHAPS wash, (7) 1% SDS wash (experiment 2).

Zymograms were used as a preliminary assay to screen the fractions for endoglucanase activity. As shown in FIG. 3, Zymograms performed on the protein extractions from the Avicel® enrichment demonstrated detectable activity in a split band at apparent molecular weights ranging from 80 to 250 kDa for the 2% CHAPS fractions. As shown in FIG. 3, subsequent washes with 1-2% SDS yielded the most activity, localized in a small number of distinct protein bands.

Figure 4:
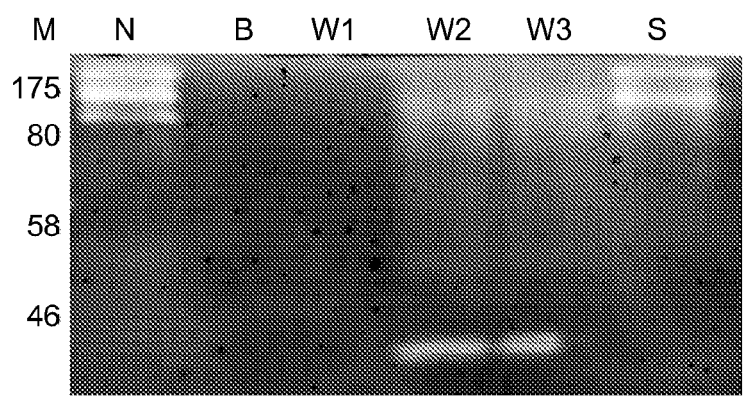
FIG. 4 shows protein extraction and detection of CMCase activity. Protein extraction and detection of CMCase activity from proteins eluted from Avicel® particles after deconstruction by enrichment at 90° C. for 8 days. Image shows SDSPAGE gradient zymogram, 10%-15% acrylimide, with 0.2% CMC embedded in gel. Lanes: M-marker, N-native whole SDS extract, B-buffer only soluble extract, W1-0.6% CHAPS extract, W2-1% CHAPS 5% Cellobiose extract #1 (1 hr incubation at 90° C.), W-3 1% CHAPS 5% Cellobiose extract #2 (1 hr incubation at 90° C.), S-1% SDS extract final wash (15 minute incubation 100° C.). For lanes B through S, the Avicel® pellet was sonicated continuously for 2 minutes in the wash solution.

The 1% CHAPS/5% cellobiose fraction showed detectable CMCase activity on zymograms. Active cellulases with apparent molecular weights of about 40 kDa and 80 kDa were detected (FIG. 4). Subsequent washes with 1% SDS at 100° C. yielded the release of additional hyperstable, high molecular weight enzymes with CMCase activity as indicated by the activity in a smaller number of more distinct bands with apparent molecular weights of about 80 kDa and 180 kDa (FIG. 4). It was apparent that this consortium was producing cellulases that could bind to Avicel® particles, and were able to withstand boiling in 1% SDS, abilities not yet observed in well-characterized cellulases from hyperthermophilic archaea. Therefore, metagenomics was employed to identify potential cellulases from this consortium.

Extraction of High Molecular Weight DNA from Avicel® Enrichment

Standard protocols were used to extract high molecular weight DNA from the Avicel® enrichment using the CTAB method (Ausubel et al., Current Protocols in Molecular Biology. Vol. 2 (John Wiley & Sons Inc., 1994) with volumes increased 4-fold. Using this method, approximately 20 μg of high molecular weight DNA was obtained from a 1.5 L enrichment grown on 5 g Avicel®/L. The average size of the DNA was determined by pulsed-field electrophoresis to be about 50 kDa.

Sequencing and Sequence Analysis

Metagenomic analysis was performed on the minimal enrichment identified multiple endoglucanase homologs in the metagenome.

Metagenomic sequencing was performed on DNA from the consortium. Library preparation and sequencing was performed at the University of Illinois, W. M. Keck Center for Comparative and Functional Genomics. Sequencing was done via Roche 454 Titanium Shotgun Sequencing. Initial automated assembly was by done at the Center by Newbler Assembly program (Newbler Assembler software, 454 Sequencing/Roche). Automated annotation was done using a local MANATEE database and the nr BLAST database, available through NCBI. In addition, further annotation was conducted through the MicrobesOnline Comparative Genomics Database (VIMSS funded by DOE Genomics:GTL), which includes protein coding prediction using CRITICA and Glimmer3, followed by annotation using the VIMSS genome pipeline composed of all publicly available sequence databases.

The consortium of three Archaea contained a dominant organism related to *Ignisphaera aggregans*, but sufficiently distinct to be assigned to a different genus, as well as two Archaea related to *Pyrobaculum islandicum* and *Thermofilum pendens*. The major organism is designated *Pyrosphaera cellulolytica* Candidatus Nov Gen Nov Sp (*P. cellulolytic*). The incomplete genome of this hyperthermophilic Archaeon shares several features of the genome of *I. aggregans*, including a pair of homologous but somewhat distantly related genes encoding reverse gyrase. The genome of *P. cellulolytica* indicates that the strain is specialized for heterotrophic utilization of a variety of carbohydrates. The draft genome has significant coding capacity for glycolytic enzymes including putative endo and exocellulases, glucosidases and hemicellulases.

Figure 5:
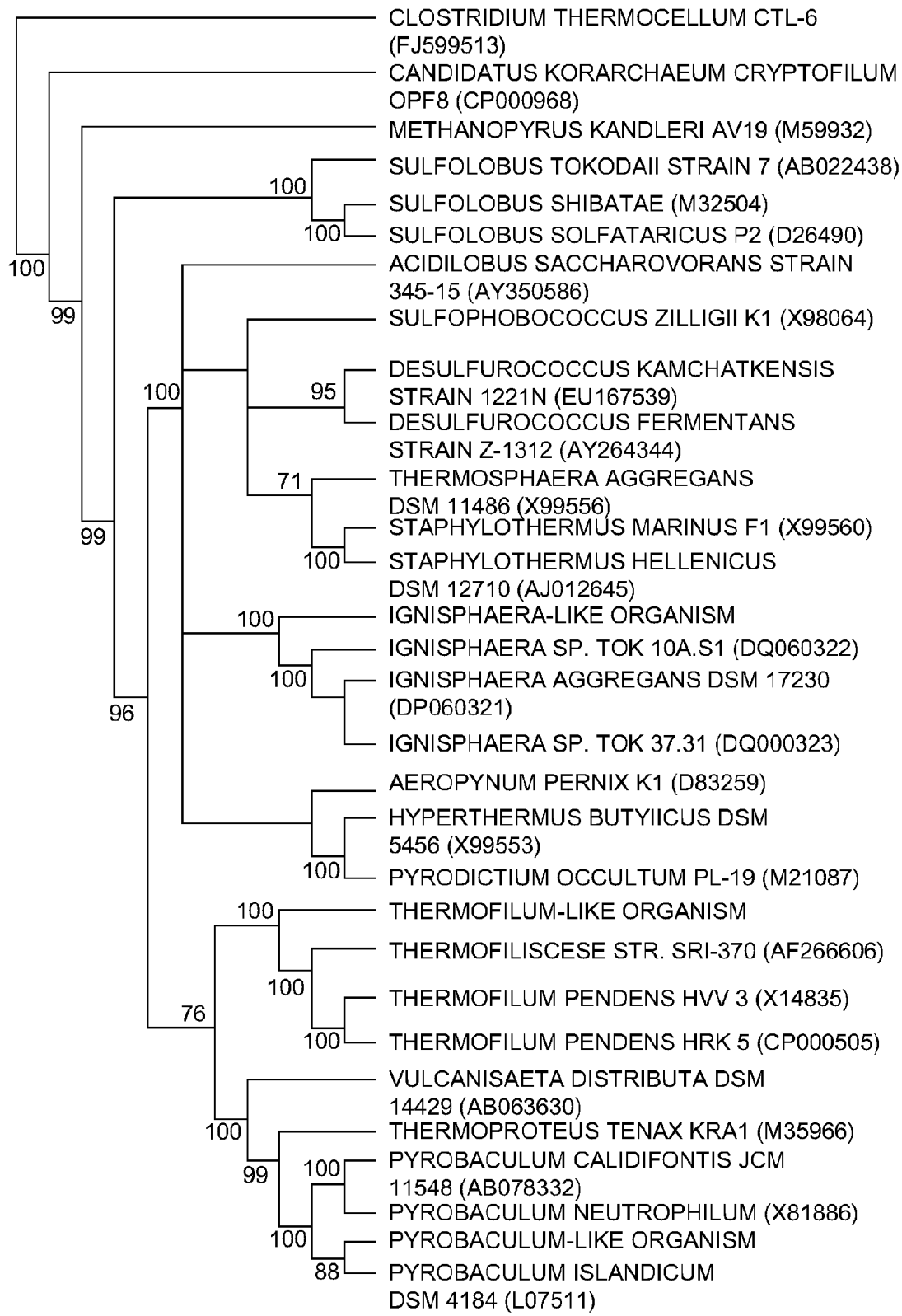
FIG. 5 depicts a maximum likelihood phylogenetic tree. Maximum likelihood 16S rRNA phylogenetic tree, showing the relationship of full-length 16S rRNAs from the three component organisms of the assembled metagenome. Branches in bold and labeled with larger type represent the three sequences from the metagenome.

Metagenomic sequencing yielded 1,283,902 reads, with a total of 497,707,575 bases. Assembly yielded 4206 contigs representing 6,954,058 bases. One complete 16S RNA and two fragmented 16S RNAs were identified, which matched most closely to characterized organisms *Ignisphaera aggregans* DSM 17320 (95%), *Pyrobaculum islandicum* DSM 4184 (98%), and *Thermofilum pendens* Hrk (93%), respectively. A maximum likelihood 16S rRNA gene phylogenetic tree is shown in FIG. 5.

Proteomics analysis was done by tandem mass spectrometry conducted at the California Institute for Quantitative Biosciences Proteomics/Mass Spectrometry Core Facility. Briefly, gel slices were prepared by vortexing with 25 mM ammonium bicarbonate 1:1 acetonitrile/water for 10 min and discarding the supernatant. This step was repeated three times. Slices were vacuum-dried, then reduced by incubation with 10 mM DTT in 25 mM ammonium bicarbonate with 10% acetonitrile and alkylated with 55 mM iodoacetamide in 25 mM ammonium bicarbonate. Proteins were then digested with one volume of trypsin for 6 h at 37° C. After digestion, the slices were washed with water and the supernatant saved. Gel slices were then washed twice with a solution of 45% water, 50% acetonitrile, and 5% formic acid; all supernatants were saved. Supernatants containing the peptides were reduced to a volume of 10 µL and then analyzed with tandem mass spectrometry. Peptide sequences were annotated using the annotated genome created by MicrobesOnline.

Figure 6:
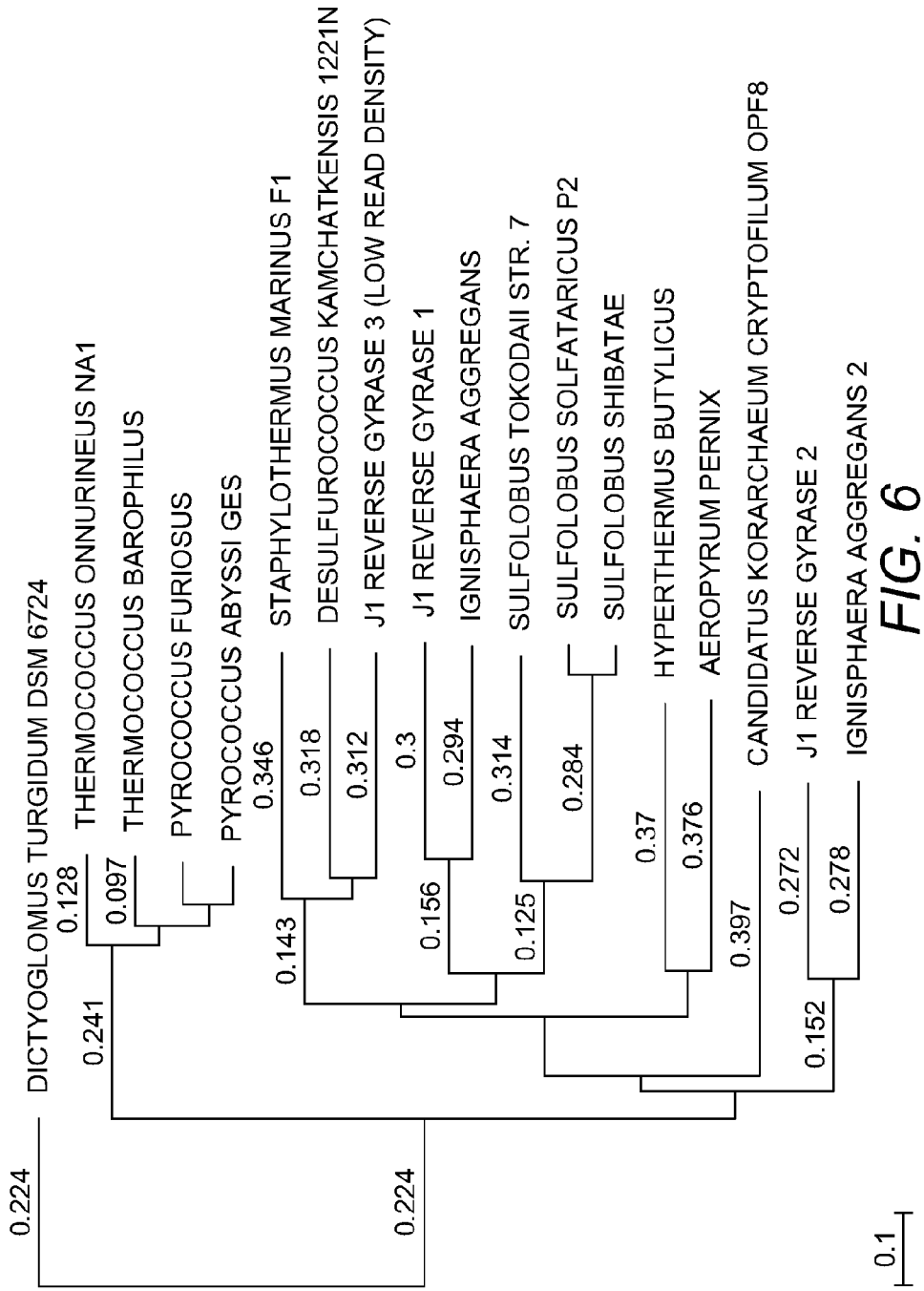
FIG. 6 displays a phylogentic tree, showing relationship of three reverse gyrases, from the metagenome described in Example 1A, to other archaeal reverse gyases. Reverse gyrase 1 and 2, found on high-read density contigs, appear closely allied with the two reverse gyrases encoded by Ignisphaera aggregans. The reverse gyrase of the bacterium Dictyoglomus turgidum was set as the root.

Similar topology and bootstrap supported was obtained for the Neighbor-joining method (results not shown) The 16S rRNA gene from the *Ignisphaera*-like organism was 99% identical to 16S rRNA clones from uncultured archaea from geothermal systems in both Nevada (accession number HM448083.1) and Montana (accession number EU635921.1). The *Ignisphaera*-like 16S RNA was 94% identical to the type species and represented the dominant organism in the enrichment, based on large number of reads per kilobase of sequence (~300) for 16S RNA and the hyperthermophilic housekeeping gene reverse gyrase, compared to read densities (<20) for 16 RNA fragments and reverse gyrases from the other organisms. Like *Ignisphaera aggregans*, the *Ignisphaera*-like organism appeared to have two reverse gyrase genes, as shown in FIG. 6. The sum of the high read density contigs represented about 1.8 Mb, or most of the expected coding sequence of a single hyperthermophile (~2.0 Mb). Sequence analysis found a large number a glycosyl hydrolases (>40) and 21 contigs containing potential cellulases, based on automated annotation.

Example 2

Identification of Carbohydrate Active Enzymes

Annotation analysis found a large number of GHs (37) and included 4 potential GH family 5 endoglucanases, based on automated annotation. Twelve of these GHs were encoded by the closed genome of the dominant strain. One predicted GH, designated EBI244 (accession number JF509452), was chosen for further study because it was a potential multi-domain cellulase, 842 amino acids in length, and a member of the TIM barrel glycosyl hydrolase superfamily (β/α)8. Large multidomain cellulases are ubiquitous amongst cellulolytic organisms but have not been previously found in hyperthermophilic archaea. The central domain of this enzyme (AA250-580) had a Pfam match (E-value $1X\ e^{-12}$) to the GH family 5 (GH5). The gene encoding EBI244 was found on the chromosome of the dominant organism and at 94 kDa EBI244 was the largest of three proteins encoded on the chromosome with Pfam hits to GH family 5 (GH5); the others were a 43 kDa Pfam match (E-value $6.3\ E^{-67}$) and a 44 kDa Pfam match (E-value $8\ E^{-52}$).

Potential homologs were gathered with PSI-BLAST (Johnson, M et al., Nucleic Acids Res. 36, W5-9, 2008) using each putative domain of EBI244 as the query sequence against the nr protein sequence database. The SAM software package (Karplus et al., Bioinformatics 14, 846-856, 1998) was used to build hidden Markov models (HMM's), score the potential homolog sequences, and create alignments for building new models. This method was used iteratively with each putative domain to build more general models in order to detect distant homologs. Jalview (Waterhouse, A. M. et al., Bioinformatics 25, 1189-1191, 2009) was used to view and edit multiple sequence alignments. The resulting alignments allowed for approximate domain boundary determination.

According to BLASTp searches EBI244 is a weak match to its closest apparent homolog, an uncharacterized hypothetical protein from *Caldicellulosiruptor saccharolyticus* (35% identity). The conserved central domain (AA250-580) had only 9 significant hits (NCBI nonredundant protein database) with BLAST E-values less then 1E-20, including proteins from *Herpetosiphon aurantiacus* ATCC 23779, *Spirochaeta thermophila* DSM 6578, *Spirochaeta thermophila* DSM 6192, *Opititus terrae* PB90-1, *Chitinophaga pinensis* DSM 2588, *Zunongwangia profunda* SM-A87, *Clostridium leptum* DSM 753, *Victivallis vadensis* ATCC BAA-548; with % identities ranging from 25-35%.

Example 3

Analysis of a Hyperthermophilic Cellulase-encoding Gene (ebi244) and Polypeptide Encoded Thereby (EBI244 Protein)

Based on sequencing and analysis, one gene and polypeptide encoded thereby were chosen for further study, based on the gene's homology to the cellulase superfamily/glycosylhydrolase family 5/EC 3.2.1.4. The gene/protein was designated ebi244/EBI244. The EBI244 protein had apparent but distant similarity to type 5 glycosyl hydrolases (cellulase superfamily). The gene mapped to a high-read density contig embedded in a sequence flanked by other assembled genes. The contig did not display synteny or detectable homology to the draft genome sequence of *I. aggregans* web site genome.ornl.gov/microbial/iag17230/.

Sequence analysis revealed that ebi244 was a putative cellulase-encoding gene, isolated from a hyperthermophilic archaeal consortium metagenome, having no global identity to any previously characterized protein or enzyme. The predicted open reading frame (ORF) encodes a protein having a deduced sequence 842 amino acids in length, set forth as SEQ ID NO: 1. The recombinant forms generally add a terminal methionine (Met) bringing the total to 843 amino acids (SEQ ID NO:14.) Achea proteins sometimes start with amino acids other than Met, such as leucine (Leu).

Sequence comparison revealed that the protein contained no close global identity to any previously characterized protein or enzyme. A central region of the protein (Domain 2) showed similarity to the known glycosyl-hydrolase family 5

(GH5) domain, present in a family of glycosyl hydrolases, which was evidence of cellulase or similar sugar hydrolase activity. Aside from this glycosyl hydrolase domain, none of the remainder of the amino acid sequence shows any similarity to any known domain or protein in the major databases.

Figure 7A:
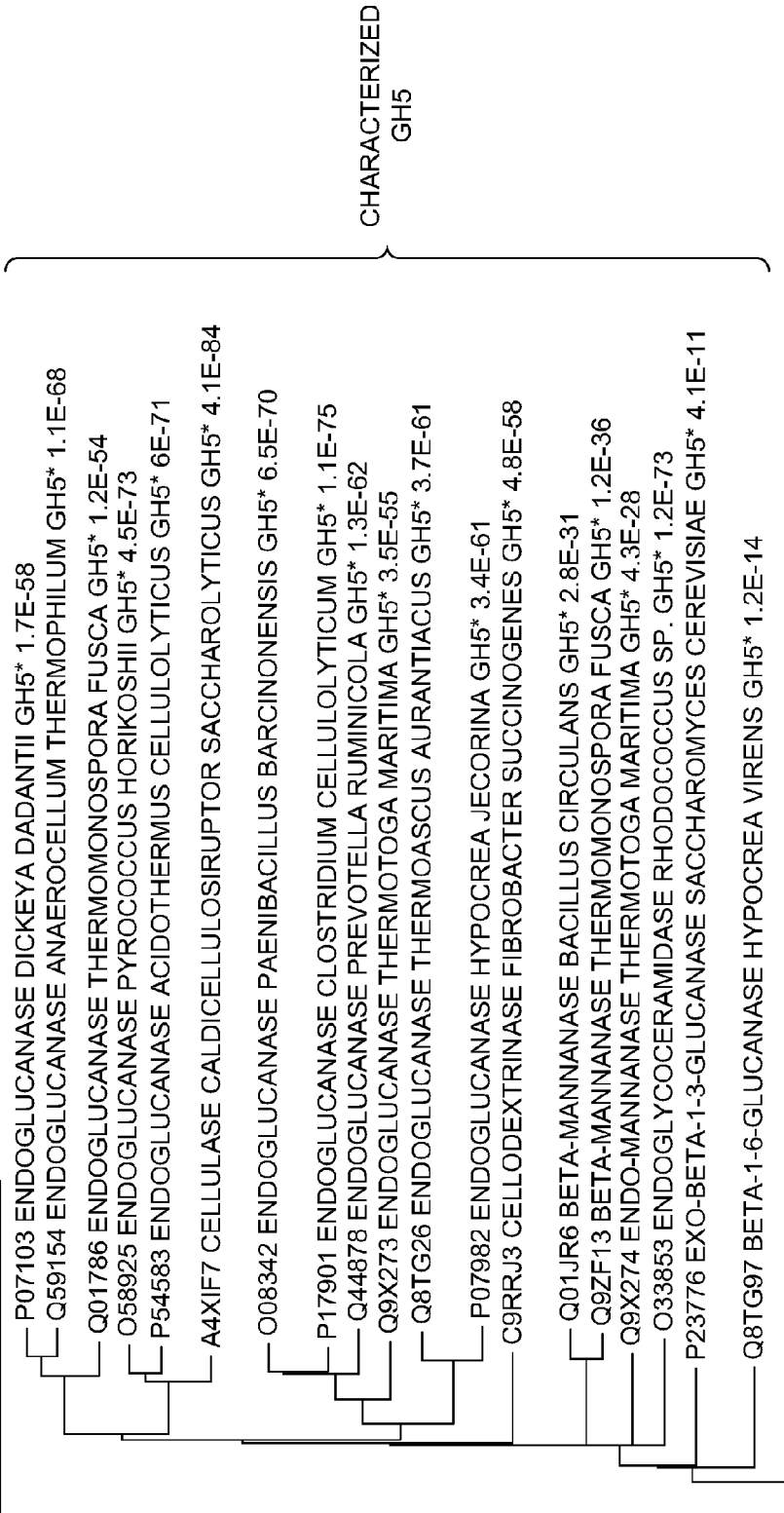
FIG. 7 depicts the phylogeny of the EBI244 protein putative catalytic domain. A phylogenetic tree was produced showing the relationship of EBI244's catalytic domain to the closest characterized GH families. Tree entry information: Uniprot identifier; enzyme function (if known); organism name; Pfam hit GH family (asterisk indicated characterized enzyme in CAZY database); and E-value (no GH listed indicates no Pfam hits).
Figure 7B:
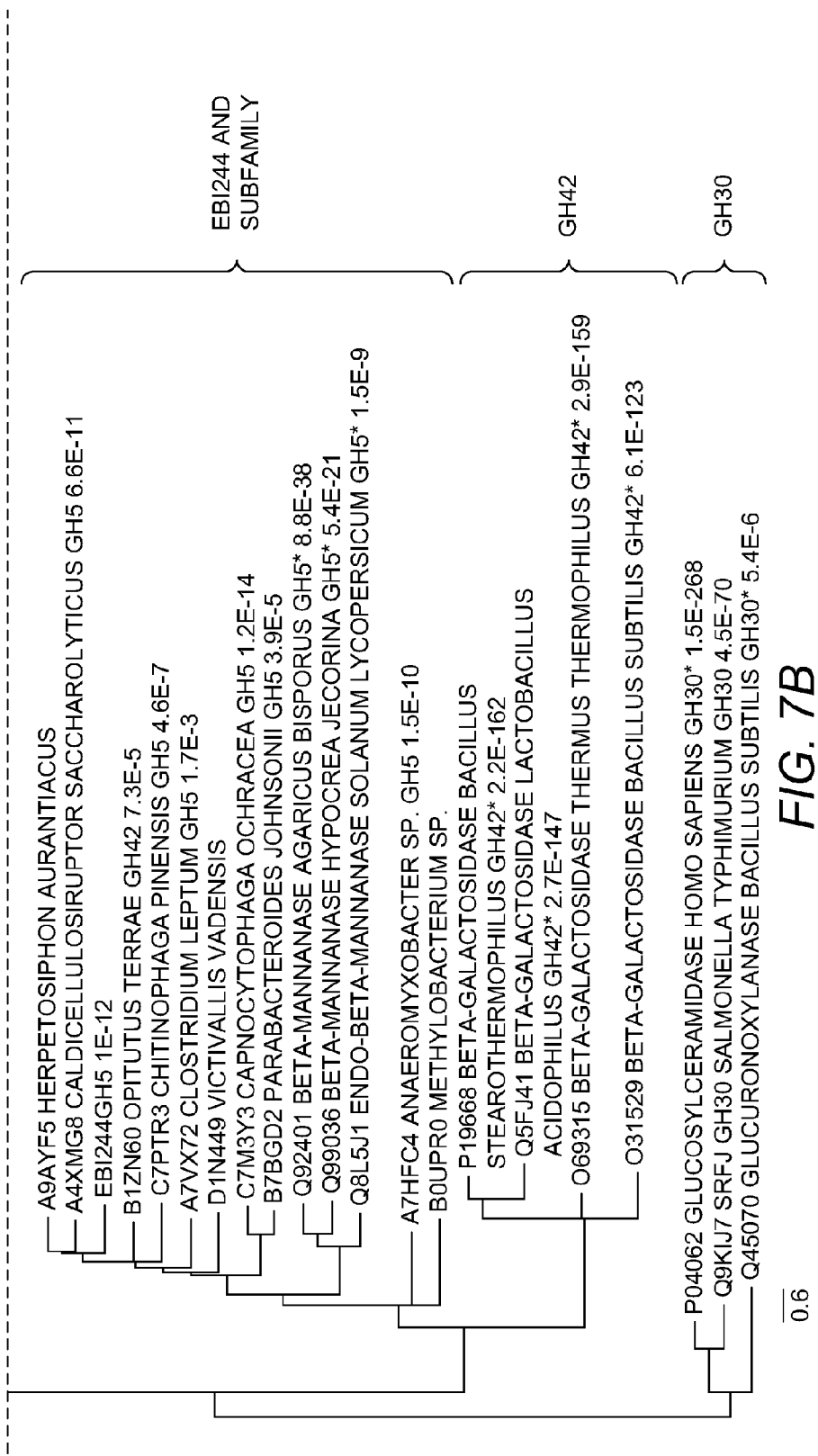

Phylogenetic analysis of EBI244 was carried out using the sequence of domain 2 (GH5 match) in order to determine its evolutionary relationship to characterized enzymes (FIG. 7). The phylogenetic tree was built using the SATCHMO-JS server (Hagopian, R et al., Nucleic Acids Res. 38, W29-34, 2010). All sequences were aligned with the Expresso server (Armougom, F. et al., Nucleic Acids Res. 34, W604-608, 2006) in order to trim sequences down to only the structurally related GH domain. All characterized GH family 5 and GH family 42 sequences in the CAZy database (Cantarel, B. et al., Nucleic Acids Res. 37, D233-238, 2009) were used initially to compare to EBI244 and its closest homologs. The size of the tree was reduced by using Jalview's remove-redundancy function, thereby also preserving the diversity of each family. The Pfam web server (Finn, R D et al., Nucleic Acids Res. 38, D211-222, 2010) was used to score the sequences against Pfam HMM models of the GH families.

The catalytic domain of EBI244 clustered with a unique subset of TIM barrel sequences that show distant relationships to both GH families 5 and 42 in the calculated phylogenetic tree. In this analysis, three members of Family 30 formed a distant out-group although they are assigned to the Clan A structural clade that includes the families GH5 and GH12. EBI244 clusters with three characterized mannanases that have been classified in the GH5 family. The eight closest homologs of the EBI244 catalytic domain include six that have a GH Pfam match (five from GH5, one from GH42), and two with no predictive matches (E-values shown in FIG. 7). Given this uncertain association, the unique architecture, and the diversity of the GH5 family, it is unclear whether the sequence cluster containing the EBI244 catalytic domain is a divergent subfamily of the GH5 family or the nucleus of a new family of glycoside hydrolases.

EBI244 Domain Architecture:

Protein database searches and bioinformatic server predictors indicated that EBI244 contains four structural domains, one unstructured region, and an N-terminal signal or lipid-anchor sequence. The domains and regions are shown schematically in FIG. 8A, with approximate amino acid positions indicated for each.

N-Terminal Sequence:

The analysis revealed that the first approximately 25 amino acids of the native EBI244 enzyme are highly hydrophobic and likely represent a signal peptide (for directing protein localization with eventual cleavage) or membrane/lipid anchor (to hold the protein on the cell surface). While signal sequence and transmembrane (TM) region prediction servers are not built with archaeal sequences, they can be useful for some guidance. Thus, various servers were used to analyze this region of EBI244, given mixed results, with some predicting a TM-region (e.g. Phobius: TM region a.a. 6-25. TMHMM: TM region a.a. 5-27), some predicting a signal peptide (e.g. SignalP 3.0: predicted cleavage between a.a. 22 and 23), and others giving inconclusive predictions (e.g. SIG-Pred: Eukaryote predicted signal sequence with cleavage between a.a. 18 and 19, but no prokaryotic signal sequence predicted).

Figures 8A, 8B:
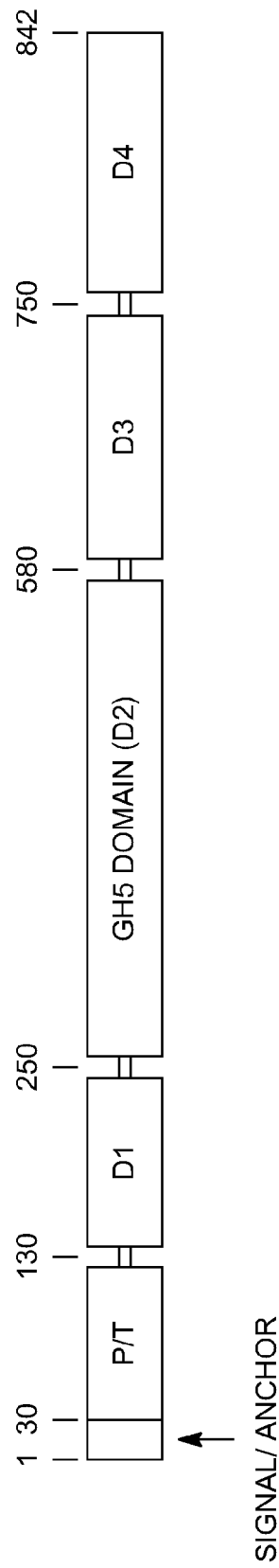
FIG. 8A displays schematically the predicted domain architecture of EBI244 protein sequence, with approximate amino acid positions of domain boundaries labeled.
FIG. 8B displays similar N-terminal protein regions among genes identified in the hyperthermophilic Archaea consortium metagenome in which EBI244 was discovered, as described in Example 1. The top sequence is EBI244, labeled VIMSS5326244 (SEQ ID NO: 38), VIMSS5324142 (SEQ ID NO: 39), VIMSS5327647 (SEQ ID NO: 40), consensus (SEQ ID NO: 41).

Given the varied results using server predictions, further studies were carried out to identify similar N-terminal protein regions among genes found in the metagenome (FIG. 8B). Two representative sequences are shown in illustration 2, VIMSS5327647 (Pfam hit: Extracellular solute-binding protein family 5) and VIMSS5324142 (Pfam hit: Extracellular solute-binding protein family 1). This type of proteins (according to Pfam's description) is known in gram(+) bacteria (containing no outer membrane) to be bound in the membrane via N-terminal lipid-anchors, indicating that EBI244 may also be attached to the extracellular side of the lipid membrane with its N-terminal hydrophobic amino-acid region.

Well-known methods, such as those employing software (free and commercially available services) may be used to predict signal sequences (see, for example, the Transmembrane helix and signal peptide prediction list available on the World Wide Web, at the URL cmgm.stanford.edu/WWW/www_predict.html, and the program "SignalP 3.0 Server," available on the World Wide Web at www.cbs.dtu.dk/services/SignalP. The SignalP 3.0 program was used to predict the location of a signal sequence for the polypeptide of SEQ ID NO: 1. Using this method, a cleavage site was predicted between amino acids 23 and 24. Thus, the predicted mature protein is 24-842 of SEQ ID NO: 1.

Proline/Threonine-rich Region

The analysis revealed that the N-terminal putative signal peptide is followed by a one hundred (100) amino acid region, rich in threonine and proline. Threonine/proline rich regions are generally highly unstructured, often serving as flexible linkers in cellulases. Such sequences are known to be found in many types of proteins, including cellulases. The size of the threonine/proline-rich region in EBI244, as well as the degree of enrichment for threonine (44%—for the region 33-126) and proline (24% for the region 33-126) are highly unusual. In many cellulases, threonine/proline rich regions serve as linker domains, connecting different domains (e.g., a catalytic domain connected to a cellulose-binding domain). In EBI244, however, this region is positioned too close to the N-terminus to be positioned between functional domains. Other deduced carbohydrate enzymes from the metagenome also showed threonine rich motifs at N- or C termini. None was as dramatic as the region from EBI244.

Domains 1-4

Based on Hidden Markov Modeling (HMM), the remainder of the protein was predicted to encode up to four structural domains (Domains 1-4).

Hidden Markov Model (HMM) searching and analysis was carried out on the domain 1 region of EBI244. This searching and analysis identified sequences of thirty-eight (38) proteins, a non-redundant sample of which is shown in FIG. 8C. Table 1 lists the ID (GenBank Accession number or UniProt ID), start and stop amino acid positions for domain with identity to domain 1, e-value, protein length, and organism for each hit. The same information also is provided for EBI244 (with VIMSS5326244 listed as the ID. VIMSS5326244 is electronically designated by the sequence analysis software (microbes on line) for specific open reading frames (orfs). Prior to this work, none of the identified proteins had been experimentally characterized; almost all had only electronically-inferred annotations. Annotations varied among sequences, with a good number of glycoside hydrolases; many had no annotations.

Global alignment of sequences identified by domain 1 HMM revealed that the next domain in the carboxy direction (domain 2 in EBI244) was related among all these sequences. Thus, based on the HMM multiple sequence analysis, Domain 1 appeared always to be accompanied by Domain 2.

TABLE 1

Protein sequence hits and e-values from domain 1 HMM searching.

| Protein ID | start | stop | e-value | length | Organism |
|---|---|---|---|---|---|
| A9AYF5_HERA2 | 60 | 168 | 7.52E−29 | 591 | *Herpetosiphon aurantiacus* (strain ATCC 23779/DSM 785) |
| VIMSS5326244 (EB144) | 157 | 273 | 1.56E−27 | 842 | 94C *Metagenome* |
| A4XMG8_CALS8 | 62 | 203 | 7.04E−27 | 611 | *Caldicellulosiruptor saccharolyticus* (strain ATCC 43494/DSM 8903) |
| YP_003585990.1 | 26 | 127 | 4.45E−26 | 531 | *Zunongwangia profunda* SM-A87 |
| C7PTR3_CHIPD | 56 | 153 | 3.35E−25 | 557 | *Chitinophaga pinensis* (strain ATCC 43595/DSM 2588/NCIB 11800/UQM 2034) |
| B1ZN60_OPITP | 52 | 169 | 2.46E−24 | 749 | *Opitutus terrae* (strain DSM 11246/PB90-1) |
| D1N449_9BACT | 214 | 330 | 4.36E−24 | 777 | *Victivallis vadensis* ATCC BAA-548 |
| ZP_03628444.1 | 63 | 157 | 2.32E−23 | 559 | bacterium Ellin514 |
| NP_870950.1 | 148 | 240 | 2.84E−23 | 634 | *Rhodopirellula baltica* SH 1 |
| ZP_03626656.1 | 66 | 170 | 4.66E−23 | 1596 | bacterium Ellin514 |
| ZP_01717989.1 | 53 | 140 | 1.13E−22 | 542 | *Algoriphagus* sp. PR1 |
| YP_003323724.1 | 24 | 121 | 2.17E−22 | 528 | *Thermobaculum terrenum* ATCC BAA-798 |
| A7VX72_9CLOT | 37 | 157 | 1.49E−21 | 787 | *Clostridium leptum* DSM 753 |
| YP_001297703.1 | | | 2.91E−21 | 534 | *Bacteroides vulgatus* ATCC 8482 |
| ZP_05256313.1 | | | 2.94E−21 | 534 | *Bacteroides* sp. 4_3_47FAA |
| ZP_06742086.1 | | | 2.94E−21 | 534 | *Bacteroides vulgatus* PC510 |
| NP_228758.1 | | | 3.68E−21 | 509 | *Thermotoga maritima* MSB8 |
| ZP_04540112.1 | | | 1.28E−20 | 518 | *Bacteroides* sp. 9_1_42FAA |
| ZP_03298724.1 | | | 1.30E−20 | 534 | *Bacteroides dorei* DSM 17855 |
| ZP_04555706.1 | | | 1.30E−20 | 534 | *Bacteroides* sp. D4 |
| YP_003548440.1 | 382 | 466 | 5.86E−20 | 1258 | *Coraliomargarita akajimensis* DSM 45221 |
| YP_001819159.1 | | | 1.26E−19 | 536 | *Opitutus terrae* PB90-1 |
| YP_003195709.1 | 52 | 137 | 4.31E−19 | 1160 | *Robiginitalea biformata* HTCC2501 |
| ZP_03628309.1 | 55 | 148 | 6.44E−19 | 725 | bacterium Ellin514 |
| YP_003243090.1 | | | 1.18E−18 | 481 | *Geobacillus* sp. Y412MC10 |
| YP_764889.1 | | | 2.53E−18 | 506 | |
| YP_001819827.1 | | | 3.02E−17 | 570 | |
| YP_002278657.1 | | | 3.46E−17 | 506 | |
| NP_869354.1 | 472 | 574 | 4.06E−17 | 1043 | *Rhodopirellula baltica* SH 1 |
| YP_001818722.1 | | | 4.95E−16 | 648 | *Opitutus terrae* PB90-1 |
| YP_826861.1 | | | 1.18E−15 | 604 | |
| YP_001820771.1 | 62 | 148 | 1.35E−15 | 859 | *Opitutus terrae* PB90-1 |
| YP_003547883.1 | | | 4.64E−15 | 606 | *Coraliomargarita akajimensis* DSM 45221 |
| A7HFC4_ANADF | 60 | 150 | 9.41E−15 | 566 | *Anaeromyxobacter* sp. (strain Fw109-5) |
| ZP_04488111.1 | | | 1.60E−14 | 526 | |
| YP_003387974.1 | | | 1.61E−14 | 534 | *Spirosoma linguale* DSM 74 |
| ZP_02918195.1 | | | 2.30E−14 | 529 | *Bifidobacterium dentium* ATCC 27678 |
| YP_003547687.1 | 718 | 821 | 1.10E−12 | 1853 | *Coraliomargarita akajimensis* DSM 45221 |
| YP_003011267.1 | | | 3.54E−09 | 554 | |
| YNP18_461130 | | | | 311 | Microbial community from Yellowstone Hot Springs (Washburn Springs #1) |
| BISONR_127760 | | | | 597 | Bison Hot Spring Pool, Yellowstone (11FEB08 BISONR) |
| BISONS_6715 | | | | 777 | Bison Hot Spring Pool, Yellowstone (14JAN08 BISONS) |

Domain 2 represents the largest predicted domain of EBI244, and is the region having similarity to the known glycosyl-hydrolase family 5 (GH5) domain family glycosyl hydrolases, evidencing the protein's cellulase or similar sugar hydrolase activity. The sequence of the GH5 domain was determined to be highly divergent (Pfam server analysis; e-value=1e-12) compared to previously characterized GH5 proteins. FIG. 8D shows a number of highly conserved residues across all sequences in the domain 2 region, including the two predicted catalytic residues of EBI244 (highlighted in yellow; glutamates 413 and 506).

Figure 9:
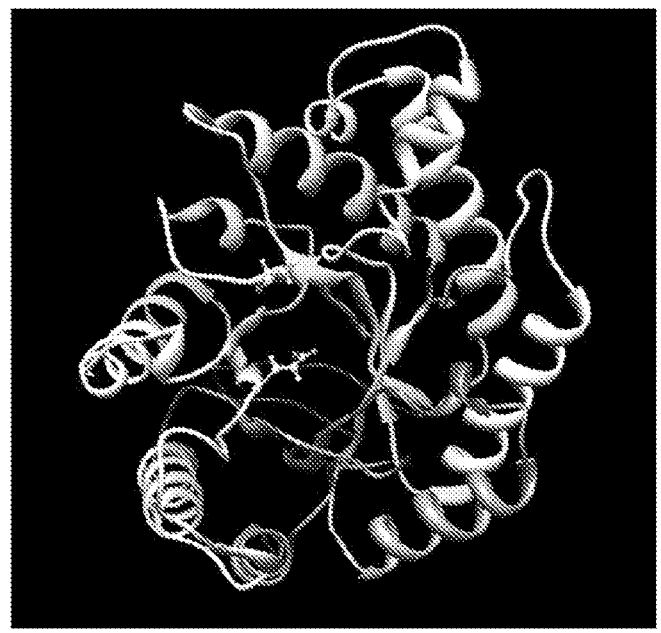
FIG. 9 shows a homology structural model of EBI244 domain 2, constructed by the I-TASSER server, built from multiple GH5 domain structures in the PDB database, showing the common TIM-barrel architecture with 8 beta sheets inside 8 alpha-helices.
Figure 10:
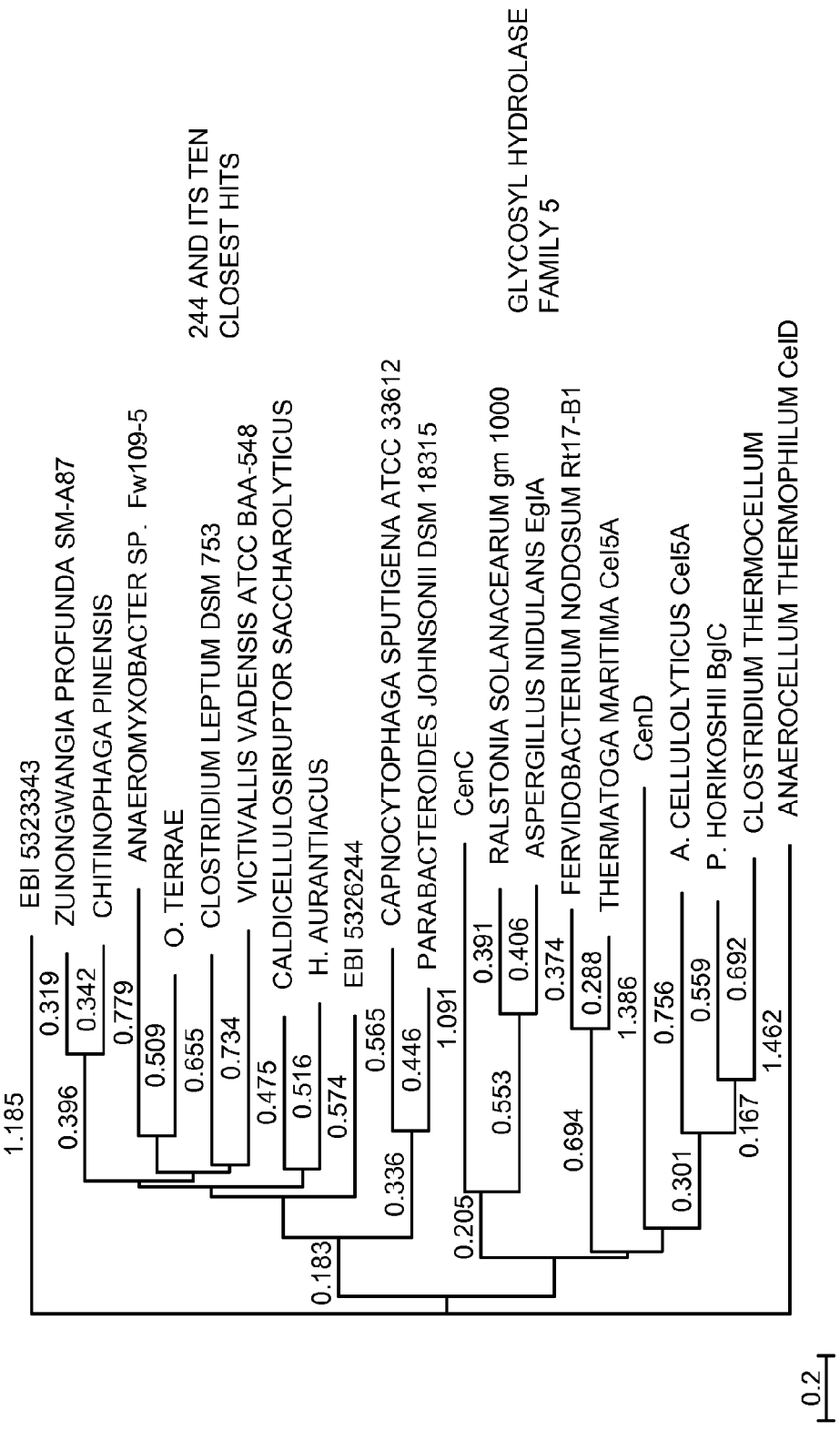
FIG. 10 shows schematically a relationship of the glycolytic domain of EBI244 to known glycosyl hydrolase family 5 proteins.

Despite low sequence identity in this region across all sequences, the conservation of key residues, including the predicted catalytic residues glutamate 413 and glutamate 506, suggests a similar fold in this region. Other structural predictions revealed that the protein is a member of the glycosidase superfamily, within the TIM-barrel fold (InterProScan; e-values~1e-27; see FIG. 9). FIG. 10 shows a schematic representation of the relationship of domain 2 of EBI244 to other glycosylhydrolases in this superfamily. Many of the known glycoside hydrolase families are within the TIM-barrel fold (the CAZY database shows at least 18), which includes GH5 (see Illustration 5). HMM analysis/searching carried out for domain 2 of EBI244 identified a very large number of significant hits.

Table 2 lists the ID (GenBank Accession number, UniProt ID), e-value, protein length, and organism for each hit, with the same information provided for EBI244 (listing VIMSS5326244 as the ID). As shown in Tables 1 and 2, many of the top hits (eight top hits) were the same protein sequences identified as top hits in the domain 1 searching. However, beyond those first eight, most of the hits were not identified in other domain searches indicating that they do not have very similar domains outside of domain 2.

Even though the sequence identity is very low in this region across all sequences, the high conservation of a number of residues, especially the predicted catalytic residues of EBI244, indicates that all of these sequences have the possibility of a similar fold in this region. The observation that the domain 1 region did not appear to be present in any protein not having this similar domain 2 region indicates that the function of the domain 1 region may be dependent on or affect the function of the domain 2 region.

TABLE 2

Protein sequence hits and E-values from domain 2 HMM searching.

| Protein ID | e-val | length |
| --- | --- | --- |
| VIMSS5326244 (EBI244) | 7.01E−143 | 842 |
| A4XMG8_CALS8 | 1.93E−134 | 611 |
| A9AYF5_HERA2 | 3.55E−125 | 591 |
| B1ZN60_OPITP | 2.46E−123 | 749 |
| A7VX72_9CLOT | 2.26E−118 | 787 |
| B7BGD2_9PORP | 1.02E−116 | 470 |
| D1N449_9BACT | 1.39E−110 | 777 |
| C7PTR3_CHIPD | 3.82E−69 | 557 |
| YP_003585990.1 | 1.01E−61 | 531 |
| ZP_04378853.1 | 1.14E−56 | 446 |
| C7M3Y3_CAPOD | 1.16E−56 | 470 |
| ZP_03390557.1 | 6.80E−54 | 466 |
| A7HFC4_ANADF | 9.39E−46 | 566 |
| B0UPR0_METS4 | 3.32E−32 | 504 |
| B9RN03_RICCO | 1.67E−28 | 404 |
| C6T835_SOYBN | 2.75E−28 | 418 |
| XP_002264115.1 | 2.44E−25 | 433 |
| C7A7X8_MALDO | 2.58E−25 | 429 |
| VIMSS9423033 | 9.82E−25 | 431 |
| MAN7_ARATH | 9.86E−25 | 431 |
| XP_002281804.1 | 1.92E−24 | 433 |
| C7A7X6_9ERIC | 2.98E−24 | 433 |
| B2BMP9_PRUPE | 3.27E−24 | 431 |
| B9H4D6_POPTR | 4.59E−24 | 420 |
| XP_002272344.1 | 4.61E−24 | 402 |
| C7A7X7_MALDO | 4.84E−24 | 428 |
| Q9FT03_COFAR | 5.55E−24 | 416 |
| Q9P893_AGABI | 5.91E−24 | 439 |
| B9GRV2_POPTR | 7.04E−24 | 415 |
| C6TAY0_SOYBN | 7.20E−24 | 431 |
| XP_002270023.1 | 1.72E−23 | 403 |
| B9R7X5_RICCO | 1.90E−23 | 432 |
| VIMSS9886800 | 2.25E−23 | 379 |

TABLE 2-continued

Protein sequence hits and E-values from domain 2 HMM searching.

| Protein ID | e-val | length |
| --- | --- | --- |
| B2BMQ0_PRUPE | 2.91E−23 | 433 |
| Q2I011_HORVD | 2.92E−23 | 380 |
| B0FPH4_9ROSA | 3.26E−23 | 433 |
| Q0ZR47_THEHA | 3.56E−23 | 431 |

HMM searching on Domain 3 revealed only one significant hit (B1zn60_OPITP), which was also a hit in searching the other three domains. This hit appears co-linear with EBI244 except for the threonine rich N-terminus. Secondary structure predictions show mostly beta-sheets. Table 3 lists the ID (GenBank Accession number or UniProt ID) for each hit. The same information also is provided for EBI244 (with VIMSS5326244 listed as the ID). The start and stop positions of domain 3 in EB244 also are listed. 03379646.1 was unlikely a true domain hit because of low sequence identity

TABLE 3

Protein sequence hits from domain 3 HMM searching.

| Domain 3 | start | stop |
| --- | --- | --- |
| VIMSS5326244 | 605 | 734 |
| B1ZN60_OPITP | | |
| YP_003379646.1 | | |

Domain 4 is the C-terminal domain of EBI244. HMM search analysis of Domain 4 returned seven significant hit. As shown in FIG. 8E, all seven of these sequences aligned globally with EBI244, except over the domain 3 and T/P rich regions. This result indicates that Domain 4 is related in some way to domains 1 and 2. Given that only one other sequence aligned in the domain 3 region, domain 3 may have been added to EBI244 at some point in evolution or it was removed from an ancestor to the other proteins. Each of these seven sequences were top hits in the domain 2 searching; 6 of them showed up in the hits of domain 1 searching, providing further evidence of the link between domain 4 and the rest of the protein. Many of the domain 1 hits do not have a related region to domain 4.

Table 4 lists the ID (GenBank Accession number or UniProt ID), start and stop amino acid positions for domain with identity to domain 4, e-value, and organism for each hit. The same information also is provided for EBI244 (with VIMSS5326244 listed as the ID).

TABLE 4

Protein sequence hits and E-values from domain 4 HMM searching.

| Domain 4 | start | stop | e-val | length | |
| --- | --- | --- | --- | --- | --- |
| A4XMG8_CALS8 | 534/557 | 604 | 5.64E−23 | 611 | *Caldicellulosiruptor saccharolyticus* (strain ATCC 43494/DSM 8903) |
| VIMSS5326244 | 759/785 | 838 | 1.87E−21 | 842 | 94C *Metagenome* |
| A7VX72_9CLOT | 519/544 | 597 | 4.65E−20 | 787 | *Clostridium leptum* DSM 753 |
| B1ZN60_OPITP | 667/692 | 745 | 1.68E−18 | 749 | *Opitutus terrae* (strain DSM 11246/PB90-1) |
| B0UPR0_METS4 | 423/447 | 501 | 1.10E−16 | 504 | *Methylobacterium* sp. (strain 4-46) |
| D1N449_9BACT | 698/718 | 771 | 4.54E−16 | 777 | *Victivallis vadensis* ATCC BAA-548 |
| A7HFC4_ANADF | 493/510 | 562 | 1.59E−15 | 566 | *Anaeromyxobacter* sp. (strain Fw109-5) |
| A9AYF5_HERA2 | 537 | 588 | 1.46E−14 | 591 | *Herpetosiphon aurantiacus* (strain ATCC 23779/DSM 785) |

In summary, no highly similar BLAST hits resulted during searches with EBI244, implying that no known and sequenced Archaea or other hyperthermophiles in the NCBI non-redundant protein database have cellulase-encoding genes with the same domain structure as this enzyme. This enzyme occupies a highly divergent sequence space with less than 30% identity to the catalytic domain of the nearest characterized endoglucanase. Consideration of the weak homologs identified established that none are biochemically characterized, and the conserved glycosyl hydrolase family 5 catalytic domains of the hyperthermophilic cellulase is extremely divergent from characterized proteins of the family, with its nearest blast hits separated from known members of this family. Thus, this enzyme may represent the first characterized member of a highly divergent branch of the glycosyl hydrolase family 5 catalytic motif, or alternatively should be classified as the prototype a new glycosyl hydrolase family.

Thus, the EBI244 cellulase appears to represent a highly unusual type of glycosidase, based on structural alignments and sequence-based homolog searches. For example, the enzyme contains a highly divergent core catalytic domain and unusual domains flanking the catalytic domain. The few distant homologs of EBI244 in the public databases are distributed in organisms that occupy a broad swath of habitats, from rice paddies to mammalian intestines.

Example 4

Expression and Analysis of Synthetic Protein

An ebi244 protein-coding region, having the nucleic acid sequence set forth in SEQ ID NO: 2 (original sequence with hyperthermophilic codon usage) was synthesized de novo by GenScript, ltd (Piscataway, N.J.). A second version of the coding region, which was codon-optimized for expression in E. coli (SEQ ID NO: 3) also was synthesized by DNA 2.0 (Menlo Park, Calif.).

Protein Expression and Purification

The 94 kDa protein was expressed by autoinduction in E. coli and purified. Expression of the recombinant EBI244 protein in E. coli was carried out by the auto-induction (Studier, F W, Protein Expres. Purif. 41, 207-234, 2005).

Using this method, EBI244 was successfully expressed in two E. coli strains, BL21 (de3) and Rosetta cells (Invitrogen, Carlsbad, Calif.), as an N-terminally His tagged protein, from the plasmid pET16b, in shaking flasks or in a 17.5 L fermenter. For expression, each strain was transformed with plasmid and plated on YT media supplemented with 0.8% glucose at 35° C. The pET16b N-terminal His-tagged gene appeared to be toxic, producing variable colony size. Only smaller colonies picked from freshly transformed plates resulted in significant expression. These were picked into a small volume of ZYP-0.8G media, 5 mL-50 mL and incubated at 25° C. until cells reached an optical density at 550 nm of ~0.4. Then about 2.5 mL was inoculated per liter of ZYP-5052 rich media for auto-induction.

Cells were then incubated with shaking at 20° C. or 25° C. for 48 hours or 36 hours respectively. Expression was optimized in 1 liter shake flask cultures, and subsequently scaled up to 17.5 L in a specialized New Brunswick Bioflow IV fermentor. Cells were grown to an OD 55 0 nm of approximately 2.5-3.0 then harvested by centrifugation at 6,000×g. Expression in the fermentor yielded 3-5 times higher levels of cellulose activity as compared with shake flasks. Cells were lysed by French Pressure Cell in 50 mM Na phosphate buffer or 50 mM HEPPS buffer and incubated for 30 min at 90° C. Denatured host proteins were removed by centrifugation at 8,000×g for 15 minutes followed by 100,000×g for 30 minutes and the cleared supernatant, representing a partially purified soluble fraction was used for immediate and downstream assays or purification Expression levels were low (50 micrograms per g cells) but the protein was readily obtained in soluble form after heating whole cell extracts to 90° C.

C-terminal poly his-tagged codon optimized gene is expressed by a similar process, using well-known methods and plasmids. Recombinant protein was purified as follows: Clarified supernatants were fractionated by ammonium sulfate precipitation. The initial supernatant was brought to 20% saturating ammonium sulfate, centrifuged at 10,000×g, and decanted. The supernatant was then brought to 40% saturating ammonium sulfate and centrifuged at 10,000×g. The pellet fraction was resuspended in 50 mM phosphate buffer. The buffer was exchanged twice on a PES membrane centrifugal concentrator (Sartorius). Ammonium sulfate was added to a concentration of 500 mM (sans potassium chloride and the protein was loaded on a hi-trap butyl-hydrophobic interaction column (GE Healthcare, Piscataway, N.J.) and eluted with a linear gradient from 1M KCl to 0M KCl in 50 mM phosphate pH 7.0. The most active fractions were then pooled, buffer exchanged in 50 mM borate (pH 9.5) and loaded on a Q sepharose fast flow column (GE Healthcare, Piscataway, N.J.) and eluted with a potassium chloride gradient from 0M to 500 mM.

Additionally, an ebi244 gene construct was generated by replacing the native signal peptide sequence of ebi244 with the ompA signal peptide sequence from E. coli. The construct was generated by two rounds of amplification by PCR with primers that collectively reconstruct the signal peptide sequence from ompA in place of the native signal peptide sequence. The construct was subcloned into pet16b and expressed in E. coli Rosetta cells by standard IPTG induction at 25° C. or autoinduction at 25° C. The replacement of the archaeal signal peptide with the ompA signal peptide resulted in increased expression of the new construct ebi 244-OA in E. coli as compared to the unmodified sequence ebi 244.

The nucleotide sequence ebi 244-OA is set forth as SEQ ID NO: 15. The amino acid sequence of the EBI244 encoded by ebi 244-OA is set forth as SEQ ID NO: 16.

The results of a comparison of the expression levels of EBI244 and EBI244-OA expression when induced with IPTG is shown in Table 5. Expression via auto-induction resulted in a 5-fold increase in the expression of EBI244-OA as compared to EBI244.

Expression Results:

TABLE 5

| EBI244-OA Expression | | |
| --- | --- | --- |
| Method (25° C.) | EBI244 | EBI244-OA |
| IPTG | N.D. | 18 µg/g cell pellet* |
| Auto-induction | 20 µg/g cell pellet | 100 µg/g cell pellet* |

Analysis of Purified Protein

Activity of the recombinant protein was analyzed by a number of methods, as follows.

Zymograms

Zymograms were performed as described above, with gels made as standard 8% SDS-PAGE gels, with 0.25% medium viscosity carboxymethyl cellulose incorporated into the gel. In the case of gradient gels the gels were 10% to 15% acrylamide and contained 0.20% CMC. Standard SDS-PAGE protocols were used, with standard loading buffer, with the exception that samples were kept at 20° C. and were not boiled prior to loading. Gels were gently agitated for 30 minutes in 50 mM tris buffer pH 6.8 with 2% triton X-100, and then for 30 minutes in 50 mM tris buffer, pH 6.8, to reactivate cellulases. Gels were then incubated in 50 mM potassium phosphate, pH 6.8, or 50 mM HEPPS buffer, pH 6.8, for 3 hours at 90° C. After incubation, the gels were cooled to 20° C. and stained with 0.5% Congo Red (sodium salt of benzidinediazo-bis-1-naphthylamine-4-sulfonic acid (formula: $C_{32}H_{22}N_6Na_2O_6S_2$; molecular weight: 696.66 g/mol), for 40 minutes, then destained with 1M Tris Buffer, pH 6.8, for approximately 15 minutes. The dye then was set in 1M $MgCl_2$.

Reducing Sugar Assays

Reducing sugar assays were performed to detect the presence of reducing sugars. Dinitrosalicylic acid (DNS) reagent was made according to International Union of Pure and Applied Chemistry (IUPAC) guidelines. Results were calibrated to standard solutions of calaboose. Assays on CMC (carboxymethyl cellulose), Avicel®, ionic liquid pretreated Avicel® and Whatman® #1 filter paper were carried out in 50 mM potassium phosphate pH 6.8 or 50 mM sodium acetate pH 5.0. Assays with high concentrations of salts or ionic liquids were carried out in Phosphate buffer. To compare activity at various pH levels, the following buffers were used 50 mM sodium acetate/acetic acid pH 3.5, 4, 4.5, 5, 5.6; 50 mM sodium phosphate buffer: pH 6, 6.5; 50 mM MOPS: pH 7, 7.5; 50 mM EPPS: pH 6.8, 8, 8.5, 9; 50 mM CAPS: pH 9.5-11.1. Assays were generally conducted in 100 μL of buffer, in dome-capped PCR tubes, for a temperature of less than 99° C., incubated in a bio-rad mycycler thermocycler with heated lid. Screw cap 1.5 mL polypropylene tubes in a silicone oil bath were used for temperature range from 99-114° C. Alternatively, assays from 100-130° C. were conducted in 10 ml sealed serum stoppered Hungate tubes overpressured with 30 psi of $N_2$ then incubated in a Binder oven. In the case of the Hungate tubes, controls were removed from the oven at the calculated time of temperature equilibration (equilibration times were calculated using standard equations for unsteady-state heat conduction, see for example, J. R. Welty, C. E. Wicks, and R. E. Wilson, *Fundamentals of Momentum, Heat, and Mass Transfer*, 3rd Edition, John Wiley & Sons, 1984, pp. 297-304) and stopped with the addition of an equal volume of cold 0.1 M sodium hydroxide.

Assays on alternative substrates described in Table 6 were done as follows: Pretreated substrates were treated as preciously described (Kim, T et al., Biotechnol. Bioeng, 2010). All cellulolytic assays for insoluble substrates were carried out in quadruplicate in a final volume of 70 μL containing 1%(w/v) substrate (glucan loading), 0.2 μM of the EBI244 and 100 mM sodium acetate buffer, pH 5.5 at 90° C. in a thermal cycler (Applied Biosystems). Cellulase activities were measured for Avicel®, Lichenan, AFEX pretreated corn stover, ionic-liquid pretreated Avicel® (IL-Avicel®), *Miscanthus* (IL-*Miscanthus*), and corn stover (IL-corn stover). The mixtures were incubated at 90° C. for 15 h after which they were cooled to 4° C. prior to measuring the amount of soluble reducing sugar released using the glucose oxidase-peroxidase assay as previously described (Kim, T et al., Biotechnol. Bioeng, 2010).

Paranitrophenol-labeled Glycosides

The chromogenic substrate 4-nitrophenyl-beta-D-glucopyranoside was utilized at 2.5 mM in sodium acetate buffer pH 5.0. Alternatively the chromogenic substrate 4-nitrophenyl-beta-D-cellobioside was utilized as a substrate in 100 mM sodium acetate buffer. Sodium acetate buffer containing 4-nitrophenol was used as a standard and reagent blank during assays at 95° C. Absorbance was measured at 410 nm. To compare activity at various pH levels, the following buffers were used at a buffer strength of 50 mM: pH 2.5-5.5 acetate/acetic acid, pH 6.5 MES, pH 7.5-8.5 HEPPS, pH 9.5-10.5 CAPS. All assays on PNP-substrates and standards were adjusted with an equal volume of 100 mM sodium hydroxide before recording the absorbance at 410 nm.

Dionex Product Analysis

For Dionex product analysis, assay conditions were the same as those utilized for the DNS assay. Reactions were stopped with the addition of an equal volume of 0.1 M sodium hydroxide.

Cellulose Binding Assay

Cellulose binding assays were carried out as follows. Soluble extract was adjusted to 50 mL in 25 mM HEPPS buffer pH 6.8 with 1 g of Avicel®, then incubated at 80° C. for 30 minutes with shaking. The suspension was centrifuged at 8,000×g, the supernatant removed and the Avicel® resuspended in 5 mL of HEPPS buffer with 0.6% CHAPS detergent added. The suspension was centrifuged at 8,000×g, the supernatant removed, and the Avicel® resuspended in 5 mL 0.6% CHAPS buffer, heated to 80° C., for 15 min with shaking. The suspension was centrifuged at 8,000×g, the supernatant removed, and the Avicel® re-suspended in 5 ml of 2.0% CHAPS at 25° C. and shaken. The suspension then was centrifuged at 8,000×g, the supernatant removed and the Avicel® re-suspended in 5 mL of 2% CHAPS and incubated at 80° C. for 15 minutes. The suspension was centrifuged at 8,000×g, the supernatant removed, and the Avicel® re-suspended in 5 mL of 2% CHAPS and incubated at 90° C. for 30 minutes. The suspension was centrifuged at 8,000×g and the supernatant removed.

Endoglucanase Activity of Recombinant EBI244 on a Wide Range of High Molecular Weight Carbohydrate Substrates Containing β1-4 Linked Glucose.

Figure 11:
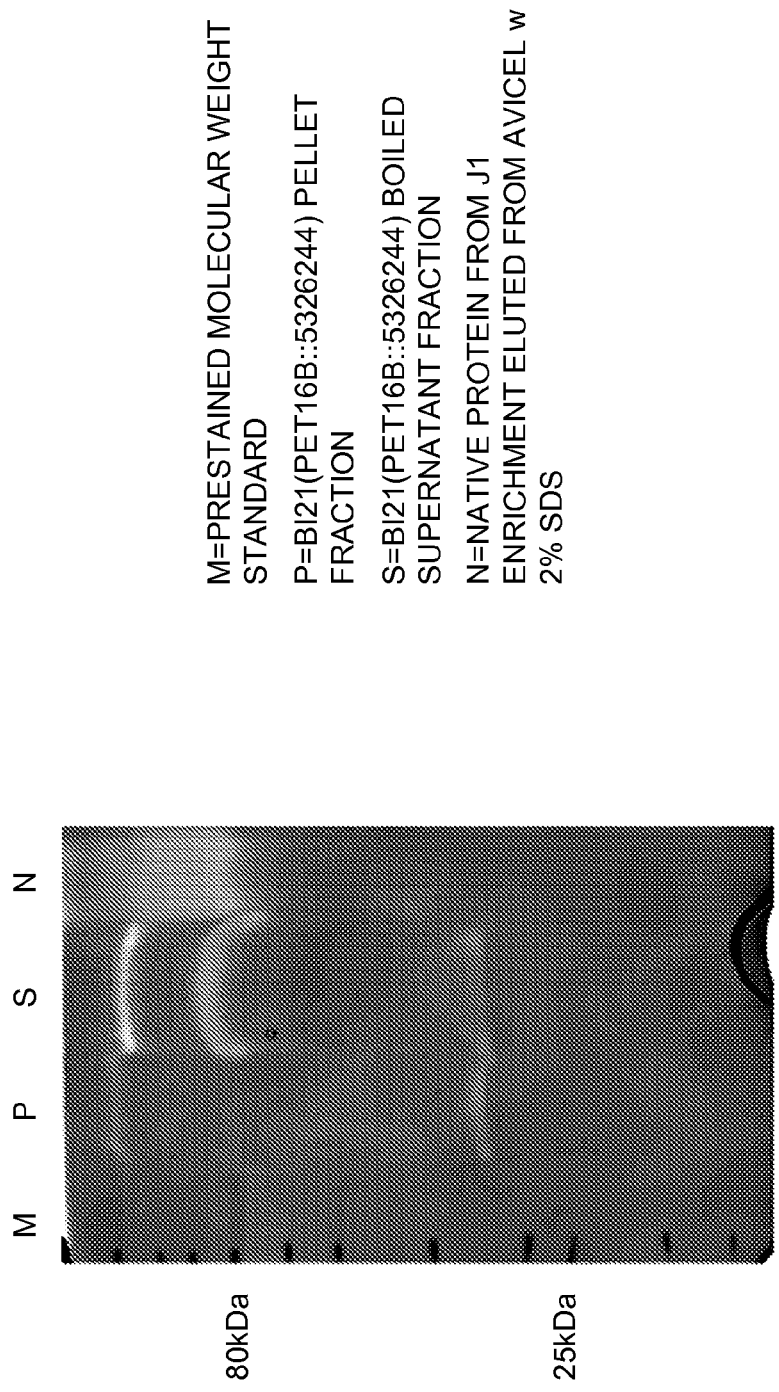
FIG. 11 shows zymogram activity of recombinant protein fractions, compared to native protein fraction. M=prestained molecular weight standard; P=B121 (pet16b:5326244 (His-tagged EBI244 protein)), pellet fraction; S=B121 (pet16b: 5326244 (His-tagged EBI244 protein)), boiled fraction; N=native protein from J1 enrichment eluted from Avicel® with 2% SDS. Cleared areas (white) represent activity, while dark areas represent intact carboxymethylcellulose. Recombinant protein fractions (P and S) were insoluble or soluble portions of the E. coli extract. Native fraction was eluted from Avicel® with boiling SDS. The lower band represents an internal control, E. coli endoglucanase.

Zymograms performed on recombinantly expressed EBI244 proteins revealed endoglucanase activity of recombinant EBI244, both with and without a refolding step. As shown in FIG. 11, the behavior of the protein on zymogram gels was similar to that observed for active endoglucanase fractions from the archaeal enrichment. The enzyme was active on carboxymethyl cellulose in liquid assays as well.

Figure 12:
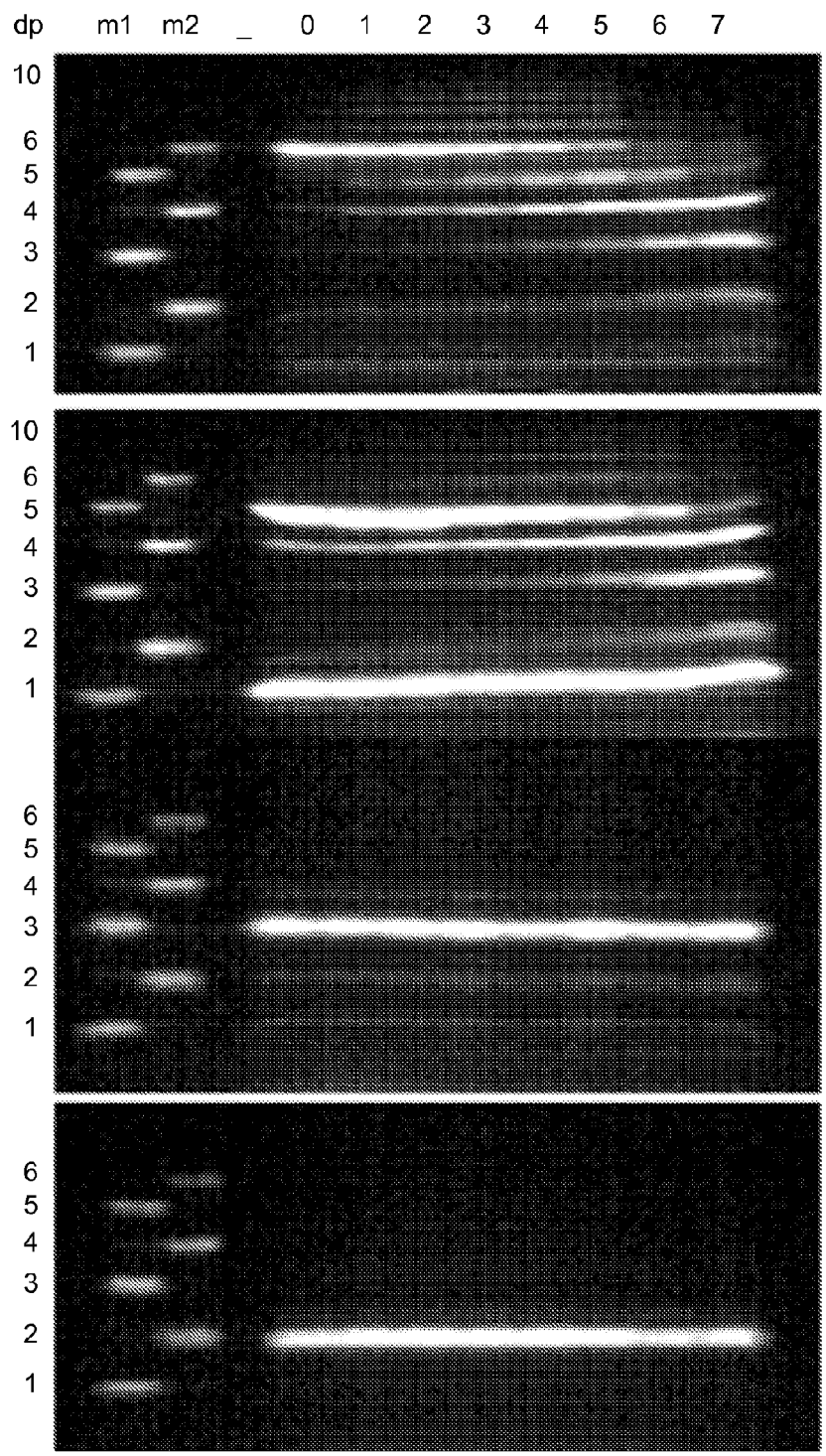
FIG. 12 shows the Fluorophore Assisted Carbohydrate Electropheresis (FACE) results of time course of EBI244 on cellohexaose. Reaction condition was 10 µg enzyme, 0.33 mM cellohexaose in 25 mM HEPPS ph 6.8, 95° C. in 100 µL volume. The experiment tracked degree of polymerization (dp) over time.

The enzyme also showed activity on a range of high molecular weight carbohydrate substrates that contained β1-4 linked glucose (Table 6). Product analysis by fluorophore-assisted carbohydrate electrophoresis (FACE) revealed release of oligomers from Avicel® (FIG. 12). Purified EBI244 was supplied with various cellulose oligomers at 95° C. and the reaction was monitored over two hours. The reactions show the conversion of higher order oligomers into mixtures of cellobiose, cellotriose and cellotetraose. The reactions show a dramatic pattern of trans-glycosylation resulting in transient formation of oligomers up to dp (degree of polymerization) of eleven when starting with cellohexaose (FIG. 12A). The transglycosylation activity was not greatly enhanced by the presence of glucose (FIG. 12B) and the enzyme showed no significant activity on cellotriose or cellobiose (FIGS. 12C and 12D).

TABLE 6

The specific activity of EBI 244 endoglucanase on different substrates.

| Substrate | Activity | Error (%) |
|---|---|---|
| pNP-cellobioside | 178[a] | 1 |
| CMC | 138[a] | 5 |
| Barley Glucan | 518[a] | 7 |
| Lichenan | 6296[b] | 5 |
| Avicel | 1241[b] | 3 |
| IL-Avicel | 8261[b] | 2 |
| IL-Miscanthus | 1002[b] | 4 |
| IL-Cornstover | 1318[b] | 2 |
| AFEX Cornstover | 89[b] | 5 |
| Xylan | NA | — |
| Mannan | NA | — |

In Table 6 above, "a" represents μmol GE/μmol Enzyme/min, "b" represents μmol GE/μmol Enzyme/15 hr, and "GE" represents glucose equivalents. Substrates pretreated with Ionic Liquid (IL) and Ammonia Fiber Expansion (AFEX) are indicated. "NA" indicates no measurable activity.

Truncated versions of the EBI244 protein were analyzed for activity on PNP-cellobiose, CMC, and Avicel® to determine potential functions for each domain. A truncation variant (EBI244 Δ1-127 V128M-hereafter EBI244ΔN) lacking the Thr/Pro rich region, maintained similar activity as the full length version on the PNP-cellbioside and CMC (data not shown). This result is expected because the threonine/proline rich region is predicted to be a highly flexible low complexity region. Domains 3 and 4 do not align to experimentally characterized domains, thus it is possible that these domains act as a cellulose binding domain (CBD) or function is protein-protein interactions. Truncations removing both domains 3 and 4, or just domain 4 alone, were constructed and expressed at higher levels than the full length protein, but were inactive against all substrates. This result indicates that domain 3, and possibly 4 as well, is required for the enzyme to remain active, possibly due to a stabilizing effect on the enzyme. Treatment of the recombinant enzyme with proteinase K at 50° C. for 30 minutes, resulted in a uniform N-terminal truncation to threonine-121, determined by N-terminal Edman degradation. The proteinase treated enzyme showed similar mobility and activity to the EBI244ΔN variant, suggesting that the remainder of the protein forms an integrated structure that is inaccessible to proteinase K at 50° C.

Amenability of the Enzyme to Ammonium Sulfate Fractionation and Purification

Figure 13:
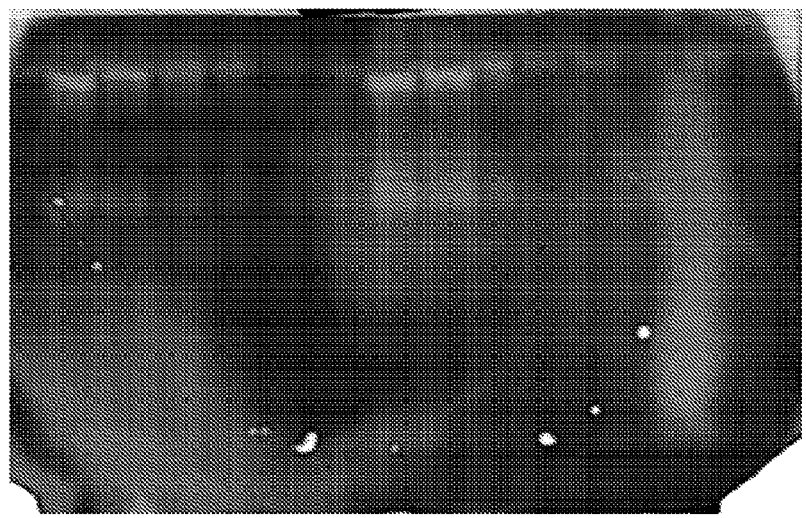
FIG. 13 shows results of a zymogram assay, showing EBI244 activity distributed among 20-40% saturating ammonium sulfate fractions. Each fraction is represented by three lanes: undiluted (1.0), dilution 2 in 5 (0.4), and dilution 1 in 5 (0.2). Initial sample was soluble recombinant protein after pretreatment at 80 C for 30 minutes. Protein was precipitated using 20, 40, 60, and 90% saturating ammonium sulfate.
Figure 14:
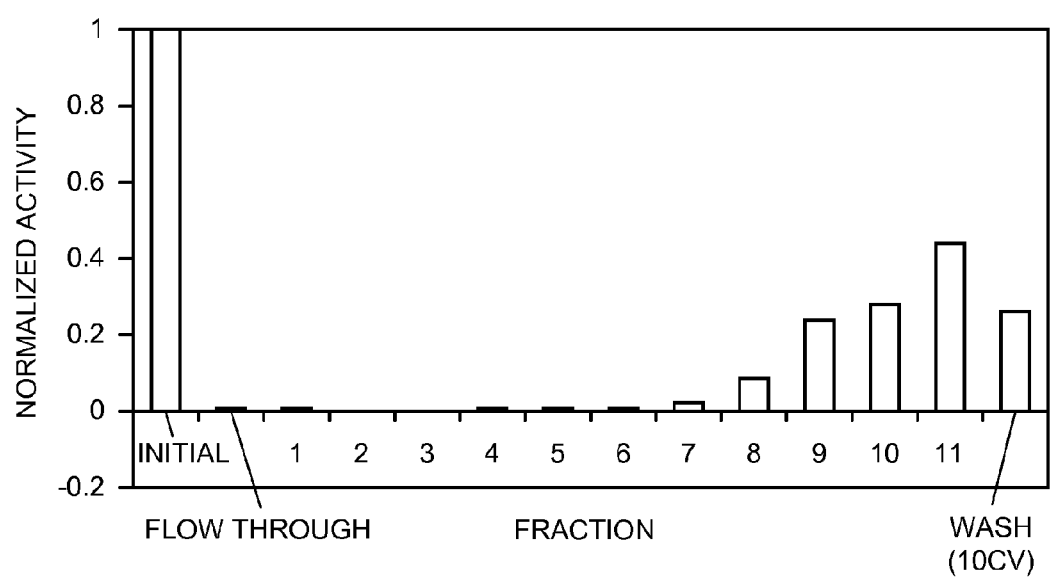
FIG. 14 shows a graph of endoglucanase activity, measured by DNS assay, with 1% low-viscosity carboxymethylcellulose as the substrate. Fractions 1-11 represent a linear gradient from 1 M to 0 M ammonium sulfate in potassium phosphate buffer, pH 7.0.

The EBI244 enzyme also proved amenable to ammonium sulfate fractionation (see FIG. 13, showing results of a zymogram assay showing activity distributed among the 20-40% saturating ammonium sulfate fractions, each represented by three lanes (undiluted (1.0), dilution 2 in 5 (0.4), and 1 in 5 (0.2); initial sample was soluble recombinant protein after pretreatment at 80° C. for 30 minutes; protein was precipitated using 20, 40, 60, and 90% saturating ammonium sulfate), hydrophobic interaction chromatography (see FIG. 14, showing results of a DNS assay using 1% low-viscosity carboxymethylcellulose as the substrate, with fractions 1-11 representing a linear gradient from 1 M to 0 M ammonium sulfate in potassium phosphate buffer, pH 7), and anion exchange chromatography.

Figure 15:
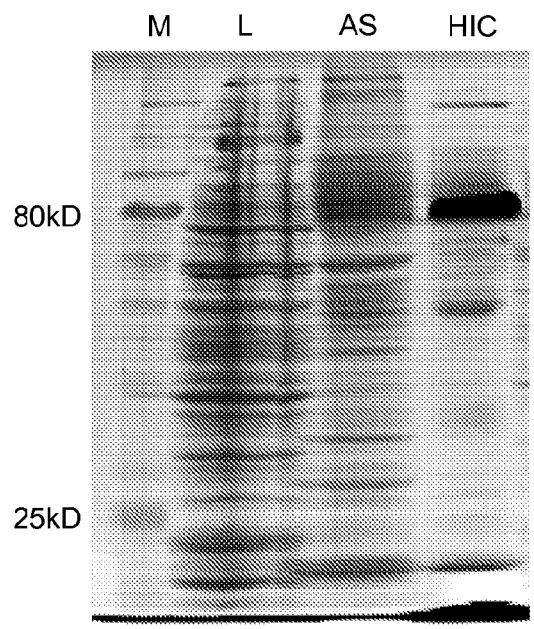
FIG. 15 shows a picture of a comassie-stained SDS-PAGE gel, demonstrating stepwise purification of EBI244 to ~60% purity. M=marker; L=whole cell lysate; AS=20-40% ammonium sulfate fraction; HIC=pooled active fraction, purified using Macro-Prep t-butyl hydrophobic interaction chromatography (HIC) support (methacrylate-based, 50 µm beads) (butyl HIC). The sample was heated to 80° C. prior to ammonium sulfate fractionation.

The N-terminal histidine tagged enzyme, however, did not interact with a nickel or cobalt affinity column, presumably because the threonine rich N-terminal region occluded the tag. FIG. 15 shows a comassie stained SDS-PAGE gel demonstrating stepwise purification to 60% purity, with the sample heated prior to ammonium sulfate fractionation. While this figure shows EBI244 that is approximately 60% pure, purities over 95% have been obtained.

Thermostability

Figure 16:
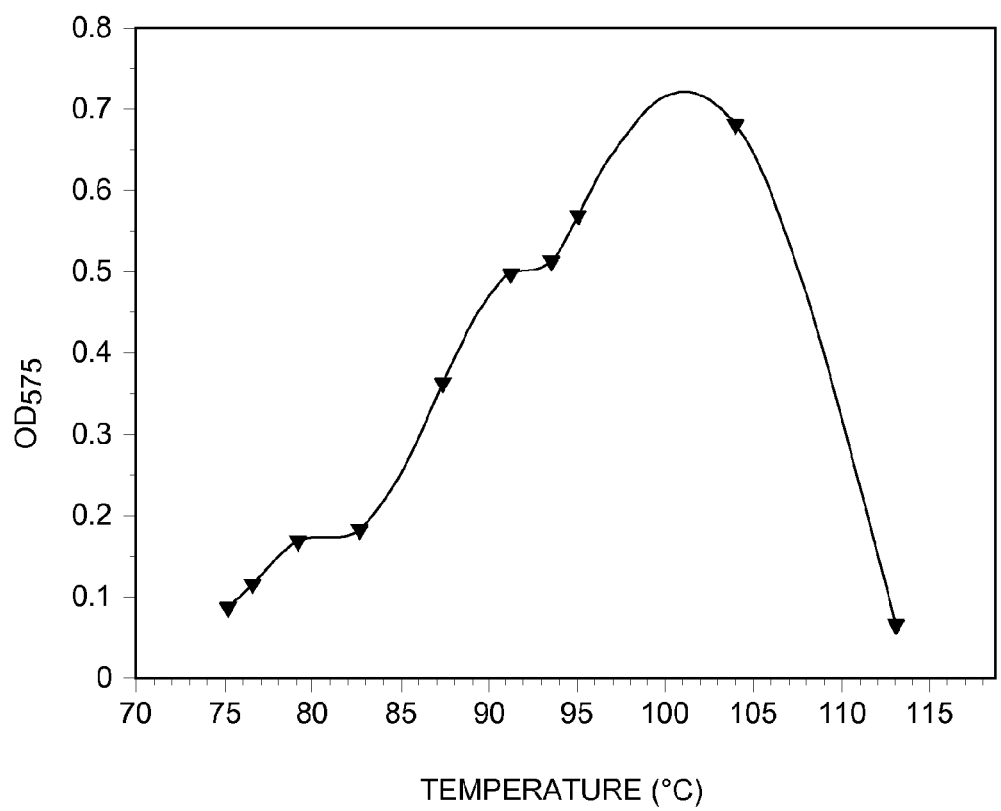
FIG. 16 shows an activity-temperature profile of EBI244 on 1% CMC (carboxymethyl cellulose) (DNS assay).
Figure 17:
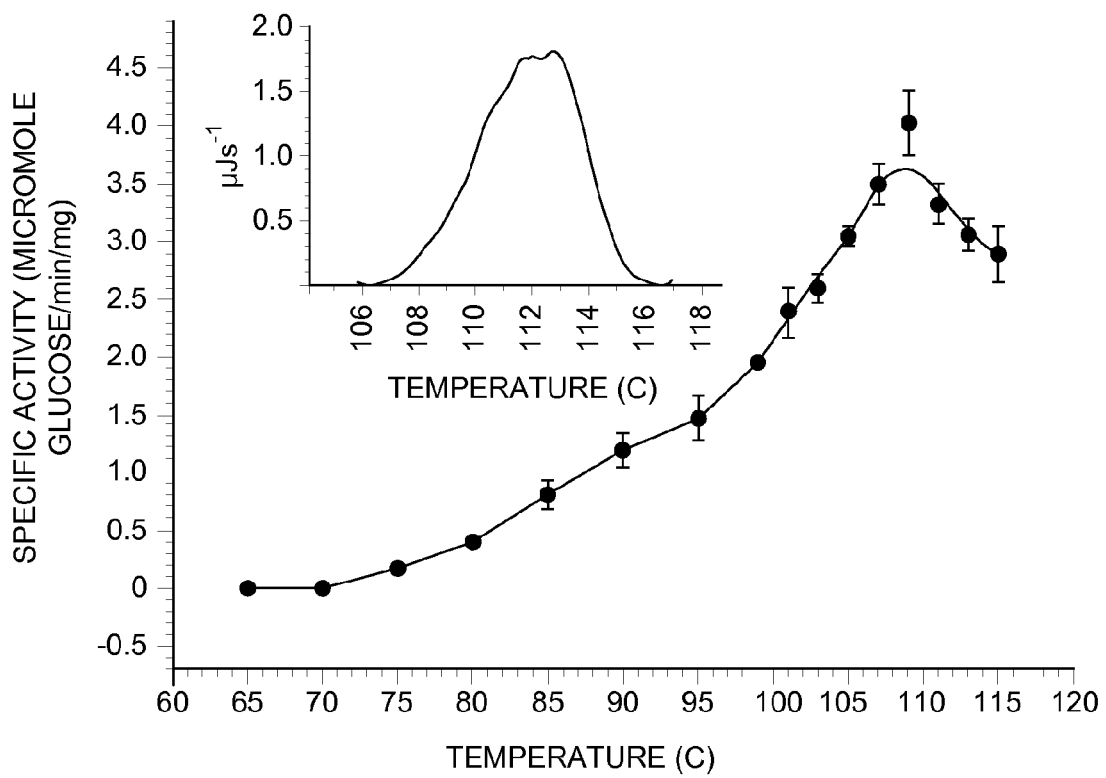
FIG. 17 shows the temperature profile of EBI244. The temperature vs. activity profile was measured by 20-min assay in 1% CMC in 25 mM sodium acetate buffer, pH 6.0. The products were detected by DNS reducing sugar assay and normalized to a cellobiose standard. Error for this experiment was below 15%. Inset: Differential scanning calorimetry results of enzyme from 102-116° C. A dual Tm was observed at 111.5° C. and 113° C.

When assayed on 1% CMC (carboxymethyl cellulose) (DNS assay), 50 mM HEPPS buffer, the enzyme demonstrated almost no activity at 75° C., 50% maximal activity at ~92° C., and maximal activity at about 109° C. The results are shown in FIGS. 16 and 17, showing activity-temperature profiles of EBI244 on 1% CMC.

Figure 18:
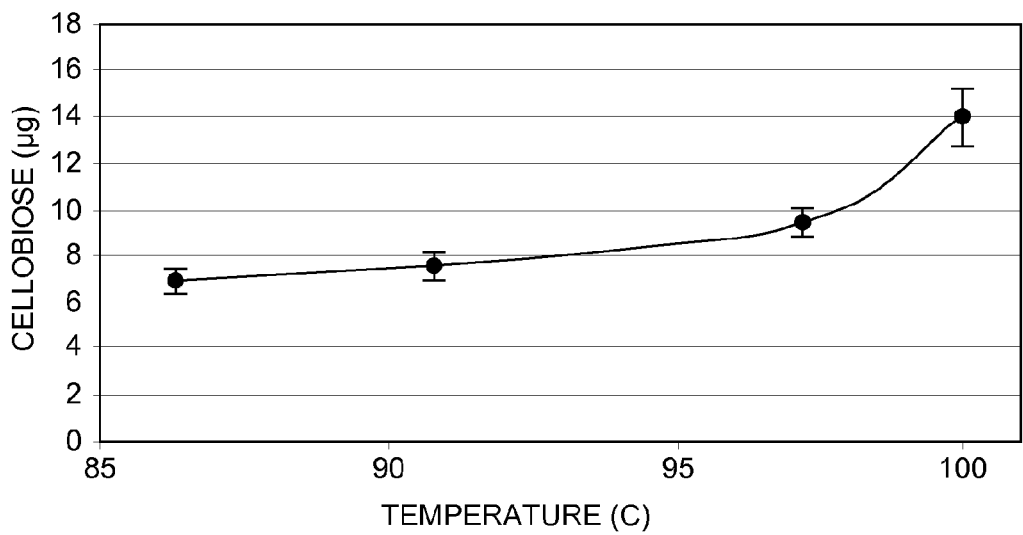
FIG. 18 shows results of a DNS assay using Whatman® #1 filter paper in 10 mM Sodium Acetate pH 5.0 curve, demonstrating enzyme activity on filter paper over a range of temperatures.

The temperature profile of the enzyme on Whatman® #1 paper showed a similar trend, with overall activity decreasing with the increasing crystalline nature of the substrate (FIG. 18).

Figure 19:
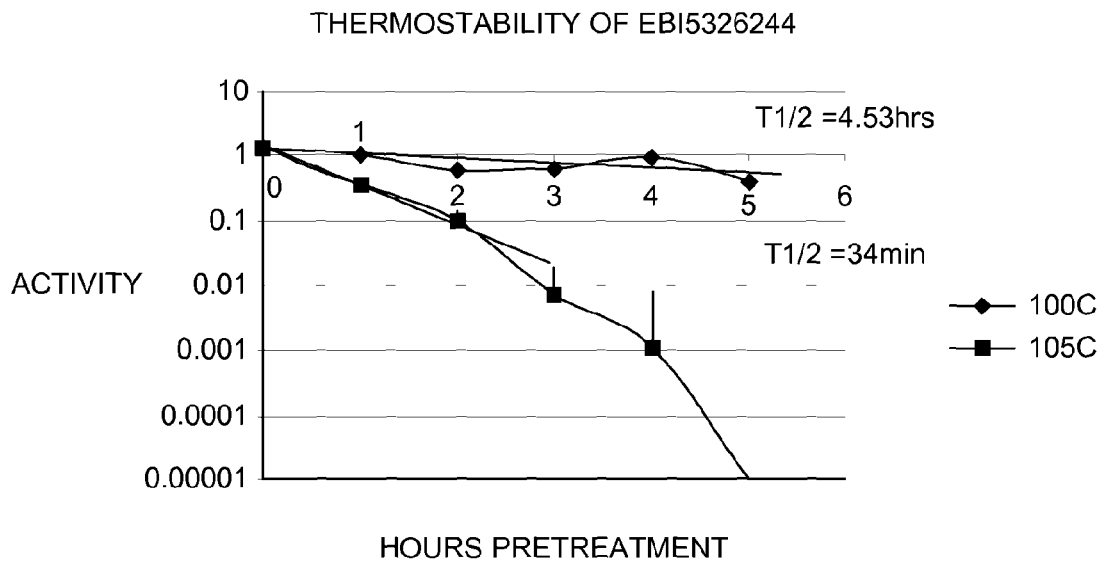
FIG. 19 shows thermostability of EBI244 activity, preincubated at 100° C. or 105° C. in buffer, then assayed for activity on 1% CMC at 95° C.
Figure 20:
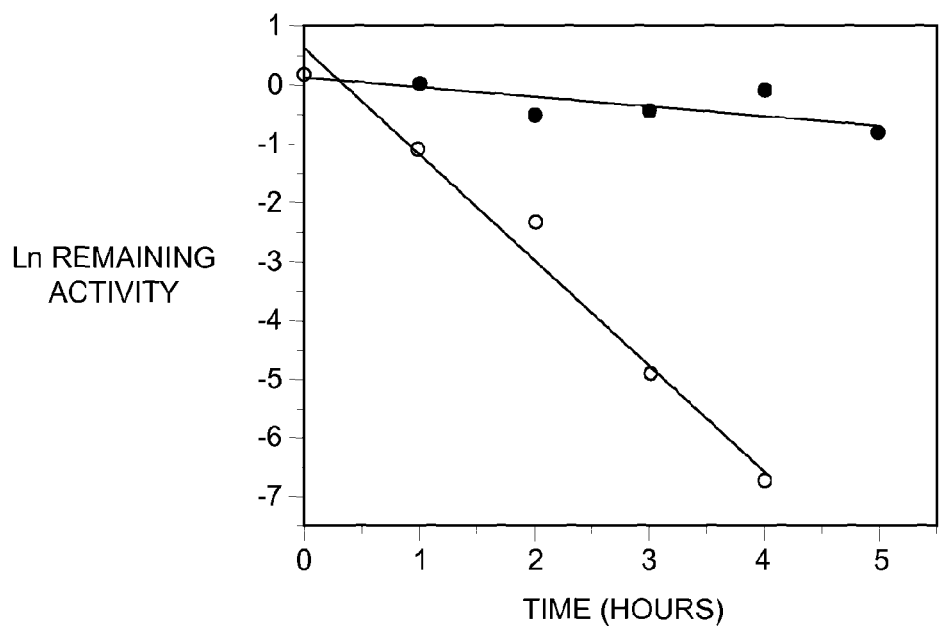
FIG. 20 shows the thermostability of EBI244 at 100° C. (●) and 105° C. (○) in 50 mM HEPPS buffer, pH 6.8. Data points represent the mean of four assays. Enzyme was incubated at the appropriate temperature, samples were collected at 1 hour intervals, and activity was measured using the DNS assay with cellobiose as a standard.
Figure 21:
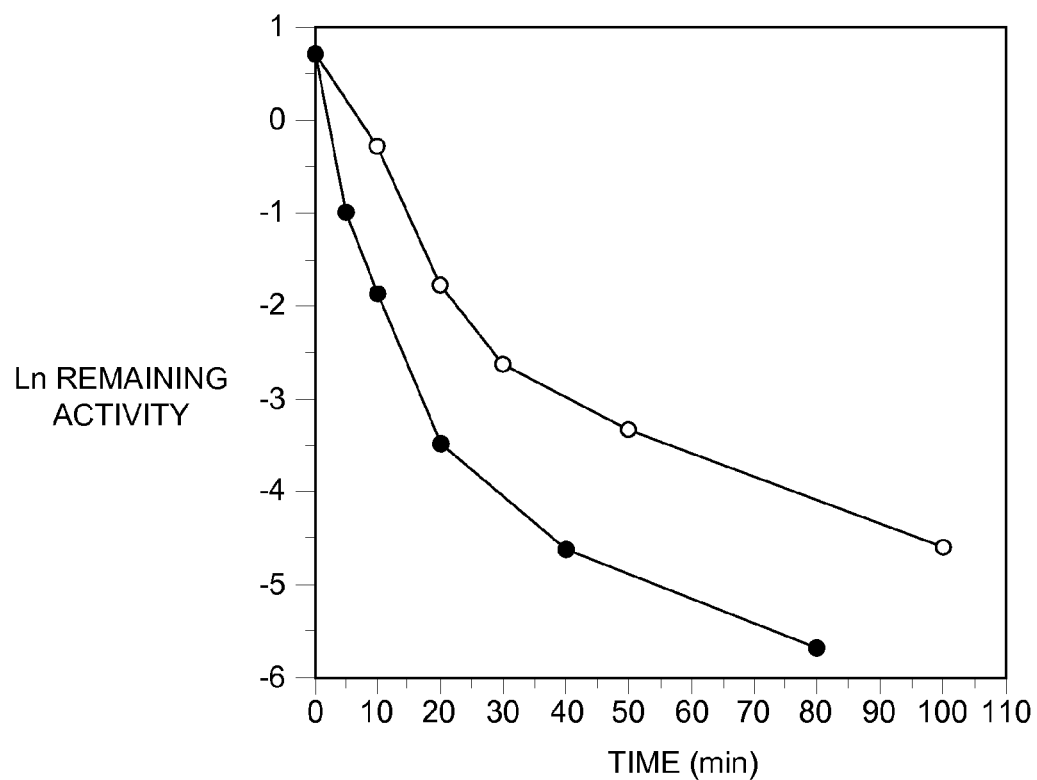
FIG. 21 shows thermostability of EBI244 at 108° C. with (○) and without (●) 0.5% w/v Avicel® in 25 mM sodium acetate buffer, pH 6.0. Enzyme was pretreated for 30 min at 90° C. prior to incubation at 108° C. to allow for interaction with the cellulose. Samples were removed at time intervals and activity was measured in triplicate using the DNS assay using cellobiose as a standard.

To assess thermostability, the enzyme was preincubated at 100° C. or 105° C. in HEPPS buffer, then assayed for activity on 1% CMC at 90° C. The results, shown in FIGS. 19 and 20, demonstrate that the enzyme had a half-life of about 4.5 hours at 100° C., and about 34 minutes at 105° C. Additionally, the enzyme had a half-life of 10 min in HEPPS buffer, pH 6.8, at 108° C. in the presence of microcrystalline cellulose (0.5% Avicel®) (FIG. 21). Differential scanning calorimetry of the enzyme (FIG. 17, inset) showed a bifurcated transition with two Tm's of 111° C. and 113° C.

Figure 22:
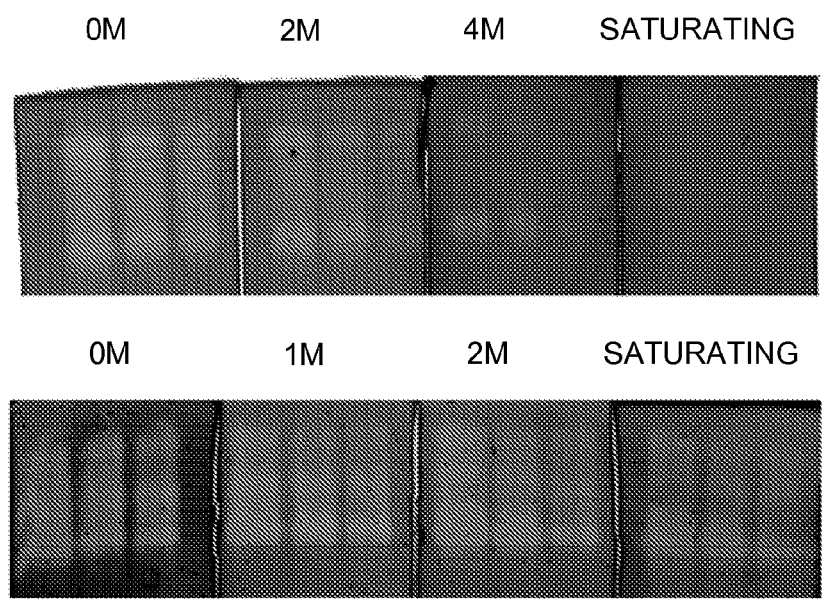
FIG. 22 shows zymogram assay results following incubation of recombinant EBI244 enzyme at 90° C. in phosphate buffer, at various salt concentrations. Upper panel: NaCl; lower panel: KCl.

Stability and Activity in High Ionic Strength,

Zymogram assays also revealed that the recombinant enzyme is active in solutions of high ionic strength. For this study, zymogram gels were made as described, then equilibrated to various salt concentrations at room temperature prior to incubation at 90° C. The results are presented in FIG. 22, showing the enzyme exhibited zymogram activity in up to 4 M sodium chloride and up to saturating potassium chloride.

Figure 23:
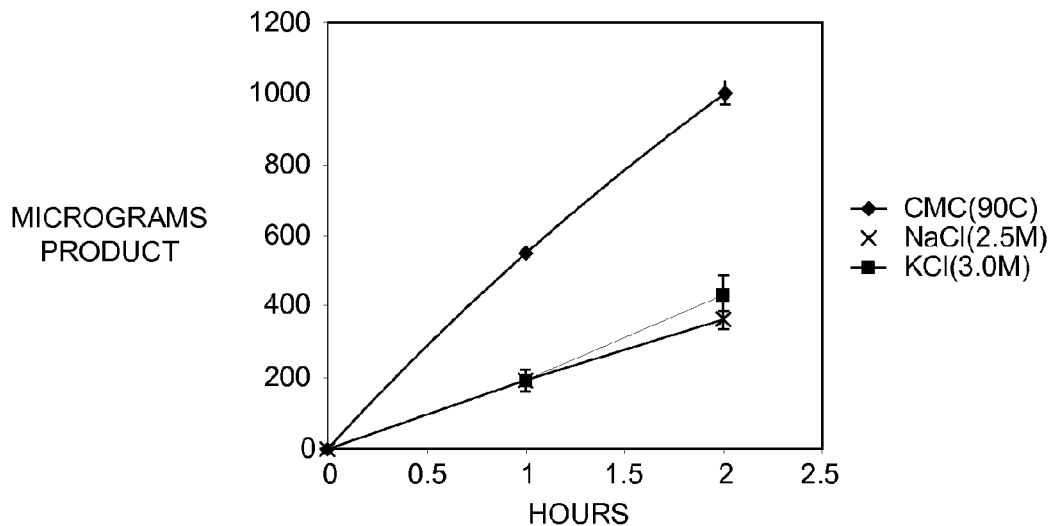
FIG. 23 shows DNS assay results showing product formation for EBI244 with 1% CMC in HEPPS buffer with no added salt, 2.5 M NaCl, or 3.0 M KCl.
Figure 24:
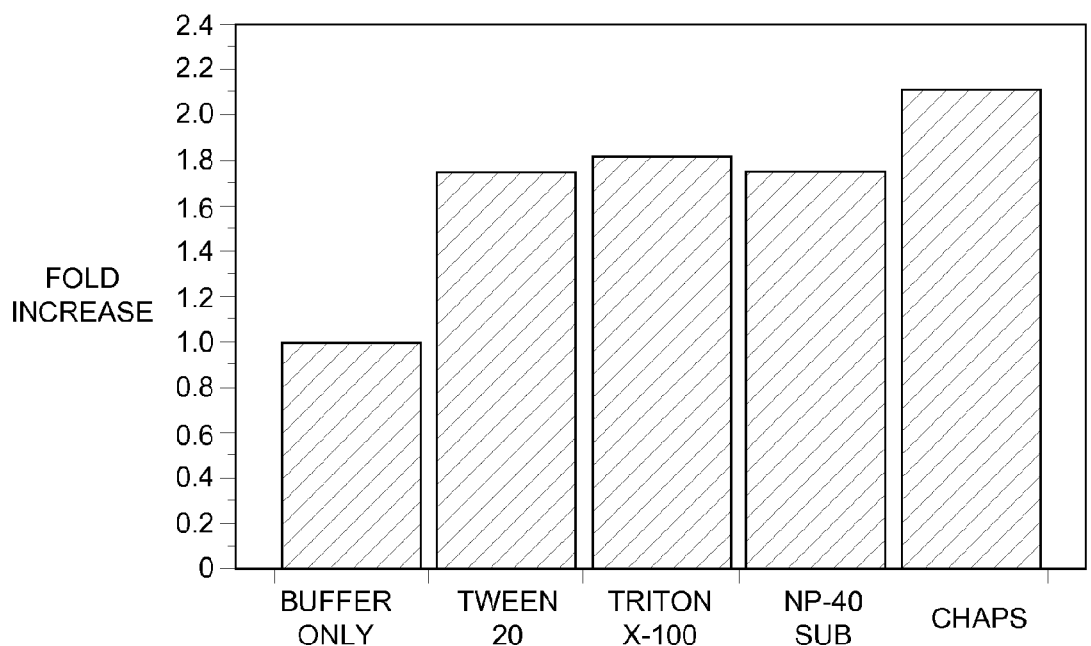
FIG. 24 depicts activity of EBI244 against PNP-cellobioside at 95° C. in the presence of various detergents. Conditions tested were 25 mM potassium phosphate buffer, pH 6.8 alone or buffer plus 0.1% of either Tween® 20, Triton® x-100, NP-40 substitute or CHAPS. After a 20 min incubation, sodium hydroxide was added to 50 mM and absorbance was measured at 410 nm. Values were calculated via paranitrophenol standard in the same buffer. Ratios were calculated based on activity in buffer alone.

A DNS assay was used to measure product formation for EBI244 with 1% CMC in HEPES buffer with no salt added, 2.5 M sodium chloride, and 3.0 M KCl. The results, shown in FIG. 23, revealed that the initial reaction kinetics of the enzyme were linear in up to 2.5 M sodium chloride and 3.0 M potassium chloride, at rates about 40% of that of buffer alone. These results indicate that the enzyme is very halotolerant but functions better at lower salt concentrations. Moreover, ionic detergents, including SDS, had little effect on enzyme activity or stability and both non-ionic and non-denaturing ionic detergents such as CHAPS stimulated activity (FIG. 24).

Figure 25:
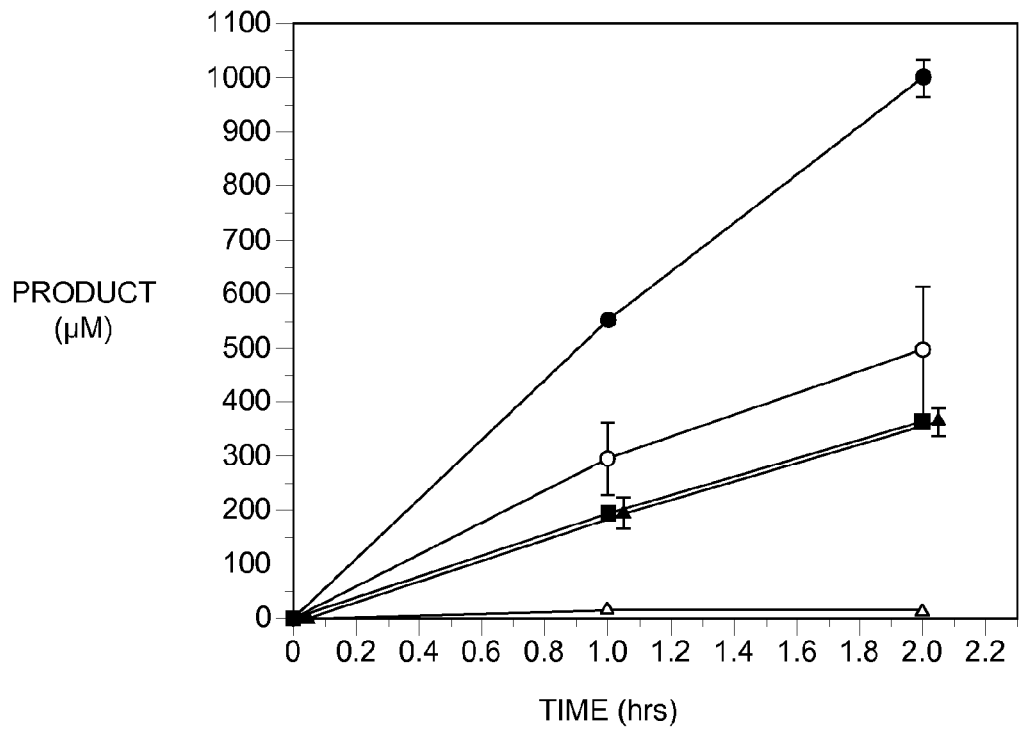
FIG. 25 depicts a time course of EBI244 activity against 1% CMC while in the presence of salts or ionic liquids. All assays were done in HEPPS buffer, pH 6.8 at 90° C. (shown with ●) and either 2.5 M sodium chloride (▲), 3.0 M potassium chloride (■), 25% (v/v) [DMM]DMP (○), or 25% (v/v) [EMM]Acetate (Δ). Activity was measured using DNS assay after each time point using cellobiose as a standard. Error bars represent the standard error of the mean of four assays.
Figure 26:
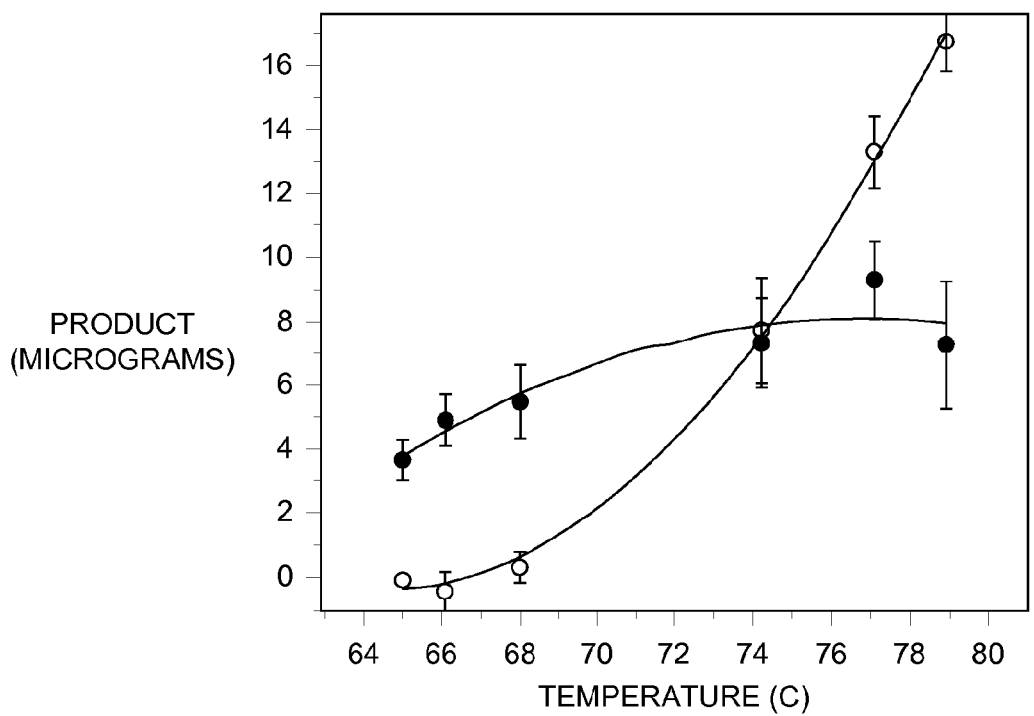
FIG. 26 depicts a temperature profiles showing CMC activity of EBI244 in 50% ionic liquid. Enzyme activity was measured in 50% (v/v) [DMIM]DMP in 25 mM phosphate, pH 6.8 (●) and 25 mM potassium phosphate buffer, pH 6.8 alone (○). Activity was measured using DNS assay after 2 hours using cellobiose as a standard.

Given that EBI244 remained active under high (NaCl) to near-saturating (KCl) salt conditions (FIG. 25), its activity was measured in the presence of the ionic liquids 1,3-dimethylimidazolium dimethyl phosphate ([DMIM]DMP) and 1-ethyl-3-methylimidazole acetate ([EMIM]OAc), which could potentially be used to pretreat substrates like *Miscanthus*17. The concentrations tested, 25% and 50% (v/v), are well above the expected residual ionic liquid of 10-15% that may be carried over after pretreatment (18). CMCase activity was demonstrated in zymograms incubated at 90° C. in 25% (v/v) of either ionic liquid (pH 6.8). EBI244 remained stable and active at 90° C. in 25% [DMIM]DMP (FIG. 23). Interestingly, in these assays, the enzyme's Topt decreased in the presence of ionic liquids (FIG. 26), suggesting that denaturing effects of the ionic liquids may stimulate activity at lower temperatures at which the enzyme would otherwise be inactive.

Figure 27:
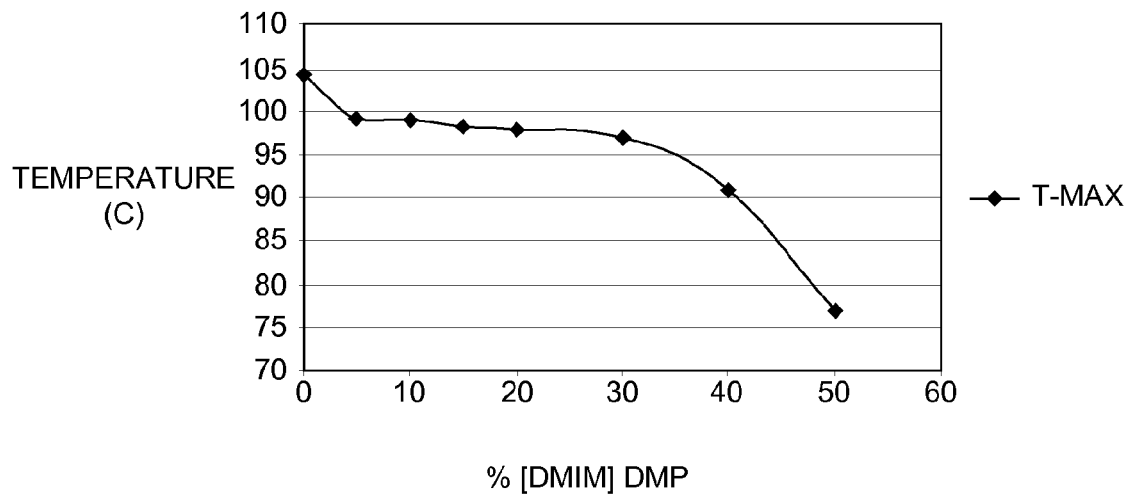
FIG. 27 shows results of a DNS assay, representing temperature optima compiled from activity-temperature profiles of EBI244 in increasing amounts of the ionic liquid [DMIM] DMP.

The enzyme was also equilibrated in buffer with ionic liquid added in both zymogram assays and liquid DNS assays, with carboxymethylcellulose as the substrate. The enzyme was tested in two different ionic liquids, [DMIM]DMP and [EMIM]OAc. Zymogram activity was detected in gels incubated in 25% of either ionic liquid at 90° C. in 50 mM phosphate buffer at pH 6.8. The enzyme was shown to be active in up to 50% 1,3-dimethylimidazolium dimethyl phosphate. The temperature of maximum activity was determined for different concentrations of this ionic liquid. FIG. 27 shows results from a DNS assay, representing temperature optima compiled from activity-temperature profiles of EBI244 in increasing amounts of the ionic liquid (DMIM) DMP. While the maximum active temperature declined with increasing ionic liquid, purified EBI244 was demonstrated to be active in liquid assays at high concentrations of ionic liquids through a wide range of temperatures.

Figure 28:
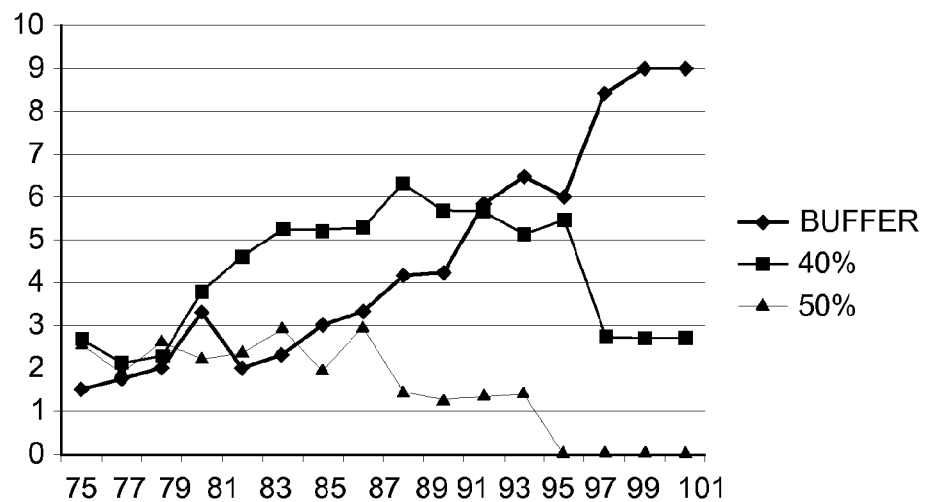
FIG. 28 shows results of a DNS assay, showing activity of EBI244 on 1% CMC in buffer alone, and in the presence of 40% and 50% [DMIM]DMP.

FIG. 28 shows the results of a DNS assay measuring activity of EBI244 on 1% CMC in buffer alone, and in the presence of 40% and 50% [DIMM] DMP. As shown, the highest activities in the low temperature range from 50-80° C. were recorded in the presence of ionic liquid, implying that the enzyme is activated at low temperature by the addition of ionic liquids.

Tolerance for Various Detergents

Figure 29:
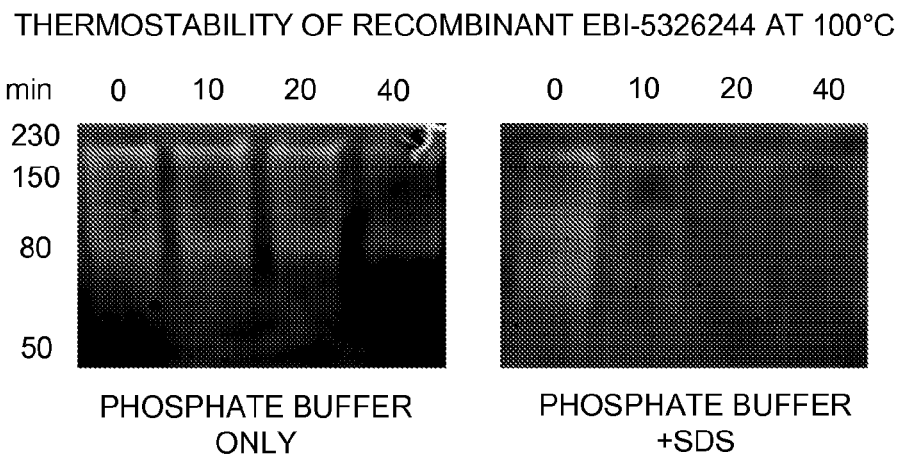
FIG. 29 shows the results of a zymogram assay of EBI244, after pretreatment in phosphate buffer or phosphate buffer plus 0.1% sodium dodecyl sulfate at 100 C, demonstrating the thermostability of recombinant EBI244.

All detergents tested, including SDS at 100° C., had little effect on enzyme stability. No loss of activity was observed in non-ionic detergents, Triton x-100, NP-40, Tween 20. The enzyme was stable in up to 2% CHAPS (ionic non-denaturing detergent). Zymogram activity was retained after SDS-PAGE without the customary wash and refold steps, indicating a tolerance for 0.1-1% SDS at room temperature. The recombinant enzyme was pretreated at 100° C. with and without the addition of 0.1% SDS, then assayed by zymography at 90° C., showing thermostability at 100° C. in the presence of 0.1% SDS (FIG. 29).

Activity Over a Broad pH Range

Figure 30:
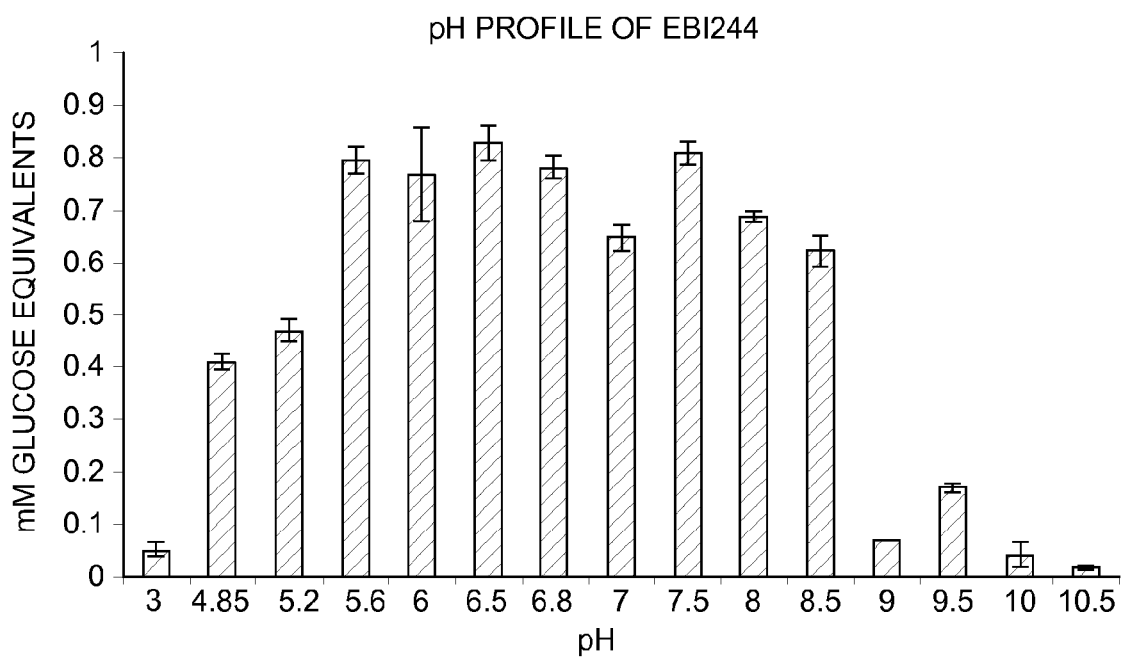
FIG. 30 shows a pH-profile of EBI244 activity, based on DNS assays of CMC hydrolysis.
Figure 31:
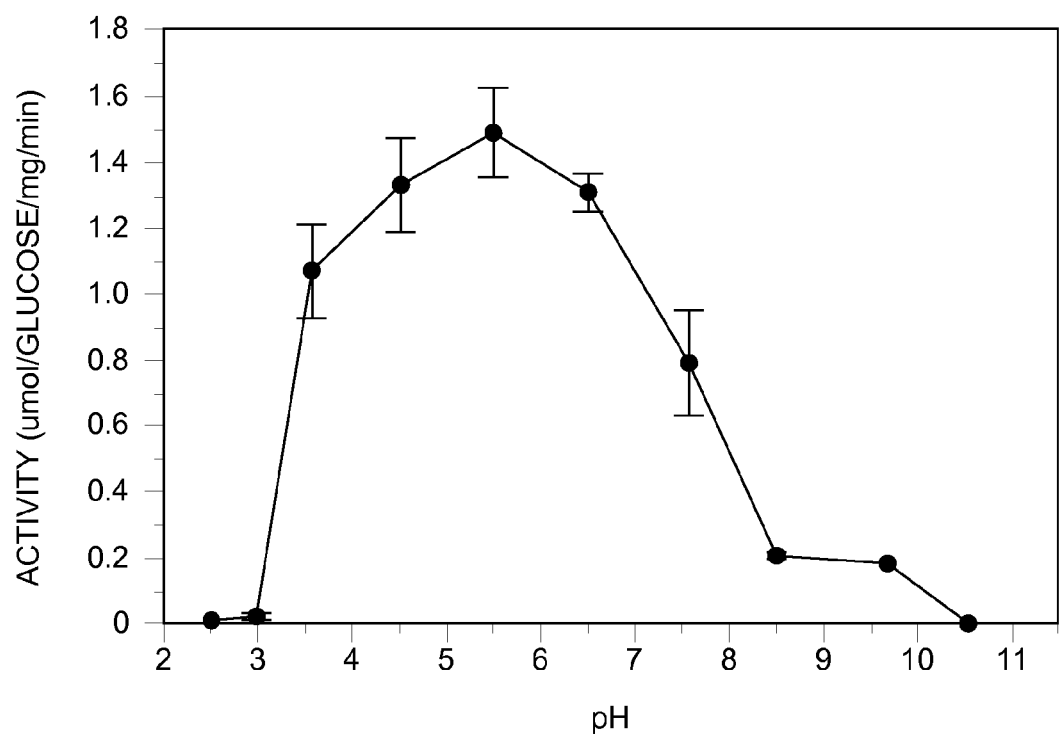
FIG. 31 shows a pH profile of EBI244 activity measured against PNP-cellobioside at 95° C. Buffers used were sodium acetate/acetic acid (pH 2.5-5.5), MED (pH 6.5), HEPPS (pH 7.5-8.5), and CAPS (pH 9.5-10.5). After 20 min incubation, sodium hydroxide to a final concentration of 50 mM and absorbance was measured at 410 nm. Values were calculated by a paranitrophenol standard in the same buffer. Error bars are standard deviations of the mean of four duplicate addays.

The enzyme retained activity over a very broad pH range with significant activity up to pH 8.5, as shown in FIG. 30 (showing results of a DNS assay of CMC hydrolysis over a broad pH range). Moreover, the enzyme had an optimum of about pH 5.5 (FIG. 31).

The results of this study demonstrate that the recombinant enzyme has cellulolytic activity, releasing reducing sugars from carboxymethyl-cellulose, microcrystalline cellulose (Avicel®) and Whatman® #1 filter paper, at reaction temperatures exceeding 105° C., with an optimal temperature range from 95-110° C. The results further demonstrate that the enzyme has a half-life of greater than five hours at 100° C. and tolerates sodium chloride in near saturating concentrations (4M) at 90° C. and potassium chloride at saturating concentration (~3.2 M) at 90° C. The results further show that the enzyme is active toward carboxymethylcellulose in the presence of the ionic detergents CHAPS (2%) and sodium dodecyl sulfate (0.1%) and to function in up 50% ionic liquids (i.e., 1,3-dimethylimidazolium dimethyl phosphate) at 90° C., and functions over an unusually broad range of pH, with greater than 50% of the maximum activity exhibited from pH 4.5-8.75.

The results demonstrate that the EBI244 enzyme is an extremely thermostable, thermoactive cellulose-binding endoglucanase, with a unique sequence composition. Because the enzyme maintains a high proportion of its activity over an exceptionally broad range of salinities, ionic strength, detergents, and pH, the enzyme is useful in providing cellulase activity suitable for long-term use under the broad and variable range of conditions encountered in industrial conditions. Furthermore, given the ability of EBI244 to bind tightly to crystalline cellulose, the enzyme will be useful in engineering hyperstable endocellulases for greater activity on crystalline substrates, for example, by the addition of thermostable cellulose binding domain, e.g., the N-terminal and/or C-terminal domain(s) of EBI244 to catalytic domains.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the compositions and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of hydrolyzing or degrading a biomass, comprising contacting said biomass with a composition comprising an isolated protein comprising amino acids 250-580 of SEQ ID NO: 1, wherein the protein is a cellulase.

2. The method of claim 1, wherein the isolated protein further comprises amino acids 130-250 of SEQ ID NO: 1.

3. The method of claim 2, wherein the isolated protein further comprises amino acids 750-842 of SEQ ID NO: 1.

4. The method of claim 3, wherein the isolated protein further comprises amino acids 580-750 of SEQ ID NO: 1.

5. The method of claim 1, wherein the isolated protein has at least 70% identity to SEQ ID NO: 1.

6. The method of claim 1, wherein the isolated protein comprises the amino acid sequence of SEQ ID NO: 1.

7. A genetically modified host cell comprising an expression vector, wherein the expression vector comprises a heterologous nucleic acid encoding a cellulase protein comprising the amino acid sequence of SEQ ID NO: 1, or enzymatically active fragments thereof.

8. A method of hydrolyzing or degrading a biomass, comprising contacting said biomass with a genetically modified host cell of claim 7.

* * * * *

SEQUENCE LISTING

```
<160> NUMBER OF SEQ ID NOS: 122

<210> SEQ ID NO 1
<211> LENGTH: 842
<212> TYPE: PRT
<213> ORGANISM: Unknown
<220> FEATURE:
<223> OTHER INFORMATION: EBI5326244 deduced protein sequence, derived
      from Archaea

<400> SEQUENCE: 1

Leu Lys Lys Val His Ile Ile Ala Ile Val Val Ile Ile Ala Ile Ala
1               5                   10                  15

Phe Ala Leu Ile Leu Ala Arg Tyr Tyr Thr Met Gln Arg Gly Tyr Glu
            20                  25                  30

Thr Val Thr Pro Thr Thr Pro Pro Gln Gln Thr Thr Thr Glu Thr
        35                  40                  45

Thr Pro Val Pro Thr Glu Ala Gly Thr Thr Thr Pro Ile Thr Glu Ala
    50                  55                  60

Thr Val Thr Gln Pro Pro Gln Thr Pro Thr Thr Pro Ser Pro Gln Thr
```

-continued

```
            65                  70                  75                  80
Pro Thr Thr Pro Thr Ala Leu Pro Thr Pro Ser Pro Thr Pro Thr Ala
                    85                  90                  95
Pro Ser Ala Thr Val Thr Glu Thr Thr Ser Pro Gln Thr Pro Thr Thr
                   100                 105                 110
Thr Ile Thr Thr Glu Thr Thr Thr Pro Ala Pro Gln Pro Gln Val
                   115                 120                 125
Val Phe Leu Lys Leu Pro Glu Gly Glu Pro Lys Phe Gly Leu Val
    130                 135                 140
Glu Ile Ala Phe Asn Ile Ser Gly Leu Ser Tyr Ser Asn Pro Phe Asp
145                 150                 155                 160
Thr Ser Asp Ile Asp Val Trp Val His Ile Glu Thr Pro Ser Gly Ser
                    165                 170                 175
Arg Val Ala Val Pro Ala Phe Tyr Phe Gln Asn Tyr Thr Val Lys Arg
                    180                 185                 190
Leu Gly Pro Gly Glu Ile Ile Val Arg Val Gly Arg Pro Tyr Trp
                195                 200                 205
Leu Ala Arg Phe Ala Pro Val Glu Gly Val His Lys Phe Tyr Val
    210                 215                 220
Lys Ala Val Asp Gly Arg Gly Ser Ala Val Val Ser Glu Ile Arg Glu
225                 230                 235                 240
Phe Met Val Lys Gly Val Ala Gly Arg Gly Phe Val Arg Val Asp Ser
                245                 250                 255
Gly Lys Arg Leu Phe Val Phe Asp Ser Gly Glu Ser Met Phe Met Leu
                260                 265                 270
Gly Ile Asp Val Ala Trp Pro Pro Asp Arg Arg Ser Ser Ile Ser Phe
            275                 280                 285
Tyr Glu Gln Trp Phe Asp Lys Leu Asn Lys Ser Gly Ile Lys Val Val
        290                 295                 300
Arg Ile Gly Leu Val Pro Trp Ala Leu Thr Leu Glu Trp Ser Lys Leu
305                 310                 315                 320
His Tyr Tyr Ser Leu Asp Asp Ala Ala Arg Ile Asp Glu Ile Val Lys
                325                 330                 335
Leu Ala Glu Lys Tyr Asp Ile Tyr Ile Val Phe Val Phe Met Trp His
                340                 345                 350
Gly Glu Leu Ala Asp Asn Trp Gly Asp Asn Pro Tyr Asn Ala Ala Arg
                355                 360                 365
Gly Gly Pro Leu Gln Ser Pro Glu Glu Phe Trp Ser Asn Ala Val Ala
    370                 375                 380
Ile Ser Ile Phe Lys Asp Lys Val Arg Tyr Ile Ala Arg Trp Gly
385                 390                 395                 400
Tyr Ser Thr His Ile Leu Ala Trp Glu Leu Ile Asn Glu Ala Asp Leu
                405                 410                 415
Thr Thr Asn Phe Phe Ser Ala Arg Ser Ala Phe Val Ser Trp Val Lys
                420                 425                 430
Glu Ile Ser Ser Tyr Ile Lys Ser Val Asp Pro Tyr Asn Arg Ile Val
            435                 440                 445
Thr Val Asn Leu Ala Asp Tyr Asn Ser Glu Pro Arg Val Trp Ser Val
            450                 455                 460
Glu Ser Ile Asp Ile Ile Asn Val His Arg Tyr Gly Pro Glu Gly Phe
465                 470                 475                 480
Lys Asp Ile Ala Leu Ala Ile Pro Ser Ile Val Glu Gly Leu Trp Asn
                485                 490                 495
```

```
Thr Tyr Arg Lys Pro Ile Ile Ile Thr Glu Phe Gly Val Asp Tyr Arg
            500                 505                 510

Trp Ile Gly Tyr Pro Gly Phe Lys Gly Thr Pro Tyr Trp Ala Tyr Asp
            515                 520                 525

Lys Ser Gly Val Gly Leu His Glu Gly Leu Trp Ser Ser Ile Phe Ser
            530                 535                 540

Leu Ser Pro Val Ser Ala Met Ser Trp Trp Trp Asp Thr Gln Ile Asp
545                 550                 555                 560

Ser Tyr Asn Leu Trp Tyr His Tyr Lys Ala Leu Tyr Glu Phe Leu Lys
                565                 570                 575

Ser Val Asp Pro Val Arg Gly Leu Gly Lys Ala Arg Ala Ser Leu
            580                 585                 590

Val Ile Thr Asp Val Thr Pro Ser Ser Ile Thr Leu Tyr Pro Leu Ala
            595                 600                 605

Gly Trp Val Trp Val Ser Pro Val Arg Glu Asn Arg Leu Val Ile Arg
610                 615                 620

Pro Asp Gly Ala Ile Glu Gly Arg Val Asp Leu Leu Ser Gly Phe Ile
625                 630                 635                 640

Tyr Gly Thr Cys His Ser Gln Arg Thr Leu Asn Pro Val Phe Thr Val
                645                 650                 655

Met Phe Ile Asp Arg Gly Arg Val Val Leu His Ile Asn Ser Val Gly
                660                 665                 670

Arg Gly Ser Ala Lys Leu Val Ile Tyr Val Asn Gly Ser Leu Ala Thr
                675                 680                 685

Gln Leu Asp Leu Pro Asp Lys Asp Gly Lys Ser Asp Gly Ser Ala Asn
            690                 695                 700

Glu Tyr Asp Met Asp Val Glu Leu Trp Phe Glu Pro Gly Thr Tyr Glu
705                 710                 715                 720

Ile Lys Ile Asp Ser Glu Ala Cys Asp Trp Phe Thr Trp Asp Tyr Ile
                725                 730                 735

Val Phe Glu Asn Ala Val Tyr Arg Ala Ala Lys Val Asp Leu Tyr Ala
                740                 745                 750

Leu Ala Asn Ser Thr Phe Ala Met Leu Trp Val Arg Asn Lys Asp Tyr
            755                 760                 765

Asn Trp Trp Asn Val Val Leu Asn Lys Thr Leu Glu Pro Ala Glu
770                 775                 780

Gly Val Glu Val Glu Ile Arg Gly Leu Gln Asp Gly Val Tyr Arg Val
785                 790                 795                 800

Glu Phe Trp Asp Thr Cys Arg Gly Val Val Val Lys Ser Met Glu Val
                805                 810                 815

Gln Val Ser Asn Gly Val Ala Arg Val Pro Val Gly Ser Val Glu Lys
            820                 825                 830

Asp Ile Ala Met Lys Ile Thr Arg Ala Gly
            835                 840

<210> SEQ ID NO 2
<211> LENGTH: 2532
<212> TYPE: DNA
<213> ORGANISM: Unknown
<220> FEATURE:
<223> OTHER INFORMATION: EBI5326244 coding region, derived from Archaea

<400> SEQUENCE: 2
atgttgaaaa aggttcacat tattgctata gtagttataa tagcgatagc ttttgcactt      60
```

```
atactagcac ggtactacac aatgcagaga ggctatgaaa cagtgacacc tacaacacca    120
cctcagcaaa ctactaccac agaaacaact ccagtgccta cagaggcagg tactacaaca    180
ccaataactg aggccactgt gactcaaccc cctcaaaccc ctacaacacc ttcaccacaa    240
acaccaacaa caccaacagc gttgcccacg ccatcaccaa cccccacagc gccctctgcc    300
acagtaacag agactacatc gcctcaaact cctacaacta caataactac agaaacaaca    360
actacaccag cccccccaacc ccaggtggtg tttctaaagc taccagaggg agaggagcca    420
aagtttggct tagttgaaat agcctttaac atatctggtc taagctactc aaaccccttt    480
gacacaagcg atattgatgt gtgggtgcac atagagacgc caagtggctc tagagtggct    540
gtaccagctt tctacttcca gaactacact gtgaaaaggc ttggaccagg ggaggagatc    600
atagtcaggg ttggaaggcc atactggctc gctaggttcg cacctgttga ggaggggtg     660 cacaagttct acgtaaaggc agttgatggc aggggagtg ctgtggtgag cgagattaga     720
gagtttatgg ttaagggggt ggctggcagg gggtttgtca gagttgacag tggcaaaagg    780
ctattcgtat ttgacagcgg tgaatcaatg tttatgctgg ggatagatgt tgcgtggcca    840
ccagatagga ggagctctat atcgttctat gagcagtggt ttgataaact aaataagagt    900
gggattaagg ttgtgagaat aggcctagtg ccctgggctc taacactaga gtggagcaag    960
ctccactact acagcttaga tgacgctgct agaatagatg agattgtgaa gcttgctgaa    1020
aagtatgaca tatacatagt gtttgtgttt atgtggcatg gagagcttgc ggataactgg    1080
ggggataacc catacaatgc agcaaggggt ggtcctcttc agagcccaga ggagttctgg    1140
agcaatgcag tagctatcag tatatttaag gataaggtga ggtacattat agctaggtgg    1200
gggtactcaa cacacatact cgcatgggag ctgataaacg aggctgacct aacaacaaac    1260
ttctttagcg ctagaagtgc tttttgtgagc tgggttaagg agataagcag ctacataaag    1320
tccgtagacc cctacaacag gattgtcact gtgaacctcg ctgactacaa ttctgagcca    1380
agggtgtgga gcgtagagtc catagacatc ataaatgtgc ataggtatgg ccagagggc     1440 tttaaggaca tagccttggc tattccaagc atagtagagg ggctttggaa cacctacaga    1500
aagcctatta taataacaga gtttggtgtt gactatcggt ggattggcta cccaggcttt    1560
aaaggaaccc cctactgggc atacgacaag agtgggggttg ggcttcatga agggctctgg    1620 agctctatt ttcagcctctc cccagttttct gctatgagct ggtggtggga tacacagata    1680
gactcttata atctgtggta ccactacaaa gccctctacg agtttctaaa gagtgtcgac    1740
cctgttagag gaggcttggg caaggccaga gcatcgctag tcattacaga tgtgaccccc    1800
tctagcataa cactataccc cttagcgggc tgggtgtggg tctcgccagt gagagaaaat    1860
aggcttgtta taaggcctga tggggctatc gagggggggg ttgatttgct aagtgggttt    1920
atctatggca cgtgccacag ccagcggaca ctaaacccag tattactgt gatgttcatt     1980 gatagaggca gggtggtgct acacataaac tctgttggca ggggctctgc aaagctcgtg    2040
atatatgtta atggctctct agctacacaa ctggacttgc ctgataagga tggtaagagt    2100
gatgggagtg caaatgagta cgacatggat gtggagctgt ggtttgagcc tggcacctac    2160
gaaataaaaa ttgatagtga agcttgcgac tggttcacat gggactacat agtgtttgaa    2220
aatgctgtgt atagagctgc taaagtagat ctctatgcac ttgcaaacag caccttttgca   2280 atgctctggg taaggaacaa ggactacaac tggtggaacg tagtggtgct gaacaagact    2340
ctagagcctg ctgagggagt agaggtagag attagaggac tgcaagatgg ggtgtacaga    2400
gtagagtttt gggacacatg cagaggggtg gtggtgaaga gcatggaggt tcaagtgtca    2460
```

```
aatggtgtag ccagggttcc ggtgggtagc gtagaaaagg acatagctat gaaaatcact    2520
agggctggct aa                                                        2532

<210> SEQ ID NO 3
<211> LENGTH: 2553
<212> TYPE: DNA
<213> ORGANISM: Unknown
<220> FEATURE:
<223> OTHER INFORMATION: EBI5326244 coding region, derived from Archaea

<400> SEQUENCE: 3
atgctgaaga aagtccacat catcgcaatc gtcgtcatca tcgccatcgc attcgcactg      60
attctggcgc gctactacac catgcagcgt ggctatgaaa cggtcactcc gaccaccccg     120
cctcaacaaa cgacgaccac cgaaaccacc ccggtgccta ccgaagcggg caccaccact     180
ccgatcactg aggcgaccgt gacccagccg cctcagacgc aacgacgcc atcgccgcaa     240 acgccgacga ccccaaccgc cctgccgacc ccgagcccga cgccgaccgc gccaagcgcc     300
acggtcactg aaacgaccag cccgcagacc ccgaccacca ccatcacgac ggaaaccact     360
accacgccgg caccgcagcc gcaggttgtg tttctgaaat gccggagggg tgaagaaccg     420
aaattcggcc tggttgagat cgctttcaac attagcggcc tgagctacag caacccttt      480 gataccagcg atattgacgt ttgggttcat attgaaaccc cgagcggtag ccgcgtggcc     540
gttccggcat tttactttca aaactacacg gtcaagcgcc tgggtccggg tgaagaaatc     600
atcgtgcgtg tgggtcgtcc gtattggctg gctcgctttg cgccggtcga agagggcgtt     660
cacaagttct acgtgaaagc ggttgatggt cgcggctccg cggtggttag cgagattcgt     720
gagtttatgg taaagggcgt tgccggtcgc ggcttcgttc gtgtggactc tggcaaacgt     780
ctgtttgtgt tcgatagcgg cgagagcatg tttatgctgg gtattgatgt cgcgtggcca     840
ccggaccgtc gttctagcat cagcttttac gagcaatggt tcgacaaatt gaacaagtct     900
ggcattaaag ttgttcgcat tggtctggtc ccgtgggcgc tgaccctgga atggagcaag     960
ctgcactact atagcctgga tgatgcggct cgcattgacg agatcgtcaa actggcagag    1020
aagtatgaca tctacattgt ctttgtgttt atgtggcatg tgagttggc agacaattgg     1080 ggcgataacc cgtataacgc ggctcgtggt ggtccgctgc agagcccgga agagttttgg    1140
agcaatgcgg tggcaattag catctttaag gacaaagttc gttatatcat cgcgcgctgg    1200
ggttatagca ctcacattct ggcgtgggag ctgattaatg aggcagactt gaccacgaac    1260 ttctttccg cccgtagcgc cttcgtcagc tgggtcaaag agatcagcag ctacattaag    1320
agcgtggacc cgtacaaccg catcgtcacc gtcaatctgg ctgattacaa ctctgaaccg    1380
cgtgtttggt ccgtggagtc catcgacatc atcaatgttc atcgctatgg tccggaaggt    1440
ttcaaggaca ttgccctggc aattccgtcg attgtcgagg gtctgtggaa cacttatcgt    1500
aagcctatca tcattaccga gttcggcgtg gattatcgtt ggattggcta tccgggtttc    1560
aaaggtaccc cgtactgggc gtatgataag agcggtgttg gcttgcacga gggcctgtgg    1620
agcagcatct tctcgctgtc cccggtaagc gcgatgtctt ggtggtggga cacccaaatt    1680
gacagctaca acctgtggta tcattacaaa gcgctgtacg agttcctgaa atccgttgac    1740
ccggttcgtg gtggcctggg taaagcccgt gcgagcttgg ttatcacgga cgtgacgccg    1800
agcagcatta ccctgtatcc gctggcgggt tgggtgtggg tgtcgccggt ccgtgagaat    1860
cgtttggtta ttcgtccaga tggcgcaatc gaaggccgcg ttgacctgct gagcggtttc    1920
```

```
atctatggta cgtgtcacag ccagcgtacc ctgaatccgg ttttttacggt catgttcatt    1980 gatcgtggtc gcgtggtgct gcacattaac agcgtgggtc gtggttctgc taagctggtg    2040
atttacgtca atggcagcct ggcgacgcaa ctggatttgc cggacaaaga cggcaagagc    2100
gacggtagcg cgaacgagta cgatatggac gtcgagctgt ggttcgagcc gggtacctac    2160
gagatcaaaa ttgattccga agcttgcgac tggttcacct gggattacat tgttttcgaa    2220
aatgcggttt atcgtgcggc aaaggttgat ctgtatgcct ggcaaacag caccttttgcc    2280 atgctgtggg tacgtaacaa ggattacaat tggtggaatg tggtggtgct gaataagacc    2340
ctggaaccgg cggagggtgt tgaagtggag atccgtggcc tgcaagacgg tgtgtaccgc    2400
gtcgaattct gggacacgtg ccgcggtgtg gttgttaaaa gcatggaagt ccaggtttct    2460
aatggtgtgg cgcgtgtccc ggttggtagc gtcgagaaag atattgcaat gaagattacc    2520
cgtgcaggcc atcatcacca tcaccactaa taa                                  2553

<210> SEQ ID NO 4
<211> LENGTH: 2529
<212> TYPE: DNA
<213> ORGANISM: Unknown
<220> FEATURE:
<223> OTHER INFORMATION: EBI5326244 coding region, derived from Archaea

<400> SEQUENCE: 4
atgctgaaga aagtccacat catcgcaatc gtcgtcatca tcgccatcgc attcgcactg      60
attctggcgc gctactacac catgcagcgt ggctatgaaa cggtcactcc gaccaccccg     120
cctcaacaaa cgacgaccac cgaaaccacc ccggtgccta ccgaagcggg caccaccact     180
ccgatcactg aggcgaccgt gacccagccg cctcagacgc caacgacgcc atcgccgcaa     240
acgccgacga ccccaaccgc cctgccgacc ccgagcccga cgccgaccgc gccaagcgcc     300
acggtcactg aaacgaccag cccgcagacc ccgaccacca ccatcacgac ggaaaccact     360
accacgccgg caccgcagcc gcaggttgtg tttctgaaat gccggagggg tgaagaaccg     420
aaattcggcc tggttgagat cgcttttcaac attagcggcc tgagctacag caacccttttt    480 gataccagcg atattgacgt ttgggttcat attgaaaccc cgagcggtag ccgcgtggcc     540
gttccggcat tttacttttca aaactacacg gtcaagcgcc tgggtccggg tgaagaaatc     600
atcgtgcgtg tgggtcgtcc gtattggctg gctcgctttg cgccggtcga agagggcgtt     660
cacaagttct acgtgaaagc ggttgatggt cgcggctccg cggtggttag cgagattcgt     720
gagtttatgg taaagggcgt tgccggtcgc ggcttcgttc gtgtggactc tggcaaacgt    780
ctgtttgtgt cgatagcgg cgagagcatg tttatgctgg gtattgatgt cgcgtggcca    840
ccggaccgtc gttctagcat cagcttttac gagcaatggt tcgacaaatt gaacaagtct    900
ggcattaaag ttgttcgcat tggtctggtc ccgtgggcgc tgaccctgga atggagcaag    960
ctgcactact atagcctgga tgatgcggct cgcattgacg agatcgtcaa actggcagag   1020
aagtatgaca tctacattgt ctttgtgttt atgtggcatg tgagttggc agacaattgg   1080 ggcgataacc cgtataacgc ggctcgtggt ggtccgctgc agagcccgga gagttttgg    1140 agcaatgcgt tggcaattag catctttaag gacaaagttc gttatatcat cgcgcgctgg   1200
ggttatagca ctcacattct ggcgtgggag ctgattaatg aggcagactt gaccacgaac   1260 ttcttttttccg cccgtagcgc cttcgtcagc tgggtcaaag agatcagcag ctacattaag   1320
agcgtggacc cgtacaaccg catcgtcacc gtcaatctgg ctgattacaa ctctgaaccg   1380 cgtgttttggt ccgtggagtc catcgacatc atcaatgttc atcgctatgg tccggaaggt   1440
```

-continued

```
ttcaaggaca ttgccctggc aattccgtcg attgtcgagg gtctgtggaa cacttatcgt    1500
aagcctatca tcattaccga gttcggcgtg gattatcgtt ggattggcta tccgggtttc    1560
aaaggtaccc cgtactgggc gtatgataag agcggtgttg gcttgcacga gggcctgtgg    1620
agcagcatct tctcgctgtc cccggtaagc gcgatgtctt ggtggtggga cacccaaatt    1680
gacagctaca acctgtggta tcattacaaa gcgctgtacg agttcctgaa atccgttgac    1740
ccggttcgtg gtggcctggg taaagcccgt gcgagcttgg ttatcacgga cgtgacgccg    1800
agcagcatta ccctgtatcc gctggcgggt tgggtgtggg tgtcgccggt ccgtgagaat    1860
cgtttggtta ttcgtccaga tggcgcaatc gaaggccgcg ttgacctgct gagcggtttc    1920
atctatggta cgtgtcacag ccagcgtacc ctgaatccgg tttttacggt catgttcatt    1980
gatcgtggtc gcgtggtgct gcacattaac agcgtgggtc gtggttctgc taagctggtg    2040
atttacgtca atggcagcct ggcgacgcaa ctggatttgc cggacaaaga cggcaagagc    2100
gacggtagcg cgaacgagta cgatatggac gtcgagctgt ggttcgagcc gggtacctac    2160
gagatcaaaa ttgattccga agcttgcgac tggttcacct gggattacat tgttttcgaa    2220
aatgcggttt atcgtgcggc aaaggttgat ctgtatgcct tggcaaacag caccttttgcc    2280 atgctgtggg tacgtaacaa ggattacaat tggtggaatg tggtggtgct gaataagacc    2340
ctggaaccgg cggagggtgt tgaagtggag atccgtggcc tgcaagacgg tgtgtaccgc    2400
gtcgaattct gggacacgtg ccgcggtgtg gttgttaaaa gcatggaagt ccaggtttct    2460
aatggtgtgg cgcgtgtccc ggttggtagc gtcgagaaag atattgcaat gaagattacc    2520
cgtgcaggc                                                           2529
```

<210> SEQ ID NO 5
<211> LENGTH: 849
<212> TYPE: PRT
<213> ORGANISM: Artificial Sequence
<220> FEATURE:
<223> OTHER INFORMATION: Synthetic Construct

<400> SEQUENCE: 5

```
Met Leu Lys Lys Val His Ile Ile Ala Ile Val Ile Ile Ala Ile
 1               5                  10                  15

Ala Phe Ala Leu Ile Leu Ala Arg Tyr Tyr Thr Met Gln Arg Gly Tyr
                20                  25                  30

Glu Thr Val Thr Pro Thr Thr Pro Gln Gln Thr Thr Thr Thr Glu
            35                  40                  45

Thr Thr Pro Val Pro Thr Glu Ala Gly Thr Thr Thr Pro Ile Thr Glu
        50                  55                  60

Ala Thr Val Thr Gln Pro Pro Gln Thr Pro Thr Thr Pro Ser Pro Gln
65                  70                  75                  80

Thr Pro Thr Thr Pro Thr Ala Leu Pro Thr Pro Ser Pro Thr Pro Thr
                85                  90                  95

Ala Pro Ser Ala Thr Val Thr Glu Thr Thr Ser Pro Gln Thr Pro Thr
            100                 105                 110

Thr Thr Ile Thr Thr Glu Thr Thr Thr Thr Pro Ala Pro Gln Pro Gln
        115                 120                 125

Val Val Phe Leu Lys Leu Pro Glu Gly Glu Glu Pro Lys Phe Gly Leu
    130                 135                 140

Val Glu Ile Ala Phe Asn Ile Ser Gly Leu Ser Tyr Ser Asn Pro Phe
145                 150                 155                 160
```

```
Asp Thr Ser Asp Ile Asp Val Trp Val His Ile Glu Thr Pro Ser Gly
            165                 170                 175

Ser Arg Val Ala Val Pro Ala Phe Tyr Phe Gln Asn Tyr Thr Val Lys
        180                 185                 190

Arg Leu Gly Pro Gly Glu Glu Ile Ile Val Arg Val Gly Arg Pro Tyr
    195                 200                 205

Trp Leu Ala Arg Phe Ala Pro Val Glu Glu Gly Val His Lys Phe Tyr
210                 215                 220

Val Lys Ala Val Asp Gly Arg Gly Ser Ala Val Ser Glu Ile Arg
225                 230                 235                 240

Glu Phe Met Val Lys Gly Val Ala Gly Arg Gly Phe Val Arg Val Asp
                245                 250                 255

Ser Gly Lys Arg Leu Phe Val Phe Asp Ser Gly Glu Ser Met Phe Met
            260                 265                 270

Leu Gly Ile Asp Val Ala Trp Pro Asp Arg Arg Ser Ser Ile Ser
        275                 280                 285

Phe Tyr Glu Gln Trp Phe Asp Lys Leu Asn Lys Ser Gly Ile Lys Val
    290                 295                 300

Val Arg Ile Gly Leu Val Pro Trp Ala Leu Thr Leu Glu Trp Ser Lys
305                 310                 315                 320

Leu His Tyr Tyr Ser Leu Asp Asp Ala Ala Arg Ile Asp Glu Ile Val
                325                 330                 335

Lys Leu Ala Glu Lys Tyr Asp Ile Tyr Ile Val Phe Val Phe Met Trp
            340                 345                 350

His Gly Glu Leu Ala Asp Asn Trp Gly Asp Asn Pro Tyr Asn Ala Ala
        355                 360                 365

Arg Gly Gly Pro Leu Gln Ser Pro Glu Glu Phe Trp Ser Asn Ala Val
    370                 375                 380

Ala Ile Ser Ile Phe Lys Asp Lys Val Arg Tyr Ile Ile Ala Arg Trp
385                 390                 395                 400

Gly Tyr Ser Thr His Ile Leu Ala Trp Glu Leu Ile Asn Glu Ala Asp
                405                 410                 415

Leu Thr Thr Asn Phe Phe Ser Ala Arg Ser Ala Phe Val Ser Trp Val
            420                 425                 430

Lys Glu Ile Ser Ser Tyr Ile Lys Ser Val Asp Pro Tyr Asn Arg Ile
        435                 440                 445

Val Thr Val Asn Leu Ala Asp Tyr Asn Ser Glu Pro Arg Val Trp Ser
    450                 455                 460

Val Glu Ser Ile Asp Ile Ile Asn Val His Arg Tyr Gly Pro Glu Gly
465                 470                 475                 480

Phe Lys Asp Ile Ala Leu Ala Ile Pro Ser Ile Val Glu Gly Leu Trp
                485                 490                 495

Asn Thr Tyr Arg Lys Pro Ile Ile Ile Thr Glu Phe Gly Val Asp Tyr
            500                 505                 510

Arg Trp Ile Gly Tyr Pro Gly Phe Lys Gly Thr Pro Tyr Trp Ala Tyr
        515                 520                 525

Asp Lys Ser Gly Val Gly Leu His Glu Gly Leu Trp Ser Ser Ile Phe
    530                 535                 540

Ser Leu Ser Pro Val Ser Ala Met Ser Trp Trp Asp Thr Gln Ile
545                 550                 555                 560

Asp Ser Tyr Asn Leu Trp Tyr His Tyr Lys Ala Leu Tyr Glu Phe Leu
                565                 570                 575

Lys Ser Val Asp Pro Val Arg Gly Gly Leu Gly Lys Ala Arg Ala Ser
```

```
                    580             585              590
Leu Val Ile Thr Asp Val Thr Pro Ser Ser Ile Thr Leu Tyr Pro Leu
            595                 600             605

Ala Gly Trp Val Trp Val Ser Pro Val Arg Glu Asn Arg Leu Val Ile
        610             615                 620

Arg Pro Asp Gly Ala Ile Glu Gly Arg Val Asp Leu Leu Ser Gly Phe
625                 630                 635                 640

Ile Tyr Gly Thr Cys His Ser Gln Arg Thr Leu Asn Pro Val Phe Thr
                645                 650                 655

Val Met Phe Ile Asp Arg Gly Arg Val Val Leu His Ile Asn Ser Val
            660                 665                 670

Gly Arg Gly Ser Ala Lys Leu Val Ile Tyr Val Asn Gly Ser Leu Ala
        675                 680                 685

Thr Gln Leu Asp Leu Pro Asp Lys Asp Gly Lys Ser Asp Gly Ser Ala
    690                 695                 700

Asn Glu Tyr Asp Met Asp Val Glu Leu Trp Phe Glu Pro Gly Thr Tyr
705                 710                 715                 720

Glu Ile Lys Ile Asp Ser Glu Ala Cys Asp Trp Phe Thr Trp Asp Tyr
                725                 730                 735

Ile Val Phe Glu Asn Ala Val Tyr Arg Ala Ala Lys Val Asp Leu Tyr
            740                 745                 750

Ala Leu Ala Asn Ser Thr Phe Ala Met Leu Trp Val Arg Asn Lys Asp
        755                 760                 765

Tyr Asn Trp Trp Asn Val Val Leu Asn Lys Thr Leu Glu Pro Ala
    770                 775                 780

Glu Gly Val Glu Val Glu Ile Arg Gly Leu Gln Asp Gly Val Tyr Arg
785                 790                 795                 800

Val Glu Phe Trp Asp Thr Cys Arg Gly Val Val Val Lys Ser Met Glu
                805                 810                 815

Val Gln Val Ser Asn Gly Val Ala Arg Val Pro Val Gly Ser Val Glu
            820                 825                 830

Lys Asp Ile Ala Met Lys Ile Thr Arg Ala Gly His His His His His
        835                 840                 845

His

<210> SEQ ID NO 6
<211> LENGTH: 611
<212> TYPE: PRT
<213> ORGANISM: Caldicellulosiruptor saccharolyticus

<400> SEQUENCE: 6

Met Arg Lys Lys Ile Thr Ser Leu Ile Ser Tyr Val Ile Ala Phe Leu
1               5                   10                  15

Ile Leu Leu Thr Leu Ser Val Thr Gly Phe Gly Ala Pro Ser Asn Ile
            20                  25                  30

Lys Ile Thr Asp Phe Lys His Leu Thr Ser Val Ala Tyr Lys Tyr Ser
        35                  40                  45

Lys Phe Glu Ile Ser Phe Lys Thr Pro Ala Phe Lys Gly Asn Cys Phe
    50                  55                  60

Asp Pro Asp Glu Ile Asp Ile Trp Gly Glu Phe Val Ser Pro Ser Gly
65                  70                  75                  80

Lys Lys Tyr Val Met Pro Ala Phe Trp Tyr Gln Asp Tyr Lys Arg Gln
                85                  90                  95

Leu Leu Pro Ile Asn Glu Lys Lys Leu Glu Arg Leu Asn Lys Asn Gly
```

```
            100             105             110
Ile Gly Gly Thr Ala Ser Asn Asn Pro Asn Glu Pro Gln Gly Lys Glu
            115             120             125

Val Leu Thr Lys Val Gly Gln Pro Glu Trp Arg Ile Arg Phe Cys Pro
130             135             140

Val Glu Ile Gly Lys Trp Lys Tyr Thr Ile Tyr Val Lys Ala Lys Gly
145             150             155             160

Arg Val Gln Asp Phe Lys Lys Gly Glu Phe Ser Val Lys Glu Ala Lys
                165             170             175

Asn His Gly Phe Ile Arg Val Glu Pro Lys Lys Arg His Phe Val
            180             185             190

Phe Asp Asp Gly Thr Pro Tyr Ile Pro Ile Gly Gln Asn Val Ala Trp
            195             200             205

Trp Thr Ser Pro Thr Arg Gly Ser Tyr Asp Tyr Asn Val Trp Phe Ser
            210             215             220

Lys Met Ala Glu Ser Gly Ala Asn Phe Ala Arg Ile Trp Met Gly Ser
225             230             235             240

Trp Ser Phe Gly Leu Tyr Trp Asn Asp Thr Gly Ile Tyr Asp Phe Thr
                245             250             255

Asn Arg Leu Asp Arg Ala Tyr Gln Leu Asp Lys Val Leu Glu Leu Ala
                260             265             270

Glu Gln Lys Gly Ile Tyr Ile Met Leu Thr Phe Ile Asn His Gly Gln
            275             280             285

Phe Ser Thr Lys Val Asn Pro Gln Trp Asn Glu Asn Pro Trp Asn Lys
            290             295             300

Lys Asn Gly Gly Ile Leu Thr Lys Pro Glu Glu Phe Phe Thr Asn Thr
305             310             315             320

Glu Ala Lys Lys Gln Phe Lys Lys Ile Ile Arg Tyr Ile Ile Ala Arg
                325             330             335

Trp Gly Tyr Ser Thr Asn Ile Met Ser Trp Glu Leu Phe Asn Glu Val
                340             345             350

Ser Trp Thr Asp Asn Tyr Asp Pro Glu Lys Ser Asn Ala Trp His Lys
            355             360             365

Glu Met Ala Leu Phe Ile Lys Ser Ile Asp Pro Tyr Lys His Leu Val
            370             375             380

Ser Ser Ser Ala Val Leu Tyr Asp Pro Leu Glu Lys Val Lys Glu
385             390             395             400

Leu Asp Phe Ile Asn Ile His Asp Tyr Gly Ile Thr Asn Phe Cys Lys
                405             410             415

Asn Ile Pro Ser Lys Gln Arg Asp Ile Ala Asp Met Tyr Asn Lys Pro
            420             425             430

Ala Phe Phe Cys Glu Met Gly Ile Ala Ser Asp Pro Thr Thr Thr Lys
            435             440             445

Arg Leu Asp Pro Lys Gly Met His Val His Leu Gly Leu Trp Ala Gly
            450             455             460

Val Met Gly Gly Gly Ala Gly Thr Gly Met Thr Trp Trp Asp Ser
465             470             475             480

Tyr Val His Pro Leu Asn Leu Tyr Thr Tyr Phe Lys Pro Val Ser Leu
                485             490             495

Tyr Val Lys Lys Ile Pro Trp Asn Asp Pro Phe Leu Lys Tyr Ile Asp
            500             505             510

Glu Met Gln Leu Asp Ile Ser Asn Phe Asp Val Gly Val His Gly Tyr
            515             520             525
```

```
Ile Lys Gln Asp Ser Ala Tyr Leu Trp Phe Tyr Asp Thr Glu Tyr Ser
        530                 535                 540

His Ile Gly Gly Ile Glu Arg Leu Phe Lys Asp Val Thr Val Arg Ile
545                 550                 555                 560

Lys Leu Asp Asn Gly Ile Tyr Gln Val Glu Trp Phe Asp Thr Phe Ser
                565                 570                 575

Gly Asn Ala Val Lys Lys Glu Asn Val Ala Val Lys Asn Lys Ile Leu
            580                 585                 590

Asn Ile Lys Met Pro Asn Trp Lys Ile Asp Ile Ala Phe Ile Ala Lys
        595                 600                 605

Lys Val Lys
    610

<210> SEQ ID NO 7
<211> LENGTH: 787
<212> TYPE: PRT
<213> ORGANISM: Clostridium leptum

<400> SEQUENCE: 7

Met Thr Gln Asp Lys Glu Leu Cys Phe Leu Trp Asp Asn Thr Ile His
1               5                   10                  15

Gly Ala Ile Pro Ala Phe Glu Lys Phe Glu Ala Ala Phe Ala Phe Glu
            20                  25                  30

Lys Val Phe Glu His Pro Tyr Cys Pro Glu Val Asp Leu Lys Ala
        35                  40                  45

Tyr Ile Leu Lys Pro Asn Gly Asp Gln Lys Gln Ile Ser Gly Phe Trp
50                  55                  60

Tyr Glu Gly Phe Gln Arg Val Leu Arg Asn Gly Arg Glu Ile Leu Ile
65                  70                  75                  80

Ser Thr Leu Glu Lys Asp Trp Arg Ile Arg Tyr Ser Ala Gln Val Pro
                85                  90                  95

Gly Glu Tyr Arg Tyr Tyr Val Thr Leu Leu Asp Lys Lys Arg His Arg
            100                 105                 110

Ser Tyr Arg Tyr Pro Glu Lys Gly Glu Leu Ser Phe Thr Val Thr Pro
        115                 120                 125

Ser Asp Arg Lys Gly Phe Leu Arg Val Ser Ala Arg Asp Pro Ala Tyr
130                 135                 140

Leu Glu Phe Ser Asp Gly Ser Pro Tyr Leu Gly Ile Gly His Asn Leu
145                 150                 155                 160

Cys Gly Trp Glu Trp Gly Gly Thr Asp Asn Arg Leu Gly Thr Tyr Glu
                165                 170                 175

Tyr Asp Arg Trp Leu Ser Ser Met Ala Gln Asn Gly Ala Asn Leu Thr
            180                 185                 190

Gln Phe Asp Phe Cys Glu Gly Asp Gln Ile Glu Trp Thr Pro Cys Asp
        195                 200                 205

Asn Glu Leu Pro Phe Ser Glu Asp Trp Lys Gly Leu Asn Glu Tyr Asn
    210                 215                 220

Gln Gln Asn Ala Trp Lys Met Asp Arg Arg Phe Gln Thr Ala Glu Glu
225                 230                 235                 240

Leu Gly Ile Phe Phe Arg Leu Ser Leu Phe His Trp Glu Asp Phe Asp
                245                 250                 255

Asp Glu Thr Glu Lys Phe Pro Asp Trp Gly Trp Asn Arg Asn Pro Tyr
            260                 265                 270

His Asp Gln Asn Gly Gly Pro Ala Lys Asn Val Ser Glu Phe Phe Glu
```

```
              275                 280                 285
Lys Pro Ala Cys Lys Lys Tyr Val Arg Tyr Tyr Leu Lys Tyr Val Ala
290                 295                 300

Ala Arg Trp Gly Tyr Ser Pro Asn Leu Met Ala Tyr Glu Leu Trp Asn
305                 310                 315                 320

Glu Ile Asp Ala Pro Glu Val Met Trp Arg Ala Gly Glu Asp Tyr Asp
                325                 330                 335

Gln Glu Ala Ser Lys Val Ile Gly Trp His Ser Glu Met Gly Ser Tyr
            340                 345                 350

Leu Lys Gln Leu Asp Ser Lys His Leu Val Thr Ser Ser Phe Ala Asp
        355                 360                 365

Ser Arg Arg Asp Leu Asn Leu Trp Gln Leu Pro Cys Ile Asp Leu Thr
370                 375                 380

Thr Val His Arg Tyr Thr Tyr Phe Asn Glu Glu Tyr Gly Gln Arg Gln
385                 390                 395                 400

Tyr Asp Thr Glu Gly Ala Leu Ser Ala Val Leu Lys Glu Arg Phe Ser
                405                 410                 415

Gln Val Glu Lys Pro Val Leu Phe Gly Glu Phe Ala Leu Ser Pro Gly
            420                 425                 430

Gly Asp Ile Gln Lys Asp Tyr Asp Pro Glu Gly Ile Glu Phe His Asn
        435                 440                 445

Gln Leu Trp Ala Ser Leu Leu Lys Ser Leu Gly Thr Ala Met His
450                 455                 460

Trp Thr Trp Gly Ser Tyr Val Asp Lys Asn Arg Leu Tyr Ser Lys Tyr
465                 470                 475                 480

Leu Pro Val Ser Arg Phe Phe Ala Gly Glu Asp Leu Arg Arg Thr Val
                485                 490                 495

Ser Phe Ser Asn Leu Asp Ala Val Thr Glu Arg Leu Leu Ile Leu Gly
            500                 505                 510

Leu Arg Lys Thr Asp Arg Ala Cys Leu Trp Ile Lys Lys Arg Asp Trp
        515                 520                 525

Gly Phe Cys Gln Ala Asn Glu Gly Lys Ser Ser Val Glu Lys Gly
530                 535                 540

Arg Thr Ala Glu Val Pro Gly Leu Lys Ala Gly Asp Tyr Gln Val Glu
545                 550                 555                 560

Phe Tyr Asp Thr Lys Thr Gly Lys Ile Leu Glu Lys Ser Thr Ile Thr
                565                 570                 575

Ala Ala Gly Glu Thr Leu Thr Leu Leu Leu Pro Gly Phe Ser Gly Asp
            580                 585                 590

Leu Ala Val Lys Leu Lys Pro Lys Glu Lys Asp Thr Leu Trp Lys Ser
        595                 600                 605

Ile Asp Phe Pro Arg Pro Lys Lys Ser Ser Arg Thr Glu Phe Leu Gln
610                 615                 620

Asp Gly Ala Ile Leu Ser Ala Gly Ala Gly Phe Cys Gly Glu Lys
625                 630                 635                 640

Glu Glu Tyr Arg Phe Val Tyr Gln Gln Ala Ser Gly Asp Phe Arg Leu
                645                 650                 655

Ser Ala Glu Ile Arg Ser Leu Thr Asn Leu Gly Glu Arg Val Ala Ala
            660                 665                 670

Gly Leu Met Val Arg Asp Ser Leu Glu Pro Glu Ser Gly Tyr Ile Ala
        675                 680                 685

Val Leu Leu His Pro Tyr Ser Lys Ala Gln Val Ile Ile Arg Arg Asp
690                 695                 700
```

```
Gly Asn Thr Glu Ile Leu Lys Glu Phe Asp Ala Gly Glu Arg Pro Cys
705                 710                 715                 720

Phe Gly Leu Asn Arg Ala Ala Gly Val Leu Thr Val Arg Leu Ala Lys
            725                 730                 735

Gln Gly Arg Glu Trp Glu Pro Val Phe Gln Ile Gln Val Ser Lys Glu
        740                 745                 750

Lys Glu Leu Leu Val Gly Leu Thr Ala Ala Ser Ser His Thr Ile Thr
    755                 760                 765

Tyr Ile Thr Ala Glu Phe His Gln Leu Arg Leu Ala Lys Ile Glu Glu
770                 775                 780

Glu Ile Leu
785

<210> SEQ ID NO 8
<211> LENGTH: 787
<212> TYPE: PRT
<213> ORGANISM: Opitutus terrae

<400> SEQUENCE: 8

Met Thr Gln Asp Lys Glu Leu Cys Phe Leu Trp Asp Asn Thr Ile His
1               5                   10                  15

Gly Ala Ile Pro Ala Phe Glu Lys Phe Glu Ala Ala Phe Ala Phe Glu
            20                  25                  30

Lys Val Phe Glu His Pro Tyr Cys Pro Glu Glu Val Asp Leu Lys Ala
        35                  40                  45

Tyr Ile Leu Lys Pro Asn Gly Asp Gln Lys Gln Ile Ser Gly Phe Trp
    50                  55                  60

Tyr Glu Gly Phe Gln Arg Val Leu Arg Asn Gly Arg Glu Ile Leu Ile
65                  70                  75                  80

Ser Thr Leu Glu Lys Asp Trp Arg Ile Arg Tyr Ser Ala Gln Val Pro
                85                  90                  95

Gly Glu Tyr Arg Tyr Tyr Val Thr Leu Leu Asp Lys Lys Arg His Arg
            100                 105                 110

Ser Tyr Arg Tyr Pro Glu Lys Gly Glu Leu Ser Phe Thr Val Thr Pro
        115                 120                 125

Ser Asp Arg Lys Gly Phe Leu Arg Val Ser Ala Arg Asp Pro Ala Tyr
    130                 135                 140

Leu Glu Phe Ser Asp Gly Ser Pro Tyr Leu Gly Ile Gly His Asn Leu
145                 150                 155                 160

Cys Gly Trp Glu Trp Gly Gly Thr Asp Asn Arg Leu Gly Thr Tyr Glu
                165                 170                 175

Tyr Asp Arg Trp Leu Ser Ser Met Ala Gln Asn Gly Ala Asn Leu Thr
            180                 185                 190

Gln Phe Asp Phe Cys Glu Gly Asp Gln Ile Glu Trp Thr Pro Cys Asp
        195                 200                 205

Asn Glu Leu Pro Phe Ser Glu Asp Trp Lys Gly Leu Asn Glu Tyr Asn
    210                 215                 220

Gln Gln Asn Ala Trp Lys Met Asp Arg Arg Phe Gln Thr Ala Glu Glu
225                 230                 235                 240

Leu Gly Ile Phe Phe Arg Leu Ser Leu Phe His Trp Glu Asp Phe Asp
                245                 250                 255

Asp Glu Thr Glu Lys Phe Pro Asp Trp Gly Trp Asn Arg Asn Pro Tyr
            260                 265                 270

His Asp Gln Asn Gly Gly Pro Ala Lys Asn Val Ser Glu Phe Phe Glu
```

-continued

```
            275                 280                 285
Lys Pro Ala Cys Lys Lys Tyr Val Arg Tyr Tyr Leu Lys Tyr Val Ala
            290                 295                 300

Ala Arg Trp Gly Tyr Ser Pro Asn Leu Met Ala Tyr Glu Leu Trp Asn
305                 310                 315                 320

Glu Ile Asp Ala Pro Glu Val Met Trp Arg Ala Gly Glu Asp Tyr Asp
                325                 330                 335

Gln Glu Ala Ser Lys Val Ile Gly Trp His Ser Glu Met Gly Ser Tyr
            340                 345                 350

Leu Lys Gln Leu Asp Ser Lys His Leu Val Thr Ser Ser Phe Ala Asp
            355                 360                 365

Ser Arg Arg Asp Leu Asn Leu Trp Gln Leu Pro Cys Ile Asp Leu Thr
370                 375                 380

Thr Val His Arg Tyr Thr Tyr Phe Asn Glu Glu Tyr Gly Gln Arg Gln
385                 390                 395                 400

Tyr Asp Thr Glu Gly Ala Leu Ser Ala Val Leu Lys Glu Arg Phe Ser
                405                 410                 415

Gln Val Glu Lys Pro Val Leu Phe Gly Glu Phe Ala Leu Ser Pro Gly
            420                 425                 430

Gly Asp Ile Gln Lys Asp Tyr Asp Pro Glu Gly Ile Glu Phe His Asn
            435                 440                 445

Gln Leu Trp Ala Ser Leu Leu Lys Ser Leu Gly Thr Ala Met His
            450                 455                 460

Trp Thr Trp Gly Ser Tyr Val Asp Lys Asn Arg Leu Tyr Ser Lys Tyr
465                 470                 475                 480

Leu Pro Val Ser Arg Phe Phe Ala Gly Glu Asp Leu Arg Arg Thr Val
                485                 490                 495

Ser Phe Ser Asn Leu Asp Ala Val Thr Glu Arg Leu Leu Ile Leu Gly
            500                 505                 510

Leu Arg Lys Thr Asp Arg Ala Cys Leu Trp Ile Lys Lys Arg Asp Trp
            515                 520                 525

Gly Phe Cys Gln Ala Asn Glu Gly Lys Ser Ser Val Glu Lys Gly
530                 535                 540

Arg Thr Ala Glu Val Pro Gly Leu Lys Ala Gly Asp Tyr Gln Val Glu
545                 550                 555                 560

Phe Tyr Asp Thr Lys Thr Gly Lys Ile Leu Glu Lys Ser Thr Ile Thr
                565                 570                 575

Ala Ala Gly Glu Thr Leu Thr Leu Leu Leu Pro Gly Phe Ser Gly Asp
            580                 585                 590

Leu Ala Val Lys Leu Lys Pro Lys Glu Lys Asp Thr Leu Trp Lys Ser
            595                 600                 605

Ile Asp Phe Pro Arg Pro Lys Lys Ser Ser Arg Thr Glu Phe Leu Gln
610                 615                 620

Asp Gly Ala Ile Leu Ser Ala Gly Ala Gly Phe Cys Gly Glu Lys
625                 630                 635                 640

Glu Glu Tyr Arg Phe Val Tyr Gln Gln Ala Ser Gly Asp Phe Arg Leu
                645                 650                 655

Ser Ala Glu Ile Arg Ser Leu Thr Asn Leu Gly Glu Arg Val Ala Ala
            660                 665                 670

Gly Leu Met Val Arg Asp Ser Leu Glu Pro Glu Ser Gly Tyr Ile Ala
            675                 680                 685

Val Leu Leu His Pro Tyr Ser Lys Ala Gln Val Ile Ile Arg Arg Asp
            690                 695                 700
```

```
Gly Asn Thr Glu Ile Leu Lys Glu Phe Asp Ala Gly Glu Arg Pro Cys
705                 710                 715                 720

Phe Gly Leu Asn Arg Ala Ala Gly Val Leu Thr Val Arg Leu Ala Lys
            725                 730                 735

Gln Gly Arg Glu Trp Glu Pro Val Phe Gln Ile Gln Val Ser Lys Glu
        740                 745                 750

Lys Glu Leu Leu Val Gly Leu Thr Ala Ala Ser Ser His Thr Ile Thr
    755                 760                 765

Tyr Ile Thr Ala Glu Phe His Gln Leu Arg Leu Ala Lys Ile Glu Glu
770                 775                 780

Glu Ile Leu
785

<210> SEQ ID NO 9
<211> LENGTH: 504
<212> TYPE: PRT
<213> ORGANISM: Unknown
<220> FEATURE:
<223> OTHER INFORMATION: Methylobacterium sp.

<400> SEQUENCE: 9

Met Thr Asp Asp Arg Ala Leu Asp Pro Asp Cys Ser Leu Ala Asp Gly
1               5                   10                  15

Pro Ser Pro Ser Pro Arg Pro Asp Pro Ala Pro Ala Arg Thr Ala Gly
            20                  25                  30

Ala Arg Gly Gly Arg Leu Pro Trp Ile Arg Val Ala Gly Pro Gly Ile
        35                  40                  45

Pro Tyr Phe Glu Thr Glu Thr Gly Ala Ala Trp Thr Pro Val Gly Gln
50                  55                  60

Asn Asp Ala Ile Ser Trp His Glu Leu Glu Gly Leu Phe Gly Arg Arg
65                  70                  75                  80

Asp Leu Ala Ala Ala Glu Ala His Leu Arg His Leu Ala Asp His Gly
                85                  90                  95

Val Thr Cys Leu Arg Leu Met Leu Glu Tyr Ala Gln Val Arg His Arg
            100                 105                 110

Tyr Ile Glu Arg Pro Val Gly Arg Phe Val Pro Ala Met Val Arg Leu
        115                 120                 125

Trp Asp Asp Leu Phe Ala Leu Cys Glu Thr Val Gly Leu Arg Ile Leu
130                 135                 140

Leu Thr Pro Phe Asp Thr Phe Trp Met Trp Leu His Trp His Arg His
145                 150                 155                 160

Pro Tyr Asn Arg Arg His Gly Gly Pro Leu Ala Glu Pro Ser Arg Phe
                165                 170                 175

Leu Leu Asp Pro Gln Val Arg Glu Ala Ile Lys Asn Arg Leu Ala Phe
            180                 185                 190

Ala Val Ala Arg Trp Gly Gly Ser Gly Ala Leu Phe Ala Trp Asp Leu
        195                 200                 205

Trp Asn Glu Ile His Pro Ala His Ala Glu Gly Ser Ala Glu Gly Phe
210                 215                 220

Ala Pro Phe Ile Ala Asp Leu Ser Arg His Val Arg Ala Leu Glu Thr
225                 230                 235                 240

Arg Leu Tyr Gly Arg Ala His Pro Gln Thr Val Ser Leu Phe Gly Pro
                245                 250                 255

Glu Leu Gly Trp Arg Pro His Leu Gly Leu Glu Glu Pro Ile Phe Arg
            260                 265                 270
```

```
His Pro Asp Leu Asp Phe Ala Thr Leu His Ile Tyr Ala Glu Gly Thr
            275                 280                 285

Ile Asp Asp Pro Arg Asn Thr Val Glu Pro Ala Ile Ala Met Gly Arg
            290                 295                 300

Ile Val Arg Glu Gly Leu Ala Gln Ile Arg Asp Gly Arg Pro Phe Leu
305                 310                 315                 320

Asp Ser Glu His Gly Pro Ile His Ser Phe Lys Asp Arg Arg Leu Thr
            325                 330                 335

Leu Pro Glu Pro Phe Asp Asp Glu Tyr Phe Arg His Met Gln Trp Ala
            340                 345                 350

His Leu Ala Ser Gly Gly Ala Gly Gly Met Arg Trp Pro Asn Arg
            355                 360                 365

His Pro His Ser Leu Thr Ala Gly Met Arg Ala Ala Gln Arg Gly Leu
            370                 375                 380

Ser Gly Phe Leu Pro Leu Ile Asp Trp Arg Arg Phe Arg Arg Arg Asn
385                 390                 395                 400

Leu Ser Gly Asp Leu Gly Asp Pro Gly Pro Gly Ala Ala Leu Phe Ala
            405                 410                 415

Cys Gly Asp Ala Glu Gln Ala Val Ile Trp Cys Leu Arg Ala Asp Ser
            420                 425                 430

Leu Ala Pro Asp Gly Arg Leu Arg Arg Asp Ala Ala Pro Leu Gly Ile
            435                 440                 445

Arg Leu Ala Leu Pro Gly Leu Arg Ala Gly Arg Tyr Ala Leu Thr Ala
450                 455                 460

Trp Asp Thr Arg Ala Gly Arg Pro Cys Gly Arg Glu Val Thr Ala
465                 470                 475                 480

Arg Asp Gly Val Ala Thr Glu Ile Glu Pro Pro Pro Phe Val Thr Asp
            485                 490                 495

Val Ala Leu Ala Val Arg Arg Val
            500

<210> SEQ ID NO 10
<211> LENGTH: 777
<212> TYPE: PRT
<213> ORGANISM: Victivallis vadensis

<400> SEQUENCE: 10

Met Arg Arg Ile Ser Ala Leu Phe Pro Thr Ile Leu Ser Leu Ala Phe
1               5                   10                  15

Leu Pro Leu Leu Asn Ala Ala Glu Leu Thr Gly Val Trp Lys Ala Asp
            20                  25                  30

Gly Thr Asn Thr Pro His Ser Ser Pro Glu Ala Pro Gly Glu Ala Ala
            35                  40                  45

Val Thr Val Arg Phe Pro Gly Ser Ala Gln Leu Tyr Arg Glu Pro Asp
    50                  55                  60

Arg Ala Thr Phe Arg Pro Ser Arg Glu Ala Phe Glu Ala Ala Glu Phe
65                  70                  75                  80

Glu Leu Glu Ala Arg Val Ile Thr Asp Thr Pro Asp Pro Val Arg Ala
                85                  90                  95

Trp Leu Phe Phe Lys Asp Lys Asp Gly Arg Trp Tyr Gln Thr Ile Glu
            100                 105                 110

Glu Tyr Arg Leu Ala Pro Gly Val Trp Gln Lys Leu Ser Ala Arg Leu
            115                 120                 125

Asp Arg Thr Gly Ala Val Trp Arg Gly Val Gly His Thr Ala Thr Phe
```

-continued

```
            130                 135                 140
Asp Ala Met Ala Ala Thr Glu Phe Tyr Ala Gly Gly Ile Ser Val Tyr
145                 150                 155                 160

Gly Glu Glu Lys Arg Glu Phe Thr Leu Glu Val Arg Asn Ala Ala Arg
                165                 170                 175

Thr Gly Lys Arg Glu Pro Gly Lys Leu Ala Leu Leu Asp Cys His Phe
            180                 185                 190

Pro Glu Gln Gly Glu Ala Asn Ala Leu Phe Gln Gly Arg Phe Arg Leu
        195                 200                 205

Leu Arg Glu Phe Phe Asn Pro Phe Asp Pro Asp Glu Val Thr Val Asp
210                 215                 220

Phe Glu Ile Lys Ala Pro Asn Gly Lys Leu Thr Arg Leu Pro Ala Phe
225                 230                 235                 240

Tyr Ser Arg Asp Tyr Glu Arg Arg Leu His His Thr Arg Glu Thr Ala
                245                 250                 255

Thr Pro Ile Gly Gln Gly Phe Trp Glu Phe Arg Phe Thr Pro Pro Val
            260                 265                 270

Pro Gly Glu Tyr Arg Leu Arg Ala Val Ile Ala Asp Lys Thr Ala Arg
        275                 280                 285

Glu Thr Val Thr Gly Ser Trp Lys Ser Phe Thr Ala Leu Pro Ser Arg
290                 295                 300

Arg Pro Gly Leu Val Arg Ala Ser Glu Lys Asp Pro Phe Phe Glu Leu
305                 310                 315                 320

Gly Thr Gly Glu Phe Phe Phe Pro Val Gly Leu Asn Ile His Thr Asn
                325                 330                 335

Thr Asp Arg Arg Ser Glu Phe Gly Phe Lys Phe Gly Gln Leu Pro Asp
            340                 345                 350

Arg Gly Thr Phe Asp Tyr Asp Tyr Leu Glu Ala Cys Gly Arg Gly
        355                 360                 365

Gly Ile Asn Ala Val Glu Ile Trp Met Ala Gly Trp Thr Tyr Ala Ile
370                 375                 380

Glu His Asp Ala Thr Arg Ala Gly Asn Tyr Gly Val Gly Arg Tyr Asn
385                 390                 395                 400

Leu Glu Ala Ala Trp Lys Leu Asp His Ile Phe Glu Gln Ala Arg Lys
                405                 410                 415

Asn Gly Ile Tyr Leu Asn Leu Ile Leu Asp Asn His Gly Arg Leu Ser
            420                 425                 430

Asp Arg Ser Asp Pro Glu Trp Gln Asp Asn Pro Ile Asn Ser Thr Thr
        435                 440                 445

Pro Tyr Ala Lys Ala Asn Gly Gly Phe Leu Ala Asn Pro Ala Asp Phe
450                 455                 460

Phe Arg Ser Glu Ala Ala Glu Lys Asn Asp Arg Lys Arg Ala Arg Tyr
465                 470                 475                 480

Ile Ala Ala Arg Trp Gly Asn Ala Pro Asn Leu Met Ala Val Glu Leu
                485                 490                 495

Trp Ser Glu Val Asp Leu Thr Glu Asp Tyr Trp Gly Arg Tyr Asn Asp
            500                 505                 510

Gly Ser Ala Ile Arg Trp Ala Glu Lys Ala Ala Phe Leu Gln Ala
        515                 520                 525

Asn Ser Arg Pro Asp Leu Pro Val Ser Ile His Phe Cys Ser Asp Tyr
530                 535                 540

Asn Asn Val Arg Arg Phe Ile Lys Leu Phe Asp Asn Pro Ser Ile Thr
545                 550                 555                 560
```

```
His Leu Ala Gly Asp Ala Tyr Arg Ser Pro Gln Ile His Phe Val Asp
            565                 570                 575

His Leu Arg Gly Tyr Glu Gln Asn Met Arg Tyr Asn Lys Pro Gln Leu
        580                 585                 590

Ile Thr Glu Phe Gly Gly Asn Pro Gln Gly Ser Ser Glu Arg Gln Val
    595                 600                 605

Leu Ala Asp Ile His Ser Gly Leu Trp Ser Ser Leu Phe Val Arg Leu
610                 615                 620

Ala Gly Thr Pro Phe Leu Trp Trp His Asp Phe Val His Leu Arg Asn
625                 630                 635                 640

His Tyr Gln His Tyr Leu Gly Phe Ser Arg Tyr Leu Ala Gly Ile Asp
                645                 650                 655

Leu Arg Gly Lys Glu Arg Val Tyr Phe Thr Pro Ala Val Ala Val Pro
            660                 665                 670

Ala Asn Gln Gln Lys Tyr Glu Ser Leu Gly Leu Ser Leu Pro Ala Ala
        675                 680                 685

Ala Tyr Gly Trp Ile Tyr Asn Arg Asn Ala Met Leu Glu Tyr Pro Asp
    690                 695                 700

Asp Pro Asn Gln Phe Pro Glu Thr Arg Pro Gly Ser Val Thr Leu Ala
705                 710                 715                 720

Gly His Asn Leu Thr Gly Gly Val Tyr Leu Leu Arg Trp Phe Val Pro
                725                 730                 735

Leu Thr Gly Glu Cys Leu Pro Gly Glu Leu Lys Leu Asn Val Glu Ala
            740                 745                 750

Gly Lys Pro Val Thr Phe Ala Val Pro Ser Phe Arg Leu Asp Leu Ala
        755                 760                 765

Phe Lys Leu Glu Lys Thr Glu Ala Lys
    770                 775

<210> SEQ ID NO 11
<211> LENGTH: 566
<212> TYPE: PRT
<213> ORGANISM: Unknown
<220> FEATURE:
<223> OTHER INFORMATION: Anaeromyxobacter sp.

<400> SEQUENCE: 11

Met Ser Gly Val Thr Thr Arg Arg Leu His Cys Thr Gly Pro Arg Ser
1               5                   10                  15

Ala Ala Ala Ala Met Leu Ala Ala Leu Ala Leu Gly Cys Ala Arg
            20                  25                  30

Ala Pro Val Arg Pro Gly Ala Asp Ala Ala Gly Gly Arg Glu Ala Ala
        35                  40                  45

Val Asn Gly Val Val Glu Leu Arg Leu Ala Val Pro Ala Gly Ala Pro
    50                  55                  60

Val Arg Ala Glu Val Leu Ala Pro Ser Gly Ala Arg Ile His Val Pro
65                  70                  75                  80

Ala Phe Pro Val Pro Gly Gly Trp Ala Ala Arg Phe Arg Pro Arg Glu
                85                  90                  95

Pro Gly Arg His Arg Trp Val Ala Arg Ser Gly Glu Gly Ala Ala Ala
            100                 105                 110

Ala Glu Val Ala Arg Gly Glu Val Met Ala Glu Asp Arg Gly Leu Ala
        115                 120                 125

Gly Gln Val Ile Val Ser Gly Gly Thr Leu Arg Thr Glu Asp Gly Arg
    130                 135                 140
```

```
Pro Phe Arg Pro Leu Gly Glu Asn Arg Phe Asn Val Tyr Asp Pro Thr
145                 150                 155                 160

Trp Ser Asp Gly Leu Ser Pro Ala Asp Tyr Val Ala Arg Met Ala Ala
                165                 170                 175

Asp Gly Met Asn Ala Leu Arg Val Phe Val Phe Thr Ala Cys Gly Arg
            180                 185                 190

Ala Gly Thr Met Pro Asn Pro Gly Cys Leu Glu Pro Val Leu Gly Ala
        195                 200                 205

Phe Asp Glu Ala Ala Ala Arg Tyr Asp Ala Ile Phe Ala Ala Ala
    210                 215                 220

Glu Ala His Gly Val Lys Val Val Leu Ser Val Phe Ala Ile Gly Phe
225                 230                 235                 240

Thr Pro Gly Asp Ala Trp Lys Gly Trp Glu Glu Asn Pro Tyr Ser Ala
                245                 250                 255

Ala Arg Gly Gly Pro Ala Ala Gly Asn Thr Asp Phe Phe Leu Asp Pro
            260                 265                 270

Arg Ala Arg Glu Ala Ala Arg Ala Arg Leu Arg Tyr Val Leu Ala Arg
        275                 280                 285

Trp Gly Ala Ser Pro Ala Leu Leu Ala Ile Asp Leu Leu Asn Glu Pro
290                 295                 300

Glu Trp Asp Gly Ala Ile Pro Glu Asp His Trp Ile Pro Trp Ala Glu
305                 310                 315                 320

Asp Leu Ala Arg Thr Trp Arg Ala Glu Asp Pro Tyr Gly His Pro Val
                325                 330                 335

Thr Ala Gly Pro Val Gly Leu His Trp Asn Val Glu Glu Asp Glu Arg
            340                 345                 350

Ala Trp Trp Ala Ser Ala Ala Cys Asp Ile Val Gln Trp His Arg Tyr
        355                 360                 365

Gly Pro Asp Val His Asp Val His Asp Leu Ala Glu Ala Leu Val Glu
    370                 375                 380

Thr Thr Arg Asp Thr Ala Arg Tyr Gly Lys Pro Val Leu Ile Gly Glu
385                 390                 395                 400

Phe Gly Trp Gly Gly Asp Ala Lys Pro Glu His Asp His Thr His Val
                405                 410                 415

Gly Ile Trp Ala Ala Thr Phe Ala Gly Ala Gly Val Leu Ser His Ser
            420                 425                 430

Ala Pro Pro Phe Thr Glu Asp Ser Asp Glu Pro Met Thr Pro Ala Arg
        435                 440                 445

Ala Arg His Phe Arg Thr Leu Ala Ala Phe Leu Arg Arg Ala Glu Ala
    450                 455                 460

Arg Gly Pro Leu Ala Pro Ala Pro Glu Pro Ala Val Arg Arg Ala Pro
465                 470                 475                 480

Gly Leu Arg Ala Leu Ala Leu Gly Gly Glu Arg Ala Ala Ala Val Trp
                485                 490                 495

Leu Leu Ala Pro Arg Pro Gly Tyr Gly Gly Arg Val Lys Gly Ala Arg
            500                 505                 510

Leu Thr Leu Ala Gly Ile Ala Pro Gly Arg Trp Arg Val Thr Trp Val
        515                 520                 525

Glu Asp Val Ser Gly Glu Val Ile Ala Val Glu Glu Arg Asp Ala Ser
    530                 535                 540

Gly Pro Leu Pro Leu Asp Val Pro Pro Phe Ala Arg His Val Ala Ala
545                 550                 555                 560
```

Leu Val Glu Arg Ile Glu
                565

<210> SEQ ID NO 12
<211> LENGTH: 591
<212> TYPE: PRT
<213> ORGANISM: Herpetosiphon aurantiacus

<400> SEQUENCE: 12

Met Arg Arg Trp Leu Tyr Arg Leu His Leu Trp Leu Val Leu Leu Leu
 1               5                  10                  15

Leu Ile Ala Ala Cys Thr Gln Val Gly Glu Ser Gly Gly Asn Gln Thr
            20                  25                  30

Leu Ser Leu Arg Thr Leu Thr Gly Asn Ala Ala Val Phe Gly Thr Ile
        35                  40                  45

Glu Leu Ala Ile Asp Thr Ile Thr Val Ala Asn Pro Tyr Asp Pro
50                  55                  60

Asn Gln Ile Asp Leu Met Val Ser Phe Ile Ser Ala Thr Gly Gln Ile
65                  70                  75                  80

Tyr Arg Val Pro Ala Phe Trp Tyr Gln Asp Phe Asp Gln Leu Ser Leu
                85                  90                  95

Gln Pro Lys Gly Asn Pro Glu Trp Arg Val Arg Phe Thr Pro Ser Glu
            100                 105                 110

Pro Gly Ala Trp Gln Val Lys Ala Glu Leu Ala Lys Pro Ala Leu Ser
        115                 120                 125

Ser Asp Val Ile Thr Ile Glu Val Ser Ala Asn Lys Gln Ser Pro Gly
    130                 135                 140

Phe Val Arg Ile Asn Thr Ser Asn Pro Arg Tyr Phe Ala Arg Gln Asp
145                 150                 155                 160

Gly Thr Phe Phe Met Pro Ile Gly Leu Asn Leu Gly Trp Ser Thr Gln
                165                 170                 175

Gln Gly Thr Gly Ile Leu Arg Glu Tyr Glu His Trp Phe Asp Gln Leu
            180                 185                 190

Ser Lys Asn Gly Gly Asn Ile Ala Arg Ile Trp Met Ala Ser Trp Ser
        195                 200                 205

Phe Gly Ile Glu Trp Gln Asp Thr Gly Leu Gly Asp Tyr Ser Lys Arg
    210                 215                 220

Met Gln Gln Ala Trp Met Leu Asp Gln Ile Phe Lys Leu Ala Glu Gln
225                 230                 235                 240

Arg Asn Ile Thr Ile Met Leu Thr Leu Ile Asn His Gly Ala Phe Ser
                245                 250                 255

Thr Ser Thr Asp Ser Glu Trp Ala Ser Asn Pro Tyr Asn Ala Ala Asn
            260                 265                 270

Gly Gly Pro Ile Ala Glu Pro Arg Leu Phe Ala Thr Asp Ile Gln Ser
        275                 280                 285

Arg Glu Val Phe Lys His Arg Val Arg Tyr Ile Ala Ala Arg Trp Ala
    290                 295                 300

His Ser Pro Ser Leu Phe Ala Trp Glu Trp Asn Glu Ala Asn Trp
305                 310                 315                 320

Thr Pro Ile Asn Asp Ala Leu Met Gln Pro Trp Ile Ser Glu Met Thr
                325                 330                 335

Arg His Leu Ala Gln Phe Asp Pro Tyr Gln His Leu Val Ser Thr Ser
            340                 345                 350

Tyr Ala Ser Asn Thr Ser Thr Ser Met Trp Val Gln Pro Glu Ile Asn
        355                 360                 365

```
Phe Thr Gln His His Asp Tyr Thr Gly Arg Asp Leu Gly Gln Ala Phe
    370                 375                 380
Pro Leu Val Ile Arg Glu Leu Asn Ala Ala Pro Gln Lys Pro Ala
385                 390                 395                 400
Leu Val Ser Glu Leu Gly Tyr Ala Gly Thr Gly Arg Asp Glu Val Ile
                405                 410                 415
Asn Arg Asp Val Trp Gln Phe His Gln Gly Leu Trp Ala Ala Pro Phe
            420                 425                 430
Ser Gly Phe Ala Gly Ser Gly Met Tyr Trp Trp Asp Thr Leu Val
        435                 440                 445
Asp Pro Asp Asn Leu Trp Ser Glu Tyr Ser Lys Leu Ala Glu Phe Phe
450                 455                 460
Lys Asp Gln Asp Leu Thr Ile Tyr Asn Pro Val Val Ala Gln Ile Ser
465                 470                 475                 480
Pro Leu Lys Ala Arg Ala Leu Ala Leu Gln Thr Lys Ser Gln Ala Leu
                485                 490                 495
Val Trp Val Arg Ser Asn Glu Tyr Glu Pro Glu Ala Leu Thr Lys Ala
            500                 505                 510
Tyr Glu Glu Ala Leu Lys Lys Arg Glu Phe Asn Asp Thr Trp Glu Tyr
        515                 520                 525
Val Pro Pro Thr Tyr Ala Asp Leu Thr Leu Lys Leu Asn Gly Leu Glu
530                 535                 540
Ala Gly Asn Tyr Gln Ala Thr Trp Tyr Asp Pro Gln Thr Gly Thr Trp
545                 550                 555                 560
Ser Gln Pro Thr Thr Val Thr Leu Glu Ala Asn Gln Ser Ser Ile Ala
                565                 570                 575
Val Pro Ser Phe Asn Tyr Asp Leu Ala Leu Lys Leu Val Lys Gln
            580                 585                 590

<210> SEQ ID NO 13
<211> LENGTH: 557
<212> TYPE: PRT
<213> ORGANISM: Chitinophaga pinensis

<400> SEQUENCE: 13

Met Lys Asn Tyr Val Lys Ala Ile Pro Cys Tyr Ala Leu Leu Met Ala
1               5                   10                  15
Thr Phe Thr Val Tyr Ala Asn Asp Ser Thr Lys Leu Gln Arg Ile Thr
                20                  25                  30
Pro Pro Ala Ala Ala Val Asn Leu Tyr Glu Lys Ala Glu Trp Thr Ile
            35                  40                  45
Asp Leu Thr Ala Asn Tyr Ser Asn Pro Tyr Asp Gln Arg Glu Ile Lys
        50                  55                  60
Leu Asp Met Cys Leu Val Ser Pro Ser Gly Lys Pro Leu Leu Leu Pro
65                  70                  75                  80
Ala Tyr Phe Asp Gln Val Asn His His Trp Gln Ser Arg Phe Ala Pro
                85                  90                  95
Gln Glu Thr Gly Gln Tyr Gln Tyr Tyr Phe Glu Leu Ile Ala Gly Lys
            100                 105                 110
Asp Thr Val Gln Ser Lys Pro Ser Val Phe Thr Val Tyr Lys Ser Thr
        115                 120                 125
Arg Lys Gly Phe Leu His Lys Asn Asp Leu Trp Thr Phe Arg Phe Asp
    130                 135                 140
Asn Gly Glu Leu Phe Arg Gly Val Gly Glu Asn Val Ala Trp Glu Ser
```

145                 150                 155                 160
Arg Ser Phe Glu Asp Asp Lys Trp Thr Tyr Asp Tyr Leu Leu Pro Ser
                165                 170                 175

Leu Ala His Asn Gly Ala Asn Phe Phe Arg Thr Trp Met Cys Tyr Trp
            180                 185                 190

Asn Leu Pro Leu Glu Trp Lys Gln Pro Arg Ser Thr Lys Arg Tyr Gln
            195                 200                 205

Pro Ser Ala Glu Tyr Phe His Pro Gly Ala Ile Arg Arg Met Asp Gln
        210                 215                 220

Leu Val Asp Met Cys Asp Ser Leu Gly Leu Tyr Phe Met Leu Thr Leu
225                 230                 235                 240

Asp Trp His Gly His Leu Met Glu His Gly Gly Trp Lys His Ser Ser
                245                 250                 255

Tyr Asn Lys Ala Asn Gly Gly Pro Ala Glu Thr Pro Thr Ala Phe Phe
            260                 265                 270

Thr Ser Gln Gln Ala Gln Glu Lys Tyr Lys Asn Lys Leu Arg Tyr Ile
            275                 280                 285

Ile Ala Arg Trp Gly Tyr Ser Ser Ile Ala Val Trp Glu Phe Phe
        290                 295                 300

Asn Glu Val Asp Asn Ala Ala Phe Thr Gln Gln Asp Ser Ile Leu Ile
305                 310                 315                 320

Pro Leu Pro Val Ile Ala Gln Trp His Leu Glu Met Ser Arg Tyr Leu
                325                 330                 335

Lys Asp Ile Asp Pro Tyr His His Leu Val Ser Thr Ser Ile Ser His
                340                 345                 350

Arg Asp Ile Ile Gly Met Asn Ala Ile Pro Tyr Ile Asp Phe Asn Gln
        355                 360                 365

Lys His Ile Tyr Lys His Thr Glu Lys Ile Pro Gly Ile Tyr Pro Asp
        370                 375                 380

Tyr Ile Gln Thr Phe Gly Lys Pro Tyr Val Val Gly Glu Phe Gly Tyr
385                 390                 395                 400

Arg Trp Glu Asp Gln Asp Pro Lys Tyr Ala Thr Glu Ala Asn Tyr Asp
                405                 410                 415

Tyr Arg Arg Gly Leu Trp Tyr Gly Met Phe Ser Pro Thr Pro Val Leu
            420                 425                 430

Pro Met Ser Trp Trp Trp Glu Leu Phe Asp Asp Gln His Met Thr Pro
            435                 440                 445

Tyr Leu Gln Ser Val Ser Thr Ile Asn Lys Met Met Leu Gln Ala Gly
        450                 455                 460

Lys Gly Gln Phe Glu Gln Leu Pro Val Gln Ala Ala Ile Leu Glu Ser
465                 470                 475                 480

Tyr Ala Ile Lys Cys Gly Asn Thr Ile Phe Val Tyr Ala Leu Asn Asn
            485                 490                 495

Thr Thr Lys Gln Gln Ser Ala Asp Ile Arg Val Asn Ile Pro Ser Gly
            500                 505                 510

Tyr Thr Leu Gln Cys Phe His Pro Leu Lys Asn Thr Trp Asn Lys Ser
        515                 520                 525

Ile Tyr Lys Arg Thr Ala Asp Gly Thr Val Gln Ile Ser Asn Thr Val
        530                 535                 540

Leu Pro Ala Lys Glu Glu Ile Ile Leu Val Phe Lys Pro
545                 550                 555

<210> SEQ ID NO 14

```
<211> LENGTH: 843
<212> TYPE: PRT
<213> ORGANISM: Unknown
<220> FEATURE:
<223> OTHER INFORMATION: EBI5326244 deduced protein sequence, derived
      from Archaea

<400> SEQUENCE: 14

Met Leu Lys Lys Val His Ile Ile Ala Ile Val Ile Ile Ala Ile
 1               5                  10                  15

Ala Phe Ala Leu Ile Leu Ala Arg Tyr Tyr Thr Met Gln Arg Gly Tyr
                20                  25                  30

Glu Thr Val Thr Pro Thr Thr Pro Gln Gln Thr Thr Thr Thr Glu
                35                  40                  45

Thr Thr Pro Val Pro Thr Glu Ala Gly Thr Thr Thr Pro Ile Thr Glu
 50                          55                      60

Ala Thr Val Thr Gln Pro Pro Gln Thr Pro Thr Thr Pro Ser Pro Gln
 65                  70                      75                  80

Thr Pro Thr Thr Pro Thr Ala Leu Pro Thr Pro Ser Pro Thr Pro Thr
                85                      90                  95

Ala Pro Ser Ala Thr Val Thr Glu Thr Thr Ser Pro Gln Thr Pro Thr
                100                 105                 110

Thr Thr Ile Thr Thr Glu Thr Thr Thr Thr Pro Ala Pro Gln Pro Gln
                115                 120                 125

Val Val Phe Leu Lys Leu Pro Glu Gly Glu Glu Pro Lys Phe Gly Leu
                130                 135                 140

Val Glu Ile Ala Phe Asn Ile Ser Gly Leu Ser Tyr Ser Asn Pro Phe
145                 150                 155                 160

Asp Thr Ser Asp Ile Asp Val Trp Val His Ile Glu Thr Pro Ser Gly
                165                 170                 175

Ser Arg Val Ala Val Pro Ala Phe Tyr Phe Gln Asn Tyr Thr Val Lys
                180                 185                 190

Arg Leu Gly Pro Gly Glu Glu Ile Ile Val Arg Val Gly Arg Pro Tyr
                195                 200                 205

Trp Leu Ala Arg Phe Ala Pro Val Glu Glu Gly Val His Lys Phe Tyr
                210                 215                 220

Val Lys Ala Val Asp Gly Arg Gly Ser Ala Val Val Ser Glu Ile Arg
225                 230                 235                 240

Glu Phe Met Val Lys Gly Val Ala Gly Arg Gly Phe Val Arg Val Asp
                245                 250                 255

Ser Gly Lys Arg Leu Phe Val Asp Ser Gly Glu Ser Met Phe Met
                260                 265                 270

Leu Gly Ile Asp Val Ala Trp Pro Pro Asp Arg Arg Ser Ser Ile Ser
                275                 280                 285

Phe Tyr Glu Gln Trp Phe Asp Lys Leu Asn Lys Ser Gly Ile Lys Val
                290                 295                 300

Val Arg Ile Gly Leu Val Pro Trp Ala Leu Thr Leu Glu Trp Ser Lys
305                 310                 315                 320

Leu His Tyr Tyr Ser Leu Asp Asp Ala Ala Arg Ile Asp Glu Ile Val
                325                 330                 335

Lys Leu Ala Glu Lys Tyr Asp Ile Tyr Ile Val Phe Val Phe Met Trp
                340                 345                 350

His Gly Glu Leu Ala Asp Asn Trp Gly Asp Asn Pro Tyr Asn Ala Ala
                355                 360                 365

Arg Gly Gly Pro Leu Gln Ser Pro Glu Glu Phe Trp Ser Asn Ala Val
```

```
                370             375             380
Ala Ile Ser Ile Phe Lys Asp Lys Val Arg Tyr Ile Ala Arg Trp
385             390             395             400

Gly Tyr Ser Thr His Ile Leu Ala Trp Glu Leu Ile Asn Glu Ala Asp
            405             410             415

Leu Thr Thr Asn Phe Phe Ser Ala Arg Ser Ala Phe Val Ser Trp Val
            420             425             430

Lys Glu Ile Ser Ser Tyr Ile Lys Ser Val Asp Pro Tyr Asn Arg Ile
            435             440             445

Val Thr Val Asn Leu Ala Asp Tyr Asn Ser Glu Pro Arg Val Trp Ser
            450             455             460

Val Glu Ser Ile Asp Ile Ile Asn Val His Arg Tyr Gly Pro Glu Gly
465             470             475             480

Phe Lys Asp Ile Ala Leu Ala Ile Pro Ser Ile Val Glu Gly Leu Trp
                485             490             495

Asn Thr Tyr Arg Lys Pro Ile Ile Ile Thr Glu Phe Gly Val Asp Tyr
            500             505             510

Arg Trp Ile Gly Tyr Pro Gly Phe Lys Gly Thr Pro Tyr Trp Ala Tyr
            515             520             525

Asp Lys Ser Gly Val Gly Leu His Glu Gly Leu Trp Ser Ser Ile Phe
            530             535             540

Ser Leu Ser Pro Val Ser Ala Met Ser Trp Trp Trp Asp Thr Gln Ile
545             550             555             560

Asp Ser Tyr Asn Leu Trp Tyr His Tyr Lys Ala Leu Tyr Glu Phe Leu
            565             570             575

Lys Ser Val Asp Pro Val Arg Gly Gly Leu Gly Lys Ala Arg Ala Ser
            580             585             590

Leu Val Ile Thr Asp Val Thr Pro Ser Ser Ile Thr Leu Tyr Pro Leu
            595             600             605

Ala Gly Trp Val Trp Val Ser Pro Val Arg Glu Asn Arg Leu Val Ile
            610             615             620

Arg Pro Asp Gly Ala Ile Glu Gly Arg Val Asp Leu Leu Ser Gly Phe
625             630             635             640

Ile Tyr Gly Thr Cys His Ser Gln Arg Thr Leu Asn Pro Val Phe Thr
                645             650             655

Val Met Phe Ile Asp Arg Gly Arg Val Val Leu His Ile Asn Ser Val
                660             665             670

Gly Arg Gly Ser Ala Lys Leu Val Ile Tyr Val Asn Gly Ser Leu Ala
            675             680             685

Thr Gln Leu Asp Leu Pro Asp Lys Asp Gly Lys Ser Asp Gly Ser Ala
            690             695             700

Asn Glu Tyr Asp Met Asp Val Glu Leu Trp Phe Glu Pro Gly Thr Tyr
705             710             715             720

Glu Ile Lys Ile Asp Ser Glu Ala Cys Asp Trp Phe Thr Trp Asp Tyr
                725             730             735

Ile Val Phe Glu Asn Ala Val Tyr Arg Ala Ala Lys Val Asp Leu Tyr
                740             745             750

Ala Leu Ala Asn Ser Thr Phe Ala Met Leu Trp Val Arg Asn Lys Asp
            755             760             765

Tyr Asn Trp Trp Asn Val Val Leu Asn Lys Thr Leu Glu Pro Ala
            770             775             780

Glu Gly Val Glu Val Glu Ile Arg Gly Leu Gln Asp Gly Val Tyr Arg
785             790             795             800
```

```
Val Glu Phe Trp Asp Thr Cys Arg Gly Val Val Lys Ser Met Glu
            805                 810                 815

Val Gln Val Ser Asn Gly Val Ala Arg Val Pro Val Gly Ser Val Glu
        820                 825                 830

Lys Asp Ile Ala Met Lys Ile Thr Arg Ala Gly
        835                 840

<210> SEQ ID NO 15
<211> LENGTH: 2516
<212> TYPE: DNA
<213> ORGANISM: Unknown
<220> FEATURE:
<223> OTHER INFORMATION: EBI5326244-OA, derived from Archaea

<400> SEQUENCE: 15
atgaaaaaga cagctatcgc gattgcagtg gcactggctg gtttcgctac cgttgcgcaa      60
gctgctatgc agagaggcta tgaaacagtg acacctacaa caccacctca gcaaactact     120
accacagaaa caactccagt gcctacagag gcaggtacta acaccaat aactgaggcc       180 actgtgactc aaccccctca aacccctaca acaccttcac cacaaacacc aacaacacca     240
acagcgttgc ccacgccatc accaaccccc acagcgccct ctgccacagt aacagagact     300
acatcgcctc aaactcctac aactacaata actacagaaa caacaactac accagccccc     360
caaccccagg tggtgtttct aaagctacca gagggagagg agccaaagtt tggcttagtt     420
gaaatagcct ttaacatatc tggtctaagc tactcaaacc cctttgacac aagcgatatt     480
gatgtgtggg tgcacataga gacgccaagt ggctctagag tggctgtacc agctttctac     540
ttccagaact acactgtgaa aaggcttgga ccaggggagg agatcatagt cagggttgga     600
aggccatact ggctcgctag gttcgcacct gttgaggagg gggtgcacaa gttctacgta     660
aaggcagttg atggcagggg gagtgctgtg gtgagcgaga ttagagagtt tatggttaag     720
ggggtggctg gcaggggttt tgtcagagtt gacagtggca aaaggctatt cgtatttgac     780
agcggtgaat caatgtttat gctggggata gatgttgcgt ggccaccaga taggaggagc     840
tctatatcgt tctatgagca gtggtttgat aaactaaata gagtgggat taaggttgtg       900 agaataggcc tagtgccctg ggctctaaca ctagagtgga gcaagctcca ctactacagc     960
ttagatgacg ctgctagaat agatgagatt gtgaagcttg ctgaaaagta tgacatatac    1020
atagtgtttg tgtttatgtg gcatggagag cttgcggata ctgggggga taacccatac     1080 aatgcagcaa ggggtggtcc tcttcagagc ccagaggagt tctggagcaa tgcagtagct    1140
atcagtatat ttaaggataa ggtgaggtac attatagcta ggtggggta ctcaacacac      1200 atactcgcat gggagctgat aaacgaggct gacctaacaa caaacttctt tagcgctaga    1260
agtgcttttg tgagctgggt taaggagata agcagctaca taaagtccgt agacccctac    1320
aacaggattg tcactgtgaa cctcgctgac tacaattctg agccaagggt gtggagcgta    1380
gagtccatag acatcataaa tgtgcatagg tatgggccag agggctttaa ggacatagcc    1440
ttggctattc caagcatagt agagggctt tggaacacct acagaaagcc tattataata     1500
acagagtttg tgttgactta tcggtggatt ggctacccag gctttaaagg aaccccctac    1560
tgggcatacg acaagagtgg ggttgggctt catgaagggc tctggagctc tattttcagc    1620
ctctccccag tttctgctat gagctggtgg tgggatacac agatagactc ttataatctg    1680
tggtaccact acaaagccct ctacgagttt ctaaagagtg tcgaccctgt tagaggaggc    1740
ttgggcaagg ccagagcatc gctagtcatt acagatgtga cccctctag cataacacta    1800
```

-continued

```
taccccttag cgggctgggt gtgggtctcg ccagtgagag aaaataggct tgttataagg   1860
cctgatgggg ctatcgaggg gagggttgat ttgctaagtg ggtttatcta tggcacgtgc   1920
cacagccagc ggacactaaa cccagtattt actgtgatgt tcattgatag aggcagggtg   1980
gtgctacaca taaactctgt tggcagggc tctgcaaagc tcgtgatata tgttaatggc    2040
tctctagcta cacaactgga cttgcctgat aaggatggta agagtgatgg gagtgcaaat   2100
gagtacgaca tggatgtgga gctgtggttt gagcctggca cctacgaaat aaaaattgat   2160
agtgaagctt gcgactggtt cacatgggac tacatagtgt ttgaaaatgc tgtgtataga   2220
gctgctaaag tagatctcta tgcacttgca aacagcacct ttgcaatgct ctgggtaagg   2280
aacaaggact acaactggtg gaacgtagtg gtgctgaaca agactctaga gcctgctgag   2340
ggagtagagg tagagattag aggactgcaa gatggggtgt acagagtaga gttttgggac   2400
acatgcagag gggtggtggt gaagagcatg gaggttcaag tgtcaaatgg tgtagccagg   2460
gttccggtgg gtagcgtaga aaaggacata gctatgaaaa tcactagggc tggcta       2516
```

<210> SEQ ID NO 16
<211> LENGTH: 838
<212> TYPE: PRT
<213> ORGANISM: Unknown
<220> FEATURE:
<223> OTHER INFORMATION: EBI5326244-0A, derived from Archaea

<400> SEQUENCE: 16

```
Met Lys Lys Thr Ala Ile Ala Val Ala Leu Ala Gly Phe Ala
 1               5                  10                  15

Thr Val Ala Gln Ala Ala Met Gln Arg Gly Tyr Glu Thr Val Thr Pro
             20                  25                  30

Thr Thr Pro Pro Gln Gln Thr Thr Thr Glu Thr Thr Pro Val Pro
         35                  40                  45

Thr Glu Ala Gly Thr Thr Thr Pro Ile Thr Glu Ala Thr Val Thr Gln
     50                  55                  60

Pro Pro Gln Thr Pro Thr Thr Pro Ser Pro Gln Thr Pro Thr Thr Pro
 65                  70                  75                  80

Thr Ala Leu Pro Thr Pro Ser Pro Thr Pro Thr Ala Pro Ser Ala Thr
                 85                  90                  95

Val Thr Glu Thr Thr Ser Pro Gln Thr Pro Thr Thr Thr Ile Thr Thr
            100                 105                 110

Glu Thr Thr Thr Thr Pro Ala Pro Gln Pro Gln Val Val Phe Leu Lys
        115                 120                 125

Leu Pro Glu Gly Glu Pro Lys Phe Gly Leu Val Glu Ile Ala Phe
    130                 135                 140

Asn Ile Ser Gly Leu Ser Tyr Ser Asn Pro Phe Asp Thr Ser Asp Ile
145                 150                 155                 160

Asp Val Trp Val His Ile Glu Thr Pro Ser Gly Ser Arg Val Ala Val
                165                 170                 175

Pro Ala Phe Tyr Phe Gln Asn Tyr Thr Val Lys Arg Leu Gly Pro Gly
            180                 185                 190

Glu Glu Ile Ile Val Arg Val Gly Arg Pro Tyr Trp Leu Ala Arg Phe
        195                 200                 205

Ala Pro Val Glu Glu Gly Val His Lys Phe Tyr Val Lys Ala Val Asp
    210                 215                 220

Gly Arg Gly Ser Ala Val Val Ser Glu Ile Arg Glu Phe Met Val Lys
225                 230                 235                 240
```

```
Gly Val Ala Gly Arg Gly Phe Val Arg Val Asp Ser Gly Lys Arg Leu
            245                 250                 255

Phe Val Phe Asp Ser Gly Glu Ser Met Phe Met Leu Gly Ile Asp Val
            260                 265                 270

Ala Trp Pro Pro Asp Arg Arg Ser Ser Ile Ser Phe Tyr Glu Gln Trp
            275                 280                 285

Phe Asp Lys Leu Asn Lys Ser Gly Ile Lys Val Val Arg Ile Gly Leu
            290                 295                 300

Val Pro Trp Ala Leu Thr Leu Glu Trp Ser Lys Leu His Tyr Tyr Ser
305                 310                 315                 320

Leu Asp Asp Ala Ala Arg Ile Asp Glu Ile Val Lys Leu Ala Glu Lys
            325                 330                 335

Tyr Asp Ile Tyr Ile Val Phe Val Phe Met Trp His Gly Glu Leu Ala
            340                 345                 350

Asp Asn Trp Gly Asp Asn Pro Tyr Asn Ala Ala Arg Gly Gly Pro Leu
            355                 360                 365

Gln Ser Pro Glu Glu Phe Trp Ser Asn Ala Val Ala Ile Ser Ile Phe
            370                 375                 380

Lys Asp Lys Val Arg Tyr Ile Ile Ala Arg Trp Gly Tyr Ser Thr His
385                 390                 395                 400

Ile Leu Ala Trp Glu Leu Ile Asn Glu Ala Asp Leu Thr Thr Asn Phe
            405                 410                 415

Phe Ser Ala Arg Ser Ala Phe Val Ser Trp Val Lys Glu Ile Ser Ser
            420                 425                 430

Tyr Ile Lys Ser Val Asp Pro Tyr Asn Arg Ile Val Thr Val Asn Leu
            435                 440                 445

Ala Asp Tyr Asn Ser Glu Pro Arg Val Trp Ser Val Glu Ser Ile Asp
450                 455                 460

Ile Ile Asn Val His Arg Tyr Gly Pro Glu Gly Phe Lys Asp Ile Ala
465                 470                 475                 480

Leu Ala Ile Pro Ser Ile Val Glu Gly Leu Trp Asn Thr Tyr Arg Lys
            485                 490                 495

Pro Ile Ile Ile Thr Glu Phe Gly Val Asp Tyr Arg Trp Ile Gly Tyr
            500                 505                 510

Pro Gly Phe Lys Gly Thr Pro Tyr Trp Ala Tyr Asp Lys Ser Gly Val
            515                 520                 525

Gly Leu His Glu Gly Leu Trp Ser Ser Ile Phe Ser Leu Ser Pro Val
            530                 535                 540

Ser Ala Met Ser Trp Trp Asp Thr Gln Ile Asp Ser Tyr Asn Leu
545                 550                 555                 560

Trp Tyr His Tyr Lys Ala Leu Tyr Glu Phe Leu Lys Ser Val Asp Pro
            565                 570                 575

Val Arg Gly Gly Leu Gly Lys Ala Arg Ala Ser Leu Val Ile Thr Asp
            580                 585                 590

Val Thr Pro Ser Ser Ile Thr Leu Tyr Pro Leu Ala Gly Trp Val Trp
            595                 600                 605

Val Ser Pro Val Arg Glu Asn Arg Leu Val Ile Arg Pro Asp Gly Ala
            610                 615                 620

Ile Glu Gly Arg Val Asp Leu Leu Ser Gly Phe Ile Tyr Gly Thr Cys
625                 630                 635                 640

His Ser Gln Arg Thr Leu Asn Pro Val Phe Thr Val Met Phe Ile Asp
            645                 650                 655
```

-continued

```
Arg Gly Arg Val Val Leu His Ile Asn Ser Val Gly Arg Gly Ser Ala
            660                 665                 670

Lys Leu Val Ile Tyr Val Asn Gly Ser Leu Ala Thr Gln Leu Asp Leu
        675                 680                 685

Pro Asp Lys Asp Gly Lys Ser Asp Gly Ser Ala Asn Glu Tyr Asp Met
    690                 695                 700

Asp Val Glu Leu Trp Phe Glu Pro Gly Thr Tyr Glu Ile Lys Ile Asp
705                 710                 715                 720

Ser Glu Ala Cys Asp Trp Phe Thr Trp Asp Tyr Ile Val Phe Glu Asn
                725                 730                 735

Ala Val Tyr Arg Ala Ala Lys Val Asp Leu Tyr Ala Leu Ala Asn Ser
            740                 745                 750

Thr Phe Ala Met Leu Trp Val Arg Asn Lys Asp Tyr Asn Trp Trp Asn
        755                 760                 765

Val Val Val Leu Asn Lys Thr Leu Glu Pro Ala Glu Gly Val Glu Val
    770                 775                 780

Glu Ile Arg Gly Leu Gln Asp Gly Val Tyr Arg Val Glu Phe Trp Asp
785                 790                 795                 800

Thr Cys Arg Gly Val Val Val Lys Ser Met Glu Val Gln Val Ser Asn
                805                 810                 815

Gly Val Ala Arg Val Pro Val Gly Ser Val Glu Lys Asp Ile Ala Met
            820                 825                 830

Lys Ile Thr Arg Ala Gly
        835

<210> SEQ ID NO 17
<211> LENGTH: 60
<212> TYPE: PRT
<213> ORGANISM: Unknown
<220> FEATURE:
<223> OTHER INFORMATION: EBI5324142, derived from Archaea

<400> SEQUENCE: 17

Met Ala Met Arg Thr Gly Leu Ala Leu Gly Ile Val Ala Leu Ile Ala
1               5                   10                  15

Val Ile Leu Ile Ala Val Leu Leu Ala Thr Gln Gln Gln Pro Thr Pro
            20                  25                  30

Thr Pro Ser Pro Thr Pro Thr Pro Ser Pro Thr Pro Thr Pro Thr Pro
        35                  40                  45

Thr Pro Thr Pro Thr Pro Thr Pro Thr Pro Thr Pro
    50                  55                  60

<210> SEQ ID NO 18
<211> LENGTH: 41
<212> TYPE: PRT
<213> ORGANISM: Unknown
<220> FEATURE:
<223> OTHER INFORMATION: EBI5327647, derived from Archaea

<400> SEQUENCE: 18

Leu Asn Lys Thr Val Ile Ala Ile Ala Val Leu Leu Val Val Val Ile
1               5                   10                  15

Ala Ala Ala Leu Ile Tyr Val Ile Tyr Tyr Pro Thr Pro Thr Thr Thr
            20                  25                  30

Thr Thr Pro Thr Val Thr Thr Pro Val
        35                  40

<210> SEQ ID NO 19
```

<211> LENGTH: 1258
<212> TYPE: PRT
<213> ORGANISM: Coraliomargarita akajimensis

<400> SEQUENCE: 19

```
Met His Arg Cys Arg Tyr Ser Ile Ser Leu Val Trp Lys Gln Leu Ser
1               5                   10                  15

Gly Arg Lys Leu Ala Leu Thr Lys Ser Lys Ala Ser Ala Ser Arg Leu
            20                  25                  30

Arg Thr Arg Gln Ser Leu Trp Ala Leu Leu Ser Ser Val Leu Leu Gly
        35                  40                  45

Phe Val Cys Ala Gly Ala Leu Gln Ala Gln Val Leu Glu Asp Ala Tyr
50                  55                  60

Leu Glu Ser Gly Gly Ala Val Val Phe Glu Val Glu Ser Glu Ala Ala
65                  70                  75                  80

Val Ser Pro Trp Met Leu Asp Asn Ser Val Ala Gly Tyr Lys Gly Thr
                85                  90                  95

Gly Tyr Phe Glu Gly Thr Ala Asp Tyr Phe Ser Thr Pro Gly Gln Gly
            100                 105                 110

Val Val Arg Tyr Pro Ile Lys Ile Thr Thr Ser Gly Arg Tyr Gln Leu
        115                 120                 125

Gln Trp Arg Ser Arg Ile Asn Phe Gly Thr Glu Thr Ser Glu His Asn
    130                 135                 140

Asp Ser Trp Ala Arg Leu Thr Asp Ala Asn Gly Asn Pro Val Ser Pro
145                 150                 155                 160

Ala Ser Asn Ser Asn Val Ala Asn Ser Gln Trp Tyr Lys Val Tyr Val
                165                 170                 175

Gly Trp Thr Gly Trp Gln Trp Gly Ser Ser Asn Lys Asp Asn Asp Pro
            180                 185                 190

Arg Ser Leu Ser Trp Asn Leu Thr Ala Gly Asp Tyr Tyr Tyr Val Glu
        195                 200                 205

Ile Ser Val Arg Ser His Tyr His Ala Leu Asp Arg Ile Val Leu Trp
    210                 215                 220

Asp His Asn Arg Leu Ala Leu Ala Asn Thr Thr Thr Gly Lys Gly Ala
225                 230                 235                 240

Asn Asn Ser Ala Leu Asp Ala Leu Pro Val Ser Ala Ile Glu Val Gln
                245                 250                 255

Glu Gly Pro Asp Val Glu Ile Thr Asp Pro Val His Gly Thr Thr Ile
            260                 265                 270

Val Pro Gly Gly Thr Val Thr Phe Thr Ala Ser Ala Ser Asp Ala Gln
        275                 280                 285

Gly Ser Val Val Ser Val Glu Phe Phe Ala Gly Thr Thr Ser Leu Gly
    290                 295                 300

Ile Asp Thr Ser Ala Pro Phe Ser Gln Ala Trp Ser Ser Ala Ala Glu
305                 310                 315                 320

Gly Val Tyr Glu Ile Thr Ala Leu Ala Thr Asp Asn Glu Gly Tyr Thr
                325                 330                 335

Thr Thr Ser Ala Pro Ile Thr Leu His Val Ala Pro Ser Met Gly Ala
            340                 345                 350

Asn Gly Thr Val Ser Gly Glu Leu Met Gln Trp His Lys Val Met Leu
        355                 360                 365

Thr Phe Asp Gly Pro Gly Thr Ser Glu Thr Ala Thr Pro Asn Pro Phe
    370                 375                 380

Arg Asp Tyr Arg Met Asp Val Thr Phe Thr Gly Pro Ser Ser Gln Ser
```

```
             385                 390                 395                 400
         Tyr Val Val Pro Gly Tyr Tyr Ala Ala Asp Gly Asn Ser Gly Glu Thr
                         405                 410                 415
         Ser Leu Gly Ser Gly Asn Arg Trp Arg Val Ala Phe Ala Pro Asp Glu
                         420                 425                 430
         Ala Gly Thr Trp Asn Tyr Ser Val Ser Phe Val Thr Gly Thr Asp Ile
                         435                 440                 445
         Ala Ala Asp Leu Ser Gly Gly Ala Ser Ala Gly Phe Phe Asp Gly Ala
                         450                 455                 460
         Thr Gly Thr Phe Ser Val Ala Ala Ser Asp Lys Ser Gly Ala Asp Leu
         465                 470                 475                 480
         Arg Ala Lys Gly Lys Leu Glu Tyr Val Gly Asp His Tyr Leu Gln Phe
                         485                 490                 495
         Arg Asn Gly Glu Tyr Phe Ile Lys Gly Gly Ala Asn Ser Pro Glu Val
                         500                 505                 510
         Leu Leu Glu Tyr Ser Gly Phe Asp Asn Thr Asp Ser Thr Arg Thr Tyr
                         515                 520                 525
         Ser Ala His Thr Ile Asn Trp Gln Leu Gly Asp Pro Thr Trp Lys Gly
                         530                 535                 540
         Gly Glu Gly Lys Gly Leu Val Gly Val Ile Asn Tyr Leu Ala Asp Leu
         545                 550                 555                 560
         Gly Leu Asn Ser His Tyr Phe Leu Leu Met Asn Ser Tyr Gly Asp Gly
                         565                 570                 575
         Lys Lys Ala Phe Pro Phe Leu Gly Glu Asp Asp Ile Trp Arg Tyr Asp
                         580                 585                 590
         Cys Ser Lys Leu Glu Gln Trp Asp Val Leu Phe Glu His Phe Asp Arg
                         595                 600                 605
         Lys Gly Met Met Met His Phe Val Met Thr Glu Gln Glu Asn Gln Gln
                         610                 615                 620
         Leu Phe Glu Val Ala Asp Pro Ala Thr Val Glu Gly Gly Phe Ser Asp
         625                 630                 635                 640
         Ser Arg Arg Ile Tyr Phe Arg Glu Met Val Ala Arg Phe Gly His His
                         645                 650                 655
         Met Ala Ile Thr Trp Asn Ile Gly Glu Glu Asn Gly Trp Glu Lys Gln
                         660                 665                 670
         Thr Arg Pro Thr Ile Tyr Ala Gly Ala Cys Ser Asp Thr Gln Arg Lys
                         675                 680                 685
         Asp Phe Ser Asp His Leu Arg Ala Leu Leu Pro Tyr Glu Asp His Ile
                         690                 695                 700
         Ser Ile His Asn Gly Pro Ser Ser Thr Asp Ala Ile Phe Asn Ala Leu
         705                 710                 715                 720
         Val Gly His Thr Ser Phe Thr Gly Pro Ala Phe Gln Trp Asn Ile Asn
                         725                 730                 735
         Thr Asn Ile Ala Ala Lys Thr Lys Gln Trp Arg Asp Ala Ser Ile Ala
                         740                 745                 750
         Ser Gly His Lys Trp Val Phe Cys Met Asp Glu Pro Tyr Leu Gly Gly
                         755                 760                 765
         Asn Pro Asn Asp Ala His Asp Thr Asn Arg Lys Gln Thr Leu Trp Pro
                         770                 775                 780
         Ala Tyr Met Ala Gly Ala Gly Val Glu Trp Tyr Ile Gly Gly Gly
         785                 790                 795                 800
         Gln Asp Leu Gln Val Gln Asp Tyr Thr Leu Tyr Glu Pro Leu Trp Thr
                         805                 810                 815
```

```
Glu Met Gly Tyr Ala Val Asp Leu Leu Glu Ile Ile Pro Phe His Ala
        820                 825                 830

Met Glu Pro Asn Asp Ala Leu Leu Thr Gly Glu Thr Gly Gly Ala Gly
        835                 840                 845

Gln Val Leu Ala Asp Leu Gly Ala Ser Tyr Leu Ala Tyr Leu Pro Asn
850                 855                 860

Ala Thr Ala Ser Ala Ser Leu Asn Leu Ser Gly Gln Ser Gly Asn Phe
865                 870                 875                 880

Asp Val Met Trp Tyr Asp Pro Arg Asn Gly Asp Leu Gln Met Gly
                885                 890                 895

Ser Val Ser Thr Val Thr Gly Gly Ile Arg Ser Leu Gly Ala Ala
        900                 905                 910

Pro Ser Ala Ser Ala Glu Asp Trp Leu Val Leu Val Phe Ala Glu Gly
        915                 920                 925

Thr Met Pro Val Met Pro Gly Asp Pro Val Pro Ala Leu Ser Tyr
    930                 935                 940

Leu Glu Ile Trp Asn Glu Gly Phe Glu Asn Ala Asn Leu Gly Ala Thr
945                 950                 955                 960

Ser Ala Ser Asn Ala Asp Leu Pro Gly Ala Val Phe Tyr Gly Arg Asn
                965                 970                 975

Gly Leu Thr Ala Glu Val Val Asn Ala Pro Ala Gly Phe Ser Ser Ala
        980                 985                 990

Ser Gly Gln Val Ile Ala Leu Ser Thr Thr Asn Ala Tyr Ala Ala
        995                 1000                1005

Ala Lys Arg Gln Glu Ser Ala Ile Asp Leu Ser Ala Leu Ser Leu Lys
        1010                1015                1020

Ala Gly Asp Thr Tyr Arg Leu Ser Phe Asp Met Tyr Ile Pro Ser Pro
1025                1030                1035                1040

Leu Ser Thr Ala Val Gly Ala Ile Ser Phe Arg Trp Arg Thr Ala Thr
                1045                1050                1055

Ala Thr Gly Asn Gly Pro Thr Asp Ser Ser Gln Ala Thr Leu Ser Ala
        1060                1065                1070

Gly Val His Arg Ile Glu Tyr Thr Gly Thr Phe Pro Val Ile Asn Gly
        1075                1080                1085

Ser Glu Ile Leu Pro Thr Ser Val Glu Pro Phe Ile Met Phe His Gln
        1090                1095                1100

Asn Gly Val Ala Ala Ser Gln His Val Tyr Leu Asp Asn Ile Leu Phe
1105                1110                1115                1120

Glu Ile Glu Ser Pro Gln Leu Ser Gly Phe Glu Lys Phe Ala Asp Asp
                1125                1130                1135

Tyr Ala Leu Ile Gly Gly Lys Thr Asp Asp Asp Leu Asp Gly Gln
        1140                1145                1150

Thr Asn Phe Met Glu Phe Ala Thr Gly Gly Asn Pro Thr Asp Pro Ser
        1155                1160                1165

Asp Ile Gly Leu Ile Arg Val Ser Phe Asp Gly Asp Gly Asn Ala Arg
        1170                1175                1180

Val Ser Val Pro Gln Arg Ile Asp Gly Asn Glu Leu Gly Leu Ser Tyr
1185                1190                1195                1200

Thr Val Tyr Asn Arg Thr Ser Leu Thr Glu Gly Ser Trp Ala Glu Leu
                1205                1210                1215

Ser Thr Asn Ala Ile Phe Thr Ser Ile Glu Gly Thr Ala Glu Tyr
        1220                1225                1230
```

```
Glu Thr Tyr Gly Tyr Arg Phe Trp Val Gly Thr Gly Ser Phe Ser Asp
        1235                1240                1245

Arg Phe Phe Arg Val Glu Ile Ser Asp Asn
    1250                1255

<210> SEQ ID NO 20
<211> LENGTH: 859
<212> TYPE: PRT
<213> ORGANISM: Opitutus terrae

<400> SEQUENCE: 20

Met Met Leu Leu Arg Thr Val Val Trp Ala Gly Ala Leu Val Leu Gly
  1               5                  10                  15

Ser Val Phe Cys Val Ser Ala Ser Gly Ala Thr Arg Asn Leu Gly Ser
             20                  25                  30

Lys Thr Thr Phe Ser Gly Glu Gln Lys Gln Trp His Lys Val Ser Leu
         35                  40                  45

Thr Phe Ala Gly Pro Ser Thr Ser Glu Thr Asn Ser Val Asn Pro Phe
     50                  55                  60

Thr Asn Tyr Arg Leu Asn Val Thr Phe Lys His Ser Ala Ser Asn Arg
 65                  70                  75                  80

Thr Leu Ile Val Pro Gly Tyr Phe Ala Ala Asp Gly Asn Ala Ala Asn
                 85                  90                  95

Thr Gly Ala Val Ser Gly Asp Lys Trp Arg Val Asp Phe Thr Pro Asp
            100                 105                 110

Ala Thr Gly Thr Trp Thr Tyr Val Ala Ser Phe Arg Thr Gly Ser Asn
        115                 120                 125

Val Ala Ala Ser Thr Ser Ala Thr Ala Gly Thr Ala Thr Ser Phe Asn
    130                 135                 140

Gly Glu Ser Gly Ser Phe Thr Ile Asp Pro Thr Asp Lys Thr Gly Ala
145                 150                 155                 160

Asp Phe Arg Ala Lys Gly Arg Leu Arg Glu Val Gly Gln His Tyr Leu
                165                 170                 175

Gln His Ala Gly Ser Lys Glu Tyr Phe Ile Lys Ser Gly Ala Gly Ser
            180                 185                 190

Pro Glu Asn Phe Leu Ala Phe Ala Asp Phe Asp Asn Thr Ser Ala Gly
        195                 200                 205

Lys Lys Ile Leu His His Tyr Thr Ala His Leu Ser Ala Tyr Arg Ser
    210                 215                 220

Gly Asp Pro Thr Trp Lys Ser Gly Lys Gly Lys Ala Ile Ile Gly Ala
225                 230                 235                 240

Leu Asn Tyr Leu Ala Ser Lys Lys Val Asn Ser Val Tyr Phe Leu Thr
                245                 250                 255

Met Asn Ile Gly Gly Asp Gly Asp Val Phe Pro Phe Val Ser Lys
            260                 265                 270

Thr Asp Arg Thr Arg Phe Asp Val Ser Lys Leu Ala Gln Trp Glu Ile
        275                 280                 285

Val Phe Ser His Met Asp Lys Leu Gly Ile Met Leu Asn Val Val Thr
    290                 295                 300

Gln Glu Gln Glu Cys Asp Gln Leu Leu Asp Gly Ser Gly Leu Gly Asn
305                 310                 315                 320

Thr Arg Lys Ile Tyr Tyr Arg Glu Leu Val Ala Arg Phe Gly His His
                325                 330                 335

Leu Gly Val Thr Trp Asn Leu Gly Glu Glu Asn Thr Asn Thr Asp Ala
            340                 345                 350
```

```
Gln Arg Glu Ala Phe Ala Asp Tyr Leu Asn Ala Leu Asp Pro Tyr Phe
        355                 360                 365

Ser Leu Ile Ala Val His Thr Tyr Pro Ser Gln Arg Asp Thr Ile Tyr
    370                 375                 380

Thr Gly His Leu Gly Ser Glu Leu Ile Ser Gly Ala Ser Leu Gln Leu
385                 390                 395                 400

Glu Ser Pro Ser Ile Val His Glu Gln Thr Leu Lys Trp Val Lys Lys
                405                 410                 415

Ser Ala Ala Gly Ser Lys Trp Val Ser Val Asp Glu Leu Gly
                420                 425                 430

Pro Ser Ser Ala Gly Val Val Pro Asp Ala Asn Asp Pro Ala His Glu
        435                 440                 445

Thr Ile Val His Arg Val Leu Trp Gly Ser Leu Leu Ala Gly Gly Ala
        450                 455                 460

Gly Val Glu Trp Tyr Phe Gly Tyr Asn Tyr Pro Gln Thr Asp Leu Thr
465                 470                 475                 480

Leu Glu Asp Trp Lys Ser Arg Asp Lys Met Trp Thr Leu Thr Gln His
                485                 490                 495

Ala Ala Gln Phe Met Arg Asp Tyr Met Pro Leu Pro Leu Val Ala Asn
            500                 505                 510

Tyr Asp Ser Ile Thr Ser Ser Thr Ser Asp Tyr Cys Phe Gly Lys Pro
        515                 520                 525

Gly Val Ala Tyr Ala Ile Tyr Leu Pro Gln Gly Ala Ile Thr Asn Ile
        530                 535                 540

Thr Val Pro Ser Gly Glu Gly Tyr Thr Val His Trp Tyr Asn Pro Arg
545                 550                 555                 560

Ala Gly Gly Ser Leu Gln Thr Gly Thr Val Lys Ser Ile Ala Gly Gly
                565                 570                 575

Thr Ala Ala Ile Gly Arg Pro Pro Thr Gln Gln Ser Glu Asp Trp Val
            580                 585                 590

Ala Leu Leu Arg Arg Thr Ser Gly Thr Thr Gly Ala Pro Ala Pro
        595                 600                 605

Ala Pro Thr Glu Pro Thr Ser Thr Ala Val Thr Gln Leu Thr Leu
    610                 615                 620

Val Asn Ala Ser Thr Glu Lys Asp Leu Arg Ala Leu Thr Asn Gly Ser
625                 630                 635                 640

Thr Ile Thr Phe Gly Thr Asp Gly Lys Ala Leu Asn Val Arg Ala Thr
                645                 650                 655

Thr Ser Gly Thr Val Gly Ser Val Ala Phe Ile Leu Asp Gly Gln Thr
            660                 665                 670

Ile Gln Thr Glu Asn Met Ala Pro Tyr Thr Leu Ala Gly Asp Ser Asn
        675                 680                 685

Gly Asp Tyr Ala Ser Trp Thr Pro Ser Val Gly Thr His Val Leu Lys
    690                 695                 700

Val Val Pro Tyr Ser Gly Arg Asp Arg Thr Gly Asn Ala Gly Thr Ala
705                 710                 715                 720

Leu Gln Val Ser Phe Thr Val Gln Ser Thr Ala Thr Glu Asp Ser Ser
                725                 730                 735

Ser Ala Pro Val Val Ser Glu Pro Ala Ser Gly Ala Ser Val Thr Lys
            740                 745                 750

Leu Thr Leu Ile Asn Ala Ser Thr Glu Lys Asp Leu Arg Ala Leu Thr
        755                 760                 765
```

```
Asn Gly Ser Thr Ile Thr Phe Gly Thr Asp Gly Lys Ala Leu Asn Val
    770                 775                 780

Arg Ala Glu Thr Ser Gly Thr Val Gly Ser Val Ala Phe Ile Leu Asp
785                 790                 795                 800

Gly Lys Thr Leu Arg Thr Glu Asn Val Ala Pro Tyr Thr Leu Ala Gly
                805                 810                 815

Asp Gly Thr Gly Asn Tyr Tyr Ser Trp Thr Pro Ser Val Gly Ser His
                820                 825                 830

Thr Leu Lys Val Val Pro Tyr Ser Gly Lys Asp Arg Thr Gly Thr Ala
                835                 840                 845

Gly Thr Ser Leu Gln Val Gly Phe Thr Val Lys
                850                 855

<210> SEQ ID NO 21
<211> LENGTH: 606
<212> TYPE: PRT
<213> ORGANISM: Coraliomargarita akajimensis

<400> SEQUENCE: 21

Met Lys Asn Thr Ile Arg Leu Thr Thr Leu Ala Leu Leu Ala Ala Ala
1               5                   10                  15

Gln Ala Ala His Ala Glu Ser Ile Ala Glu Val Ser Gly Ser Leu Arg
                20                  25                  30

Thr Trp His Lys Val Thr Leu Ser Trp Asn Gly Pro Gln Thr Asn Glu
            35                  40                  45

Leu Ala Thr Pro Asn Pro Phe Thr Asp Tyr Arg Leu Asp Val Arg Phe
    50                  55                  60

Thr His Gln Gln Ser Gly Thr Ser Tyr Leu Val Pro Gly Tyr Tyr Ala
65                  70                  75                  80

Ala Asp Gly Asp Ala Ala Asn Thr Gly Ala Asp Ser Gly Ser Val Trp
                85                  90                  95

Arg Val His Phe Ala Pro Asp Ala Ile Gly Asn Trp Asp Tyr Ala Val
                100                 105                 110

Ser Phe Arg Thr Gly Glu Ala Val Ala Met Ala Gln His Pro Gln Val
            115                 120                 125

Gly Asp Gly Thr His Phe Asp Gly Asp Ser Gly Thr Leu Asn Ile Arg
    130                 135                 140

Pro Ser Ala Gln Lys Ala Pro Asp Leu Arg Ala Lys Gly Arg Leu Gln
145                 150                 155                 160

Tyr Val Gly Glu His Tyr Leu Lys Phe Ala Ser Gly Glu Tyr Phe
                165                 170                 175

Leu Lys Gln Gly Ala Asp Ala Pro Glu Asn Phe Leu Ser Tyr Lys Gly
                180                 185                 190

Phe Asp Gly Asp Phe Lys Ser Asp Gly Ile Asn Asp His Leu Val Lys
            195                 200                 205

Asp Trp Glu Pro His Val Gln Asp Trp Lys Asp Gly Asp Pro Ser Trp
    210                 215                 220

Ala Asp Gly Gln Gly Lys Gly Ile Ile Gly Ala Val Asn Tyr Leu Ala
225                 230                 235                 240

Ser Glu Gly Leu Asn Ala Phe Ser Phe Leu Thr Met Asn Ile Glu Gly
                245                 250                 255

Asp Asp Arg Asn Val Phe Pro Tyr Thr Thr Tyr Lys Glu Arg Tyr Arg
                260                 265                 270

Met Asp Cys Ser Lys Leu Ala Gln Trp Glu Val Val Phe Glu His Ala
            275                 280                 285
```

Asp Ser Lys Gly Met Phe Leu His Phe Lys Thr Gln Glu Thr Glu Asn
290                 295                 300

Glu Cys Leu Leu Asp Asn Gly Asp Thr Gly Pro Met Arg Arg Leu Tyr
305                 310                 315                 320

Tyr Arg Glu Leu Val Ala Arg Phe Gly His His Leu Ala Leu Asn Trp
            325                 330                 335

Asn Leu Gly Glu Glu Asn Gly Lys Trp Asp Trp Pro Gly His Val Lys
        340                 345                 350

Glu His Phe Gln Ser Thr Glu Gln Arg Gln Ala Met Ala Gln Trp Phe
    355                 360                 365

Tyr Asp Asn Asp Pro Tyr Lys His His Leu Val Ile His Asn Gly Gln
370                 375                 380

Ser Pro Asn Asp Leu Leu Gly Asp Ala Ser Lys Leu Thr Gly Phe Ser
385                 390                 395                 400

Leu Gln Thr Asn Leu Glu Asp Phe Ala Asn Val Pro Gly Thr Val Ala
            405                 410                 415

Ser Trp Ile Arg Lys Ser Ala Glu Ala Gly Lys Pro Trp Ala Val Ala
        420                 425                 430

Cys Asp Glu Pro Gly Asp Ala Ser His Ala Ile Arg Pro Asp Asp Asn
    435                 440                 445

Ala Gly Ser Ser His Glu Asn Gly Arg Arg Asn Ala Leu Trp Gly Cys
450                 455                 460

Leu Met Asn Gln Gly Tyr Gly Ser Glu Tyr Tyr Phe Gly Tyr Lys Asn
465                 470                 475                 480

Ala His Ser Asp Leu Thr Cys Asn Asp Tyr Arg Ser Arg Asp Lys Trp
            485                 490                 495

Trp Asp Tyr Cys Arg Tyr Ala Leu Glu Phe Phe His Asn His Lys Val
        500                 505                 510

Ala Ile Trp Glu Leu Ala Pro Ala His Lys Leu Ser Ser Asn Ser Glu
    515                 520                 525

Ser Trp Cys Leu Ala Lys Thr Gly Glu Thr Tyr Leu Ile Tyr Ile Lys
530                 535                 540

Asp Gly Ala Thr Thr Asn Leu Asp Leu Ser Gly Asp Ser Gly Lys Phe
545                 550                 555                 560

Gln Val Gln Trp Tyr Asp Thr Arg Lys Gly Gly Ser Leu Leu Ala Gly
            565                 570                 575

Ser Glu Lys Lys Ile Lys Ala Gly Glu Ala Val Ser Ile Gly Lys Pro
        580                 585                 590

Pro Tyr Asp Pro Asp Arg Asp Trp Leu Val Leu Val Ser Lys
    595                 600                 605

<210> SEQ ID NO 22
<211> LENGTH: 1853
<212> TYPE: PRT
<213> ORGANISM: Coraliomargarita akajimensis

<400> SEQUENCE: 22

Met Met Lys Leu Leu Gln Leu Phe Thr Leu Cys Leu Leu Ser Met Ala
1               5                   10                  15

Thr Phe Ala Gln Thr Ala Leu Gly Gln Asp Thr Val Asp Leu Ser Gln
            20                  25                  30

Leu Pro Thr Ser Leu Thr Pro Gln Thr Ser Tyr Thr Val Ser Val Pro
        35                  40                  45

Tyr Thr Ala Ser Val Asp Arg Asp Ile Ala Val Glu Phe Trp Lys Gly

```
            50                  55                  60
Gly Ala Trp Val Thr Ala Lys Thr Thr Thr Val Thr Ala Gly Ser Gly
 65                  70                  75                  80

Thr Ala Ser Val Thr Leu Thr Leu Ala Thr Ala Pro Val Glu Gly Thr
                 85                  90                  95

Asp Tyr Leu Trp Lys Ala Asn Ile Arg Pro Val Gly Thr Asp Trp Thr
                100                 105                 110

Gln Asn Leu Asn Gly Gly Val Val Glu Asn Val Val Ser Leu Pro
                115                 120                 125

Val Thr Glu Asp Thr Ile Asp Leu Thr Glu Leu Pro Thr Ser Met Pro
130                 135                 140

Pro Gln Ser Ser Tyr Thr Val Thr Val Pro Tyr Thr Ala Leu Glu Ser
145                 150                 155                 160

Arg Asp Ile Ala Leu Ser Leu Tyr Lys Gly Gly Ile Trp Gln Thr Gly
                165                 170                 175

Leu Thr Gln Thr Val Ala Ala Gly Arg His Thr Ala Ser Phe Thr Leu
                180                 185                 190

Asn Leu Gly Ser Gln Ala Ala Glu Asp Thr Asp Tyr Glu Trp Arg Cys
                195                 200                 205

Gly Ile Arg Pro Val Gly Ala Asp Trp Thr Gln Asn Leu Asp Ala Gly
210                 215                 220

Thr Ile Asp Asn Val Val Val Ser Ser Gly Ser Ser Gly Gly Gly Ser
225                 230                 235                 240

Gly Asn Gly Ala Trp Ile Glu Ser Gly Gly Met Val Val Ile Glu Ala
                245                 250                 255

Glu Asn Val Asp Leu Thr Ser Asp Trp Val Ala Arg Pro Ser Thr His
                260                 265                 270

Gly Ala Ala Asn Ala Met Gly Gly Ser Leu Gly Asp Gly Trp Leu Glu
                275                 280                 285

Trp Thr Gly Ala Gln Tyr Tyr Gly Asn Thr Gln Thr Glu Ala Gln Ala
                290                 295                 300

Val Ala Ile Leu Thr Phe Glu Phe Glu Ile Thr Asn Pro Gly Asp Tyr
305                 310                 315                 320

Tyr Phe Arg Trp Arg Ser Lys Gln Tyr Asn Asn Val Gly Ser Gly Asp
                325                 330                 335

Ala Gly Asn Asp Ser Tyr Val Ser Leu Thr Ser Gly Thr Pro Val Ala
                340                 345                 350

Gly Tyr Gln Asp Phe Gly Gln Phe His Lys Val Trp Val Gln Ser Gln
                355                 360                 365

Gln Ala Trp Ser Trp Gln Thr Thr Phe Glu Pro His His Gly Glu His
                370                 375                 380

Tyr Ala Asn Asn Leu Val Arg Arg His Tyr Glu Ala Gly Thr His Thr
385                 390                 395                 400

Ile Arg Leu Ala Ala Arg Ser Pro Gly His Ala Ile Asp Arg Ile Val
                405                 410                 415

Leu His Arg Thr Asp Val Pro Phe Asn Gln Ala Thr Phe Glu Ser Ala
                420                 425                 430

Ala Glu Ser Glu Arg Ala Ala Gly Ile Gly Asp Thr Ile Thr Tyr Arg
                435                 440                 445

Ala Thr Glu Asp Phe Pro Thr Leu Asn Ile Tyr Gly Thr Glu Ala Arg
                450                 455                 460

Gly Thr Val Gln Val Asn Pro Gly Ala Gly Ala Val Asn Tyr Asp Asp
465                 470                 475                 480
```

```
Thr Val Phe Ala Ser Ala Thr Arg Thr Phe Asp Gly Pro Thr Gly Thr
                485                 490                 495

Tyr Asp Ile Asp Leu Thr Thr Trp Val Glu Tyr Asp Gly Glu Ser Thr
            500                 505                 510

Tyr Arg Leu Leu Val Asn Gly Ser Gln Val Ala Ser Tyr Gln Asn Pro
        515                 520                 525

Gln Val Thr Glu Ala Thr Asp Leu Thr Pro Asn Thr His Thr Trp Ser
    530                 535                 540

Asn Ile Val Leu Thr Gln Gly Asp Ser Ile Thr Val Gln Ser Asn Ala
545                 550                 555                 560

His Ser Asn Asn Ile Ile Pro Glu Ala Gly Pro Pro Asn Gly Phe Ala
                565                 570                 575

Trp Ala Arg Gly Arg Trp Glu Gln Ile Glu Leu Thr Phe Val Ser Val
            580                 585                 590

Asn Val Gly Ile Pro Thr Val Asp Ala Gly Pro Asp Gln Ser Val Ser
        595                 600                 605

Thr Thr Gln Gly Ser Ala Thr Leu Asn Gly Thr Ala Ser Asp Asn Gly
    610                 615                 620

Ser Ile Thr Asn Tyr Ala Trp Thr Gln Val Ser Gly Pro Asn Thr Ala
625                 630                 635                 640

Thr Leu Ser Gly Gln Ser Thr Val Asp Leu Thr Ala Ser Asn Leu Ile
                645                 650                 655

Ser Gly Thr Tyr Thr Phe Arg Leu Thr Val Thr Asp Asn Glu Ser Asn
            660                 665                 670

Thr Ala Ser Asp Asp Ala Ile Val His Val Val Ser Thr Gly Asn Gly
        675                 680                 685

Ala Val Ala Ile Thr Gly Asp Leu Met Gln Trp His Asn Val Ile Leu
    690                 695                 700

Thr Met Asn Gly Pro Asn Ser Ser Glu Ser Ala Thr Pro Asn Pro Phe
705                 710                 715                 720

Lys Asp Tyr Arg Met Asn Val Thr Phe Thr His Pro Asn Ser Gly Leu
                725                 730                 735

Ser Tyr Thr Val Pro Gly Tyr Phe Ala Ala Asp Gly Asn Ala Gly Gln
            740                 745                 750

Thr Gly Ala Thr Ser Gly Gly Lys Trp Arg Ala His Leu Cys Pro Asp
        755                 760                 765

His Ala Gly Gln Trp Thr Tyr Ser Val Ser Phe Arg Ser Gly Thr Asp
    770                 775                 780

Val Ala Val Asn Asn Ser Leu Ser Ala Gly Thr Ala Phe Ala Gly Leu
785                 790                 795                 800

Asp Gly Lys Thr Gly Ser Phe Thr Val Val Ala Thr Asn Lys Thr Gly
                805                 810                 815

Arg Asp His Arg Gly Lys Gly Arg Leu Gln Tyr Asp Gly Thr Arg Tyr
            820                 825                 830

Leu Lys Phe Ala Gly Ser Gly Glu Ala Phe Leu Lys Thr Gly Ala Asp
        835                 840                 845

Ala Pro Glu Asn Phe Leu Asn Tyr Thr Glu Phe Asp Asn Thr Tyr Thr
    850                 855                 860

His Gly Ala Asn Tyr Leu Lys Asp Trp Ser Ala His Val Gly Asp Trp
865                 870                 875                 880

Asn Ala Gly Asp Pro Thr Trp His Gly Thr Lys Gly Lys Gly Ile Ile
                885                 890                 895
```

```
Gly Ala Ile Asn Tyr Leu Ala Ser Glu Gly Gln Asn Val Phe Ser Phe
            900                 905                 910

Leu Thr Tyr Asn Ala Gly Gly Asp Ser Lys Asp Val Trp Pro Tyr Val
            915                 920                 925

Ser His Thr Asn Pro Leu Gln Phe Asp Cys Ser Lys Leu Asp Gln Trp
            930                 935                 940

Asp Ile Val Phe Ser His Gly Asp Lys Met Gly Met Tyr Leu His Phe
945                 950                 955                 960

Lys Thr Gln Glu Arg Glu Asn Asp Asp Leu Asp Gly Pro Gly Ser Ala
            965                 970                 975

Tyr Ala Leu Asp Gly Gly Asn Val Gly Thr Glu Arg Lys Leu Tyr Tyr
            980                 985                 990

Arg Glu Leu Ile Ala Arg Phe Gly His His Leu Ala Leu Asn Trp Asn
            995                 1000                1005

Leu Gly Glu Glu Asn Thr Gln Ser Thr Ser Gln Arg Gln Ala Met Ala
            1010                1015                1020

Gln Tyr Phe Arg Asp Thr Asp Pro Tyr Gly His Asn Ile Val Leu His
1025                1030                1035                1040

Thr Tyr Pro Gly Glu Trp Glu Gln Val Tyr Arg Pro Leu Leu Gly Ser
            1045                1050                1055

Ala Ser Glu Leu Thr Gly Ala Ser Ile Gln Thr Asn Tyr Asn Thr Val
            1060                1065                1070

His Ser Arg Thr Leu Gln Trp Leu Asn Glu Ser Thr Ala Ala Gly Lys
            1075                1080                1085

Val Trp Val Val Ala Asn Asp Glu Gln Gly Pro Ala Ser His Ala Asn
            1090                1095                1100

Pro Pro Asp Asn Gly Trp Pro Gly Tyr Thr Gly Ser Thr Thr Pro Ser
1105                1110                1115                1120

Gln Lys Gln Met Arg Trp Gln Thr Val Trp Gly Asn Tyr Met Ala Gly
            1125                1130                1135

Gly Ala Gly Ile Glu Leu Tyr Ala Gly Tyr Gln Asn Pro Gln Ser Asp
            1140                1145                1150

Leu Thr Leu Asp Asp Phe Arg Ser Arg Asp Arg Met Trp Asp Tyr Cys
            1155                1160                1165

Arg His Ala Asn Thr Phe Phe Thr Glu His Leu Pro Phe Trp Glu Met
1170                1175                1180

Ala Asn Ala Asn Ser Leu Ile Gly Asn Thr Ser Asn Asn Asp Lys
1185                1190                1195                1200

Tyr Cys Phe Ala Lys Thr Gly Glu Tyr Tyr Ala Ile Tyr Leu Pro Asn
            1205                1210                1215

Gly Gly Thr Thr Asn Leu Asn Leu Ser Gly Ala Thr Gly Thr Phe Asp
            1220                1225                1230

Ile Leu Trp Tyr Asp Pro Arg Asn Gly Gly Ala Leu Gln Ala Gly Thr
            1235                1240                1245

Val Ser Ser Val Ile Gly Gly Ser Asn Val Ser Val Gly Asn Ala Pro
            1250                1255                1260

Ser Ser Thr Thr Asp Asp Trp Ala Ile Leu Val Val Lys Gln Gly Leu
1265                1270                1275                1280

Gly Thr Gly Leu Leu Val Asp Ala Gly Ala Ala Lys Thr Ile Ile Leu
            1285                1290                1295

Pro Thr Asn Gln Val Thr Leu Asn Gly Ser Ser Ser Asp Asp Gly Thr
            1300                1305                1310

Ile Thr Ser Arg Leu Trp Thr Gln Ile Ser Gly Pro Asn Thr Ala Ala
```

```
            1315                1320                1325
Leu Ser Gly Gln Thr Ser Asn Thr Leu Gln Ala Ser Ser Leu Ile Ala
            1330                1335                1340
Gly Ser Tyr Val Phe Arg Leu Thr Val Thr Asp Asn Asp Ser Asn Thr
1345                1350                1355                1360
Ala Tyr Asp Gln Thr Thr Val Thr Val Glu Val Asp Ser Ala Pro Ser
                1365                1370                1375
Ile Thr Thr Ser Ser Leu Pro Asp Gly Thr Val Ser Ala Ser Tyr Ser
            1380                1385                1390
Gln Thr Leu Ala Ala Ser Gly Gly Asn Pro Gln Leu Ala Trp Ser Ile
            1395                1400                1405
Ile Glu Gly Ser Leu Pro Thr Gly Leu Ser Ile Asn Ser Ser Gly Val
    1410                1415                1420
Ile Ser Gly Thr Pro Thr Ala Thr Gly Leu Ser Val Phe Lys Val Gln
1425                1430                1435                1440
Thr Gln Asp Ala Asn Gly Asp Thr Asp Asp Ala Val Phe Ser Ile Lys
                1445                1450                1455
Val Val Glu Val Thr Thr Ser Thr Lys Thr Phe Asn Pro Thr Asp Asp
            1460                1465                1470
Ala Phe Ile Glu Trp Ser Thr Pro Tyr Asn Thr Thr Gln Leu Lys Ile
        1475                1480                1485
Glu Asn Gly Ser Arg Val Gly Tyr Met Lys Phe Asn Ile Thr Gly Ile
    1490                1495                1500
Thr Thr Gln Val Glu Ser Ala Val Leu Ser Met Arg Val Ala Gly Asp
1505                1510                1515                1520
Ser Gly Asn Gly Thr Ile Arg Phe Tyr Leu Gly Ser His Asn Asn Trp
            1525                1530                1535
Thr Glu Ala Thr Ile Thr Thr Ala Asn Arg Pro Ala Lys Gly Ala Gln
            1540                1545                1550
Val Gly Ser Met Thr Gly Ser Phe Ser Asn Asn Thr Thr Tyr Gln Ala
            1555                1560                1565
Asp Ile Thr Ser Met Leu Asn Gly Ser Gly Asp Gly Val Tyr Thr Leu
    1570                1575                1580
Val Ile Glu Met Asp Ser Gly Gly Asn Asp Ala Trp Phe Ser Ser Thr
1585                1590                1595                1600
Glu Gly Ala Asn Pro Pro Ser Leu Val Val Asn Tyr Ser Asp Gly Ser
                1605                1610                1615
Thr Asp Glu Ile Pro Val Ala Asn Ala Gly Ala Asp Lys Ala Ile Thr
            1620                1625                1630
Leu Pro Thr Asn Gln Val Leu Ile Asn Gly Ser Gly Thr Asp Asp Gly
            1635                1640                1645
Ser Ile Ser Ser Tyr Ala Trp Ser Gln Val Met Gly Pro Asn Thr Ala
            1650                1655                1660
Ser Leu Ser Gly Ala Phe Ser Ala Lys Leu Ile Ala Thr Gly Leu Ile
1665                1670                1675                1680
Ala Gly Glu Tyr Ala Phe Val Leu Thr Val Thr Asp Asn Thr Ala Asn
                1685                1690                1695
Glu Asp Ser Asp Met Val Ile Val Val Asn Pro Ala Val Gly Ser
            1700                1705                1710
Gly Ser Ala Tyr Thr Asn Trp Ala Ser Asn Gln Phe Ala Gly Leu Ser
            1715                1720                1725
Gly Gly Ala Thr Asn Pro Leu Ala Ala Phe Asp Ala Ser Tyr Met Gly
            1730                1735                1740
```

```
Asn Gly Leu Pro Asn Gly Leu Ile Tyr Ala Met Gly Asn Pro His
1745                1750                1755                1760

Glu Ala Asn Asn Asp Ile Arg Ala Met Leu Pro Glu Ala Arg Gly Asp
                1765                1770                1775

Arg Val Glu Phe Thr Leu Pro Asp Ser Ile Pro Ala Gly Val Ser Val
            1780                1785                1790

Arg Leu Tyr Gln Ala Ser Asp Leu Thr Ala Val Ser Pro Trp Ser Glu
        1795                1800                1805

Thr His Val Arg Asn Ser Asn Gly Thr Trp Thr Pro Ser Leu Ser Ser
    1810                1815                1820

Ser Ala Asn Gly Asp Gly Thr Ser Thr Phe Thr Leu Pro Leu Gly Gly
1825                1830                1835                1840

Gly Ser Thr Gly Phe Tyr Leu Leu Asp Phe Ser Ala Glu
                1845                1850

<210> SEQ ID NO 23
<211> LENGTH: 648
<212> TYPE: PRT
<213> ORGANISM: Opitutus terrae

<400> SEQUENCE: 23

Met Arg Ile Arg His Ser Ser Ile Cys Ala Leu Ala Ser Ala Ala Ile
1               5                   10                  15

Tyr Ala Val Phe Thr Pro Ala Ala Gly Ala Ala Ala Leu Val Ala
            20                  25                  30

Gly Lys Leu Glu Gln Trp His Lys Ile Thr Leu Ser Ile Asp Gly Pro
        35                  40                  45

Glu Ala Arg Glu Thr Asp Thr Ser Pro Asn Pro Phe Leu Asp Tyr Arg
    50                  55                  60

Met Asp Val Thr Phe Thr His Glu Ser Gly Ala Pro Ser Tyr Arg Val
65                  70                  75                  80

Pro Gly Tyr Phe Ala Val Asp Gly Asn Ala Ala Glu Thr Ser Ala Phe
                85                  90                  95

Ala Gly Arg Ile Trp Arg Ala His Leu Ala Pro Asp Lys Pro Gly Met
            100                 105                 110

Trp Arg Tyr Ala Val Ser Phe Arg Arg Gly Pro Glu Val Ala Val Ser
        115                 120                 125

Thr Leu Glu Ala Gly Ala Pro Val Asp Gly Cys Asp Gly Ile Ser Gly
    130                 135                 140

Glu Phe Thr Val Val Pro Thr Asp Lys Thr Gly Arg Asp Phe Arg Ala
145                 150                 155                 160

His Gly Arg Leu Asp Tyr Val Gly Gly Arg Tyr Leu Arg Phe Ala Gly
                165                 170                 175

Ser Gly Glu Tyr Phe Leu Lys Val Gly Ala Asp Ser Pro Glu Asn Leu
            180                 185                 190

Leu Gly Tyr Ser Asp Phe Asp Gly Thr Arg Ser Asn Lys Pro Gly Thr
        195                 200                 205

Pro Ala Arg Pro Asp Glu Ala Ala Pro Pro Ser Leu Leu Lys Thr Trp
    210                 215                 220

Gln Pro His Val Arg Asp Trp Arg Glu Gly Asp Pro Thr Trp Gln His
225                 230                 235                 240

Arg Lys Gly Lys Gly Leu Ile Gly Ala Leu Asn Tyr Leu Ala Ser Thr
                245                 250                 255

Gly Cys Asn Ala Phe Ser Phe Leu Thr Tyr Asn Ala Gly Gly Asp Gly
```

```
                260                 265                 270
Asp Asp Val Trp Pro Phe Val Glu Arg Asp Pro Leu His Phe Asp
            275                 280                 285
Cys Ser Lys Leu Asp Gln Trp Gln Ile Ile Phe Asp His Ala Thr Ala
            290                 295                 300
Leu Gly Leu His Leu His Phe Lys Leu Glu Thr Glu Asn Asp Asp
305                 310                 315                 320
Asn Arg Pro Gly Gly Asp Gly Gln Ile Gly Asp Val Pro Thr Ala Leu
            325                 330                 335
Asp Arg Gly Lys Thr Gly Val Glu Arg Lys Leu Tyr Leu Arg Glu Leu
            340                 345                 350
Ile Ala Arg Phe Ala His Glu Leu Ala Leu Asn Trp Asn Leu Gly Glu
            355                 360                 365
Glu Asn Thr Leu Ser Thr Glu Gln Gln Gln Ala Met Ala Ala Phe Ile
            370                 375                 380
Arg Asp Thr Asp Pro Tyr His His Pro Ile Val Leu His Thr Phe Pro
385                 390                 395                 400
Asp Trp Gln Glu Arg Val Tyr Arg Pro Leu Leu Gly Asp Arg Ser Ala
            405                 410                 415
Leu Thr Gly Val Ser Leu Gln Thr Gly Trp Glu Gln Ser His Arg Arg
            420                 425                 430
Val Leu Gln Trp Ile Glu Glu Ser Ala Ala Gly Lys Gln Trp Val
            435                 440                 445
Val Ala His Asp Glu Gln Asn Pro His Tyr Thr Gly Val Pro Pro Asp
450                 455                 460
Thr Gly Trp Glu Gly Phe Asp Gly Thr Ala Arg Pro Glu Lys Tyr Ser
465                 470                 475                 480
Arg Pro Tyr Thr Ala Asp Asp Val Arg Lys His Thr Leu Trp Gly Ser
            485                 490                 495
Leu Leu Ala Gly Gly Ala Gly Val Glu Tyr Tyr Phe Gly Tyr Thr Leu
            500                 505                 510
Pro Gln Asn Asp Leu Gly Ala Gln Asp Trp Arg Ser Arg Ala Gln Ser
            515                 520                 525
Trp Lys Trp Cys Asp Leu Ala Leu Arg Phe Phe Arg Glu Asn Ala Ile
            530                 535                 540
Pro Phe Trp Asn Met His Asn Ala Asp Glu Leu Val Gly Asn Pro Ser
545                 550                 555                 560
His Asp Asn Ser Arg Tyr Cys Phe Ala Gln Pro Gly Glu Ile Tyr Val
            565                 570                 575
Val Tyr Leu Pro Asn Gly Gly Ser Ala Glu Leu Asp Leu Gly Arg Gly
            580                 585                 590
Ala Asp Gly Ala Thr Phe Gln Val Arg Trp Phe Asn Pro Arg Glu Gly
            595                 600                 605
Gly Pro Leu Gln Ser Gly Asn Val Ser Glu Val Arg Gly Ser Gly Arg
            610                 615                 620
Val Ser Leu Gly Glu Pro Pro Ala Asp Ala Ala Asp Trp Val Val
625                 630                 635                 640
Leu Val Ala Arg Ala Pro Arg Pro
            645

<210> SEQ ID NO 24
<211> LENGTH: 1043
<212> TYPE: PRT
<213> ORGANISM: Rhodopirellula baltica
```

<400> SEQUENCE: 24

```
Met Val Ala Pro Ile Thr Pro Ser Arg Ser Pro Asn Thr Met Gln Val
 1               5                  10                  15

Cys Arg Leu Arg Lys Phe Leu Thr Leu Gln Thr Val Phe Ala Leu Ala
             20                  25                  30

Val Thr Ala Thr Trp Cys Val Ser Val Ala Ala Gln Lys Pro Asp Ala
         35                  40                  45

Val Phe Thr Glu Ala Asn Gly Phe Leu Lys Val Ala Glu Asp Phe
     50                  55                  60

Ala Ser Gln Thr Asn Thr Asp Lys Arg Ala Phe Tyr Leu Thr Thr Ala
 65                  70                  75                  80

Glu Ser Ala Pro Ser Val Gln Pro Asp Gly Asp Pro Ser His Ala Ser
                 85                  90                  95

Asp Ala Ser Gly Gly Ala Tyr Leu Glu Ile Leu Pro Asp Thr Arg Arg
            100                 105                 110

Thr His Ala Asp Lys Leu Ile His Gly Thr Asn Phe Ser Pro Gln Pro
        115                 120                 125

Gly Lys Met Ala Val Leu Thr Tyr Arg Val Asn Val Gln Thr Pro Gly
130                 135                 140

Arg Tyr Tyr Val Trp Val Arg Ala Tyr Ser Thr Gly Ser Glu Asp Asn
145                 150                 155                 160

Gly Leu His Val Gly Ile Asp Gly Thr Trp Pro Glu Ser Gly Gln Arg
                165                 170                 175

Leu Gln Trp Cys Gln Gly Lys His Ser Trp Tyr Trp Asp Ser Lys Gln
            180                 185                 190

Arg Thr Glu Ala Gln His Cys Gly Glu Pro Gly Lys Ile Phe Leu Asp
        195                 200                 205

Ile His Glu Pro Gly Glu His Lys Ile His Phe Ser Met Arg Glu Asp
210                 215                 220

Gly Phe Glu Phe Asp Gln Trp Leu Met Thr Thr Asp Ser Ser Phe Gln
225                 230                 235                 240

Arg Pro Pro Ala Gly Lys Ser Asn Lys Pro Lys Glu Asn Ala Thr Thr
                245                 250                 255

Gln Val Leu Ser Leu Pro Ala Lys Glu Phe Glu Phe Lys Ser Gly Gly
            260                 265                 270

Tyr Tyr Leu Asp Gln Gly Lys Trp Leu Ala Ile Asn Pro Asp Arg Asn
        275                 280                 285

Gln Ser Ala Ala Lys Lys Val Phe Pro Phe Pro Ser Gly Arg Tyr
290                 295                 300

Asp Val Thr Leu Lys Ala Val Gly Glu Asn Asp Gly Gln Ser Thr Tyr
305                 310                 315                 320

Ser Val Ser Ala Asp Lys Glu Ser Ile Gly Ser Phe Thr Cys Pro Met
                325                 330                 335

Ala Asp Gln Thr Phe Ala Glu Gly Lys Gln Phe His Thr Phe Ala
            340                 345                 350

Asn Val Gln Ile Thr Glu Gly Ala Glu Leu Glu Val Ala Ser Lys Ile
        355                 360                 365

Ala Ser Ala Asp Gly Ala Glu Tyr Ser Arg Ala Arg Trp Ser Glu Leu
370                 375                 380

Thr Phe Thr Pro Ala Asn Glu Ala Thr Ala Lys Ala Ala Asn Phe
385                 390                 395                 400

Ala Lys Glu Asn His Leu Val Ala Ala Lys Thr Ser Ala Glu Ser Asn
```

```
            405                 410                 415
Asp Arg Thr Gly Ser Pro Thr Lys Pro Val Ser Asp Gln Pro Leu Gln
            420                 425                 430

Met Pro Arg Glu Lys Asp Gly Asp Ser Val Gln Val Thr Gly Glu
            435                 440                 445

Lys Arg Met Trp His Lys Val Thr Val Thr Leu Asn Gly Pro Tyr Ala
            450                 455                 460

His Glu Gln Asp Asn Thr Pro Asn Pro Tyr Leu Asp His Arg Met Glu
465                 470                 475                 480

Val Glu Phe Lys His Glu Ser Gly Lys Gln Tyr Leu Val Pro Gly Tyr
                485                 490                 495

Phe Ala Ala Asp Gly Asn Ala Ala Asn Thr Ser Ala Glu Ser Gly Thr
                500                 505                 510

Gln Trp Arg Ala His Phe Ala Pro Asp Glu Thr Gly Glu Trp Thr Tyr
                515                 520                 525

Thr Val His Phe Ala Thr Gly Lys Asp Ala Ala Ile Asp Arg Asp Ala
                530                 535                 540

Ser Ala Lys Thr Val Ala Ala Phe Asn Gly Lys Thr Gly Thr Phe Asn
545                 550                 555                 560

Val Ala Lys Thr Asn Lys Ser Gly Arg Asp Phe Arg Ala His Gly Arg
                565                 570                 575

Leu Arg Tyr Val Asn Gln Ser His Leu Gln Phe Ala Gly Thr Gly Gln
                580                 585                 590

Tyr Phe Leu Lys Ala Gly Ala Asp Ala Pro Glu Thr Leu Leu Gly Tyr
                595                 600                 605

Ala Glu Phe Asp Gly Thr Val Ala Gly Lys Pro Gly Lys Val Pro Leu
                610                 615                 620

Lys Lys Tyr Glu Pro His Leu Gly Asp Trp Arg Arg Gly Asp Pro Thr
625                 630                 635                 640

Trp Lys Asp Gly Gln Gly Lys Gly Leu Ile Gly Ala Val Asn Tyr Leu
                645                 650                 655

Ser Ser Lys Gly Cys Asn Ala Phe Ser Phe Leu Thr Tyr Asn Ala Gly
                660                 665                 670

Gly Asp Gly Asp Asn Val Trp Pro Phe Ile Gln Arg Asp Asp Lys Leu
                675                 680                 685

His Tyr Asp Cys Ser Lys Leu Asp Gln Trp Gly Ile Val Phe Asp His
                690                 695                 700

Gly Thr Glu Asn Gly Met Tyr Leu His Phe Lys Leu Gln Glu Thr Glu
705                 710                 715                 720

Asn Asp Asp His Arg Gln Gly Gln Lys Ala Lys Gly Phe Lys Pro Glu
                725                 730                 735

Ser Leu Asp Gly Lys Leu Gly Ser Gln Arg Lys Leu Tyr Leu Arg
                740                 745                 750

Glu Ile Ile Ala Arg Phe Gly His Asn Leu Ala Leu Asn Trp Asn Leu
                755                 760                 765

Ala Glu Glu Thr Thr Gln Thr Thr Asp Glu His Leu Ala Met Leu Asn
                770                 775                 780

Tyr Ile Glu Glu Met Asp Pro Tyr Gly His His Arg Val Leu His Thr
785                 790                 795                 800

Tyr Pro Gly Glu Gln Asp Lys Lys Tyr Asp Pro Leu Leu Gly Asp Lys
                805                 810                 815

Ser Asn Leu Thr Gly Val Ser Leu Gln Asn Ser His Ile Lys Asp Thr
                820                 825                 830
```

His Trp Gln Thr Val Lys Trp Ser Glu Lys Ala Arg Glu Ala Gly Lys
            835                 840                 845

Pro Trp Val Val Ala Phe Asp Glu Ser Gly Ser Ala Ala His Gly Gln
        850                 855                 860

Cys Pro Asp Leu Gly Tyr Arg Gly Tyr Asp Gly Arg Asp Lys Thr Gly
865                 870                 875                 880

Lys Met Thr Tyr Thr Gln His Glu Val Arg Lys Gln Thr Leu Trp Gly
                885                 890                 895

Asn Phe Met Gly Gly Gly Gly Val Glu Tyr Tyr Phe Gly Tyr Gln
            900                 905                 910

Tyr Asp Glu Asn Asp Leu Gly Cys Glu Asp Trp Arg Ser Arg Asp Gln
        915                 920                 925

Ser Trp Asp Ala Cys Arg Val Ala Ile Glu Phe Phe Gln Asn Asn Ala
    930                 935                 940

Val Pro Phe Trp Glu Met Val Asn Ala Asp Glu Leu Val Gly Asn Glu
945                 950                 955                 960

Lys His Asp Asn Ser Lys Tyr Cys Leu Ala Lys Ala Gly Glu Ala Tyr
                965                 970                 975

Val Val Tyr Leu Pro Asn Gly Gly Thr Thr Ser Ile Asp Leu Ser Asp
            980                 985                 990

Ala Asp Gly Glu Phe Gln Val His Trp Tyr Asn Ala Arg Ile Gly Gly
        995                 1000                1005

Asp Leu Gln Ser Gly Ser Val Lys Thr Val Ser Gly Gly Gly Ser Val
    1010                1015                1020

Glu Ile Gly Gln Pro Pro Ala Asp Ala Asp Gln Asp Trp Ala Val Leu
1025                1030                1035                1040

Leu Arg Lys

<210> SEQ ID NO 25
<211> LENGTH: 1160
<212> TYPE: PRT
<213> ORGANISM: Robiginitalea biformata

<400> SEQUENCE: 25

Met Ser Pro Arg Asn Leu Leu Leu Ser Leu Thr Leu Phe Val Phe Ala
1               5                   10                  15

Thr Ala Gly Leu Arg Ala Gln Gly Gln Val Thr Gly Glu Leu Gln Lys
            20                  25                  30

Trp His Arg Ile Gln Ile Leu Phe Asp Gly Pro Gln Thr Ser Glu Ser
        35                  40                  45

Ala Ser Gln Asn Pro Phe Leu Asn Tyr Arg Leu Asn Val Leu Phe Thr
    50                  55                  60

Ala Pro Asp Gly Arg Glu Phe Thr Val Pro Gly Phe Phe Ala Ala Asp
65                  70                  75                  80

Gly Asn Ala Ala Glu Ser Ser Ala Thr Ser Gly Asn Lys Trp Ala Val
                85                  90                  95

Arg Phe Ser Pro Asp Gln Val Gly Thr Trp Thr Tyr Thr Ala Ser Phe
            100                 105                 110

Arg Thr Gly Asp Glu Val Ala Ile Ser Leu Asp Pro Asn Ala Gly Thr
        115                 120                 125

Ala Thr Gly Phe Asp Gly Ala Ser Gly Ser Phe Gln Ile Gly Leu Ser
    130                 135                 140

Thr Lys Ser Ala Pro Asp Asn Arg Ser Lys Gly Arg Leu Glu Tyr Val
145                 150                 155                 160

-continued

```
Gly Glu Arg Tyr Leu Arg Phe Arg Glu Asn Gly Thr Tyr Phe Leu Lys
            165                 170                 175
Ala Gly Ala Asp Ser Pro Glu Asn Leu Leu Ala Tyr Ala Asp Phe Asp
            180                 185                 190
Asn Thr Val Ala Ser Lys Thr Trp Ser Pro His Leu Gly Asp Trp Gln
            195                 200                 205
Gln Gly Asp Ala Glu Trp Lys Asn Gly Lys Gly Arg Ala Leu Ile Gly
            210                 215                 220
Ala Val Asn Tyr Leu Ala Ser Lys Gly Met Asn Ala Phe Ser Phe Leu
225                 230                 235                 240
Thr Met Ser Val Ile Gly Asp Gly Lys Asp Val Trp Pro Trp Val Ser
            245                 250                 255
Thr Thr His Ser Gly Leu Asp Glu Pro Gly Gly Gln Asp Ala Ala Asn
            260                 265                 270
Arg Leu Arg Tyr Asp Val Ser Lys Leu Glu Gln Trp Glu Ile Leu Phe
            275                 280                 285
Gln His Ala Asp Ser Lys Gly Met Phe Leu His Phe Lys Thr Gln Glu
            290                 295                 300
Glu Glu Asn Asp Arg Leu Leu Asp Gly Gly Leu Gly Val Gln Arg
305                 310                 315                 320
Lys Leu Tyr Tyr Arg Glu Leu Val Ala Arg Phe Gly His His Leu Ala
            325                 330                 335
Leu Asn Trp Asn Leu Gly Glu Glu Asn Asp Leu Tyr Asp Glu Leu Gly
            340                 345                 350
Asp Thr Asn Asn Thr Arg Val Arg Ala Tyr Ala Ser Tyr Ile Lys Ser
            355                 360                 365
Leu Asp Pro Tyr Asn His His Ile Val Ile His Ser Tyr Pro Asn Ser
            370                 375                 380
Gln Ser Glu Leu Tyr Glu Pro Leu Leu Gly Asp Ser Asp Leu Thr Gly
385                 390                 395                 400
Pro Ser Leu Gln Ile Gln Ile Asn Asn Ile His Arg Asp Val Lys Arg
            405                 410                 415
Trp Ile Asn Asp Ser Lys Ala Ser Gly Lys Gln Trp Val Val Thr Asn
            420                 425                 430
Asp Glu Gln Gly Asp His Thr Thr Gly Val Ala Ala Asp Ala Ser Tyr
            435                 440                 445
Gly Gly Asp Lys Gly Ser Arg Gly Asp Asn Arg Ser Asp Val Arg His
            450                 455                 460
Lys Thr Leu Trp Gly Thr Leu Met Ala Gly Ala Gly Val Glu Tyr
465                 470                 475                 480
Tyr Phe Gly Tyr Gln Thr Gly Val Thr Asp Leu Thr Ala Glu Asp Trp
            485                 490                 495
Arg Ser Arg Lys Thr Lys Trp Glu Asp Ala Lys Leu Ala Leu Asp Phe
            500                 505                 510
Phe Asn Asp Tyr Leu Pro Phe Trp Ala Met Glu Ser Arg Asp Glu Leu
            515                 520                 525
Ile Ser Lys Ser Gly Ser Tyr Cys Phe Ala Lys Thr Gly Glu Ile Tyr
            530                 535                 540
Val Val Tyr Ile Pro Ser Ser Gly Thr Glu Ser Leu Asn Leu Ser Gly
545                 550                 555                 560
Val Ser Gly Thr Tyr Ser Val Arg Trp Tyr Asn Pro Arg Ser Gly Gly
            565                 570                 575
```

```
Ser Leu Lys Gln Gly Ser Val Ala Thr Ile Asn Gly Gly Val Arg
            580                 585                 590

Asn Leu Gly Thr Ala Pro Thr Asp Thr Gly Ala Asp Trp Val Ala Leu
        595                 600                 605

Val Glu Lys Thr Ser Asp Ser Gly Asp Gly Gly Thr Gly Asn
610                 615                 620

Cys Glu Ala Asp Phe Glu Gln Asn Gly Arg Val Ile Glu Ala
625                 630                 635                 640

Glu Asn Leu Asp Leu Ala Gln Gly Trp Asn Thr Gly Asn Ser Phe Ala
            645                 650                 655

Asp Ala Thr Gly Ser Gly Tyr Ile Val Trp Lys Gly Asn Ser Phe
        660                 665                 670

Ser Ser Pro Gly Asn Gly Thr Ile Ser Thr Ser Ile Ile His Thr
        675                 680                 685

Pro Gly Thr Tyr Arg Phe Glu Trp Arg Asn Lys Val Gly His Gly Thr
        690                 695                 700

Asn Ser Thr Glu Ala Asn Asp Ser Trp Val Arg Phe Pro Asp Ala Asp
705                 710                 715                 720

Asp Phe Tyr Gly Glu Lys Asn Gly Ser Arg Val Tyr Pro Lys Gly Ser
                725                 730                 735

Gly Lys Thr Pro Asn Pro Ala Gly Ala Ser Ala Asp Gly Trp Phe Lys
            740                 745                 750

Val Tyr Leu Ser Gly Thr Thr Asp Trp Thr Trp Ser Thr Asn Thr Ser
        755                 760                 765

Asp His Asp Ala His Gln Ile Tyr Ala Glu Phe Asp Thr Pro Gly Val
        770                 775                 780

Tyr Thr Leu Gln Ile Ser Gly Arg Ser Asn Asp His Leu Ile Asp Arg
785                 790                 795                 800

Ile Thr Leu Ala Leu Ala Gly Gln Ser Ala Thr Asp Leu Ser Leu Gly
                805                 810                 815

Glu Thr Leu Cys Glu Gly Gly Ser Glu Thr Val Ala Val Thr Gly Val
            820                 825                 830

Thr Val Thr Pro Gly Asp Ala Thr Leu Leu Ile Gly Glu Thr Leu Gln
        835                 840                 845

Phe Thr Ala Ala Val Leu Pro Ala Asp Ala Thr Asn Lys Ser Val Ser
850                 855                 860

Trp Ser Ser Ser Asp Pro Ser Val Ala Ile Val Ser Gly Asn Gly Thr
865                 870                 875                 880

Val Gln Ala Leu Ser Glu Gly Gln Val Glu Ile Thr Ala Thr Ala
            885                 890                 895

Asp Gly Asn Phe Thr His Ser Ala Leu Leu Thr Val Glu Ala Ala Asp
                900                 905                 910

Pro Pro Gly Gly Asp Thr Gly Asp Gly Gly Ser Gly Glu Asp Pro Gly
        915                 920                 925

Asn Asp Gly Gly Ser Gly Glu Asp Pro Gly Asn Asp Gly Gly Ser Gly
        930                 935                 940

Glu Asp Pro Gly Asn Asp Gly Ser Gly Glu Asp Pro Asp Gly Asp
945                 950                 955                 960

Gly Ser Gly Glu Glu Pro Gly Asp Gly Ala Ala Gln Ala Ala Ile Gln
                965                 970                 975

Ala Val Asp Val Arg Gln Thr Glu Gly Arg Pro Leu Ile Phe Glu Phe
            980                 985                 990

Ala Leu Ser Gln Pro Val Ser Glu Arg Ile Val Leu Glu Leu Glu Phe
```

```
              995                1000               1005
Val Asp Ile Thr Thr Glu Gln Ser Asp Tyr Val Val Ser Glu Thr Glu
        1010               1015               1020

Leu Val Phe Glu Pro Gly Ser Gln Gln Ala Phe Leu Glu Val Arg Thr
1025                1030               1035               1040

Ile Ser Asp Leu Lys Thr Glu Asp Glu Ser Phe Gln Ile Lys Val
                1045               1050               1055

Val Arg Val Val Ser Gly Gln Val Thr Val Pro Asp Ile Leu Ala Thr
                1060               1065               1070

Gly Thr Ile Leu Asp Asp Arg Asp Met Lys Val Ser Pro Asn Pro
                1075               1080               1085

Ala Thr Ser Tyr Ser Leu Val Gln Met Ser Asn Val Gln Glu Gly Thr
                1090               1095               1100

Tyr Glu Leu Glu Ile Phe Ala Ala Ser Gly His Leu Met Gln Arg Glu
1105                1110               1115               1120

Thr Val Thr Ala Asp Gly Ser Gly Ile Ala Ser Val Thr Leu Ala Gly
                1125               1130               1135

Met Ala Lys Gly Leu Tyr Ile Val Lys Leu Thr Gly Ile Asp Tyr Ala
                1140               1145               1150

Tyr Thr Ala Lys Met Leu Val Lys
                1155               1160

<210> SEQ ID NO 26
<211> LENGTH: 528
<212> TYPE: PRT
<213> ORGANISM: Thermobaculum terrenum

<400> SEQUENCE: 26

Met Ser Ile Arg Ser Leu Pro Arg Arg Thr Val Gly Glu Trp Glu Val
 1               5                  10                  15

Thr Ser Thr Arg Glu Tyr Glu Asn Pro Phe Val Asp Val Glu Val Ile
            20                  25                  30

Gly Arg Phe Ile Ser Pro Ser Gly Arg Glu Trp Arg Val Pro Gly Phe
        35                  40                  45

Tyr Asp Gly Asp Gly Val Trp Lys Val Arg Phe Asn Pro Gly Glu Glu
    50                  55                  60

Gly Arg Trp Ala Tyr Arg Leu Glu Ser Tyr Pro Glu Asp Pro Glu Leu
65                  70                  75                  80

Arg Ala Glu Gly Thr Phe Glu Val Leu Pro Arg Glu Ala Arg Gly Phe
                85                  90                  95

Leu Arg Ser Val Pro Gly Gln Ala Trp Gly Phe Ile Tyr Glu Ser Gly
            100                 105                 110

Glu Pro Val Phe Ile Leu Gly Asp Thr Val Tyr Asn Leu Phe Gly Met
        115                 120                 125

Ala His Cys Gly Ala Asp Val Glu Ala Phe Leu Glu Arg Arg Ala Ser
    130                 135                 140

Gln Gly Phe Asn Leu Leu Arg Val Arg Val Pro Val Ser Pro Phe His
145                 150                 155                 160

Pro Pro Lys Gly Tyr Ser Glu Trp Gln Thr Arg Arg Thr Trp Pro Trp
                165                 170                 175

Glu Gly Ser Glu Gln Ala Pro Val Phe Asp Arg Phe Asn Leu Glu Tyr
            180                 185                 190

Phe Ala Thr Val Asp Arg Val Val Arg Lys Val Glu Glu Leu Gly Leu
        195                 200                 205
```

```
Gly Leu Glu Val Ile Met Glu Ala Trp Gly Phe Glu Phe Pro Phe Asn
210                 215                 220

Ser Arg His Ile Phe Val Ala Glu Trp Glu Glu Leu Trp Met Arg Tyr
225                 230                 235                 240

Leu Val Ala Arg Tyr Asp Ala Tyr Ser Cys Val Tyr Phe Trp Thr Pro
                245                 250                 255

Met Asn Glu Tyr Glu Phe Tyr Pro Asn Gly Asp Trp His Tyr Lys Pro
            260                 265                 270

Thr Ala Asp Arg Trp Ala Ile Ile Ala Arg Trp Leu Arg Ala Asn
        275                 280                 285

Ala Pro His Gly His Ile Val Ser Leu His Asn Gly Pro Trp Asp Pro
290                 295                 300

Pro Phe Ala His Arg Phe Arg Ser Asp Pro Lys Ala Ile Asp Thr Ile
305                 310                 315                 320

Met Phe Gln Phe Trp Gly Thr Thr Gly Arg Asp Asp Ala Trp Leu Ala
                325                 330                 335

Ala Gly Ile Glu Asp Arg Ile Ala Tyr Ser Leu Gly Gly Trp Tyr Gly
            340                 345                 350

Thr Ala Val Phe Ala Glu Tyr Gly Tyr Glu Arg Asn Pro Ala Leu Pro
        355                 360                 365

Leu Asn Ile Pro Gly His Glu Phe Cys Asp Pro Glu His Thr Arg Arg
370                 375                 380

Gly Ala Trp Arg Gly Ala Phe Cys Gly Leu Gly Val Ile His Gly Phe
385                 390                 395                 400

Glu Asn Ser Trp Gly Pro Phe Met Val Leu Glu Glu Asp Gln Pro Gly
                405                 410                 415

Leu Glu Tyr Leu Leu His Leu Arg Arg Phe Phe Thr Glu Val Val Pro
            420                 425                 430

Phe His Arg Leu Leu Pro Asp Ala Ser Leu Val Val Ser Asp Ile Ser
        435                 440                 445

Glu Gln Gly Gly Lys Pro Leu Ala Leu Ser Ser Pro Glu Arg Asp Val
    450                 455                 460

Leu Ala Val Tyr Leu Pro Arg Gly Gly Glu Phe Lys Leu Ser Val Asn
465                 470                 475                 480

Pro Pro Ala Asp Pro Cys Trp Tyr Asp Pro Arg Thr Gly Glu Val Leu
                485                 490                 495

Ala Ala Glu Ala Ser Pro Ser Gly Gly Trp Val Ala Pro Gln Ser Gly
            500                 505                 510

Pro Ala Asp Arg Pro His Asp Trp Val Trp Phe Ser Thr Ser Gly Arg
        515                 520                 525

<210> SEQ ID NO 27
<211> LENGTH: 529
<212> TYPE: PRT
<213> ORGANISM: Bifidobacterium dentium

<400> SEQUENCE: 27

Met Ala Glu Tyr Lys Thr Gln Val Glu Gln His Arg Leu Phe Glu Ile
1               5                   10                  15

Asn Leu Thr Gly Thr Thr Glu Gly Asn Pro Tyr Gln Asp Val Thr Leu
                20                  25                  30

Ser Ala Asp Phe Thr Asn Ala Glu Thr Gly Gln Ile Val Val Val Gly
            35                  40                  45

Gly Phe Tyr Arg Gly Asn Gly Asn Tyr Ser Val Arg Phe Met Ala Ser
        50                  55                  60
```

```
Ser Ala Gly Arg Trp Ala Phe Thr Thr Arg Ser Thr Asp Pro Ala Leu
 65                  70                  75                  80

Asp Gly Gln Thr Gly Val Phe Thr Val Thr Pro Ala Thr Gln Asp Asn
                 85                  90                  95

His Gly Arg Val Leu Thr Ala Thr Glu Ala Leu Ser Gly Lys Ala Arg
                100                 105                 110

Glu Ala Tyr Gly Ser Glu Leu Lys Tyr Arg Phe Thr Tyr Glu Asp Gly
            115                 120                 125

Thr Pro Tyr Gln Pro Tyr Gly Thr Cys Tyr Ala Trp Val Ser Gln
130                 135                 140

Pro Thr Asp Val Gln Asp Arg Thr Val Ala Thr Leu Ala Lys Ala Pro
145                 150                 155                 160

Phe Asn Lys Ile Arg Met Cys Val Phe Pro Lys Phe Tyr Asp Phe Asn
                165                 170                 175

Thr Ala Asp Pro Trp Ala Tyr Ala Tyr Pro Gly Thr Arg Glu Thr Gly
                180                 185                 190

Phe Asp His Thr Cys Phe Asp Glu Glu Phe Phe Ala Asn Leu Asp Cys
            195                 200                 205

Arg Ile Ala Gln Leu Asp Glu Leu Gly Ile Glu Ala Asp Ile Ile Leu
210                 215                 220

Leu His Pro Tyr Asp Lys Pro Asp Trp Gly Phe Ser Lys Met Thr Lys
225                 230                 235                 240

Val Glu Asp Glu Met Tyr Leu Ala Tyr Met Ala Arg Arg Tyr Gly Ala
                245                 250                 255

Tyr Lys Asn Val Trp Trp Ser Leu Ala Asn Glu Tyr Asp Leu Met Pro
                260                 265                 270

Gln Lys Ser Leu Glu Asp Trp Arg Glu Tyr Ala Arg Val Val Met Ala
            275                 280                 285

Asn Asp Ala Phe Gly His Leu Arg Ser Ile His Asn Cys Ile Pro Ile
    290                 295                 300

Tyr Asp Tyr Asn Glu Pro Trp Cys Thr His Cys Ser Ile Gln Arg Val
305                 310                 315                 320

Asp Val Thr Arg Thr Thr Glu Cys Ile Ala Asp Trp Arg Lys Ala Tyr
                325                 330                 335

Gly Lys Pro Val Val Cys Asp Glu Pro Gly Tyr Glu Gly Asn Ile Tyr
                340                 345                 350

Trp Gly Trp Gly Asn Leu Thr Gly Glu Glu Leu Met Arg Arg Phe Trp
            355                 360                 365

Glu Gly Ala Met Arg Gly Gly Tyr Val Thr His Gly Glu Thr Phe Ile
370                 375                 380

Asp Glu Asp Glu Gln Ile Trp Trp Ala His Gly Gly Glu Leu His Gly
385                 390                 395                 400

Asp Ala Pro Ala Arg Ile Ala Phe Met Arg Ser Ile Phe Asp Val
                405                 410                 415

Pro Leu Asp Ala Thr Pro Leu Asp Gly Asp Leu Asp Ala Asp Arg Ala
                420                 425                 430

Trp Pro Ile Ala Asn Pro Ile Asn Gly Ser Val Asn Val Ala Pro Ala
            435                 440                 445

Val Glu Lys Ala Ala Gln Tyr Trp Asp Val Pro Val Leu Arg Gly Gly
        450                 455                 460

Asp Asp Tyr Gln Leu Ile Tyr Phe Gly Trp Phe Arg Pro Lys Tyr Arg
465                 470                 475                 480
```

```
Glu Ile Pro Leu Pro Ala Gly Ser Ala Tyr Val Val Asp Val Ile Asp
                485                 490                 495

Thr Trp Asn Met Thr Val Glu Thr Leu Pro Asp Ala Tyr Glu Asn Ser
            500                 505                 510

Val Arg Val Asp Leu Gly Arg Gln Tyr Met Ala Val Arg Ile Arg Lys
        515                 520                 525

Ala

<210> SEQ ID NO 28
<211> LENGTH: 536
<212> TYPE: PRT
<213> ORGANISM: Opitutus terrae

<400> SEQUENCE: 28

Met Asn Leu Arg Thr Phe Glu Val Ala Pro Trp Leu Ala Leu Leu Leu
  1               5                  10                  15

Ala Leu Ala Ala Pro Met Glu Gly Gly Thr Val Glu Glu Ser Pro Ala
             20                  25                  30

Val Glu Arg Trp Asn Thr Phe Glu Leu Thr Leu His Gly Pro Ala Thr
         35                  40                  45

Gly Asn Pro Phe Val Asp Val Arg Leu Gly Ala Arg Phe Thr Asp Gly
     50                  55                  60

Thr Arg Thr Ile Glu Val Pro Gly Phe Tyr Asp Gly Asp Gly Val Tyr
 65                  70                  75                  80

Arg Val Arg Phe Met Pro Asp Ala Thr Gly Ala Trp His Tyr Glu Thr
                 85                  90                  95

Ser Ser Asn Asp Pro Leu Leu Ala Gly Gln Arg Gly Glu Phe Thr Val
            100                 105                 110

Thr Pro Ala Arg Arg Gly Asn His Gly Pro Val Arg Val Arg Asn Thr
        115                 120                 125

Tyr His Phe Ala Tyr Ala Asp Gly Thr Pro Phe Lys Pro Ile Gly Thr
    130                 135                 140

Thr Ile Tyr Asn Trp Thr Asp Ala Pro Glu Glu Val Gln Glu Gln Thr
145                 150                 155                 160

Leu Arg Thr Leu Ala Thr Ala Pro Phe Asn Lys Ala Arg Met Leu Leu
                165                 170                 175

Thr Pro Gln Ser Val Ala Tyr Arg Arg Gln Phe Ala Pro Pro Arg Trp
            180                 185                 190

Pro Phe Ala Gly Gln Pro Pro Arg Asp Trp Asp Phe Ala Arg Phe Asn
        195                 200                 205

Pro Glu Tyr Phe Arg Ala Phe Glu Lys Arg Val Ala Gln Leu Arg Glu
    210                 215                 220

Leu Gly Ile Glu Ala Asp Leu Ile Leu Phe His Pro Tyr Gly Lys Ala
225                 230                 235                 240

Trp Gly Phe Glu Ala Met Asp Ala Ala Ala Asp Glu Arg Tyr Val Arg
                245                 250                 255

Tyr Val Val Ala Arg Phe Ala Ala Phe Arg Asn Val Trp Trp Ser Leu
            260                 265                 270

Ala Asn Glu Tyr Asp Leu Val Arg Thr Lys Thr Glu Glu His Trp Asp
        275                 280                 285

Gln Leu Gly Arg Leu Val Gln Ala Thr Asp Pro Phe Asp His Leu Arg
    290                 295                 300

Ser Ile His His Ser Gln Leu Leu Phe Asp Asn Arg Gln Pro Trp Val
305                 310                 315                 320
```

```
Thr His Ala Ser Ile Gln Asn Gly Ser Ala Val Glu Glu Pro Gly Arg
            325                 330                 335

Ala Glu Leu Tyr Arg Asp Val Trp Arg Lys Pro Val Val Tyr Asp Glu
        340                 345                 350

Val Lys Tyr Glu Gly Asn Ala Arg Arg Trp Gly Gln Leu Ser Gly
    355                 360                 365

Pro Glu Met Val His Arg Phe Trp Cys Gly Thr Val Ala Gly Thr Tyr
370                 375                 380

Val Gly His Gly Asp Phe Phe Gly Val Glu Asp Ala Pro Asp Thr Trp
385                 390                 395                 400

Thr Ser Phe Gly Gly Val Leu Arg Gly Glu Ser Ala Pro Arg Leu Ala
            405                 410                 415

Phe Leu Arg Thr Ile Leu Glu Ser Gly Pro Ala Asp Gly Leu Asp Pro
        420                 425                 430

Val Asp Lys Trp Gln Asn Val Thr Val Ala Gly Val Pro Gly Glu Tyr
    435                 440                 445

Tyr Leu Val Tyr Leu Gly Arg Glu Ser Ala Thr Ala Trp Pro Phe Arg
450                 455                 460

Leu Phe Arg Ser Gly Leu Lys Asp Gly Met Arg Phe Lys Val Glu Val
465                 470                 475                 480

Ile Asp Thr Trp Ala Met Thr Ile Thr Pro Val Glu Arg Glu Phe Val
            485                 490                 495

Ile Thr Lys Ser Asp Asp Tyr Thr Phe Val Ala Val Asp Gly Gly Ser
        500                 505                 510

Ile Ala Leu Pro Gly Lys Pro Gly Ile Ala Leu Arg Ile Gln Arg Thr
    515                 520                 525

Ala Pro Ala Lys Phe Leu Lys Glu
530                 535

<210> SEQ ID NO 29
<211> LENGTH: 534
<212> TYPE: PRT
<213> ORGANISM: Bacteroides vulgatus

<400> SEQUENCE: 29

Met Ser Thr Lys Phe Tyr Val Ile Ala Val Trp Thr Leu Leu Ser Phe
1               5                   10                  15

Val Val Lys Val Asn Ala Gln Asp Lys Val Glu Cys Trp Asp Arg Phe
            20                  25                  30

Glu Leu Ser Phe Lys Gln Val Thr Lys Gly Asn Pro Phe Asp Ile Arg
        35                  40                  45

Leu Ser Ala Thr Phe Val Cys Gly Lys Glu Lys Lys Thr Val Glu Gly
    50                  55                  60

Phe Tyr Asp Gly Glu Asn Thr Tyr Arg Ile Arg Phe Met Pro Ala Val
65                  70                  75                  80

Ala Gly Glu Trp Arg Tyr Val Thr Ser Ser Ile Gly Ala Met Asn
            85                  90                  95

Gly Arg Lys Gly Thr Phe Thr Val Ile Pro Ala Gly Lys Asp Asn His
        100                 105                 110

Gly Met Val Leu Val Asp Gly Glu His Asn Phe Lys Tyr Ala Asp Gly
    115                 120                 125

Thr Arg Tyr Tyr Pro Met Gly Thr Thr Ala Tyr Ala Trp Thr His Met
130                 135                 140

Lys Glu Thr Thr Gln Glu Ala Thr Leu Lys Ser Phe Gly Glu Ala Gly
145                 150                 155                 160
```

Phe Asn Lys Val Arg Met Cys Val Phe Pro Lys Asn Tyr Ser Leu Val
            165                 170                 175

Lys Asp Glu Pro Ala Leu Tyr Pro Phe Glu Ile Arg Lys Thr Ile Lys
        180                 185                 190

Asp Lys Glu Gly Asn Glu Arg Lys Glu Trp Asp Phe Asp Arg Phe Asp
    195                 200                 205

Pro Ala Phe Phe Gln His Leu Glu Lys Arg Ile Asp Gln Leu Asn Arg
210                 215                 220

Leu Gly Ile Glu Ala Asp Leu Ile Leu Phe His Pro Tyr Asp Lys Gly
225                 230                 235                 240

Arg Trp Gly Phe Asp Ala Met Ser Asn Glu Val Asn Val Arg Tyr Ile
                245                 250                 255

Lys Tyr Ile Thr Ala Arg Leu Ala Ser Phe Arg Asn Val Trp Trp Ser
                260                 265                 270

Met Ala Asn Glu Trp Asp Tyr Val Lys Ala Lys Thr Val Asp Asp Trp
            275                 280                 285

Lys Leu Leu Thr Lys Thr Val Val Glu Asn Asp Pro Tyr Arg His Leu
        290                 295                 300

Cys Ser Ile His Gly Ala Thr Ala Thr Tyr Phe Asp Tyr Trp Met Pro
305                 310                 315                 320

Glu Phe Thr His Val Ser Ile Gln Asp Glu Ala Pro Val Leu Ser Ser
                325                 330                 335

Thr Ala Ser Ala Thr Leu Arg Lys Ile Tyr Arg Lys Pro Val Ile Cys
                340                 345                 350

Asp Glu Val Gly Tyr Glu Gly Asn Leu Pro Tyr Arg Trp Gly Arg Leu
            355                 360                 365

Ser Pro Gln Gln Met Thr Cys Phe Ile Leu Asn Gly Leu Leu Gly Gly
        370                 375                 380

Ile Tyr Val Thr His Gly Glu Cys Tyr Gln Gln Gly Asn Glu Pro Ile
385                 390                 395                 400

Phe Trp Ala Gln Gly Gly Ser Leu Lys Gly Glu Ser Trp Lys Arg Val
                405                 410                 415

Lys Phe Leu Arg Thr Ile Ile Glu Ala Ala Pro His Pro Leu Glu Met
                420                 425                 430

Ala Asp Ile Ser Arg Asp Leu Val Thr Ser Thr Ala Gly Pro Asp Tyr
            435                 440                 445

Tyr Leu Val Asn Met Gly Lys Asp Val Lys Gly Phe Trp Thr Phe Asn
        450                 455                 460

Leu Pro Val Lys Asn Ala Asp Tyr Asn Lys Leu Gln Lys Asn Lys Arg
465                 470                 475                 480

Phe Lys Val Glu Ile Ile Asp Val Trp Ala Met Thr Val Thr Glu Tyr
                485                 490                 495

Pro Val Ile Phe Glu Thr Thr Glu Glu Leu Asp Tyr Arg Val Phe Asp
            500                 505                 510

Ile His His Arg Gly Val Arg Ile Pro Asp Ala Pro Tyr Ile Val Leu
        515                 520                 525

Arg Ile Thr Glu Val Lys
    530

<210> SEQ ID NO 30
<211> LENGTH: 534
<212> TYPE: PRT
<213> ORGANISM: Spirosoma linguale

```
<400> SEQUENCE: 30

Met Asn Tyr Arg Leu Phe Ser Leu Leu Val Leu Gly Leu Leu Phe Ser
 1               5                  10                  15

Lys Ser Leu Ile Ala Gln Glu Val Glu Gln Trp Gly Arg Phe Glu Lys
             20                  25                  30

Thr Phe Thr Ala Lys Ala Thr Gly Asn Pro Phe Thr Glu Val Thr Leu
         35                  40                  45

Thr Ala Glu Leu Ser Asn Gly Tyr Thr Thr Tyr Ser Val Ala Gly Phe
     50                  55                  60

Tyr Asp Gly Lys Asp Thr Phe Lys Ile Arg Phe Met Pro Pro Lys Thr
 65                  70                  75                  80

Gly Lys Trp Arg Tyr Lys Thr Ser Ser Asn Val Ala Gly Leu Thr Asn
                 85                  90                  95

Lys Lys Gly Glu Phe Thr Cys Val Ala Ala Arg Gly Asn Ser Gly
            100                 105                 110

Pro Val Arg Val Ser Asp Met Tyr Ala Phe Lys Tyr Ala Asp Gly Thr
            115                 120                 125

Asn Tyr Tyr Pro Phe Gly Thr Thr Ala Tyr Ala Trp Thr His Met Gly
130                 135                 140

Glu Glu Thr Gln Glu Ile Thr Leu Asn Thr Leu Lys Asn Ser Gly Phe
145                 150                 155                 160

Asn Lys Leu Arg Met Cys Val Phe Pro Lys Asn Tyr Glu Leu Val Lys
                165                 170                 175

Glu Ala Pro Asp Leu Phe Pro Phe Glu Ile Lys Glu Gln Lys Lys Asp
            180                 185                 190

Ala Asp Gly Lys Pro Tyr Thr Val Trp Asn Phe Asp Lys Phe Asn Pro
            195                 200                 205

Ala Phe Phe Gln His Leu Glu Lys Arg Ile Asp Asp Leu Asn Lys Leu
210                 215                 220

Gly Ile Glu Ala Asp Leu Ile Leu Phe His Pro Tyr Asp Lys Gly Arg
225                 230                 235                 240

Trp Gly Phe Asp Ala Met Pro Asn Glu Val Asn Ile Arg Tyr Leu Lys
                245                 250                 255

Tyr Leu Leu Ala Arg Leu Ser Ser Tyr Lys Asn Val Trp Trp Ser Leu
            260                 265                 270

Ala Asn Glu Trp Asp Tyr Val Lys Ser Lys Thr Val Ser Asp Trp Asp
            275                 280                 285

Leu Leu Ala Lys Thr Val Ala Gln Asn Asp Pro Tyr Lys His Leu Cys
290                 295                 300

Ser Ile His Gly Ala Thr Ala Thr Tyr Tyr Asp Tyr Arg Lys Pro Glu
305                 310                 315                 320

Phe Thr His Val Ser Ile Gln Asp Glu Thr Pro Val Gln Ser Pro Asn
                325                 330                 335

Ala Ala Ala Met Leu Arg His Ile Tyr His Lys Pro Val Ile Ala Asp
            340                 345                 350

Glu Val Gly Tyr Glu Gly Asn Leu Lys Ser Arg Trp Gly Arg Tyr Ser
            355                 360                 365

Pro Glu Glu Met Thr Tyr Leu Val Trp Asn Gly Val Leu Gly Gly Thr
370                 375                 380

Tyr Val Thr His Gly Glu Cys Tyr Met Ala Ala Pro Thr Asp Thr Ile
385                 390                 395                 400

Phe Trp Ala Lys Gly Gly Met Phe Lys Gly Thr Ser Trp Lys Arg Ile
                405                 410                 415
```

```
Ala Phe Leu Arg Gln Ile Val Glu Ala Phe Pro Asn Pro Leu Ser Leu
            420                 425                 430

Ser Asp Val Ser Arg Asp Asn Val Thr Ala Thr Ala Gly Asp Gly Gln
            435                 440                 445

Tyr Leu Val Tyr Phe Gly Lys Gln Thr Asn Asp Ser Trp Leu Phe Asn
450                 455                 460

Leu Pro Ala Lys Asn Ser Ser Phe Gln Lys Leu Thr Ala Gly Gln Arg
465                 470                 475                 480

Phe Lys Val Glu Val Ile Asp Thr Trp Asp Met Thr Ile Gln Pro Asp
            485                 490                 495

Pro Gln Ile Phe Glu Thr Ala Ser Glu Asn Asp Tyr Arg Leu Tyr Asp
            500                 505                 510

Lys Thr Leu Lys Lys Val Arg Leu Pro Leu Lys Pro Tyr Val Ala Leu
            515                 520                 525

Arg Ile Thr Glu Ile Lys
            530

<210> SEQ ID NO 31
<211> LENGTH: 481
<212> TYPE: PRT
<213> ORGANISM: Unknown
<220> FEATURE:
<223> OTHER INFORMATION: Geobacillus sp.

<400> SEQUENCE: 31

Met Glu Gly Ser Ala Ser Ala Leu Met Gly Met Gln Glu Val Glu Arg
 1               5                  10                  15

Trp Gly Ile Phe Glu Val Ala Leu Ser Gly Pro Ser Ala Gly Asn Pro
                20                  25                  30

Phe Glu Val Ala Val Ser Ala Thr Phe Glu Tyr Arg Asn Asp Arg
                35                  40                  45

Val Glu Val Glu Gly Phe Tyr Asp Gly Asp Gly Ile Tyr Arg Val Arg
            50                  55                  60

Phe Met Pro Asp Arg Glu Gly Thr Trp Arg Tyr Val Thr Lys Ser Gly
65                  70                  75                  80

Thr Ser Glu Leu Asp Gly Ala Thr Gly Ser Phe Leu Cys Thr Ser Pro
                85                  90                  95

Ser Lys Gly Asn His Gly Pro Val Arg Val Lys Asp Gly Tyr Leu Phe
                100                 105                 110

Ala Phe Glu Asp Gly Thr Pro Tyr Met Pro Phe Gly Thr Thr Cys Tyr
            115                 120                 125

His Trp Thr His Thr Gly Ser Lys Glu His Glu Leu Gln Thr Leu Glu
        130                 135                 140

Glu Leu Gly Gln Ser Pro Phe Asn Lys Val Arg Met Cys Leu Leu Pro
145                 150                 155                 160

Thr Arg Asp Met Arg Pro Glu Met Val Ala Phe Ala Gly Thr Cys Pro
                165                 170                 175

Glu Asp Ala Asp Thr Thr Arg Phe Asn Pro Ala Phe Ala His Leu
            180                 185                 190

Glu Glu Arg Ile Gly Asp Leu Met Lys Leu Gly Val Glu Ala Asp Leu
            195                 200                 205

Ile Leu Phe His Pro Tyr Asp Lys Gln Gly Gly Trp Gly Phe Asn Ser
        210                 215                 220

Met Ser Arg Glu Gln Asp Phe Tyr Tyr Leu Arg Tyr Val Ile Ala Arg
225                 230                 235                 240
```

```
Leu Gly Ala Tyr Arg Asn Val Trp Trp Ser Leu Ser Asn Glu Tyr Asp
                245                 250                 255

Phe Asn Lys Met Lys Thr Ile Glu Asp Trp Asp Arg Leu Leu Gln Tyr
            260                 265                 270

Val Gln Arg Lys Asp Pro Tyr Gln Arg Leu Arg Ser Ile His Asn Gly
        275                 280                 285

Thr Lys Met Tyr Glu Gln Ser Ser Leu Tyr Asp Phe Ser Lys Ser Trp
    290                 295                 300

Leu Thr His Gln Ser Ile Gln His Trp Asp Thr Ser Pro Thr Thr Glu
305                 310                 315                 320

Trp Arg Glu Ala Val Arg Lys Pro Ile Val Asp Glu Ile Ser Tyr
                325                 330                 335

Glu Gly Asn Val Ala Lys Arg Trp Gly Asn Ile Thr Gly Leu Glu Leu
                340                 345                 350

Ile His Arg Tyr Trp Glu Gly Leu Thr Lys Gly Gly Phe Val Ala His
                355                 360                 365

Gly Glu Cys Phe Glu Asn Lys Pro Thr Arg Ala Trp Ile Ser Ser Gly
        370                 375                 380

Gly Lys Met Tyr Gly Ser Pro Glu Arg Ile Arg Phe Leu Arg Gln
385                 390                 395                 400

Val Met Glu Glu Gly Pro Glu Asp Trp Met Gln Ala Arg Glu Glu Gly
                405                 410                 415

Gly Tyr Ala Leu Leu Tyr Leu Gly Lys Tyr Arg Leu Ser Ser Tyr Lys
                420                 425                 430

Leu Pro Leu Ser Gln Asp Arg Glu Tyr Arg Ile Glu Leu Ile Asp Ile
            435                 440                 445

Trp Lys Met Thr Ile Thr Pro Leu Asp Gly Thr Phe Thr Gly Gln Ser
    450                 455                 460

Asp Leu Ala Leu Pro Ala Arg Pro Tyr Ile Ala Leu Arg Ala Gln Ala
465                 470                 475                 480

Val

<210> SEQ ID NO 32
<211> LENGTH: 509
<212> TYPE: PRT
<213> ORGANISM: Thermotoga maritima

<400> SEQUENCE: 32

Met Ile Ser Met Thr Gln Asn Asn Val Glu Lys Trp Gly Thr Tyr Glu
1               5                   10                  15

Ile Thr Leu Lys Gly Lys Ala Glu Gly Asn Pro Phe Thr Asp Val Glu
            20                  25                  30

Ile Lys Ala Val Phe Thr Ser Glu Ala Gly Asp Ser Phe Glu Val Glu
        35                  40                  45

Gly Phe Tyr Asp Gly Glu Asp Thr Phe Lys Ile Arg Phe Met Pro Asn
    50                  55                  60

Arg Thr Gly Leu Trp Lys Tyr Glu Val Arg Ser Asp Ile Lys Asp Leu
65                  70                  75                  80

Asp Gly Met Lys Gly Glu Phe Leu Cys Val Asp Pro Ser Glu Gly Asn
                85                  90                  95

His Gly Pro Val Arg Val Cys Asn Thr Tyr His Phe Cys Tyr Glu Asp
            100                 105                 110

Gly Thr Pro Tyr His Pro Phe Gly Thr Thr Leu Tyr Ala Trp Val His
        115                 120                 125
```

```
Gln Arg Glu Glu Leu Ile Gln Gln Thr Leu Glu Ser Leu Arg Asn Ser
    130                 135                 140

Pro Phe Asn Lys Val Arg Met Cys Val Phe Pro Lys Tyr Tyr Ala Tyr
145                 150                 155                 160

Asn Arg Glu Glu Pro Pro Met Leu Pro Met Ser Trp Arg Glu Glu Asp
                165                 170                 175

Gly Arg Tyr Gln Val Glu Phe Asn Val Lys Phe Phe Gln His Phe Glu
                180                 185                 190

Arg Leu Val Lys Glu Leu Met Asp Met Gly Ile Glu Ala Asp Val Ile
            195                 200                 205

Leu Phe His Pro Tyr Asp Lys Trp Gly Phe Cys Ser Met Pro Glu Glu
    210                 215                 220

Val Asp Lys Ala Tyr Leu Arg Tyr Leu Ile Ala Arg Ile Ser Ser Tyr
225                 230                 235                 240

Arg Asn Val Trp Trp Ser Met Ala Asn Glu Tyr Asp Leu Ile Lys Pro
                245                 250                 255

Gln Lys Asp Trp Asp Gly Tyr Phe His Phe Ile Val Glu Lys Asp Pro
                260                 265                 270

Tyr Asn His Leu Arg Ser Val His Gln Cys Phe Lys Phe Tyr Asp His
            275                 280                 285

Thr Lys Pro Trp Ile Thr His Ala Ser Ile Gln Trp Gln Gly Ser Leu
    290                 295                 300

Arg Ser Trp Ser Gly Glu Pro Glu Ile Asp Ile Gly Ile Asn Leu Ile
305                 310                 315                 320

Pro Lys Trp Arg Glu Met Tyr Lys Lys Pro Val Ile Ile Asp Glu Cys
                325                 330                 335

Gly Tyr Glu Gly Asn Ile Glu Tyr Gly Trp Gly Asn Leu Pro Pro Gln
                340                 345                 350

Glu Met Met Asn Arg Phe Trp Glu Gly Val Thr Ser Gly Gly Tyr Val
            355                 360                 365

Thr His Gly Glu Thr Tyr Tyr Ser Glu Asp Glu Val Leu Trp Trp Ser
    370                 375                 380

Lys Gly Gly Arg Leu Lys Gly Glu Ser Pro Lys Arg Ile Ala Phe Leu
385                 390                 395                 400

Arg Thr Ile Ile Glu Glu Ala Pro Pro Phe Leu Lys Pro Ile Lys Leu
                405                 410                 415

Asp Pro Met Met Asp Trp Asp Val His Cys Ile Gly Lys Glu Gly Glu
                420                 425                 430

Tyr Tyr Leu Ile Tyr Phe Asp Ile Asn Arg Pro Val Lys Arg Thr Leu
            435                 440                 445

Lys Leu Pro Glu Gly Lys Tyr Arg Val Asp Leu Val Asp Cys Trp Glu
    450                 455                 460

Thr Glu Ile His Ser Leu Gly Ile Phe Gln Gly Gln Val Val Ile Arg
465                 470                 475                 480

Leu Pro Gly Lys Ser Tyr Val Ala Leu Arg Ile Gln Lys Met Glu Asn
                485                 490                 495

Asn Asp Asp Trp Ile Ile Leu Arg Glu Asp Ala Lys Leu
                500                 505

<210> SEQ ID NO 33
<211> LENGTH: 725
<212> TYPE: PRT
<213> ORGANISM: Unknown
<220> FEATURE:
```

<223> OTHER INFORMATION: bacterium Ellin514 (ZP_03628309.1)

<400> SEQUENCE: 33

```
Met Ala Tyr Leu Lys Met Pro Ile Ala Leu Leu Ala Leu Phe Ile Cys
 1               5                  10                  15

Leu Glu Gly Thr Ala Phe Ala Leu Asn Ala Asp Gly Pro Gly Ser Ala
            20                  25                  30

Leu Ala Asn Gln Met Val Glu Trp Thr Phe Thr Ser Thr Arg Pro Tyr
        35                  40                  45

Lys Asp Pro Phe Asn Gln Ile Glu Leu Asn Val Thr Phe Thr Thr Pro
    50                  55                  60

Ser Gly Lys Lys Leu Leu Val Pro Ala Phe Trp Asp Gly Gly Asp Ile
65                  70                  75                  80

Trp His Val Arg Tyr Ser Ser Thr Glu Thr Gly Ile His His Phe Ser
                85                  90                  95

Thr Val Cys Ser Asp Ser Arg Asn Thr Ser Leu His Ala Val Ala Gly
            100                 105                 110

Lys Val Glu Ile Lys Pro Tyr Val Gly Thr Asn Ala Phe Tyr Leu His
        115                 120                 125

Gly Pro Ile Gln Val Ala Lys Asp Lys Asn His Phe Glu His Ala Asp
    130                 135                 140

Gly Thr Pro Phe Phe Trp Leu Ser Asp Ser Trp Tyr Met Ser Leu Cys
145                 150                 155                 160

Lys Arg Leu Lys Trp Ser Glu Glu Phe Asn Thr Leu Thr Gln Asp Arg
                165                 170                 175

Val Ala Lys Gly Phe Asn Val Val Gln Val Val Ala Gly Leu Tyr Pro
            180                 185                 190

Asp Met Gly Ala Phe Asp Glu Arg Ser Ala Asn Glu Gly Gly Phe Pro
        195                 200                 205

Trp Glu Thr Asn Phe Thr Arg Ile Asn Pro Lys Tyr Phe Gln Ala Ala
    210                 215                 220

Asp Gln Arg Ile Ala Phe Leu Val Asp Ser Gly Leu Ala Pro Cys Leu
225                 230                 235                 240

Phe Gly Ala Trp Gly Tyr Tyr Leu Pro Trp Met Gly Glu Lys Lys Met
                245                 250                 255

Lys Gln His Trp Arg Tyr Leu Val Ala Arg Tyr Gly Ala Tyr Pro Met
            260                 265                 270

Phe Trp Cys Ile Ala Gly Glu Ala Thr Arg Pro Trp Tyr Leu Ser Asn
        275                 280                 285

Thr Arg Ala Lys Asp Gln Ala Gln Leu Leu Lys Ser Trp Thr Lys Val
    290                 295                 300

Thr Arg Tyr Val Arg Gln Val Asp Pro Tyr His Arg Pro Leu Ser Ile
305                 310                 315                 320

His Pro Pro Ile Glu Leu Gly Arg Gln Gln Val Ser Asp Pro Asn Leu
                325                 330                 335

Leu Asp Phe Glu Met Leu Gln Ser Gly His Asp Asp Arg Ala Ser Val
            340                 345                 350

Pro Tyr Thr Ile Ser Leu Val Arg Arg Ser Arg Ser Ser Pro Arg
        355                 360                 365

Met Pro Thr Ile Asp Ala Glu Val Cys Tyr Glu Gly Ile Leu Gly Asn
    370                 375                 380

Cys Glu Ala Asp Val Gln Arg Tyr Met Glu Trp Arg Cys Leu Leu Gly
385                 390                 395                 400
```

```
Gly Thr Ala Gly His Ser Tyr Gly Ala Asn Gly Val Trp Gln Ile Asn
                405                 410                 415

Gln Arg Asn Gln Pro Phe Gly Thr Ser Pro Gly Asn Asn Trp Gly
            420                 425                 430

Asn Thr Cys Trp Gln Glu Ala Met Arg Leu Pro Gly Ser Gly Gln Met
            435                 440                 445

Gly Leu Gly Arg His Ile Leu Glu Lys Tyr Lys Trp Trp Glu Phe Asp
        450                 455                 460

Cys His Pro Glu Trp Val Ser Gln Asp Ser Glu Gly Ser Phe Lys
465                 470                 475                 480

Trp Gly Asn Trp Ile Trp Ser Pro Asp Ala Glu Ser Ala Phe Ala Ala
                485                 490                 495

Pro Ser Gly Arg Arg Cys Phe Arg Lys Ser Phe Thr Leu Thr Ser Thr
            500                 505                 510

Ser Gln Ile Thr Gln Ala Leu Leu His Leu Ala Val Asp Asp Asn Ala
        515                 520                 525

Glu Val Phe Leu Asn Gly Thr Arg Leu Gly Gly Leu Val Gly Trp Asn
        530                 535                 540

Pro Tyr Arg Glu Leu Glu Val Thr Ser Leu Leu Lys Ser Gly Pro Asn
545                 550                 555                 560

Ile Leu Ala Ile His Ala Val Asn Ile Gln Ser Gly Thr Thr Gln Lys
                565                 570                 575

Asn Pro Ala Gly Leu Leu Val Asn Leu Asp Ile His Phe Asn Asp Asp
            580                 585                 590

Ser Arg Lys Gln Ile Val Ser Asp Ala Ser Trp Phe Cys Ser Glu Gln
        595                 600                 605

Glu Ser Ser Gly Trp Gln Asp Ala Asn Phe Asp Asp Arg Asn Trp Thr
        610                 615                 620

Ser Ala Lys Ser Leu Ala Glu Pro Gly Gln Gly Pro Trp Lys Ile Leu
625                 630                 635                 640

Thr Ser Pro Asn Tyr His Leu Asn Pro Gly Ala Ala Gly Ile Val Lys
                645                 650                 655

Lys Ile Arg Leu Ile Tyr Leu Ala Thr Lys Ala Pro Ala Lys Val Glu
            660                 665                 670

Lys Leu Glu Ala Gly Ile Asn Tyr Arg Ala Thr Phe Ile Asn Pro Gln
        675                 680                 685

Asn Gly Asn Ser Ala Ser Ala Gly Ile Ala Lys Ala Asp Ala Asp Gln
        690                 695                 700

Lys Trp Thr Ile Pro Thr Arg Pro Pro Gln Ser Lys Asp Trp Leu Leu
705                 710                 715                 720

Leu Leu Glu Ala Glu
            725

<210> SEQ ID NO 34
<211> LENGTH: 1596
<212> TYPE: PRT
<213> ORGANISM: Unknown
<220> FEATURE:
<223> OTHER INFORMATION: bacterium Ellin514 (ZP_03626656.1)

<400> SEQUENCE: 34

Met Asp Asp Ser Ser His Tyr Pro Leu Lys Pro Met Ser Lys Ile Asn
1               5                   10                  15

Pro Asn Lys Thr Trp Trp Ser Gln Leu Val Leu Val Trp Phe Leu Gly
            20                  25                  30
```

```
Phe Gly Leu Pro Phe Trp Thr Met Ala Ala Asp Ala Gly Leu Thr Thr
             35                  40                  45

Ser Ala Asn Val Met Val Glu Val Ser Phe Thr Ala Asn Arg Thr Tyr
 50                  55                  60

Ser Asp Pro Phe Asn Glu Val Thr Leu Asp Val Thr Phe Ile Asp Pro
 65                  70                  75                  80

Lys Gly Gln Glu Leu Arg Val Pro Ala Phe Trp Ala Gly Lys Asn Val
                 85                  90                  95

Trp Lys Val Arg Tyr Ala Ser Pro Val Val Gly Thr His Ser Phe Gln
                100                 105                 110

Ser Glu Cys Ser Glu Ala Gly Asp Lys Gly Leu His Gly Ile Arg Gly
            115                 120                 125

Lys Val Glu Val Lys Pro Tyr Ser Gly Gln Asn Leu Leu Tyr Val His
        130                 135                 140

Gly Pro Ile Arg Val Ala Ala Asn His Arg Phe Glu His Ala Asp
145                 150                 155                 160

Gly Thr Pro Phe Phe Trp Leu Gly Asp Thr Trp Trp Met Gly Leu Ser
                165                 170                 175

Gly Arg Leu His Trp Pro Glu Asp Phe Gln Lys Leu Thr Ala Asp Arg
            180                 185                 190

Lys Ala Lys Gly Phe Asn Val Ile Gln Leu Val Ala Gly Leu Phe Pro
        195                 200                 205

Asp Met His Pro Phe Asp Pro Arg Gly Ala Asn Glu Ala Gly Tyr Pro
    210                 215                 220

Trp Glu Thr Asn Tyr Thr Arg Ile Arg Pro Glu Tyr Phe Asp Ala Ala
225                 230                 235                 240

Asp Lys Arg Met Met His Leu Val Asp Gln Gly Phe Thr Pro Cys Ile
                245                 250                 255

Val Gly Ala Trp Gly Tyr Phe Leu Pro Leu Met Gly Val Asp Lys Ala
            260                 265                 270

Arg Ala His Trp Arg Tyr Leu Ile Ala Arg Tyr Gly Ala Leu Pro Val
        275                 280                 285

Val Trp Cys Thr Ala Gly Glu Ala Asn Leu Pro Trp Tyr Leu Ala Lys
    290                 295                 300

Gly Phe Pro Tyr Asp Asp Arg Lys Gln Val Lys Gly Trp Thr Glu Val
305                 310                 315                 320

Thr Arg Tyr Met Arg Ala Thr Asp Pro Phe His Arg Pro Ile Thr Ile
                325                 330                 335

His Pro Thr Gly Ile Gly Arg Leu Ser Ala Arg His Ala Met Asp Asp
            340                 345                 350

Leu Ser Leu Ile Asp Ile Asp Met Leu Gln Thr Pro His Gly Gln Arg
        355                 360                 365

Asp Ala Val Ala Pro Thr Val His Thr Met Arg Glu Ser Tyr Ala Asp
    370                 375                 380

Lys Pro Val Met Pro Val Ile Asn Gly Glu Ala Ser Phe Glu Met Leu
385                 390                 395                 400

Ser Asp Ser Leu Pro Thr Glu Trp Thr Arg Arg Met Phe Trp Leu Cys
                405                 410                 415

Leu Met Asn Gly Ala Ala Gly His Thr Tyr Gly Ala Asn Gly Ile Trp
            420                 425                 430

Gln Val Asn Arg Arg Gly Asp Pro His Gly Pro Ser Pro His His Asn
        435                 440                 445

Gly Gly Asn Gly Tyr Gly Val Ile Pro Trp Asp Asp Ala Met Asn Leu
```

-continued

```
            450             455             460
Pro Gly Ser Gly Gln Val Ala Phe Gly Lys Lys Leu Leu Glu Gln Tyr
465                 470                 475                 480

Pro Trp Gln Gln Phe Arg Pro His Pro Glu Trp Ala Ala Phe Ala Asn
                485                 490                 495

Lys Ala Ser Leu Ser Phe Glu Gly Cys Arg Trp Ile Trp Phe Pro Glu
            500                 505                 510

Gly Asn Pro Ala Gln Asp Ala Pro Ala Glu Lys Arg Phe Phe Arg Lys
                515                 520                 525

Ser Phe Val Leu Pro Glu Gly Lys Val Val Lys Ser Ala Gln Leu Arg
            530                 535                 540

Val Ser Ala Asp Asp Gln Phe Ile Ala Arg Leu Asn Gly Lys Glu Val
545                 550                 555                 560

Gly Ala Ser Asn Ser Gly Ala Glu Thr Trp Arg Val Gly Lys Gln Phe
                565                 570                 575

Asn Asp Phe Ser Asn Trp Leu Lys Thr Gly Thr Asn Val Leu Ala Ile
                580                 585                 590

Met Ala Gln Asn Met Pro Ala Thr Gly Ala Asn Pro Ala Gly Leu Ile
            595                 600                 605

Gly Arg Leu Glu Ile Arg Phe Thr Asp Gly Glu Leu Leu Thr Val Val
            610                 615                 620

Ser Asp Thr Trp His Ser Met Lys Ser Glu Val Ala Gly Trp Asp
625                 630                 635                 640

Ala Thr Gly Phe Asp Asp Arg Met Cys Glu Arg Ala Lys Val Val Ala
                645                 650                 655

Lys Tyr Gly Asp Ser Pro Trp Gly Asn Leu Asp Pro Leu Asn Asn Asp
                660                 665                 670

Asp Val Phe Gly Pro Gln Ser Ala Gly Val Pro Gly Val Val Arg Ile
            675                 680                 685

Ile Tyr Val Pro Asp Cys Glu Ser Ile Val Val Lys Asn Leu Gly Arg
            690                 695                 700

Asp Ala Glu Tyr Ala Ala Thr Tyr Phe Asp Pro Val Asp Gly Thr Lys
705                 710                 715                 720

Thr Gln Ala Thr Pro Val Arg Ala Asp Asn Thr Gly Ser Trp Ile Cys
                725                 730                 735

Pro Pro Pro Gly Gly Val Ala His Asp Trp Val Leu Ile Leu Glu Gly
            740                 745                 750

Lys Ser Lys Gly Asp Ala Ser Tyr Ser Lys Gln Lys Ala Gly Ile Ser
            755                 760                 765

Asn Thr Arg Gln Leu Thr Leu Ala Asn Asp Gln Leu Ala Trp Tyr Phe
            770                 775                 780

Asp Trp Asn Asp Gly His Leu Ser Ser Arg Tyr Phe Glu Asn Lys Leu
785                 790                 795                 800

Ser His His Arg Phe Gly Leu Ser Gly Val Gln Glu Leu Ser Leu Asn
            805                 810                 815

Phe Ser Ala Ser Leu Asp Ser Val Ala Gln Pro Phe Val Arg Leu Thr
            820                 825                 830

Asp Phe Gln Val Glu Gly Ala Gln Leu Ala Asp Ser His His Ala Ile
            835                 840                 845

Phe Lys Leu Arg Ser Pro Ser Leu Ala Val Glu Ala Asp Val His Phe
            850                 855                 860

Glu Leu Asp Gly Pro Thr Arg Arg Lys Trp Val Glu Val Thr Asn Lys
865                 870                 875                 880
```

-continued

```
Thr Gly Lys Glu Leu Leu Leu Asp Val Glu Leu Asp Phe Thr
            885                 890                 895
Thr Asp Gly Ile Ala Ser Gly Gly Glu Gly Ala Pro Val Phe Val
            900                 905                 910
Glu Gly Glu Phe Phe Ala Ala Ile Glu His Pro Ala Gly Val Asn Gln
            915                 920                 925
Gly Asp Lys Gly Arg Val Gln Leu Ala His Tyr Pro Gly Arg Arg Leu
930                 935                 940
Ala Pro Asp Ala Ser Phe Arg Ser His Val Ala Leu Val Ser Val Ala
945                 950                 955                 960
Lys Ala Gly Gln Ala Glu Glu His Phe Val Ser Tyr Ile Gln Ala Lys
            965                 970                 975
Ser Leu Arg Pro Lys Lys Ala Ile Ser Val Tyr Thr Pro Phe Gly Ile
            980                 985                 990
Asn Asn Leu Trp Gly Gly Cys Pro Ala Leu Asp Asp Glu Gln Thr Leu
            995                 1000                1005
Asp Val Leu Ser Val Leu Glu Lys Trp Gln Lys Lys Gly Met Arg Phe
            1010                1015                1020
Asp Tyr Phe Thr Leu Asp Thr Gly Trp Val Asp Pro Thr Ser Asp Leu
1025                1030                1035                1040
Thr Arg Phe Arg Pro Thr Cys Tyr Pro Asn Gly Pro Gly Lys Ile Val
            1045                1050                1055
Asp Arg Val Thr Gly Leu Asn Met Lys Phe Gly Leu Trp Phe Ala Thr
            1060                1065                1070
Ser Trp Gly Ala Gln Ser Ala Trp Asp Tyr Pro Pro Ala Phe Pro Asp
            1075                1080                1085
Gly His Pro Pro Gly Leu Pro Trp Arg Glu Gly Tyr Pro Ile Thr Arg
            1090                1095                1100
Glu Gly Ile Thr Phe Cys Leu Gly Thr Glu Gln Tyr His Gly Met Leu
1105                1110                1115                1120
Lys Lys Ala Val Leu Tyr His Ile Lys Glu Asn His Leu Arg Leu Leu
            1125                1130                1135
Lys Phe Asp Gly Gly Asp Tyr Phe Cys Asp His Ala Glu His Gly His
            1140                1145                1150
Leu Pro Gly Lys Tyr Ser Val Glu Pro Arg Phe Ala Asn Leu Ile Asp
            1155                1160                1165
Ile Ala Asn Cys Ala Arg Glu Ala Ala Pro Asp Val Phe Ile Met Trp
            1170                1175                1180
Tyr Trp Gly Leu Arg Ser Pro Phe Trp Ala Leu Tyr Gly Asp Met Leu
1185                1190                1195                1200
Phe Glu Ser Gly Leu His Met Glu Gly Ser Ala Thr Ser Ser Phe Pro
            1205                1210                1215
Thr Leu Tyr Tyr Arg Asp Ser Val Ser Leu Ala Gln Asp Gln Asn Ala
            1220                1225                1230
Gln Tyr Ala Lys Thr Ile Pro Pro Ile Val Lys Asp Ser Leu Gly Val
            1235                1240                1245
Trp Leu Ala Asp Asp Arg Trp Gly Asn Phe Met Gly Lys Glu Arg Trp
            1250                1255                1260
Arg Glu Ala Leu Val Met Asp Leu Gly Arg Gly Asn Leu Phe Leu Pro
1265                1270                1275                1280
Asn Leu Trp Gly Asp Leu Tyr Leu Leu Asn Asp Glu Asp Ile Ser Phe
            1285                1290                1295
```

```
Met Ala Arg Ile Thr Ala Leu Ala Lys Lys His Glu Ser Met Met Leu
                1300                1305                1310

His Arg Arg Asn Ile Leu Gly Asp Pro Phe Arg Asn Glu Val Tyr Gly
        1315                1320                1325

Tyr Ala Tyr Gly Gln Gly Ala His Gly Leu Leu Phe Leu Asn Asn Asp
            1330                1335                1340

His Phe Ala Ser Arg Arg Ala Glu Leu Arg Leu Asp Ala Ser Ile Gly
1345                1350                1355                1360

Ile Glu Ala Lys Pro Gly Thr Thr Leu His Val Val Ser His Phe Pro
                1365                1370                1375

Asn Gln Thr Arg Leu Leu Arg Pro Asp Gly Lys Pro Phe Lys Val Gly
            1380                1385                1390

Asp Ser Leu Gly Met Trp Leu Arg Pro Phe Glu Phe Leu Met Leu Glu
        1395                1400                1405

Val Thr Pro Asp Gly Lys Glu Gly Lys Gly Leu Pro Thr Arg Ser Ile
    1410                1415                1420

Thr Arg Gln Gln Ala Ala Asp Leu Gly Val Leu Leu Thr Leu Lys Pro
1425                1430                1435                1440

Gln Pro Leu Asp Ala Arg Met Asp Ile Arg Phe Ala Asp Ala Asn Gln
            1445                1450                1455

Phe Glu Gly Gln Lys Phe Lys Lys Val Tyr Ala Phe Glu Thr Thr
        1460                1465                1470

Leu Pro Ala Leu Glu Gly Asp Gln Pro Ile Leu Ala Val Ala Ile Arg
    1475                1480                1485

Leu Arg Lys Gly Gly Ala Glu Trp Arg Tyr Ala Pro Thr Val Val Arg
    1490                1495                1500

Val Val Gln Ala Leu Ala Arg Ile Gly Asp Gln Asn Val Gln Met Val
1505                1510                1515                1520

Pro Val Pro Asp Ser Arg Gln Tyr Gly Asn Thr Gln Ala Glu Gly Cys
            1525                1530                1535

Ser Trp Val Val Tyr Lys Val Arg Leu Ser Ser Lys Trp Ser His Thr
        1540                1545                1550

Gln Leu Lys Ile Ala Val Gln Ala Tyr Leu Pro Asp Gly Val Glu Ala
        1555                1560                1565

Glu Ile Glu Ser Trp Val Val Lys Arg Trp Gln Glu Asp Ala Arg
    1570                1575                1580

Pro Ala Ser Asp Gly Tyr Phe Thr Asp Glu Pro Ser
1585                1590                1595

<210> SEQ ID NO 35
<211> LENGTH: 542
<212> TYPE: PRT
<213> ORGANISM: Unknown
<220> FEATURE:
<223> OTHER INFORMATION: Algoriphagus sp.

<400> SEQUENCE: 35

Met Lys Val Leu Gln Ile Ala Phe Phe Leu Ile Val Leu Ser Ser
  1               5                  10                  15

His Phe Ser Phe Cys Gln Val Lys Lys Tyr Asp Arg Phe Glu Glu Glu
            20                  25                  30

Phe Gln Ser Asp Lys Thr Tyr Glu Asn Pro Leu Tyr Asp Val Ser Glu
        35                  40                  45

Phe Asp Val Lys Phe Ile Ser Pro Ser Gly Arg Glu Gln Val Val Arg
    50                  55                  60
```

```
Gly Phe Trp Asp Gly Gly Ser Thr Trp Arg Val Arg Phe Met Pro Asp
 65                  70                  75                  80

Glu Ile Gly Thr Trp Gln Phe Ser Thr Ser Ala Ser Asp Lys Asn Asn
                 85                  90                  95

Thr Gly Leu Asn Gly Val Lys Gly Ser Phe Asn Cys Ile Glu Asn Asp
            100                 105                 110

Ser Pro Leu Asn Leu Phe Gln Lys Gly Asn Ile Ile His Thr Lys Gly
            115                 120                 125

Thr Tyr His Leu Ser Tyr Ala Asp Gly Thr Pro Phe Phe Trp Thr Ala
            130                 135                 140

Cys Thr Ala Trp Asn Gly Ala Leu Lys Ser Thr Asp Glu Glu Trp Asp
145                 150                 155                 160

Tyr Tyr Leu Asn His Arg Val Glu Asn Asn Tyr Asn Thr Ile Gln Leu
                165                 170                 175

Val Thr Thr Gln Trp Arg Gly Gly Thr Lys Asn Ser Glu Gly Glu Val
            180                 185                 190

Ala Phe Thr Gly Ser Gly Lys Ile Ser Leu Asn Pro Glu Phe Phe Asp
            195                 200                 205

Arg Ile Asp Gln Lys Ile Glu Glu Ala Asn Ala Lys Gly Leu Leu Val
210                 215                 220

Ser Pro Val Val Leu Trp Ala Leu Pro Phe Gly Gln Gly Thr Glu Tyr
225                 230                 235                 240

Ser Pro Gly Tyr Tyr Leu Pro Ile Arg Glu Ala Val Ile Leu Ala Lys
                245                 250                 255

Tyr Ile Val Ala Arg Tyr Gln Gly Asn His Val Leu Trp Thr Leu Gly
            260                 265                 270

Gly Asp Gly Lys Tyr Tyr Gly Asp Leu Glu Asp Arg Trp Lys Ser Ile
            275                 280                 285

Gly Ser Gln Val Phe Gly Asp Gly Lys His Gln Gly Leu Val Thr Leu
            290                 295                 300

His Pro His Gly Leu Ser Trp Ile Gly Asp Ile Tyr Glu Asn Gln Asp
305                 310                 315                 320

Trp Tyr Asp Val Ile Thr Tyr Gln Ser Ser His Ser Asn Ser Glu Asn
                325                 330                 335

Thr Val Asn Trp Ile Asn Lys Gly Pro Ile Ala Lys Gln Trp Asp Asn
            340                 345                 350

Leu Arg Pro Met Pro Leu Ile Asn Thr Glu Pro Asn Tyr Glu Glu Ile
            355                 360                 365

Phe Phe Arg Ile Thr Ala Lys Asp Val Arg Asn Ala Ser Tyr Trp Ser
370                 375                 380

Val Phe Ala Ala Pro Ser Gly Ile Thr Tyr Gly Ala Asn Gly Ile
385                 390                 395                 400

Trp Pro Trp Leu Arg Glu Gly Glu Asp Ile Glu Asn His Glu Ser Ala
                405                 410                 415

Ile Gly Thr His Ser Trp Lys Ser Leu Asp Phe Glu Gly Ser Lys
            420                 425                 430

Gln Ile Gly Tyr Leu Asn Glu Phe Ile Asn Gln Phe Asp Trp Trp Asn
            435                 440                 445

Phe Lys Pro Ala Asn Asp Leu Val Asp Gln Pro Gly Asp Glu Lys
            450                 455                 460

Phe Asp Gln Phe Val Ser Val Ser Asn Glu Glu Lys Ser Lys Ile
465                 470                 475                 480

Leu Ile Tyr Ser Pro Val Lys Gln Pro Phe Lys Leu Phe Asn Ile Asn
```

```
                    485                 490                 495
Gly Asn Thr Tyr Gln Leu Arg Trp Phe Asn Pro Ile Asp Asn Thr Tyr
                500                 505                 510

Met Glu Gly Asn Leu Ser Pro Lys Asp Pro Ile Leu Glu Phe Glu Asn
            515                 520                 525

Pro Leu Asp Gln Asp Met Val Leu Val Leu Glu Arg Lys Glu
530                 535                 540

<210> SEQ ID NO 36
<211> LENGTH: 559
<212> TYPE: PRT
<213> ORGANISM: Unknown
<220> FEATURE:
<223> OTHER INFORMATION: bacterium Ellin514 (ZP_03628444.1)

<400> SEQUENCE: 36

Met Ile Pro Asp His Tyr Met Lys Arg Thr Ser Trp Arg Leu Trp Arg
1               5                   10                  15

Phe Leu Ser Ile Ile Cys Phe Phe Leu Ser Asn Thr Cys Phe Cys Gln
            20                  25                  30

Ala Lys Val Ile Pro Trp Pro Val Ile Ala Lys Trp Gly Val Phe Glu
        35                  40                  45

Lys Glu Phe Arg Ser Ser Val Thr Tyr Ala Asn Pro Leu Gln Asp Ile
    50                  55                  60

Thr Leu Ser Val Glu Phe Thr Ser Pro Gln Gly Lys Ile Lys Thr
65                  70                  75                  80

Tyr Gly Phe Trp Asp Gly Ala Arg Ile Trp Lys Phe Arg Phe Ser Pro
                85                  90                  95

Asp Gln Ala Gly Lys Trp Thr Tyr Gln Thr Ser Cys Ser Asp Ala Ala
            100                 105                 110

Asn Thr Asn Leu Asn Lys Val Ile Gly Glu Phe Leu Cys Val Lys Thr
        115                 120                 125

Thr Arg Lys Ser Arg Phe Asp Leu His Gly Pro Ile Gln Leu Ser His
    130                 135                 140

Asp Gln Val Cys Leu Glu His Gln Asp His Thr Pro Phe Leu Trp Leu
145                 150                 155                 160

Ala Asp Ile Ala Trp Ser Gly Ala Leu Leu Ser Lys Ser Thr Glu Trp
                165                 170                 175

Glu Thr Tyr Ala Gly Gln Arg Ala Lys Gln Ser Phe Thr Ala Val Gln
            180                 185                 190

Trp Val Ala Ala Pro Gly Arg Asn Ser Arg Asn Gln Ser Val Phe Glu
        195                 200                 205

Ser Thr Ser Thr Thr Leu Thr Ile Asn Leu Asn Leu Phe Gln Gln Leu
    210                 215                 220

Asp Ser Arg Ile Glu Thr Leu Asn Arg Ala Gly Leu Leu Ser Ala Ile
225                 230                 235                 240

Leu Pro Leu Arg Asp Leu Glu Ala Gln Ala Pro Gly Leu Glu Thr Ile
                245                 250                 255

Pro Glu Glu Gln Ala Val Gln Leu Leu Arg Tyr Met Val Ala Arg Trp
            260                 265                 270

Gly Ala Tyr Asn Val Ala Trp Ile Ile Met Cys Glu Gly Asp Asn Leu
        275                 280                 285

Ser Thr Gln Val Ala Arg Trp Lys Arg Val Gly Arg Ser Val Phe Ala
    290                 295                 300

Asn Gln His His Ala Pro Val Ile Leu His Pro Gly Thr Thr Tyr Trp
```

```
            305                 310                 315                 320
Val Leu Asp Glu Phe Arg Ala Glu Pro Trp Val Asp Val Leu Ser Tyr
                325                 330                 335

Gln Ser Gly Gln Glu Ala Asp Asp Asn Ala Leu Gln Trp Leu Leu Ala
                340                 345                 350

Gly Pro Leu Ala Ile Asp Trp Gln Arg Val Pro Leu Lys Pro Phe Ile
                355                 360                 365

Asn Leu Ala Pro Tyr Tyr Glu Asn Ser Ser Ala Pro Ala Ser Val Thr
            370                 375                 380

Gln Thr Ser Met Val Arg Arg Leu Ile Tyr Trp Ser Leu Leu Asn Ala
385                 390                 395                 400

Pro Thr Ala Gly Val Ser Tyr Gly Ala Asp Gly Val Trp Asn Trp Gln
                405                 410                 415

Lys Glu Ala Ala Asn Lys Arg Pro Asn Ser Asn Ala Gly Ser Pro Val
                420                 425                 430

Trp Gln Lys Asn Leu Thr Met Pro Val Ala Glu Gln Met Lys Ile Val
                435                 440                 445

Gly Gln Ile Phe Asn Ser Ile Glu Phe Trp Arg Leu Arg Pro Ala Pro
            450                 455                 460

Gly Met Leu Val Val Gln Pro Gly Asp Glu His Pro Ala Arg His Ile
465                 470                 475                 480

Ser Ala Thr Gln Ser Ser Leu Lys Asp Leu Ser Val Ile Tyr Ile Pro
                485                 490                 495

Glu Glu Arg Ser Val Asp Leu Lys Ala Thr Thr Ile Pro Thr Pro Leu
                500                 505                 510

Lys Ala Thr Trp Ile Asn Ala Arg Thr Gly Asp Arg Met Asp Ala Val
                515                 520                 525

Gly Tyr Val Ala Gly Pro Ile Cys Arg Phe Ile Thr Pro Gln Pro Gly
            530                 535                 540

Asp Trp Leu Leu Leu Ile Gln Pro Asp Pro Leu Pro Ser Ala His
545                 550                 555
```

<210> SEQ ID NO 37
<211> LENGTH: 531
<212> TYPE: PRT
<213> ORGANISM: Zunongwangia profunda

<400> SEQUENCE: 37

```
Met Lys Leu Lys Thr Ala Gln Pro Met Leu Tyr Glu Arg Thr Asp Phe
1               5                   10                  15

Asn Ile Ser Leu Asn Glu Gln Trp Glu Asn Pro Tyr Leu Ala Glu Asp
                20                  25                  30

Ile Ala Val Asp Ile Lys Met Gln Ser Pro Ser Gly Lys Glu Ile Leu
            35                  40                  45

Leu Pro Cys Phe Tyr Val Ser Gly Glu Ser Gly Glu Ala Ser Glu Trp
        50                  55                  60

Glu Ala Arg Phe Ala Pro Gln Glu Ile Gly Arg Tyr Thr Tyr His Leu
65                  70                  75                  80

Val Val Ser Lys Lys Gly Glu Glu Met Val Phe Asp Glu Asn Glu Phe
                85                  90                  95

Thr Val Glu Asn Ser Glu Asn Lys Gly Phe Leu His Ala Glu Asn Asn
            100                 105                 110

Trp Ile Leu Arg Tyr Asp Asn Gly Asp Pro Phe Arg Gly Ile Gly Glu
        115                 120                 125
```

```
        Asn Ile Gly Trp Glu Ser Arg Thr Asn Asp Asp Ser Lys Phe Phe His
            130                 135                 140

Glu Leu His Glu Lys Lys Lys Tyr Asn Tyr Asn Tyr Leu Leu Gly Glu
        145                 150                 155                 160

Leu Ser Arg Asn Gly Gly Asn Phe Phe Arg Thr Trp Ile Cys Ser Trp
                        165                 170                 175

Asn Leu Pro Leu Asp Trp Lys Asp Asn Phe Asn Asn Ser Arg Tyr Thr
                    180                 185                 190

Ala Ser Asp Ala Tyr Tyr Asn Pro Ser Ala Val Ala Lys Leu Asp Ser
                    195                 200                 205

Leu Val Asp Leu Ser Lys Lys Leu Asp Leu His Met Met Leu Thr Leu
        210                 215                 220

Gly Pro Gly Asn Tyr Ser Lys Glu Asp Gly Gly Phe Ala Glu Ser Thr
        225                 230                 235                 240

Ala Asp Phe Phe Val Asn Pro Lys Ser Arg Gln Arg Tyr Lys Asn Arg
                        245                 250                 255

Leu Arg Tyr Ile Ile Ala Arg Trp Gly Tyr Ser Thr Ser Ile Ala Ala
                    260                 265                 270

Trp Glu Leu Phe Asn Glu Ile Asp Asn Val Gln Tyr Arg Asn Arg Asp
                    275                 280                 285

Asn Pro Ile Asp Ala Lys Thr Ile Val Asp Trp His Glu Glu Met Ser
        290                 295                 300

Asn Tyr Ile Asp Lys Ile Asp Pro Tyr Asn His Ile Ile Thr Thr Ser
        305                 310                 315                 320

Ile Ser His Arg Asp Leu Glu Gly Leu Asn Ser Leu Pro Ala Ile Asp
                        325                 330                 335

Ile Asn Gln Lys His Ile Tyr Asn Arg Thr Lys Asp Ile Pro Gly Glu
                    340                 345                 350

Ile Ile Asp Tyr Glu Lys Arg Phe Gly Lys Pro Tyr Val Ile Gly Glu
                    355                 360                 365

Phe Ser Tyr Glu Trp Asp Trp Ser Lys Asn Phe Asp Glu Phe Pro Glu
                    370                 375                 380

Glu Met Asp Ser Asp Phe Lys Arg Gly Leu Trp Tyr Gly Met Phe Thr
        385                 390                 395                 400

Ser Thr Pro Ile Leu Pro Leu Ser Trp Trp Trp Glu Tyr Phe Asp Glu
                        405                 410                 415

Arg Gly Met Thr Ser Tyr Phe Arg Gly Val Ser Lys Ile Asn Asp Met
                    420                 425                 430

Met Leu Lys Ala Gly Asn Gly Lys Phe Glu Lys Val Ser Phe Lys Thr
                    435                 440                 445

Gly Asn Gln Leu Glu Ser Phe Gly Val Lys Cys Gly Asn Lys Ile Phe
        450                 455                 460

Ile Tyr Leu Tyr Asn Pro Leu Asp Lys Ala Leu Asn Tyr His Val Glu
        465                 470                 475                 480

Val Pro Glu Leu Arg Asp Ala Ser Tyr Glu Val Gln Ser Phe His Pro
                        485                 490                 495

Leu Asn Leu Glu Phe Ser Gln Glu Lys Thr Arg Glu Gly Ile Glu Val
                    500                 505                 510

Ala Ala Gly Lys Ser Leu Asp Ala Gly Lys Glu Ile Leu Leu Ile Ile
                    515                 520                 525

Asp Phe Asp
        530
```

```
<210> SEQ ID NO 38
<211> LENGTH: 64
<212> TYPE: PRT
<213> ORGANISM: Unknown
<220> FEATURE:
<223> OTHER INFORMATION: VIMSS5326244, derived from Archaea

<400> SEQUENCE: 38

Leu Lys Lys Val His Ile Ile Ala Ile Val Ile Ile Ala Ile Ala
1               5                   10                  15

Phe Ala Leu Ile Leu Ala Arg Tyr Tyr Thr Met Gln Arg Gly Tyr Glu
                20                  25                  30

Thr Val Thr Pro Thr Thr Pro Pro Gln Gln Thr Thr Thr Glu Thr
                35                  40                  45

Thr Pro Val Pro Thr Glu Ala Gly Thr Thr Thr Pro Ile Thr Glu Ala
            50                  55                  60

<210> SEQ ID NO 39
<211> LENGTH: 60
<212> TYPE: PRT
<213> ORGANISM: Unknown
<220> FEATURE:
<223> OTHER INFORMATION: VIMSS5324142, derived from Archaea

<400> SEQUENCE: 39

Met Ala Met Arg Thr Gly Leu Ala Leu Gly Ile Val Ala Leu Ile Ala
1               5                   10                  15

Val Ile Leu Ile Ala Val Leu Leu Ala Thr Gln Gln Gln Pro Thr Pro
                20                  25                  30

Thr Pro Ser Pro Thr Pro Thr Pro Ser Pro Thr Pro Thr Pro Thr Pro
                35                  40                  45

Thr Pro Thr Pro Thr Pro Thr Pro Thr Pro Thr Pro
            50                  55                  60

<210> SEQ ID NO 40
<211> LENGTH: 41
<212> TYPE: PRT
<213> ORGANISM: Unknown
<220> FEATURE:
<223> OTHER INFORMATION: VIMSS5327647, derived from Archaea

<400> SEQUENCE: 40

Leu Asn Lys Thr Val Ile Ala Ile Ala Val Leu Leu Val Val Val Ile
1               5                   10                  15

Ala Ala Ala Leu Ile Tyr Val Ile Tyr Tyr Pro Thr Thr Pro Thr Thr
                20                  25                  30

Thr Thr Pro Thr Val Thr Thr Pro Val
            35                  40

<210> SEQ ID NO 41
<211> LENGTH: 61
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 4, 6, 7, 10, 11, 12, 14, 15, 18, 22, 24, 28, 30,
      31, 32, 33, 35, 36, 42, 43, 55, 56, 57, 59
<223> OTHER INFORMATION: Xaa = Any Amino Acid

<400> SEQUENCE: 41

Xaa Xaa Lys Xaa Val Xaa Xaa Ile Ala Xaa Xaa Xaa Val Xaa Xaa Ile
1               5                   10                  15
```

```
Ala Xaa Ala Leu Ile Xaa Val Xaa Tyr Tyr Thr Xaa Gln Xaa Xaa Xaa
         20              25              30

Xaa Thr Xaa Xaa Pro Thr Thr Pro Xaa Xaa Thr Thr Thr Thr
         35              40              45

Pro Thr Pro Thr Pro Thr Xaa Xaa Xaa Thr Xaa Thr Pro
 50              55              60
```

<210> SEQ ID NO 42
<211> LENGTH: 88
<212> TYPE: PRT
<213> ORGANISM: Coraliomargarita akajimensis

<400> SEQUENCE: 42

```
Met Gln Trp His Lys Val Met Leu Thr Phe Asp Gly Pro Gly Thr Ser
 1               5                   10                  15

Thr Ala Thr Pro Asn Pro Phe Arg Asp Tyr Arg Met Asp Val Thr Phe
             20                  25                  30

Thr Gly Pro Ser Ser Gln Ser Tyr Val Val Pro Gly Tyr Tyr Ala Ala
         35                  40                  45

Asp Gly Asn Ser Gly Glu Thr Ser Leu Gly Ser Gly Asn Arg Trp Arg
 50                  55                  60

Val Ala Phe Ala Pro Asp Glu Ala Gly Thr Trp Asn Tyr Ser Val Ser
65                   70                  75                  80

Phe Val Thr Gly Thr Asp Ile Ala
                 85
```

<210> SEQ ID NO 43
<211> LENGTH: 90
<212> TYPE: PRT
<213> ORGANISM: Opitutus terrae

<400> SEQUENCE: 43

```
Lys Gln Trp His Lys Val Ser Leu Thr Phe Ala Gly Pro Ser Thr Ser
 1               5                   10                  15

Glu Thr Asn Ser Val Asn Pro Phe Thr Asn Tyr Arg Leu Asn Val Thr
             20                  25                  30

Phe Lys His Ser Ala Ser Asn Arg Thr Leu Ile Val Pro Gly Tyr Phe
         35                  40                  45

Ala Ala Asp Gly Asn Ala Ala Asn Thr Gly Ala Val Ser Gly Asp Lys
 50                  55                  60

Trp Arg Val Asp Phe Thr Pro Asp Ala Thr Gly Thr Trp Thr Tyr Val
65                   70                  75                  80

Ala Ser Phe Arg Thr Gly Ser Asn Val Ala
                 85                  90
```

<210> SEQ ID NO 44
<211> LENGTH: 89
<212> TYPE: PRT
<213> ORGANISM: Coraliomargarita akajimensis

<400> SEQUENCE: 44

```
Arg Thr Trp His Lys Val Thr Leu Ser Trp Asn Gly Pro Gln Thr Asn
 1               5                   10                  15

Glu Leu Ala Thr Pro Asn Pro Phe Thr Asp Tyr Arg Leu Asp Val Arg
             20                  25                  30

Phe Thr His Gln Ser Gly Thr Ser Tyr Leu Val Pro Gly Tyr Tyr Ala
         35                  40                  45
```

```
Ala Asp Gly Asp Ala Ala Asn Thr Gly Ala Asp Ser Gly Ser Val Trp
 50                  55                  60

Arg Val His Phe Ala Pro Asp Ala Ile Gly Asn Trp Asp Tyr Ala Val
 65                  70                  75                  80

Ser Phe Arg Thr Gly Glu Ala Val Ala
                 85

<210> SEQ ID NO 45
<211> LENGTH: 89
<212> TYPE: PRT
<213> ORGANISM: Coraliomargarita akajimensis

<400> SEQUENCE: 45

Met Gln Trp His Asn Val Ile Leu Thr Met Asn Gly Pro Asn Ser Ser
 1               5                  10                  15

Ser Ala Thr Pro Asn Pro Phe Lys Asp Tyr Arg Met Asn Val Thr Phe
                 20                  25                  30

Thr His Pro Asn Ser Gly Leu Ser Tyr Thr Val Pro Gly Tyr Phe Ala
             35                  40                  45

Ala Asp Gly Asn Ala Gly Gln Thr Gly Ala Thr Ser Gly Gly Lys Trp
 50                  55                  60

Arg Ala His Leu Cys Pro Asp His Ala Gly Gln Trp Thr Tyr Ser Val
 65                  70                  75                  80

Ser Phe Arg Ser Gly Thr Asp Val Ala
                 85

<210> SEQ ID NO 46
<211> LENGTH: 90
<212> TYPE: PRT
<213> ORGANISM: Opitutus terrae

<400> SEQUENCE: 46

Glu Gln Trp His Lys Ile Thr Leu Ser Ile Asp Gly Pro Glu Ala Arg
 1               5                  10                  15

Thr Asp Thr Ser Pro Asn Pro Phe Leu Asp Tyr Arg Met Asp Val Thr
                 20                  25                  30

Phe Thr His Glu Ser Gly Ala Pro Ser Tyr Arg Val Pro Gly Tyr Phe
             35                  40                  45

Ala Val Asp Gly Asn Ala Ala Glu Thr Ser Ala Phe Ala Gly Arg Ile
 50                  55                  60

Trp Arg Ala His Leu Ala Pro Asp Lys Pro Gly Met Trp Arg Tyr Ala
 65                  70                  75                  80

Val Ser Phe Arg Arg Gly Pro Glu Val Ala
                 85                  90

<210> SEQ ID NO 47
<211> LENGTH: 89
<212> TYPE: PRT
<213> ORGANISM: Rhodopirellula baltica

<400> SEQUENCE: 47

Arg Met Trp His Lys Val Thr Val Thr Leu Asn Gly Pro Tyr Ala His
 1               5                  10                  15

Gln Asp Asn Thr Pro Asn Pro Tyr Leu Asp His Arg Met Glu Val Glu
                 20                  25                  30

Phe Lys His Glu Ser Gly Lys Gln Tyr Leu Val Pro Gly Tyr Phe Ala
             35                  40                  45

Ala Asp Gly Asn Ala Ala Asn Thr Ser Ala Glu Ser Gly Thr Gln Trp
```

```
                    50                  55                  60

Arg Ala His Phe Ala Pro Asp Glu Thr Gly Glu Trp Thr Tyr Thr Val
 65                  70                  75                  80

His Phe Ala Thr Gly Lys Asp Ala Ala
                 85

<210> SEQ ID NO 48
<211> LENGTH: 89
<212> TYPE: PRT
<213> ORGANISM: Robiginitalea biformata

<400> SEQUENCE: 48

Gln Lys Trp His Arg Ile Gln Ile Leu Phe Asp Gly Pro Gln Thr Ser
  1               5                  10                  15

Glu Ser Ala Ser Gln Asn Pro Phe Leu Asn Tyr Arg Leu Asn Val Leu
                 20                  25                  30

Phe Thr Ala Pro Asp Gly Arg Glu Phe Thr Val Pro Gly Phe Phe Ala
             35                  40                  45

Ala Asp Gly Asn Ala Ala Glu Ser Ser Ala Thr Ser Gly Asn Lys Trp
         50                  55                  60

Ala Val Arg Phe Ser Pro Asp Gln Val Gly Thr Trp Thr Tyr Thr Ala
 65                  70                  75                  80

Ser Phe Arg Thr Gly Asp Glu Val Ala
                 85

<210> SEQ ID NO 49
<211> LENGTH: 61
<212> TYPE: PRT
<213> ORGANISM: Thermobaculum terrenum

<400> SEQUENCE: 49

Gly Glu Trp Glu Val Thr Ser Thr Arg Glu Tyr Glu Asn Pro Phe Val
  1               5                  10                  15

Asp Val Glu Val Ile Gly Arg Phe Ile Ser Pro Ser Gly Arg Glu Trp
                 20                  25                  30

Arg Val Pro Gly Phe Tyr Asp Gly Asp Gly Val Trp Lys Val Arg Phe
             35                  40                  45

Asn Pro Gly Glu Glu Gly Arg Trp Ala Tyr Arg Leu Glu
         50                  55                  60

<210> SEQ ID NO 50
<211> LENGTH: 65
<212> TYPE: PRT
<213> ORGANISM: Bifidobacterium dentium

<400> SEQUENCE: 50

Glu Gln His Arg Leu Phe Glu Ile Asn Leu Thr Gly Thr Thr Glu Gly
  1               5                  10                  15

Asn Pro Tyr Gln Asp Val Thr Leu Ser Ala Asp Phe Thr Asn Glu Thr
                 20                  25                  30

Gly Gln Ile Val Val Val Gly Gly Phe Tyr Arg Gly Asn Gly Asn Tyr
             35                  40                  45

Ser Val Arg Phe Met Ala Ser Ser Ala Gly Arg Trp Ala Phe Thr Thr
         50                  55                  60

Arg
 65

<210> SEQ ID NO 51
```

```
<211> LENGTH: 64
<212> TYPE: PRT
<213> ORGANISM: Opitutus terrae

<400> SEQUENCE: 51

Glu Arg Trp Asn Thr Phe Glu Leu Thr Leu His Gly Pro Ala Thr Gly
1               5                   10                  15

Asn Pro Phe Val Asp Val Arg Leu Gly Ala Arg Phe Thr Asp Gly Thr
            20                  25                  30

Arg Thr Ile Glu Val Pro Gly Phe Tyr Asp Gly Asp Gly Val Tyr Arg
        35                  40                  45

Val Arg Phe Met Pro Asp Ala Thr Gly Ala Trp His Tyr Glu Thr Ser
    50                  55                  60

<210> SEQ ID NO 52
<211> LENGTH: 63
<212> TYPE: PRT
<213> ORGANISM: Bacteroides vulgatus

<400> SEQUENCE: 52

Glu Cys Trp Asp Arg Phe Glu Leu Ser Phe Lys Gln Val Thr Lys Gly
1               5                   10                  15

Asn Pro Phe Asp Ile Arg Leu Ser Ala Thr Phe Val Cys Gly Lys Glu
            20                  25                  30

Lys Lys Thr Val Glu Gly Phe Tyr Asp Gly Glu Asn Thr Tyr Arg Ile
        35                  40                  45

Arg Phe Met Pro Ala Val Ala Gly Glu Trp Arg Tyr Val Thr Ser
    50                  55                  60

<210> SEQ ID NO 53
<211> LENGTH: 64
<212> TYPE: PRT
<213> ORGANISM: Spirosoma linguale

<400> SEQUENCE: 53

Glu Gln Trp Gly Arg Phe Glu Lys Thr Phe Thr Ala Lys Ala Thr Gly
1               5                   10                  15

Asn Pro Phe Thr Glu Val Thr Leu Thr Ala Glu Leu Ser Asn Gly Tyr
            20                  25                  30

Thr Thr Tyr Ser Val Ala Gly Phe Tyr Asp Gly Lys Asp Thr Phe Lys
        35                  40                  45

Ile Arg Phe Met Pro Pro Lys Thr Gly Lys Trp Arg Tyr Lys Thr Ser
    50                  55                  60

<210> SEQ ID NO 54
<211> LENGTH: 64
<212> TYPE: PRT
<213> ORGANISM: Unknown
<220> FEATURE:
<223> OTHER INFORMATION: Geobacillus sp.

<400> SEQUENCE: 54

Glu Arg Trp Gly Ile Phe Glu Val Ala Leu Ser Gly Pro Ser Ala Gly
1               5                   10                  15

Asn Pro Phe Glu Glu Val Ala Val Ser Ala Thr Phe Gly Tyr Arg Asn
            20                  25                  30

Asp Arg Val Glu Val Glu Gly Phe Tyr Asp Gly Asp Gly Ile Tyr Arg
        35                  40                  45

Val Arg Phe Met Pro Asp Arg Glu Gly Thr Trp Arg Tyr Val Thr Lys
    50                  55                  60
```

<210> SEQ ID NO 55
<211> LENGTH: 65
<212> TYPE: PRT
<213> ORGANISM: Thermotoga maritima

<400> SEQUENCE: 55

Glu Lys Trp Gly Thr Tyr Glu Ile Thr Leu Lys Gly Lys Ala Glu Gly
1               5                   10                  15

Asn Pro Phe Thr Asp Val Glu Ile Lys Ala Val Phe Thr Ser Glu Ala
            20                  25                  30

Gly Asp Ser Phe Glu Val Glu Gly Phe Tyr Asp Gly Glu Asp Thr Phe
        35                  40                  45

Lys Ile Arg Phe Met Pro Asn Arg Thr Gly Leu Trp Lys Tyr Glu Val
    50                  55                  60

Arg
65

<210> SEQ ID NO 56
<211> LENGTH: 63
<212> TYPE: PRT
<213> ORGANISM: Unknown
<220> FEATURE:
<223> OTHER INFORMATION: bacterium Ellin514 (ZP_03628309.1)

<400> SEQUENCE: 56

Leu Ala Asn Gln Met Val Glu Trp Thr Phe Thr Ser Thr Arg Pro Tyr
1               5                   10                  15

Lys Asn Gln Ile Glu Leu Asn Val Thr Phe Thr Pro Ser Gly Lys
            20                  25                  30

Lys Leu Leu Val Pro Ala Phe Trp Asp Gly Gly Asp Ile Trp His Val
        35                  40                  45

Arg Tyr Ser Ser Thr Glu Thr Gly Ile His His Phe Ser Thr Val
    50                  55                  60

<210> SEQ ID NO 57
<211> LENGTH: 66
<212> TYPE: PRT
<213> ORGANISM: Unknown
<220> FEATURE:
<223> OTHER INFORMATION: bacterium Ellin514 (ZP_03626656.1)

<400> SEQUENCE: 57

Ser Ala Asn Val Met Val Glu Val Ser Phe Thr Ala Asn Arg Thr Tyr
1               5                   10                  15

Ser Asp Pro Phe Asn Glu Val Thr Leu Asp Val Thr Phe Ile Asp Pro
            20                  25                  30

Lys Gly Gln Glu Leu Arg Val Pro Ala Phe Trp Ala Gly Lys Asn Val
        35                  40                  45

Trp Lys Val Arg Tyr Ala Ser Pro Val Val Gly Thr His Ser Phe Gln
    50                  55                  60

Ser Glu
65

<210> SEQ ID NO 58
<211> LENGTH: 66
<212> TYPE: PRT
<213> ORGANISM: Unknown
<220> FEATURE:
<223> OTHER INFORMATION: Algoriphagus sp.

-continued

```
<400> SEQUENCE: 58

Lys Lys Tyr Asp Arg Phe Glu Glu Phe Gln Ser Asp Lys Thr Tyr
1               5                   10                  15

Glu Asn Pro Leu Tyr Asp Val Glu Phe Asp Val Lys Phe Ile Ser Pro
                20                  25                  30

Ser Gly Arg Glu Gln Val Val Arg Gly Phe Trp Asp Gly Ser Thr
            35                  40                  45

Trp Arg Val Arg Phe Met Pro Asp Glu Ile Gly Thr Trp Gln Phe Ser
50                      55                  60

Thr Ser
65

<210> SEQ ID NO 59
<211> LENGTH: 66
<212> TYPE: PRT
<213> ORGANISM: Unknown
<220> FEATURE:
<223> OTHER INFORMATION: bacterium Ellin514 (ZP_03628444.1)

<400> SEQUENCE: 59

Ala Lys Trp Gly Val Phe Glu Lys Glu Phe Arg Ser Ser Val Thr Tyr
1               5                   10                  15

Ala Asn Pro Leu Gln Asp Ile Thr Leu Ser Val Glu Phe Thr Ser Pro
                20                  25                  30

Gln Gly Glu Lys Ile Lys Thr Gly Phe Trp Asp Gly Ala Arg Ile
            35                  40                  45

Trp Lys Phe Arg Phe Ser Pro Asp Gln Ala Gly Lys Trp Thr Tyr Gln
50                      55                  60

Thr Ser
65

<210> SEQ ID NO 60
<211> LENGTH: 58
<212> TYPE: PRT
<213> ORGANISM: Unknown
<220> FEATURE:
<223> OTHER INFORMATION: Anaeromyxobacter sp.

<400> SEQUENCE: 60

Ala Val Asn Gly Val Val Glu Leu Arg Leu Ala Val Pro Ala Gly Ala
1               5                   10                  15

Pro Val Arg Ala Glu Val Leu Ala Pro Ser Gly Ala Arg Ile His Val
                20                  25                  30

Pro Ala Phe Pro Val Pro Gly Gly Trp Ala Ala Arg Phe Arg Pro Arg
            35                  40                  45

Glu Pro Gly Arg His Arg Trp Val Ala Arg
50                      55

<210> SEQ ID NO 61
<211> LENGTH: 69
<212> TYPE: PRT
<213> ORGANISM: Chitinophaga pinensis

<400> SEQUENCE: 61

Asn Leu Tyr Glu Lys Ala Glu Trp Thr Ile Asp Leu Thr Ala Asn Tyr
1               5                   10                  15

Ser Asn Pro Tyr Asp Gln Arg Glu Ile Lys Leu Asp Met Cys Leu Val
                20                  25                  30

Ser Pro Ser Gly Lys Pro Leu Leu Leu Pro Ala Tyr Phe Asp Gln Val
```

```
                35                  40                  45
Asn His His Trp Gln Ser Arg Phe Ala Pro Gln Glu Thr Gly Gln Tyr
    50                  55                  60

Gln Tyr Tyr Phe Glu
65

<210> SEQ ID NO 62
<211> LENGTH: 73
<212> TYPE: PRT
<213> ORGANISM: Zunongwangia profunda

<400> SEQUENCE: 62

Met Leu Tyr Glu Arg Thr Asp Phe Asn Ile Ser Leu Asn Glu Gln Trp
 1               5                  10                  15

Glu Asn Pro Tyr Leu Ala Glu Asp Ile Ala Val Asp Ile Lys Met Gln
            20                  25                  30

Ser Pro Ser Gly Lys Glu Ile Leu Leu Pro Cys Phe Tyr Val Ser Gly
        35                  40                  45

Glu Ser Gly Glu Ala Ser Glu Trp Glu Ala Arg Phe Ala Pro Gln Glu
    50                  55                  60

Ile Gly Arg Tyr Thr Tyr His Leu Val
65                  70

<210> SEQ ID NO 63
<211> LENGTH: 79
<212> TYPE: PRT
<213> ORGANISM: Unknown
<220> FEATURE:
<223> OTHER INFORMATION: VIMSS5326244, derived from Archaea

<400> SEQUENCE: 63

Pro Lys Phe Gly Leu Val Glu Ile Ala Phe Asn Ile Ser Gly Leu Ser
 1               5                  10                  15

Ser Asn Pro Phe Asp Thr Ser Asp Ile Asp Val Trp Val His Ile Glu
            20                  25                  30

Thr Pro Ser Gly Ser Arg Val Ala Val Pro Ala Phe Tyr Phe Gln Asn
        35                  40                  45

Tyr Thr Val Glu Ile Ile Val Arg Val Gly Arg Pro Tyr Trp Leu Ala
    50                  55                  60

Arg Phe Ala Pro Val Glu Glu Gly Val His Lys Phe Tyr Val Lys
65                  70                  75

<210> SEQ ID NO 64
<211> LENGTH: 83
<212> TYPE: PRT
<213> ORGANISM: Victivallis vadensis
<220> FEATURE:
<221> NAME/KEY: VARIANT
<222> LOCATION: 11
<223> OTHER INFORMATION: Xaa = Pyrrolysine

<400> SEQUENCE: 64

Pro Glu Gln Gly Glu Ala Asn Ala Leu Phe Xaa Gly Arg Phe Arg Leu
 1               5                  10                  15

Leu Arg Glu Phe Phe Asn Pro Phe Asp Pro Asp Glu Val Thr Val Asp
            20                  25                  30

Phe Glu Ile Lys Ala Pro Asn Gly Lys Leu Thr Arg Leu Pro Ala Phe
        35                  40                  45

Tyr Ser Arg Asp Tyr Glu Arg Glu Thr Ala Thr Pro Ile Gly Gln Gly
    50                  55                  60
```

Phe Trp Glu Phe Arg Phe Thr Pro Pro Val Pro Gly Glu Tyr Arg Leu
65                  70                  75                  80

Arg Ala Val

<210> SEQ ID NO 65
<211> LENGTH: 79
<212> TYPE: PRT
<213> ORGANISM: Clostridium leptum

<400> SEQUENCE: 65

Pro Ala Phe Glu Lys Phe Glu Ala Ala Phe Ala Phe Glu Lys Val Phe
1               5                   10                  15

Glu Asn Pro Tyr Cys Pro Glu Val Asp Leu Lys Ala Tyr Ile Leu
            20                  25                  30

Lys Pro Asn Gly Asp Gln Lys Gln Ile Ser Gly Phe Trp Tyr Glu Gly
            35                  40                  45

Phe Gln Arg Glu Ile Leu Ile Ser Thr Leu Lys Asp Trp Arg Ile
    50                  55                  60

Arg Tyr Ser Ala Gln Val Pro Gly Glu Tyr Arg Tyr Tyr Val Thr
65                  70                  75

<210> SEQ ID NO 66
<211> LENGTH: 79
<212> TYPE: PRT
<213> ORGANISM: Herpetosiphon aurantiacus

<400> SEQUENCE: 66

Ala Val Phe Gly Thr Ile Glu Leu Ala Ile Asp Thr Thr Ile Thr Val
1               5                   10                  15

Ala Asn Pro Tyr Asp Pro Asn Gln Ile Asp Leu Met Val Ser Phe Ile
            20                  25                  30

Ser Ala Thr Gly Gln Ile Tyr Arg Val Pro Ala Phe Trp Tyr Gln Asp
            35                  40                  45

Phe Asp Gln Leu Ser Leu Gln Pro Lys Gly Asn Pro Glu Trp Arg Val
    50                  55                  60

Arg Phe Thr Pro Ser Glu Pro Gly Ala Trp Gln Val Lys Ala Glu
65                  70                  75

<210> SEQ ID NO 67
<211> LENGTH: 79
<212> TYPE: PRT
<213> ORGANISM: Caldicellulosiruptor saccharolyticus

<400> SEQUENCE: 67

Tyr Lys Tyr Ser Lys Phe Glu Ile Ser Phe Lys Thr Pro Ala Phe Lys
1               5                   10                  15

Gly Asn Cys Phe Asp Pro Asp Glu Ile Asp Ile Trp Gly Glu Phe Val
            20                  25                  30

Ser Pro Ser Gly Lys Lys Tyr Val Met Pro Ala Phe Tyr Gln Asp
            35                  40                  45

Tyr Lys Arg Glu Val Leu Thr Lys Val Gly Gln Pro Glu Trp Arg Ile
    50                  55                  60

Arg Phe Cys Pro Val Glu Ile Gly Lys Trp Lys Tyr Thr Ile Tyr
65                  70                  75

<210> SEQ ID NO 68
<211> LENGTH: 79
<212> TYPE: PRT

<213> ORGANISM: Opitutus terrae

<400> SEQUENCE: 68

His Ala Trp Glu Gly Ala Glu Phe Arg Ile Ala Gly Ala Pro Val Ala
1               5                   10                  15

Glu Asn Asn Phe Asp Pro Asp Gln Ile Arg Leu Asp Ala Ile Phe Thr
            20                  25                  30

Gly Pro Ser Gly Glu Thr Arg Ser Val Ala Ala Phe Trp Tyr Gln Asp
        35                  40                  45

Tyr Thr Arg Glu Val Leu Thr Pro Gln Gly Thr Pro Glu Trp Arg Leu
50                  55                  60

Arg Tyr Thr Pro Thr Glu Ala Gly Glu His Arg Val Thr Leu His
65                  70                  75

<210> SEQ ID NO 69
<211> LENGTH: 89
<212> TYPE: PRT
<213> ORGANISM: Coraliomargarita akajimensis
<220> FEATURE:
<221> NAME/KEY: VARIANT
<222> LOCATION: 14, 34, 35, 38, 68, 86
<223> OTHER INFORMATION: Xaa = Pyrrolysine

<400> SEQUENCE: 69

Asp Ile Trp Arg Tyr Asp Cys Ser Lys Leu Cys Asp Trp Xaa Val Leu
1               5                   10                  15

Phe Cys His Phe Asp Arg Lys Cys Asn Met Met His Phe Val Met Thr
            20                  25                  30

Cys Xaa Xaa His Cys Xaa Leu Phe Glu Tyr Ala Asp Pro Ala Thr Val
        35                  40                  45

Glu Gly Gly Phe Ser Asp Ser Arg Arg Thr Tyr Phe Arg Glu Asn Val
    50                  55                  60

Ala Arg Phe Xaa Asn His Asn Ala Ile Thr Trp His Leu Gly Leu Glu
65                  70                  75                  80

Glu Gly Trp Cys Lys Xaa Thr Arg Pro
                85

<210> SEQ ID NO 70
<211> LENGTH: 75
<212> TYPE: PRT
<213> ORGANISM: Opitutus terrae
<220> FEATURE:
<221> NAME/KEY: VARIANT
<222> LOCATION: 21, 32, 61
<223> OTHER INFORMATION: Xaa = Pyrrolysine

<400> SEQUENCE: 70

Asp Arg Thr Arg Phe Asp Val Ser Lys Leu Ala Asp Trp Glu Ile Val
1               5                   10                  15

Phe Ser His Met Xaa Lys Leu Gly Ile Asn Leu His Val Val Thr Xaa
            20                  25                  30

Glu Cys Cys Cys Asp Cys Leu Leu Asp Gly Ala Ser Leu Gly Asn Thr
        35                  40                  45

Arg Lys Ile Tyr Tyr Arg Glu Leu Val Ala Arg Phe Xaa Asn His Leu
    50                  55                  60

Gly Val Thr Trp His Leu Gly Leu Glu Asn Thr
65                  70                  75

<210> SEQ ID NO 71
<211> LENGTH: 82

```
<212> TYPE: PRT
<213> ORGANISM: Coraliomargarita akajimensis
<220> FEATURE:
<221> NAME/KEY: VARIANT
<222> LOCATION: 6, 21, 32, 35, 61, 78
<223> OTHER INFORMATION: Xaa = Pyrrolysine

<400> SEQUENCE: 71

Glu Arg Tyr Arg Asn Xaa Cys Ser Lys Leu Ala Asp Trp Cys Val Val
1               5                   10                  15

Phe Cys His Ala Xaa Ser Lys Cys His Phe Leu His Phe Lys Thr Xaa
                20                  25                  30

Glu Thr Xaa His Glu Cys Leu Leu Asp Asn Gly Asp Thr Gly Ala Met
            35                  40                  45

Arg His Leu Tyr Tyr Arg Cys Cys Val Ala Arg Phe Xaa Asn His Leu
        50                  55                  60

Ala Leu His Trp His Leu Gly Leu Glu Asn Thr Lys Trp Xaa Trp Pro
65              70                  75                  80

Cys His

<210> SEQ ID NO 72
<211> LENGTH: 83
<212> TYPE: PRT
<213> ORGANISM: Coraliomargarita akajimensis
<220> FEATURE:
<221> NAME/KEY: VARIANT
<222> LOCATION: 4, 11, 21, 32, 35, 69
<223> OTHER INFORMATION: Xaa = Pyrrolysine

<400> SEQUENCE: 72

His Pro Leu Xaa Phe Asp Cys Ser Lys Leu Xaa Asp Trp Cys Ile Val
1               5                   10                  15

Phe Ser His Gly Xaa Lys Met Cys Asn Tyr Leu Met Phe Lys Thr Xaa
                20                  25                  30

Leu His Xaa His Glu Cys Leu Asp Cys Pro Gly Ser Ala Val Ala Leu
            35                  40                  45

Asp Gly Gly Asn Val Gly Thr Glu Pro Lys Leu Tyr Tyr Arg Glu Leu
        50                  55                  60

Thr Ala Arg Phe Xaa Asn His Leu Ala Leu His Trp His Leu Gly Leu
65              70                  75                  80

Glu Asn Thr

<210> SEQ ID NO 73
<211> LENGTH: 89
<212> TYPE: PRT
<213> ORGANISM: Opitutus terrae
<220> FEATURE:
<221> NAME/KEY: VARIANT
<222> LOCATION: 11, 18, 46, 49
<223> OTHER INFORMATION: Xaa = Pyrrolysine

<400> SEQUENCE: 73

Asp Pro Leu His Phe Asp Cys Ser Lys Leu Xaa Asp Trp Cys Ile Ile
1               5                   10                  15

Phe Xaa His Ala Thr Ala Leu Cys Leu His Leu Met Phe Lys Leu Cys
                20                  25                  30

Cys Thr Cys His Asp Cys Asn His Pro Gly Gly Cys Gly Xaa Ile Gly
            35                  40                  45

Xaa Val Pro Thr Ala Leu Asp Arg Gly Lys Thr Gly Val Cys Arg Lys
        50                  55                  60
```

```
Leu Tyr Leu Arg Leu Leu Ile Ala Arg Phe Ala His Cys Leu Ala Leu
 65                  70                  75                  80

His Trp His Leu Gly Leu Glu Asn Thr
                     85

<210> SEQ ID NO 74
<211> LENGTH: 88
<212> TYPE: PRT
<213> ORGANISM: Rhodopirellula baltica
<220> FEATURE:
<221> NAME/KEY: VARIANT
<222> LOCATION: 1, 11, 18, 32, 37, 41, 43, 61
<223> OTHER INFORMATION: Xaa = Pyrrolysine

<400> SEQUENCE: 74

Xaa Lys Leu His Tyr Asp Cys Ser Lys Leu Xaa Asp Trp Cys Ile Val
 1               5                  10                  15

Phe Xaa His Gly Thr Glu Asn Cys His Tyr Leu Met Phe Lys Leu Xaa
                 20                  25                  30

Glu Thr Glu His Xaa Cys His Arg Xaa Gly Xaa Lys Ala Lys Gly Phe
             35                  40                  45

Lys Pro Glu Ser Leu Asp Gly Gly Lys Leu Gly Ser Xaa Arg Lys Leu
 50                  55                  60

Tyr Leu Arg Glu Leu Ile Ala Arg Phe Gly His Asn Leu Ala Leu His
 65                  70                  75                  80

Trp His Leu Ala Glu Glu Thr Thr
                     85

<210> SEQ ID NO 75
<211> LENGTH: 87
<212> TYPE: PRT
<213> ORGANISM: Robiginitalea biformata
<220> FEATURE:
<221> NAME/KEY: VARIANT
<222> LOCATION: 7, 28, 31, 42, 58, 85
<223> OTHER INFORMATION: Xaa = Pyrrolysine

<400> SEQUENCE: 75

Gly Leu Phe Pro Gly Gly Xaa Asp Ser Ser Asn Arg Leu Arg Tyr Asp
 1               5                  10                  15

Val Ser Lys Leu Glu Asp Trp Leu Ile Leu Phe Xaa His Ala Xaa Ser
                 20                  25                  30

Lys Cys His Phe Leu Met Phe Lys Thr Xaa Phe Phe Glu Asn Cys Ala
             35                  40                  45

Leu Leu Asp Gly Gly Phe Leu Gly Val Xaa Arg Lys Leu Tyr Tyr Arg
 50                  55                  60

Glu Leu Val Ala Arg Phe Gly His Asn Leu Ala Leu His Trp His Leu
 65                  70                  75                  80

Gly Leu Glu Asn Xaa Leu Tyr
                     85

<210> SEQ ID NO 76
<211> LENGTH: 84
<212> TYPE: PRT
<213> ORGANISM: Thermobaculum terrenum
<220> FEATURE:
<221> NAME/KEY: VARIANT
<222> LOCATION: 14, 84
<223> OTHER INFORMATION: Xaa = Pyrrolysine

<400> SEQUENCE: 76

Ala Pro Val Arg Phe Asn Leu Glu Tyr Phe Ala Thr Trp Xaa Arg Val
```

```
                1               5                  10                 15
Val Arg Lys Val Glu Glu Leu Cys Leu Gly Leu Glu Val Ile His Glu
                20                 25                 30

Ala Trp Cys Phe Glu Phe Phe His Ser Arg His Ile Phe Val Ala
        35                 40                 45

Glu Trp Glu Glu Leu Tyr Asn Arg Tyr Leu Val Ala Arg Tyr Asp Ala
        50                 55                 60

Tyr Ser Cys Val Tyr Phe Trp Thr Pro His Asn Phe Tyr Glu Phe Tyr
65                 70                 75                 80

Pro His Cys Xaa

<210> SEQ ID NO 77
<211> LENGTH: 80
<212> TYPE: PRT
<213> ORGANISM: Bifidobacterium dentium
<220> FEATURE:
<221> NAME/KEY: VARIANT
<222> LOCATION: 5, 32, 40
<223> OTHER INFORMATION: Xaa = Pyrrolysine

<400> SEQUENCE: 77

Glu Thr Gly Phe Xaa His Thr Cys Phe Asp Glu Glu Phe Phe Ala His
1               5                  10                 15

Leu Cys Cys Arg Ile Ala Cys Leu Asp Glu Leu Cys Ile Glu Ala Xaa
                20                 25                 30

Ile Thr Leu Leu His Pro Tyr Xaa Lys Pro Ile Trp Cys Phe Ser Lys
        35                 40                 45

Met Thr Lys Val Glu Asp Glu Met Tyr Leu Ala Tyr His Ala Ala Arg
        50                 55                 60

Tyr Gly Ala Tyr Lys Asn Trp Trp Trp Ser Leu Ala Asn Glu Tyr Asp
65                 70                 75                 80

<210> SEQ ID NO 78
<211> LENGTH: 79
<212> TYPE: PRT
<213> ORGANISM: Opitutus terrae
<220> FEATURE:
<221> NAME/KEY: VARIANT
<222> LOCATION: 32
<223> OTHER INFORMATION: Xaa = Pyrrolysine

<400> SEQUENCE: 78

Pro Arg Asp Trp Asp Phe Ala Arg Phe Asn Pro Glu Tyr Phe Arg Ala
1               5                  10                 15

Phe Cys Lys Ala Val Ala Cys Leu Arg Glu Leu Cys Ile Glu Ala Xaa
                20                 25                 30

Ile Thr Leu Thr His Pro Tyr Gly Lys Ala Trp Cys Phe Glu Lys Met
        35                 40                 45

Asp Ala Ala Ala Asp Glu Arg Tyr Leu Ala Tyr His Ala Ala Arg Tyr
        50                 55                 60

Gly Ala Tyr Arg Asn Trp Trp Trp Ser Leu Ala Asn Glu Tyr Asp
65                 70                 75

<210> SEQ ID NO 79
<211> LENGTH: 86
<212> TYPE: PRT
<213> ORGANISM: Bacteroides vulgatus
<220> FEATURE:
<221> NAME/KEY: VARIANT
<222> LOCATION: 29, 46
<223> OTHER INFORMATION: Xaa = Pyrrolysine
```

<400> SEQUENCE: 79

Lys Asp Glu Gly His Glu Arg Lys Glu Trp Asp Phe Asp Arg Phe Asp
1               5                   10                  15

Pro Ala Phe Phe Gln His Leu Cys Lys Arg Ile Asp Xaa Leu His Arg
            20                  25                  30

Leu Cys Ile Glu Ala Asp Leu Thr Leu Phe His Pro Tyr Xaa Lys Gly
        35                  40                  45

Arg Trp Cys Phe Asp Ala Met Ser His Glu Val Asn Val Arg Tyr Ile
    50                  55                  60

Lys Tyr Ile Thr Ala Arg Leu Ala Ser Phe Arg Asn Trp Trp Trp Ser
65                  70                  75                  80

Leu Ala Asn Glu Tyr Asp
                85

<210> SEQ ID NO 80
<211> LENGTH: 86
<212> TYPE: PRT
<213> ORGANISM: Spirosoma linguale
<220> FEATURE:
<221> NAME/KEY: VARIANT
<222> LOCATION: 29, 46
<223> OTHER INFORMATION: Xaa = Pyrrolysine

<400> SEQUENCE: 80

Lys Asp Asp Gly Lys Pro Val Thr Val Trp His Phe Asp Arg Phe Asp
1               5                   10                  15

Pro Ala Phe Phe Gln His Leu Cys Lys Arg Ile Asp Xaa Leu His Arg
            20                  25                  30

Leu Cys Ile Glu Ala Asp Leu Thr Leu Phe His Pro Tyr Xaa Lys Gly
        35                  40                  45

Arg Trp Cys Phe Asp Ala Met Pro His Glu Val His Ile Arg Tyr Leu
    50                  55                  60

Lys Tyr Leu Leu Ala Arg Leu Ser Ser Tyr Lys Asn Trp Trp Trp Ser
65                  70                  75                  80

Leu Ala Asn Glu Tyr Asp
                85

<210> SEQ ID NO 81
<211> LENGTH: 85
<212> TYPE: PRT
<213> ORGANISM: Unknown
<220> FEATURE:
<223> OTHER INFORMATION: Geobacillus sp.
<220> FEATURE:
<221> NAME/KEY: VARIANT
<222> LOCATION: 46, 58
<223> OTHER INFORMATION: Xaa = Pyrrolysine

<400> SEQUENCE: 81

Ala Gly Thr Cys Pro Glu Pro Ala Asp Thr Thr Arg Phe Asn Pro Ala
1               5                   10                  15

Phe Phe Ala His Leu Cys Glu Arg Ile Gly Asp Leu Met Lys Leu Cys
            20                  25                  30

Val Glu Ala Asp Leu Ile Leu Phe His Pro Tyr Asp Lys Xaa Gly Arg
        35                  40                  45

Trp Cys Phe Asn Ser His Ser Arg Glu Xaa Asp Phe Tyr Tyr Leu Arg
    50                  55                  60

Tyr Val Ile Ala Arg Leu Gly Ala Tyr Arg Asn Trp Trp Trp Ser Leu
65                  70                  75                  80

Ala Asn Glu Tyr Asp
             85

<210> SEQ ID NO 82
<211> LENGTH: 77
<212> TYPE: PRT
<213> ORGANISM: Thermotoga maritima
<220> FEATURE:
<221> NAME/KEY: VARIANT
<222> LOCATION: 14, 51
<223> OTHER INFORMATION: Xaa = Pyrrolysine

<400> SEQUENCE: 82

Glu Glu Asp Gly Arg Tyr Glu Phe Asn Val Lys Phe Phe Xaa His Phe
1               5                   10                  15

Cys Arg Leu Val Lys Glu Leu His Asp Met Cys Ile Glu Ala Asp Val
            20                  25                  30

Ile Leu Phe His Pro Tyr Asp Lys Trp Cys Phe Cys Ser His Pro Glu
        35                  40                  45

Glu Val Xaa Lys Ala Tyr Leu Arg Tyr Leu Ile Ala Arg Ile Ser Ser
    50                  55                  60

Tyr Arg Asn Trp Trp Trp Ser Leu Ala Asn Glu Tyr Asp
65                  70                  75

<210> SEQ ID NO 83
<211> LENGTH: 85
<212> TYPE: PRT
<213> ORGANISM: Unknown
<220> FEATURE:
<223> OTHER INFORMATION: bacterium Ellin514 (ZP_03628309.1)

<400> SEQUENCE: 83

Glu Gly Gly Phe Pro Trp Glu Thr His Phe Thr Arg Ile Asn Pro Lys
1               5                   10                  15

Tyr Phe Gln His Pro Cys Asp Arg Ile Ala Phe Leu Trp Asp Ser Cys
            20                  25                  30

Leu Ala Pro Cys Leu Phe Gly Arg Trp Cys Tyr Tyr Leu Pro Trp Met
        35                  40                  45

Gly Glu Lys Lys His Lys Cys His Leu Arg Tyr Leu Ile Ala Arg Tyr
    50                  55                  60

Trp Ala Tyr Pro Met Phe Trp Cys Ile Ala Leu Glu Ala Thr Trp Tyr
65                  70                  75                  80

Leu Ser His Thr Arg
            85

<210> SEQ ID NO 84
<211> LENGTH: 85
<212> TYPE: PRT
<213> ORGANISM: Unknown
<220> FEATURE:
<223> OTHER INFORMATION: bacterium Ellin514 (ZP_03626656.1)
<220> FEATURE:
<221> NAME/KEY: VARIANT
<222> LOCATION: 19
<223> OTHER INFORMATION: Xaa = Pyrrolysine

<400> SEQUENCE: 84

Glu Ala Gly Tyr Pro Trp Glu Thr His Tyr Thr Arg Ile Arg Pro Glu
1               5                   10                  15

Tyr Phe Xaa Ala Ala Cys Lys Arg Met Met His Leu Val Asp Cys Cys
            20                  25                  30

```
Phe Thr Pro Cys Ile Val Gly Arg Trp Cys Tyr Phe Leu Pro Leu Met
         35                  40                  45

Gly Val Asp Lys Ala Arg Ala His Trp Arg Tyr Leu Ile Ala Arg Tyr
 50                  55                  60

Trp Ala Leu Pro Val Val Trp Cys Ile Ala Leu Glu Ala Asn Trp Tyr
 65                  70                  75                  80

Leu Ala Lys Gly Phe
             85

<210> SEQ ID NO 85
<211> LENGTH: 87
<212> TYPE: PRT
<213> ORGANISM: Unknown
<220> FEATURE:
<223> OTHER INFORMATION: Algoriphagus sp.
<220> FEATURE:
<221> NAME/KEY: VARIANT
<222> LOCATION: 19, 47
<223> OTHER INFORMATION: Xaa = Pyrrolysine

<400> SEQUENCE: 85

Gly Glu Val Ala Phe Thr Gly Ser Gly Lys Ile Ser Leu Asn Pro Glu
 1               5                  10                  15

Phe Phe Xaa Arg Ile Cys Gln Lys Ile Glu Glu Ala Asn Ala Lys Cys
                 20                  25                  30

Leu Leu Val Ser Pro Val Val Leu Trp Ala Leu Pro Phe Gly Xaa Gly
             35                  40                  45

Thr Glu Tyr Ser Pro Gly Tyr Tyr Leu Pro Ile Arg Glu Ala Val Ile
 50                  55                  60

Leu Ala Lys Tyr Ile Val Ala Arg Tyr Cys Cys His His Val Leu Trp
 65                  70                  75                  80

Thr Leu Cys Leu Asp Gly Lys
             85

<210> SEQ ID NO 86
<211> LENGTH: 83
<212> TYPE: PRT
<213> ORGANISM: Unknown
<220> FEATURE:
<223> OTHER INFORMATION: bacterium Ellin514 (ZP_03628444.1)
<220> FEATURE:
<221> NAME/KEY: VARIANT
<222> LOCATION: 1, 19, 20, 46, 57, 60, 83
<223> OTHER INFORMATION: Xaa = Pyrrolysine

<400> SEQUENCE: 86

Xaa Ser Val Phe Glu Ser Thr Ser Thr Thr Leu Thr Ile Asn Leu His
 1               5                  10                  15

Leu Phe Xaa Xaa Leu Cys Ser Arg Ile Glu Thr Leu Asn Arg Ala Cys
                 20                  25                  30

Leu Leu Ser Ala Ile Leu Pro Leu Arg Asp Leu Glu Ala Xaa Ala Pro
             35                  40                  45

Gly Leu Glu Thr Ile Pro Glu Glu Xaa Ala Val Xaa Leu Leu Arg Tyr
 50                  55                  60

Asn Val Ala Arg Trp Gly Ala Tyr Asn Val Ala Trp Ile Ile Met Leu
 65                  70                  75                  80

Glu Gly Xaa

<210> SEQ ID NO 87
<211> LENGTH: 104
<212> TYPE: PRT
```

```
<213> ORGANISM: Unknown
<220> FEATURE:
<223> OTHER INFORMATION: Anaeromyxobacter sp.

<400> SEQUENCE: 87

Glu Pro Val Ala Phe Asp Glu Ala Ala Ala Arg Tyr Cys Ala Ile Phe
 1               5                  10                  15

Ala Ala Ala Glu Ala His Cys Val Lys Val Val Leu Ser Val Phe Ala
            20                  25                  30

Ile Gly Phe Thr Pro Gly Asp Ala Leu Ile Lys Gly Trp Glu Glu Asn
        35                  40                  45

Pro Tyr Ser Ala Ala Arg Gly Gly Pro Ala Ala Gly His Thr Asp Phe
50                  55                  60

Phe Leu Asp Pro Arg Ala Arg Glu Ala Ala Arg Ala Arg Leu Arg Tyr
65                  70                  75                  80

Val Leu Ala Arg Trp Gly Ala Ser Pro Ala Leu Leu Ala Ile Asp Leu
                85                  90                  95

Leu Asn Glu Pro Glu Trp Asp Gly
            100

<210> SEQ ID NO 88
<211> LENGTH: 113
<212> TYPE: PRT
<213> ORGANISM: Chitinophaga pinensis
<220> FEATURE:
<221> NAME/KEY: VARIANT
<222> LOCATION: 23, 110, 111
<223> OTHER INFORMATION: Xaa = Pyrrolysine

<400> SEQUENCE: 88

Pro Arg Thr Lys Arg Tyr Gln Pro Ser Ala Glu Tyr Phe His Pro Gly
 1               5                  10                  15

Ala Ile Arg Arg Tyr Cys Xaa Leu Val Asp Asn Cys Asp Ser Leu Cys
            20                  25                  30

Leu Tyr Phe Met Leu Thr Asp Trp His Gly His Leu His Glu His Gly
        35                  40                  45

Gly Trp Lys His Ser Ser Tyr His Lys Ala Asn Gly Gly Pro Ala Glu
50                  55                  60

Thr Pro Thr Ala Phe Phe Thr Ser Gln Cys Ala Asp Glu Lys Tyr Lys
65                  70                  75                  80

Asn Lys Leu Arg Tyr Ile Ile Ala Arg Trp Gly Tyr Ser Ser Ser Ile
                85                  90                  95

Ala Val Trp Glu Phe Phe Asn Glu Val Asp Phe Thr Gln Xaa Xaa Ser
            100                 105                 110

Ile

<210> SEQ ID NO 89
<211> LENGTH: 101
<212> TYPE: PRT
<213> ORGANISM: Zunongwangia profunda

<400> SEQUENCE: 89

Asn Phe Asn Ser Arg Tyr Thr Ala Ser Asp Ala Tyr Tyr Asn Pro Ser
 1               5                  10                  15

Ala Val Ala Lys Leu Cys Ser Leu Val Asp Leu Ser Lys Lys Cys Leu
            20                  25                  30

His Met Asn Leu Thr Leu Gly Pro Gly Asn Tyr Ser Lys Glu Asp Gly
        35                  40                  45
```

```
Gly Phe Ala Glu Ser Thr Ala Asp Phe Phe Val Asn Pro Lys Ser Arg
 50                  55                  60

Asp Arg Tyr Lys Asn Arg Leu Arg Tyr Ile Ile Ala Arg Trp Gly Tyr
 65                  70                  75                  80

Ser Thr Ser Ile Ala Ala Trp Glu Glu Phe Asn Glu Ile Asp Gln Tyr
                 85                  90                  95

Arg Asn Arg Cys Asn
            100

<210> SEQ ID NO 90
<211> LENGTH: 101
<212> TYPE: PRT
<213> ORGANISM: Unknown
<220> FEATURE:
<223> OTHER INFORMATION: VIMSS5326244, derived from Archaea

<400> SEQUENCE: 90

Leu His Tyr Tyr Ser Leu Asp Asp Ala Ala Arg Ile Cys Glu Ile Val
 1               5                  10                  15

Lys Leu Ala Glu Lys Tyr Asp Ile Tyr Ile Val Phe Val Phe His Trp
                 20                  25                  30

His Gly Glu Leu Ala Asp Asn Trp Gly Asp Asn Pro Tyr His Arg Ala
             35                  40                  45

Arg Gly Gly Pro Leu Gln Ser Pro Glu Glu Phe Trp Ser Asn Ala Val
 50                  55                  60

Ala Ile Ser Ile Phe Lys Asp Lys Val Arg Tyr Ile Ile Ala Arg Trp
 65                  70                  75                  80

Gly Tyr Ser Thr His Ile Leu Ala Trp Glu Leu Ile Asn Glu Ala Asp
                 85                  90                  95

Leu Thr Thr Asn Phe
            100

<210> SEQ ID NO 91
<211> LENGTH: 113
<212> TYPE: PRT
<213> ORGANISM: Victivallis vadensis

<400> SEQUENCE: 91

Thr Arg Ala Gly Asn Tyr Gly Arg Tyr Asn Leu Glu Ala Ala Leu Ile
 1               5                  10                  15

Lys Leu Cys His Ile Phe Glu Gln Ala Arg Lys Asn Gly Ile Tyr Leu
                 20                  25                  30

Asn Leu Ile Leu Asp Asn His Gly Arg Leu Ser Asp Arg Ser Asp Pro
             35                  40                  45

Glu Trp Gln Thr Thr Pro Tyr Ala Lys Ala Asn Gly Gly Phe Leu Ala
 50                  55                  60

Asn Pro Ala Gln Phe Phe Arg Ser Glu Ala Ala Glu Lys Asn Asp Arg
 65                  70                  75                  80

Lys Arg Ala Arg Tyr Ile Ala Ala Arg Trp Gly Asn Ala Pro Asn Leu
                 85                  90                  95

Asn Ala Val Glu Leu Trp Glu Glu Val Asp Leu Thr Glu Asp Tyr Trp
            100                 105                 110

Gly

<210> SEQ ID NO 92
<211> LENGTH: 109
<212> TYPE: PRT
<213> ORGANISM: Clostridium leptum
```

```
<220> FEATURE:
<221> NAME/KEY: VARIANT
<222> LOCATION: 6, 17
<223> OTHER INFORMATION: Xaa = Pyrrolysine

<400> SEQUENCE: 92

Leu His Glu Tyr Asn Xaa Asp Asn Ala Leu Lys Leu Cys Arg Arg Phe
  1               5                  10                  15

Xaa Thr Ala Glu Glu Leu Gly Ile Phe Phe Arg Leu Ser Leu Phe His
                 20                  25                  30

Trp Glu Asp Phe Asp Asp Glu Thr Glu Lys Phe Pro Asp Trp Gly Arg
             35                  40                  45

Asn Pro Tyr His Cys Gln Asn Gly Gly Pro Ala Lys Asn Val Ser Glu
         50                  55                  60

Phe Phe Glu Lys Pro Ala Cys Lys Lys Tyr Trp Arg Tyr Tyr Leu Lys
 65                  70                  75                  80

Tyr Trp Ala Ala Arg Trp Gly Tyr Ser Pro Asn Leu Asn Ala Tyr Glu
                 85                  90                  95

Leu Trp Asn Glu Ile Asp Trp Arg Ala Gly Glu Asp Tyr
                100                 105

<210> SEQ ID NO 93
<211> LENGTH: 106
<212> TYPE: PRT
<213> ORGANISM: Herpetosiphon aurantiacus
<220> FEATURE:
<221> NAME/KEY: VARIANT
<222> LOCATION: 11, 12, 18
<223> OTHER INFORMATION: Xaa = Pyrrolysine
<220> FEATURE:
<221> NAME/KEY: VARIANT
<222> LOCATION: 21
<223> OTHER INFORMATION: Xaa = Any Amino Acid
<220> FEATURE:
<221> NAME/KEY: VARIANT
<222> LOCATION: 72
<223> OTHER INFORMATION: Xaa = Pyrrolysine

<400> SEQUENCE: 93

Thr Gly Leu Gly Asp Tyr Ser Lys Arg Met Xaa Xaa Ala Leu Met Leu
  1               5                  10                  15

Cys Xaa Ile Phe Xaa Leu Ala Glu Gln Arg Asn Ile Thr Ile Asn Leu
                 20                  25                  30

Thr Leu Ile Asn His Gly Ala Phe Ser Thr Ser Thr Asp Ser Glu Trp
             35                  40                  45

Ala Ser Asn Pro Tyr His Ala Ala Asn Gly Gly Pro Ile Ala Glu Pro
         50                  55                  60

Arg Leu Phe Ala Thr Asp Ile Xaa Ser Arg Glu Val Phe Lys His Arg
 65                  70                  75                  80

Val Arg Tyr Ile Ala Ala Arg Trp Ala His Ser Pro Ser Leu Phe Ala
                 85                  90                  95

Trp Glu Trp Trp Asn Glu Phe His His Thr
                100                 105

<210> SEQ ID NO 94
<211> LENGTH: 106
<212> TYPE: PRT
<213> ORGANISM: Caldicellulosiruptor saccharolyticus
<220> FEATURE:
<221> NAME/KEY: VARIANT
<222> LOCATION: 15, 25, 39, 47, 76
<223> OTHER INFORMATION: Xaa = Pyrrolysine
```

<400> SEQUENCE: 94

| Thr | Gly | Ile | Tyr | Asp | Phe | Thr | Asn | Ala | Leu | Asp | Arg | Ala | Tyr | Xaa | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Lys | Val | Leu | Glu | Leu | Ala | Glu | Xaa | Lys | Gly | Ile | Tyr | Ile | His | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Phe | Ile | Asn | His | Gly | Xaa | Phe | Ser | Thr | Lys | Val | Asn | Pro | Xaa | Trp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asn | Glu | Asn | Pro | Trp | Asn | Lys | Lys | Asn | Gly | Gly | Ile | Leu | Thr | Lys | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Glu | Phe | Phe | Thr | Asn | Thr | Glu | Ala | Lys | Lys | Xaa | Phe | Lys | Lys | Ile |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Arg | Tyr | Ile | Ile | Ala | Arg | Trp | Gly | Tyr | Ser | Thr | Asn | Ile | Asn | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Trp | Glu | Leu | Phe | Asn | Glu | Val | Ser | Trp | Thr |
|-----|-----|-----|-----|-----|-----|-----|-----|-----|-----|
|     |     |     | 100 |     |     |     |     | 105 |     |

<210> SEQ ID NO 95
<211> LENGTH: 107
<212> TYPE: PRT
<213> ORGANISM: Opitutus terrae
<220> FEATURE:
<221> NAME/KEY: VARIANT
<222> LOCATION: 8, 12, 15, 32, 66, 74, 94
<223> OTHER INFORMATION: Xaa = Pyrrolysine

<400> SEQUENCE: 95

| Lys | Gly | Thr | His | Tyr | Pro | Leu | Xaa | Ala | Ala | Trp | Xaa | Leu | Cys | Xaa | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Ala | Leu | Ala | Glu | Thr | Arg | Gly | Leu | Tyr | Leu | Leu | Leu | Cys | Phe | Xaa |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | His | Gln | Tyr | Tyr | His | Ala | Asn | Asp | Pro | Ala | Trp | Gly | Ala | Asn | Pro |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Ala | His | Glu | Asn | Gly | Gly | Pro | Cys | Val | Ser | Pro | Asn | Ala | Phe | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Xaa | Pro | Pro | Ala | Arg | Ala | Leu | Tyr | Xaa | Lys | Arg | Leu | Arg | Tyr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Ala | Arg | Tyr | Gly | Gly | Ser | Pro | Arg | Leu | Leu | Ala | Trp | Xaa | Phe | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Glu | Ile | Asp | Asn | Ala | Tyr | Ile | Pro | Arg | Ser |
|-----|-----|-----|-----|-----|-----|-----|-----|-----|-----|-----|
|     |     |     | 100 |     |     |     |     | 105 |     |     |

<210> SEQ ID NO 96
<211> LENGTH: 95
<212> TYPE: PRT
<213> ORGANISM: Coraliomargarita akajimensis
<220> FEATURE:
<221> NAME/KEY: VARIANT
<222> LOCATION: 10, 56, 69
<223> OTHER INFORMATION: Xaa = Pyrrolysine
<220> FEATURE:
<221> NAME/KEY: VARIANT
<222> LOCATION: 70
<223> OTHER INFORMATION: Xaa = Selenocysteine

<400> SEQUENCE: 96

| Thr | Ile | Tyr | Ala | Gly | Ala | Cys | Ser | Asp | Xaa | Arg | Lys | Asp | Phe | Ser | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| His | Gly | Arg | Ala | Leu | Leu | Pro | Tyr | Glu | Asp | His | Ile | Ser | Ile | His | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Pro | Ser | Ser | Thr | Asp | Ala | Ile | Phe | Asn | Ala | Leu | Val | Gly | His | Thr |

-continued

```
                35                  40                  45
Ser Phe Thr Gly Pro Ala Phe Xaa Trp Asn Ile Asn Thr Asn Ile Ala
 50                  55                  60

Ala Lys Thr Lys Xaa Xaa Arg Asp Ala Ser Ile Ala Ser Gly His Lys
 65                  70                  75                  80

Trp Val Phe Cys Met Asp Glu Pro Tyr Leu Gly Gly Asn Pro Asn
                 85                  90                  95

<210> SEQ ID NO 97
<211> LENGTH: 99
<212> TYPE: PRT
<213> ORGANISM: Opitutus terrae
<220> FEATURE:
<221> NAME/KEY: VARIANT
<222> LOCATION: 5, 31, 51, 61
<223> OTHER INFORMATION: Xaa = Pyrrolysine

<400> SEQUENCE: 97

Asn Thr Asp Ala Xaa Arg Glu Ala Phe Ala Asp Tyr Leu Asn Ala Leu
 1               5                  10                  15

Asp Pro Tyr Phe Ser Leu Ile Ala Val His Thr Tyr Pro Ser Xaa Pro
                20                  25                  30

Asp Thr Ile Tyr Thr Gly His Leu Gly Ser Glu Leu Ile Ser Gly Ala
                35                  40                  45

Ser Leu Xaa Leu Glu Ser Pro Ser Ile Val His Glu Xaa Thr Leu Lys
 50                  55                  60

Trp Val Lys Lys Ser Ala Ala Ala Gly Ser Lys Trp Val Val Ser Val
 65                  70                  75                  80

Asp Glu Leu Gly Pro Ser Ser Ala Gly Val Val Pro Asp Ala Asn Asp
                85                  90                  95

Pro Ala His

<210> SEQ ID NO 98
<211> LENGTH: 103
<212> TYPE: PRT
<213> ORGANISM: Coraliomargarita akajimensis
<220> FEATURE:
<221> NAME/KEY: VARIANT
<222> LOCATION: 6, 10, 12, 16, 34, 52, 88, 97
<223> OTHER INFORMATION: Xaa = Pyrrolysine

<400> SEQUENCE: 98

Val Lys Glu His Phe Xaa Ser Thr Glu Xaa Arg Xaa Ala Met Ala Xaa
 1               5                  10                  15

Trp Phe Tyr Asp Asn Asp Pro Tyr Lys His Met Leu Val Ile His Asn
                20                  25                  30

Gly Xaa Ser Pro Asn Asp Leu Leu Gly Asp Ala Ser Lys Leu Thr Gly
                35                  40                  45

Phe Ser Leu Xaa Thr Asn Leu Glu Asp Phe Ala Asn Val Pro Gly Thr
 50                  55                  60

Val Ala Ser Trp Ile Arg Lys Ser Ala Glu Ala Gly Lys Pro Trp Ala
 65                  70                  75                  80

Val Ala Cys Asp Glu Pro Gly Xaa Ala Ser His Ala Ile Arg Pro Asp
                85                  90                  95

Xaa Asn Ala Gly Ser Ser His
                100

<210> SEQ ID NO 99
<211> LENGTH: 105
```

<212> TYPE: PRT
<213> ORGANISM: Coraliomargarita akajimensis
<220> FEATURE:
<221> NAME/KEY: VARIANT
<222> LOCATION: 1, 5, 7, 11, 34, 52, 64, 83, 105
<223> OTHER INFORMATION: Xaa = Pyrrolysine

<400> SEQUENCE: 99

Xaa Ser Thr Ser Xaa Arg Xaa Ala Met Ala Xaa Tyr Phe Arg Asp Thr
 1               5                  10                  15

Asp Pro Tyr Gly His Asn Ile Val Leu His Thr Tyr Pro Gly Glu Trp
            20                  25                  30

Glu Xaa Val Tyr Arg Pro Leu Leu Gly Ser Ala Ser Glu Leu Thr Gly
        35                  40                  45

Ala Ser Ile Xaa Thr Asn Tyr Asn Thr Val His Ser Arg Thr Leu Xaa
    50                  55                  60

Trp Leu Asn Glu Ser Thr Ala Ala Gly Lys Val Trp Val Val Ala Asn
65                  70                  75                  80

Asp Glu Xaa Gly Pro Ala Ser His Ala Asn Pro Asp Asn Gly Trp
                85                  90                  95

Pro Gly Tyr Thr Gly Ser Thr Ser Xaa
            100                 105

<210> SEQ ID NO 100
<211> LENGTH: 105
<212> TYPE: PRT
<213> ORGANISM: Opitutus terrae
<220> FEATURE:
<221> NAME/KEY: VARIANT
<222> LOCATION: 5, 6, 7, 32, 52, 64, 75
<223> OTHER INFORMATION: Xaa = Pyrrolysine

<400> SEQUENCE: 100

Leu Ser Thr Glu Xaa Xaa Xaa Ala Met Ala Ala Phe Ile Arg Asp Thr
 1               5                  10                  15

Asp Pro Tyr His His Pro Ile Val Leu His Thr Phe Pro Asp Trp Xaa
            20                  25                  30

Glu Arg Val Tyr Arg Pro Leu Leu Gly Asp Arg Ser Ala Leu Thr Gly
        35                  40                  45

Val Ser Leu Xaa Thr Gly Trp Glu Gln Ser His Arg Arg Val Leu Xaa
    50                  55                  60

Trp Ile Glu Glu Ser Ala Ala Ala Gly Lys Xaa Trp Val Val Ala His
65                  70                  75                  80

Asp Glu Gln Asn Pro His Tyr Thr Gly Val Pro Pro Asp Thr Gly Trp
                85                  90                  95

Glu Gly Phe Asp Gly Thr Ala Thr Ala
            100                 105

<210> SEQ ID NO 101
<211> LENGTH: 106
<212> TYPE: PRT
<213> ORGANISM: Rhodopirellula baltica
<220> FEATURE:
<221> NAME/KEY: VARIANT
<222> LOCATION: 1, 32, 52, 62, 106
<223> OTHER INFORMATION: Xaa = Pyrrolysine

<400> SEQUENCE: 101

Xaa Thr Thr Asp Glu His Leu Ala Met Leu Asn Tyr Ile Glu Glu Met
 1               5                  10                  15

Asp Pro Tyr Gly His Met Arg Val Leu His Thr Tyr Pro Gly Glu Xaa

```
                    20                  25                  30
Asp Lys Lys Tyr Asp Pro Leu Leu Gly Asp Lys Ser Asn Leu Thr Gly
                35                  40                  45

Val Ser Leu Xaa Asn Ser His Ile Lys Asp Thr His Trp Xaa Thr Val
 50                  55                  60

Lys Trp Ser Glu Lys Ala Arg Glu Ala Gly Lys Pro Trp Val Val Ala
 65                  70                  75                  80

Phe Asp Glu Ser Gly Ser Ala Ala His Gly Gln Cys Pro Asp Leu Gly
                85                  90                  95

Tyr Arg Gly Tyr Asp Gly Arg Asp Thr Xaa
                100                 105

<210> SEQ ID NO 102
<211> LENGTH: 109
<212> TYPE: PRT
<213> ORGANISM: Robiginitalea biformata
<220> FEATURE:
<221> NAME/KEY: VARIANT
<222> LOCATION: 37, 56, 58, 79, 87
<223> OTHER INFORMATION: Xaa = Pyrrolysine

<400> SEQUENCE: 102

Asp Glu Leu Gly Asp Thr Asn Asn Thr Arg Val Arg Ala Tyr Ala Ser
 1               5                  10                  15

Tyr Ile Lys Ser Leu Asp Pro Tyr Asn His Met Ile Val Ile His Ser
                20                  25                  30

Tyr Pro Asn Ser Xaa Ser Glu Leu Tyr Glu Pro Leu Leu Gly Asp Ser
                35                  40                  45

Asp Leu Thr Gly Pro Ser Leu Xaa Ile Xaa Ile Asn Asn Ile His Arg
 50                  55                  60

Asp Val Lys Arg Trp Ile Asn Asp Ser Lys Ala Ser Gly Lys Xaa Trp
 65                  70                  75                  80

Val Val Thr Asn Asp Glu Xaa Gly Asp Trp Thr Thr Gly Val Ala Ala
                85                  90                  95

Asp Ala Ser Tyr Gly Gly Asp Lys Gly Ser Arg Asn Arg
                100                 105

<210> SEQ ID NO 103
<211> LENGTH: 100
<212> TYPE: PRT
<213> ORGANISM: Thermobaculum terrenum
<220> FEATURE:
<221> NAME/KEY: VARIANT
<222> LOCATION: 47, 100
<223> OTHER INFORMATION: Xaa = Pyrrolysine

<400> SEQUENCE: 103

Trp His Tyr Lys Pro Thr Ala Asp Arg Trp Ala Ile Arg Ile Ala Arg
 1               5                  10                  15

Trp Leu Arg Ala Asn Ala Pro Trp Gly His Ile Val Ser Leu His Asn
                20                  25                  30

Gly Pro Trp Asp Pro Pro Phe Ala His Arg Phe Arg Ser Asp Xaa Phe
                35                  40                  45

Trp Gly Gly Arg Asp Asp Ala Trp Leu Ala Ala Gly Ile Glu Asp Arg
 50                  55                  60

Ile Ala Tyr Ser Leu Gly Gly Trp Tyr Gly Thr Ala Val Phe Ala Glu
 65                  70                  75                  80

Tyr Gly Tyr Glu Arg Asn Pro Ala Leu Pro Leu Asn Ile Pro Gly His
                85                  90                  95
```

Glu Phe Cys Xaa
            100

<210> SEQ ID NO 104
<211> LENGTH: 93
<212> TYPE: PRT
<213> ORGANISM: Bifidobacterium dentium
<220> FEATURE:
<221> NAME/KEY: VARIANT
<222> LOCATION: 1
<223> OTHER INFORMATION: Xaa = Selenocysteine
<220> FEATURE:
<221> NAME/KEY: VARIANT
<222> LOCATION: 4, 49, 74
<223> OTHER INFORMATION: Xaa = Pyrrolysine

<400> SEQUENCE: 104

Xaa Met Pro Xaa Lys Ser Leu Glu Asp Trp Arg Glu Tyr Ala Arg Val
 1               5                  10                  15

Val Met Ala Asn Asp Ala Phe Gly His Leu Arg Ser Ile His Asn Cys
            20                  25                  30

Ile Pro Ile Tyr Asp Tyr Asn Glu Pro Trp Cys Thr His Cys Ser Ile
        35                  40                  45

Xaa Arg Val Asp Val Thr Arg Thr Thr Glu Cys Ile Ala Asp Trp Arg
 50                  55                  60

Lys Ala Tyr Gly Lys Pro Val Val Cys Xaa Glu Pro Gly Tyr Glu Gly
65                  70                  75                  80

Asn Ile Tyr Trp Gly Trp Gly Asn Leu Thr Gly Glu Glu
            85                  90

<210> SEQ ID NO 105
<211> LENGTH: 93
<212> TYPE: PRT
<213> ORGANISM: Opitutus terrae
<220> FEATURE:
<221> NAME/KEY: VARIANT
<222> LOCATION: 11, 12, 18, 40, 49, 88
<223> OTHER INFORMATION: Xaa = Pyrrolysine

<400> SEQUENCE: 105

Leu Val Arg Thr Lys Thr Glu Glu His Trp Xaa Xaa Leu Gly Arg Leu
 1               5                  10                  15

Val Xaa Ala Thr Asp Pro Phe Asp His Leu Arg Ser Ile His His Ser
            20                  25                  30

Gln Leu Leu Phe Asp Asn Arg Xaa Pro Trp Val Thr His Ala Ser Ile
        35                  40                  45

Xaa Asn Gly Ser Ala Val Glu Glu Pro Gly Arg Ala Glu Leu Tyr Arg
 50                  55                  60

Asp Val Trp Arg Lys Pro Val Val Tyr Asp Val Lys Tyr Glu Gly
65                  70                  75                  80

Asn Ala Arg Arg Arg Trp Gly Xaa Leu Ser Gly Pro Glu
            85                  90

<210> SEQ ID NO 106
<211> LENGTH: 93
<212> TYPE: PRT
<213> ORGANISM: Bacteroides vulgatus
<220> FEATURE:
<221> NAME/KEY: VARIANT
<222> LOCATION: 50, 75
<223> OTHER INFORMATION: Xaa = Pyrrolysine

<400> SEQUENCE: 106

```
Tyr Val Lys Ala Lys Thr Val Asp Asp Trp Lys Leu Leu Thr Lys Thr
1               5                   10                  15

Val Val Glu Asn Asp Pro Tyr Arg His Leu Cys Ser Ile His Gly Ala
                20                  25                  30

Thr Ala Thr Tyr Phe Asp Tyr Trp Met Pro Glu Phe Thr His Val Ser
            35                  40                  45

Ile Xaa Asp Glu Ala Pro Val Leu Ser Ser Thr Ala Ser Ala Thr Leu
        50                  55                  60

Arg Lys Ile Tyr Arg Lys Pro Val Ile Cys Xaa Glu Tyr Gly Tyr Glu
65                  70                  75                  80

Gly Asn Leu Pro Tyr Arg Trp Gly Arg Leu Ser Pro Gln
                85                  90
```

<210> SEQ ID NO 107
<211> LENGTH: 93
<212> TYPE: PRT
<213> ORGANISM: Spirosoma linguale
<220> FEATURE:
<221> NAME/KEY: VARIANT
<222> LOCATION: 19, 50, 56, 75
<223> OTHER INFORMATION: Xaa = Pyrrolysine

<400> SEQUENCE: 107

```
Tyr Val Lys Ser Lys Thr Val Ser Asp Trp Asp Leu Leu Ala Lys Thr
1               5                   10                  15

Val Ala Xaa Asn Asp Pro Tyr Lys His Leu Cys Ser Ile His Gly Ala
                20                  25                  30

Thr Ala Thr Tyr Tyr Asp Tyr Arg Lys Pro Glu Phe Thr Met Val Ser
            35                  40                  45

Ile Xaa Asp Glu Thr Pro Val Xaa Ser Pro Asn Ala Ala Ala Met Leu
        50                  55                  60

Arg His Ile Tyr Asn Lys Pro Val Ile Ala Xaa Glu Val Gly Tyr Glu
65                  70                  75                  80

Gly Asn Leu Lys Ser Arg Trp Gly Arg Tyr Ser Pro Glu
                85                  90
```

<210> SEQ ID NO 108
<211> LENGTH: 90
<212> TYPE: PRT
<213> ORGANISM: Unknown
<220> FEATURE:
<223> OTHER INFORMATION: Geobacillus sp.
<220> FEATURE:
<221> NAME/KEY: VARIANT
<222> LOCATION: 11, 18
<223> OTHER INFORMATION: Xaa = Pyrrolysine
<220> FEATURE:
<221> NAME/KEY: VARIANT
<222> LOCATION: 20
<223> OTHER INFORMATION: Xaa = Any Amino Acid
<220> FEATURE:
<221> NAME/KEY: VARIANT
<222> LOCATION: 47, 50, 53, 71
<223> OTHER INFORMATION: Xaa = Pyrrolysine

<400> SEQUENCE: 108

```
Phe Asn Lys His Lys Thr Ile Glu Asp Trp Xaa Arg Leu Leu Gln Val
1               5                   10                  15

Tyr Xaa Arg Xaa Asp Pro Tyr Gln Arg Leu Arg Ser Ile His Asn Gly
                20                  25                  30

Thr Lys Ser Leu Tyr Asp Phe Ser Lys Ser Trp Leu Thr His Xaa Ser
            35                  40                  45
```

```
Ile Xaa His Trp Xaa Thr Ser Pro Thr Thr Cys Trp Arg Glu Ala Val
    50                  55                  60

Arg Lys Pro Ile Val Val Xaa Glu Ile Ser Tyr Glu Gly Asn Val Ala
 65                  70                  75                  80

Lys Arg Trp Gly Asn Ile Thr Gly Leu Glu
                85                  90

<210> SEQ ID NO 109
<211> LENGTH: 100
<212> TYPE: PRT
<213> ORGANISM: Thermotoga maritima
<220> FEATURE:
<221> NAME/KEY: VARIANT
<222> LOCATION: 5, 9
<223> OTHER INFORMATION: Xaa = Pyrrolysine
<220> FEATURE:
<221> NAME/KEY: VARIANT
<222> LOCATION: 18
<223> OTHER INFORMATION: Xaa = Any Amino Acid
<220> FEATURE:
<221> NAME/KEY: VARIANT
<222> LOCATION: 29, 47, 99
<223> OTHER INFORMATION: Xaa = Pyrrolysine

<400> SEQUENCE: 109

Leu Ile Lys Pro Xaa Lys Asp Trp Xaa Gly Tyr Phe Asn Phe Ile Val
  1               5                  10                  15

Glu Xaa Asp Pro Tyr Asn His Leu Arg Ser Val His Xaa Cys Phe Lys
                 20                  25                  30

Phe Tyr Asp His Thr Lys Pro Trp Ile Thr His Ala Ser Ile Xaa Trp
             35                  40                  45

Gly Ser Leu Arg Ser Trp Ser Gly Glu Pro Gly Ile Asp Ile Gly Ile
 50                  55                  60

His Leu Ile Pro Lys Trp Arg Glu Met Val Lys Lys Pro Val Ile Ile
 65                  70                  75                  80

Asp Phe Cys Gly Tyr Glu Gly Asn Ile Glu Tyr Gly Trp Gly Asn Leu
                 85                  90                  95

Pro Pro Xaa Glu
            100

<210> SEQ ID NO 110
<211> LENGTH: 106
<212> TYPE: PRT
<213> ORGANISM: Unknown
<220> FEATURE:
<223> OTHER INFORMATION: bacterium Ellin514 (ZP_03628309.1)
<220> FEATURE:
<221> NAME/KEY: VARIANT
<222> LOCATION: 4, 6, 19, 36, 37, 50, 92
<223> OTHER INFORMATION: Xaa = Pyrrolysine

<400> SEQUENCE: 110

Ala Lys Asp Xaa Ala Xaa Leu Leu Lys Trp Thr Lys Val Thr Arg Tyr
  1               5                  10                  15

Val Arg Xaa Val Asp Pro Tyr Asn Arg Pro Leu Ser Ile His Pro Pro
                 20                  25                  30

Ile Glu Arg Xaa Xaa Val Ser Asp Pro Asn Leu Leu Asp Phe Asp Met
             35                  40                  45

Leu Xaa Ser Gly Trp Asp Asp Arg Ala Ser Val Pro Tyr Thr Ile Ser
 50                  55                  60

Leu Val Arg Arg Ser Arg Ser Ser Ser Pro Arg Met Pro Thr Ile Asp
 65                  70                  75                  80
```

-continued

```
Ala Glu Val Cys Tyr Glu Gly Ile Leu Asn Cys Xaa Arg Tyr Met Glu
                85                  90                  95

Trp Arg Cys Leu Leu Gly Gly Thr Ala Gly
            100                 105

<210> SEQ ID NO 111
<211> LENGTH: 111
<212> TYPE: PRT
<213> ORGANISM: Unknown
<220> FEATURE:
<223> OTHER INFORMATION: bacterium Ellin514 (ZP_03626656.1)
<220> FEATURE:
<221> NAME/KEY: VARIANT
<222> LOCATION: 4, 7, 50, 55, 60
<223> OTHER INFORMATION: Xaa = Pyrrolysine

<400> SEQUENCE: 111

Pro Tyr Asp Xaa Arg Lys Xaa Val Lys Trp Thr Glu Val Thr Arg Tyr
1               5                   10                  15

Asn Arg Ala Thr Asp Pro Phe Asn Arg Pro Ile Thr Ile His Pro Thr
                20                  25                  30

Gly Ile Gly Arg Leu Ser Ala Arg His Ala Met Asp Asp Leu Ser Leu
            35                  40                  45

Ile Xaa Ile Asp Met Leu Xaa Thr Pro His Gly Xaa Arg Asp Ala Val
50                  55                  60

Ala Pro Thr Val His Thr Met Arg Glu Ser Tyr Ala Asp Lys Pro Val
65                  70                  75                  80

Met Pro Val Ile Asn Gly Glu Ala Ser Phe Glu Met Leu Ser Ser Leu
                85                  90                  95

Thr Arg Arg Met Phe Trp Leu Cys Leu Met Asn Gly Ala Ala Gly
            100                 105                 110

<210> SEQ ID NO 112
<211> LENGTH: 107
<212> TYPE: PRT
<213> ORGANISM: Unknown
<220> FEATURE:
<223> OTHER INFORMATION: Algoriphagus sp.
<220> FEATURE:
<221> NAME/KEY: VARIANT
<222> LOCATION: 14, 42, 51, 72
<223> OTHER INFORMATION: Xaa = Pyrrolysine

<400> SEQUENCE: 112

Tyr Tyr Gly Asp Leu Glu Asp Trp Lys Ser Ile Gly Ser Xaa Val Thr
1               5                   10                  15

Gly Asp Gly Lys His Gln Gly Leu Val Thr Leu His Pro His Gly Leu
                20                  25                  30

Ser Trp Ile Gly Asp Ile Tyr Glu Asn Xaa Cys Trp Tyr Asp Val Ile
            35                  40                  45

Thr Tyr Xaa Ser Ser Asn Ser Asn Ser Glu Asn Thr Val Asn Trp Ile
50                  55                  60

Asn Lys Gly Pro Ile Ala Lys Xaa Trp Asp Asn Leu Arg Pro Met Pro
65                  70                  75                  80

Leu Ile Asn Thr Glu Pro Asn Tyr Glu Cys Phe Ile Thr Arg Asn
                85                  90                  95

Ala Ser Tyr Trp Ser Val Phe Ala Ala Pro Pro
            100                 105

<210> SEQ ID NO 113
```

```
<211> LENGTH: 104
<212> TYPE: PRT
<213> ORGANISM: Unknown
<220> FEATURE:
<223> OTHER INFORMATION: bacterium Ellin514 (ZP_03628444.1)
<220> FEATURE:
<221> NAME/KEY: VARIANT
<222> LOCATION: 5, 20, 34, 51, 59, 91
<223> OTHER INFORMATION: Xaa = Pyrrolysine

<400> SEQUENCE: 113

Asn Leu Ser Thr Xaa Val Ala Arg Trp Lys Arg Val Gly Arg Ser Val
 1               5                  10                  15

Thr Ala Asn Xaa His His Ala Pro Val Ile Leu His Pro Gly Thr Thr
            20                  25                  30

Leu Xaa Glu Phe Arg Ala Glu Pro Trp Val Asp Val Leu Ser Tyr Gln
        35                  40                  45

Ser Gly Xaa Glu Ala Asp Asp Asn Ala Leu Xaa Trp Leu Leu Ala Gly
    50                  55                  60

Pro Leu Ala Ile Asp Trp Gln Arg Val Pro Leu Lys Pro Phe Ile Asn
65                  70                  75                  80

Leu Ala Pro Tyr Tyr Glu Asn Ser Ser Thr Xaa Arg Arg Leu Ile Tyr
                85                  90                  95

Trp Ser Leu Leu Asn Ala Pro Thr
                100

<210> SEQ ID NO 114
<211> LENGTH: 97
<212> TYPE: PRT
<213> ORGANISM: Unknown
<220> FEATURE:
<223> OTHER INFORMATION: Anaeromyxobacter sp.
<220> FEATURE:
<221> NAME/KEY: VARIANT
<222> LOCATION: 48, 51
<223> OTHER INFORMATION: Xaa = Pyrrolysine

<400> SEQUENCE: 114

Ala Ile Pro Glu Asp His Trp Ile Pro Trp Ala Glu Asp Leu Ala Arg
 1               5                  10                  15

Thr Trp Arg Ala Glu Asp Pro Tyr Gly His Pro Val Ile Ala Gly Pro
            20                  25                  30

Val Gly Leu His Trp Tyr Val Glu Trp Trp Ala Ser Ala Ala Cys Xaa
        35                  40                  45

Ile Val Xaa Trp His Arg Tyr Gly Pro Asp Val His Asp Val His Asp
    50                  55                  60

Leu Ala Glu Ala Leu Val Glu Thr Thr Arg Asp Thr Ala Arg Tyr Gly
65                  70                  75                  80

Lys Pro Val Leu Ile Gly Glu Phe Gly Trp Gly Gly Asp Ala Lys Pro
                85                  90                  95

Glu

<210> SEQ ID NO 115
<211> LENGTH: 97
<212> TYPE: PRT
<213> ORGANISM: Chitinophaga pinensis
<220> FEATURE:
<221> NAME/KEY: VARIANT
<222> LOCATION: 9, 47, 50, 69, 87
<223> OTHER INFORMATION: Xaa = Pyrrolysine

<400> SEQUENCE: 115
```

-continued

```
Leu Ile Pro Leu Pro Val Ile Ala Xaa Trp Met Leu Cys His Ser Arg
1               5                   10                  15

Tyr Leu Lys Asp Ile Asp Pro Tyr His His Leu Val Ser Thr Ser Ile
            20                  25                  30

Ser His Arg Asp Ile Ile Gly Met Asn Ala Ile Pro Tyr Ile Xaa Phe
        35                  40                  45

Asn Xaa Lys His Ile Tyr Lys His Thr Glu Lys Ile Pro Gly Ile Tyr
    50                  55                  60

Pro Asp Tyr Ile Xaa Thr Phe Gly Lys Pro Tyr Val Val Gly Glu Phe
65                  70                  75                  80

Gly Tyr Arg Trp Glu Asp Xaa Asp Pro Lys Tyr Ala Thr Glu Ala Asn
            85                  90                  95

Tyr
```

<210> SEQ ID NO 116
<211> LENGTH: 97
<212> TYPE: PRT
<213> ORGANISM: Zunongwangia profunda
<220> FEATURE:
<221> NAME/KEY: VARIANT
<222> LOCATION: 50
<223> OTHER INFORMATION: Xaa = Pyrrolysine

<400> SEQUENCE: 116

```
Pro Ile Asp Ala Lys Thr Ile Val Asp Trp Met Cys Cys Met Ser Asn
1               5                   10                  15

Tyr Ile Asp Lys Ile Asp Pro Tyr Asn His Ile Ile Thr Thr Ser Ile
            20                  25                  30

Ser His Arg Asp Leu Glu Gly Leu Asn Ser Leu Pro Ala Ile Asp Ile
        35                  40                  45

Asn Xaa Lys His Ile Tyr Asn Arg Thr Lys Asp Ile Pro Gly Glu Ile
    50                  55                  60

Ile Asp Tyr Glu Lys Arg Phe Gly Lys Pro Tyr Val Ile Gly Glu Phe
65                  70                  75                  80

Ser Tyr Asp Trp Asp Trp Ser Lys Asn Phe Asp Glu Phe Pro Glu Glu
            85                  90                  95

Asn
```

<210> SEQ ID NO 117
<211> LENGTH: 106
<212> TYPE: PRT
<213> ORGANISM: Unknown
<220> FEATURE:
<223> OTHER INFORMATION: VIMSS5326244, derived from Archaea
<220> FEATURE:
<221> NAME/KEY: VARIANT
<222> LOCATION: 34, 48
<223> OTHER INFORMATION: Xaa = Pyrrolysine

<400> SEQUENCE: 117

```
Phe Ser Ala Arg Ser Ala Phe Val Ser Trp Val Lys Cys Ile Ser Ser
1               5                   10                  15

Tyr Ile Lys Ser Val Asp Pro Tyr Asn Arg Ile Val Thr Val Asn Leu
            20                  25                  30

Ala Xaa Tyr Asn Ser Glu Pro Arg Val Trp Ser Val Ser Ile Xaa
        35                  40                  45

Ile Ile Asn Val Asn Arg Tyr Gly Pro Glu Gly Phe Lys Asp Ile Ala
    50                  55                  60

Leu Ala Ile Pro Ser Ile Val Glu Gly Leu Trp Asn Thr Tyr Arg Lys
```

```
                65                  70                  75                  80
Pro Ile Ile Ile Thr Glu Phe Gly Val Asp Tyr Arg Trp Ile Gly Lys
                    85                  90                  95
Gly Thr Pro Tyr Trp Ala Tyr Asp Lys Ser
                100                 105

<210> SEQ ID NO 118
<211> LENGTH: 99
<212> TYPE: PRT
<213> ORGANISM: Victivallis vadensis
<220> FEATURE:
<221> NAME/KEY: VARIANT
<222> LOCATION: 4, 19, 31, 71
<223> OTHER INFORMATION: Xaa = Pyrrolysine
<220> FEATURE:
<221> NAME/KEY: VARIANT
<222> LOCATION: 80
<223> OTHER INFORMATION: Xaa = Selenocysteine

<400> SEQUENCE: 118

Arg Tyr Asn Xaa Gly Ser Ala Ile Arg Trp Ala Cys Lys Ala Ala Ala
  1               5                  10                  15

Phe Leu Xaa Ala Asn Ser Pro Val Ser Ile His Phe Cys Ser Xaa Tyr
                20                  25                  30

Asn Asn Val Arg Arg Phe Ile Lys Leu Phe Asp Asn Pro Ser Ile Thr
                35                  40                  45

His Leu Ala Gly Asp Ala Tyr Arg Ser Pro Gln Ile Asn Phe Val Asp
 50                  55                  60

His Leu Arg Gly Tyr Glu Xaa Asn Met Arg Tyr Asn Lys Pro Gln Xaa
 65                  70                  75                  80

Ile Thr Glu Phe Gly Gly Asn Pro Gln Gly Ser Ser Glu Arg Gln Val
                85                  90                  95

Leu Ala Asp

<210> SEQ ID NO 119
<211> LENGTH: 105
<212> TYPE: PRT
<213> ORGANISM: Clostridium leptum
<220> FEATURE:
<221> NAME/KEY: VARIANT
<222> LOCATION: 20, 33, 42, 63, 80, 99
<223> OTHER INFORMATION: Xaa = Pyrrolysine

<400> SEQUENCE: 119

Asp Asp Glu Ala Ser Lys Val Ile Gly Trp Met Ser Cys His Gly Ser
  1               5                  10                  15

Tyr Leu Lys Xaa Leu Asp Ser Lys His Leu Val Thr Ser Ser Phe Ala
                20                  25                  30

Xaa Ser Arg Arg Asp Leu Asn Leu Trp Xaa Leu Pro Cys Ile Asp Leu
                35                  40                  45

Thr Thr Val His Arg Tyr Thr Tyr Glu Glu Tyr Gly Gln Arg Xaa Tyr
 50                  55                  60

Asp Thr Glu Gly Ala Leu Ser Ala Val Leu Lys Glu Arg Glu Ser Xaa
 65                  70                  75                  80

Val Glu Lys Pro Val Leu Phe Gly Glu Phe Ala Leu Ser Pro Gly Gly
                85                  90                  95

Asp Ile Xaa Lys Asp Tyr Asp Pro Glu
                100                 105

<210> SEQ ID NO 120
```

```
<211> LENGTH: 100
<212> TYPE: PRT
<213> ORGANISM: Herpetosiphon aurantiacus
<220> FEATURE:
<221> NAME/KEY: VARIANT
<222> LOCATION: 8, 20, 43
<223> OTHER INFORMATION: Xaa = Pyrrolysine

<400> SEQUENCE: 120
```

Pro Ile Asn Asp Ala Leu His Xaa Pro Trp Ile Ser Cys His Thr Arg
 1               5                  10                  15

Trp Leu Ala Xaa Phe Asp Pro Tyr Cys His Leu Val Ser Thr Ser Tyr
             20                  25                  30

Ala Ser Asn Thr Ser Thr Ser Met Trp Val Xaa Pro Glu Ile Asn Phe
             35                  40                  45

Thr Gln His His Asp Tyr Thr Gly Arg Asp Leu Gly Gln Ala Phe Pro
             50                  55                  60

Leu Val Ile Arg Glu Leu Asn Ala Ala Ala Pro Gln Lys Pro Ala Leu
65                  70                  75                  80

Val Ser Glu Leu Gly Tyr Ala Gly Thr Gly Arg Asp Val Ile Asn
             85                  90                  95

Arg Asp Val Trp
            100

```
<210> SEQ ID NO 121
<211> LENGTH: 97
<212> TYPE: PRT
<213> ORGANISM: Caldicellulosiruptor saccharolyticus
<220> FEATURE:
<221> NAME/KEY: VARIANT
<222> LOCATION: 4, 97
<223> OTHER INFORMATION: Xaa = Pyrrolysine
<220> FEATURE:
<221> NAME/KEY: VARIANT
<222> LOCATION: 97
<223> OTHER INFORMATION: Xaa = Any Amino Acid

<400> SEQUENCE: 121
```

Asp Asn Tyr Xaa Pro Glu Lys Ser Asn Trp Met Lys Asp His Ala Leu
 1               5                  10                  15

Phe Ile Lys Ser Ile Asp Pro Tyr Lys His Leu Val Ser Ser Ser Ser
             20                  25                  30

Ala Val Leu Tyr Asp Pro Leu Glu Lys Val Lys Glu Leu Asp Phe Ile
             35                  40                  45

Asn Ile Asn Asp Tyr Gly Ile Thr Asn Phe Cys Lys Asn Ile Pro Ser
             50                  55                  60

Lys Gln Arg Asp Ile Ala Asp Met Tyr Asn Lys Pro Ala Phe Phe Cys
65                  70                  75                  80

Glu Asn Gly Ile Ala Ser Asp Pro Thr Thr Thr Lys Arg Leu Asp Arg
             85                  90                  95

Xaa

```
<210> SEQ ID NO 122
<211> LENGTH: 98
<212> TYPE: PRT
<213> ORGANISM: Opitutus terrae
<220> FEATURE:
<221> NAME/KEY: VARIANT
<222> LOCATION: 25, 43
<223> OTHER INFORMATION: Xaa = Pyrrolysine

<400> SEQUENCE: 122
```

-continued

```
Asp Leu Val His Ala Asp Val Val Ala Trp Met Arg Asp His Ala Arg
 1               5                   10                  15

Trp Leu Pro Ala His Asp Pro Tyr Xaa His Leu Ile Thr Thr Ser Leu
             20                  25              30

Thr Gly Gly Ser Asp Arg Pro Glu His Trp Xaa Leu Pro Glu Met Glu
         35                  40              45

Phe Ser Met Tyr His Ser Tyr Trp Asp Pro Ala Pro Ala Arg Lys Ala
     50                  55              60

Ala Val Leu Ala Glu Asp Phe His His Arg Tyr Gly Lys Pro Val Met
 65                  70                  75                  80

Ile Gly Glu Phe Gly Val Ser Gly Ala Asn Trp Ala Arg Pro Met Asp
             85                  90                  95

Pro His
```